US010149443B2

(12) United States Patent
Shoham et al.

(10) Patent No.: US 10,149,443 B2
(45) Date of Patent: Dec. 11, 2018

(54) SYSTEMS AND METHODS FOR CULTIVATING AND DISTRIBUTING AQUATIC ORGANISMS

(71) Applicant: GreenOnyx LTD, Ganey Tikva (IL)

(72) Inventors: Tsipi Shoham, Ganey Tikva (IL); Benjamin Shoham, Ganey Tikva (IL)

(73) Assignee: GreenOnyx LTD, Tel Aviv (IL)

( * ) Notice: Subject to any disclaimer, the term of this patent is extended or adjusted under 35 U.S.C. 154(b) by 172 days.

(21) Appl. No.: 15/008,012

(22) Filed: Jan. 27, 2016

(65) Prior Publication Data

US 2016/0135380 A1 May 19, 2016

Related U.S. Application Data

(63) Continuation of application No. 14/635,949, filed on Mar. 2, 2015.
(Continued)

(51) Int. Cl.
*G06K 9/00* (2006.01)
*A01G 31/02* (2006.01)
(Continued)

(52) U.S. Cl.
CPC .............. *A01G 31/02* (2013.01); *A01G 7/02* (2013.01); *A01G 27/003* (2013.01); *A01G 33/00* (2013.01);
(Continued)

(58) Field of Classification Search
CPC ...... C12M 21/02; C12M 23/14; C12M 23/24; C12M 23/44; C12M 23/48; Y10S 47/06;
(Continued)

(56) References Cited

U.S. PATENT DOCUMENTS 3,889,639 A 6/1975 Day et al.
4,146,993 A 4/1979 Freeman, Sr.
(Continued)

FOREIGN PATENT DOCUMENTS

AU 670331 B2 11/1996
AU 2009213072 A1 4/2010
(Continued)

OTHER PUBLICATIONS

International Preliminary Report on Patentability issued in International Appl. No. PCT/US2013/046346, dated Dec. 23, 2014.
(Continued)

*Primary Examiner* — Aklilu Woldemariam
(74) *Attorney, Agent, or Firm* — Sterne, Kessler, Goldstein & Fox P.L.L.C.

(57) ABSTRACT

System and methods for monitoring the growth of an aquatic plant culture and detecting real-time characteristics associated with the aquatic plant culture aquatic plants. The systems and methods may include a control unit configured to perform an analysis of at least one image of an aquatic plant culture. The analysis may include processing at least one collected image to determine at least one physical characteristic or state of an aquatic plant culture. Systems and methods for distributing aquatic plant cultures are also provided. The distribution systems and methods may track and control the distribution of an aquatic plant culture based on information received from various sources. Systems and methods for growing and harvesting aquatic plants in a controlled and compact environment are also provided. The systems may include a bioreactor having a plurality of vertically stacked modules designed to contain the aquatic plants and a liquid growth medium.

35 Claims, 67 Drawing Sheets

Related U.S. Application Data

(60) Provisional application No. 61/947,787, filed on Mar. 4, 2014, provisional application No. 62/036,509, filed on Aug. 12, 2014, provisional application No. 62/096,269, filed on Dec. 23, 2014.

(51) Int. Cl.
| | | |
|---|---|---|
| *A01K 61/10* | (2017.01) | |
| *A01G 33/00* | (2006.01) | |
| *A01K 61/00* | (2017.01) | |
| *G06T 7/00* | (2017.01) | |
| *C12M 1/34* | (2006.01) | |
| *C12M 1/36* | (2006.01) | |
| *A01G 7/02* | (2006.01) | |
| *A01G 27/00* | (2006.01) | |
| *A01K 63/00* | (2017.01) | |
| *B01D 46/00* | (2006.01) | |
| *A01K 61/54* | (2017.01) | |
| *A01K 61/59* | (2017.01) | |
| *G06T 7/90* | (2017.01) | |

(52) U.S. Cl.
CPC .............. *A01K 61/00* (2013.01); *A01K 61/10* (2017.01); *A01K 61/54* (2017.01); *A01K 61/59* (2017.01); *A01K 63/003* (2013.01); *B01D 46/00* (2013.01); *C12M 1/34* (2013.01); *C12M 1/3446* (2013.01); *C12M 41/48* (2013.01); *G06T 7/0004* (2013.01); *G06T 7/0016* (2013.01); *G06T 7/90* (2017.01); *G06K 9/00* (2013.01); *G06T 2207/10016* (2013.01); *G06T 2207/10024* (2013.01); *G06T 2207/10152* (2013.01); *G06T 2207/30004* (2013.01); *G06T 2207/30128* (2013.01); *Y02A 40/81* (2018.01); *Y02P 60/642* (2015.11)

(58) Field of Classification Search
CPC ........ A01N 25/10; A01N 37/46; A01N 63/02; A01G 1/001; A01G 31/02; A01G 33/00; A01G 27/003; A01G 7/02; A01G 9/1073; A01K 61/00; A01K 63/00; A01K 61/10; A01K 61/54; A01K 61/59; A01K 63/003; G06T 2207/10016; G06T 2207/10024; G01N 15/14; G01N 15/1434; G01N 15/1436; G01N 15/147; G01N 15/1484; G01N 2015/0065; G01N 2015/1454; G01N 2015/149; G01N 2015/1497; G01N 2021/3595; G01N 21/3577; G01N 21/532; G01N 2201/06113; G01N 15/12; G01N 15/1404; G01N 2015/1409; G01N 2015/1415; G01N 2015/142; G01N 21/1702; G01N 21/64; G01N 21/6428; G01N 21/645; G01N 2291/02416; G01N 2291/02809; A61M 1/3678; A47J 31/402; B05B 7/2408; B05B 7/2443; B05B 7/2481; A47L 15/4418; A47L 15/4463; A47L 2301/08; A47L 2401/20; A47L 2501/07; B01F 13/1058; B01F 13/1066; B01F 13/1069; B01F 5/0496; B44D 3/06
See application file for complete search history.

(56) References Cited

U.S. PATENT DOCUMENTS

| | | | |
|---|---|---|---|
| 4,441,145 A | 4/1984 | Antkowiak | |
| 4,669,217 A * | 6/1987 | Fraze | A01G 31/02 47/64 |
| 5,087,353 A * | 2/1992 | Todd | C02F 1/32 210/151 |
| 5,197,263 A | 3/1993 | Midtling et al. | |
| 5,269,819 A | 12/1993 | Porath | |
| 5,469,810 A * | 11/1995 | Chiang | A01K 63/003 119/225 |
| 5,993,030 A | 11/1999 | Barcel | |
| 6,192,833 B1 | 2/2001 | Brune et al. | |
| 6,905,838 B1 | 6/2005 | Bittner | |
| 7,094,562 B2 | 8/2006 | Bittner | |
| 7,176,024 B2 | 2/2007 | Branson et al. | |
| 7,287,488 B2 | 10/2007 | Taylor et al. | |
| 7,415,144 B2 | 8/2008 | Imaizumi et al. | |
| 7,499,573 B2 | 3/2009 | Tanabata et al. | |
| 7,531,350 B2 | 5/2009 | Shiau | |
| 7,582,415 B2 | 9/2009 | Straus | |
| 7,643,134 B2 | 1/2010 | Berndt | |
| 7,690,330 B2 | 4/2010 | Miller | |
| 7,824,904 B1 | 11/2010 | Dimanshteyn | |
| 7,997,025 B1 | 8/2011 | Masse | |
| 8,022,373 B2 | 9/2011 | Maiya | |
| 8,064,661 B2 | 11/2011 | Komori et al. | |
| 8,159,675 B2 | 4/2012 | Kiyota | |
| 8,175,327 B2 * | 5/2012 | Beaty | G06T 7/20 209/509 |
| 8,245,440 B2 | 8/2012 | Ryan et al. | |
| 8,523,385 B2 | 9/2013 | Lu et al. | |
| 8,569,050 B1 | 10/2013 | Ericsson | |
| 8,605,149 B2 | 12/2013 | Conrad et al. | |
| 8,713,850 B2 | 5/2014 | Seebo | |
| 8,800,202 B2 | 8/2014 | Rusiniak | |
| 8,993,314 B2 | 3/2015 | Eckelberry et al. | |
| 9,021,739 B2 | 5/2015 | Koo et al. | |
| 9,058,518 B2 | 6/2015 | Conrad et al. | |
| 9,165,189 B2 | 10/2015 | Conrad et al. | |
| 2005/0034676 A1 | 2/2005 | Taylor et al. | |
| 2005/0074146 A1 | 4/2005 | Jones et al. | |
| 2005/0180608 A1 | 8/2005 | Tanabata et al. | |
| 2006/0102851 A1 | 5/2006 | Jalink et al. | |
| 2006/0122794 A1* | 6/2006 | Sprague | G06Q 10/06 702/32 |
| 2006/0143731 A1 | 6/2006 | Timmis et al. | |
| 2006/0240544 A1 | 10/2006 | Shiau | |
| 2007/0092962 A1 | 4/2007 | Sheppard | |
| 2007/0094926 A1 | 5/2007 | Branson et al. | |
| 2007/0151522 A1 | 7/2007 | Brauman | |
| 2008/0173249 A1 | 7/2008 | Miller | |
| 2008/0173705 A1* | 7/2008 | Girard | A47J 31/402 235/375 |
| 2008/0230010 A1* | 9/2008 | Buck | A01G 9/00 119/256 |
| 2009/0113790 A1 | 5/2009 | Erd | |
| 2009/0148927 A1* | 6/2009 | Schroeder | A01G 33/00 435/257.1 |
| 2009/0291485 A1 | 11/2009 | Shigematsu et al. | |
| 2010/0005711 A1 | 1/2010 | McNeff | |
| 2010/0028977 A1 | 2/2010 | Ng et al. | |
| 2010/0162621 A1 | 7/2010 | Seebo | |
| 2011/0051414 A1 | 3/2011 | Bailey et al. | |
| 2011/0116688 A1 | 5/2011 | Li et al. | |
| 2011/0216953 A1 | 9/2011 | Callahan et al. | |
| 2011/0290202 A1 | 12/2011 | Smith et al. | |
| 2012/0003728 A1 | 1/2012 | Lanoue et al. | |
| 2012/0034679 A1* | 2/2012 | Falber | A01G 33/00 435/257.1 |
| 2012/0043907 A1 | 2/2012 | Lu et al. | |
| 2012/0149091 A1 | 6/2012 | Wilkerson et al. | |
| 2012/0155714 A1* | 6/2012 | Douglass | G06K 9/00657 382/110 |
| 2012/0192799 A1* | 8/2012 | Bazemore, Sr. | A01K 63/006 119/264 |
| 2012/0282677 A1 | 11/2012 | Brod et al. | |
| 2013/0038727 A1 | 2/2013 | Clark | |
| 2013/0045531 A1 | 2/2013 | Weaver et al. | |
| 2013/0252237 A1* | 9/2013 | Wagner | G01N 15/14 435/6.1 |
| 2013/0283683 A1 | 10/2013 | Ringbom et al. | |
| 2014/0234896 A1 | 8/2014 | McHugh | |

(56) References Cited

U.S. PATENT DOCUMENTS

| | | |
|---|---|---|
| 2014/0268635 A1 | 9/2014 | Aikala et al. |
| 2015/0089867 A1 | 4/2015 | Abbott et al. |
| 2015/0234394 A1 | 8/2015 | Shoham et al. |
| 2015/0250113 A1* | 9/2015 | Shoham ............... G06T 7/0004 47/62 R |

FOREIGN PATENT DOCUMENTS

| | | |
|---|---|---|
| DE | 19845883 A1 | 5/1999 |
| EP | 1154370 B1 | 1/2008 |
| JP | 2005056657 A | 3/2005 |
| JP | 2008283937 A | 11/2008 |
| JP | 2010267591 A | 11/2010 |
| JP | 2011120557 A | 6/2011 |
| TW | 201304677 A1 | 2/2013 |
| WO | 9407361 | 4/1994 |
| WO | 2006042371 A1 | 4/2006 |
| WO | 2009142765 A2 | 11/2009 |
| WO | 2010115655 A1 | 10/2010 |
| WO | 2010123943 A1 | 10/2010 |
| WO | 2010132812 A2 | 11/2010 |
| WO | 2011022349 A1 | 2/2011 |
| WO | 2013192195 A1 | 12/2013 |
| WO | 2014006233 A1 | 1/2014 |
| WO | 2014057233 A2 | 4/2014 |
| WO | 2015132661 A3 | 9/2015 |

OTHER PUBLICATIONS

Written Opinion of the International Searching Authority issued in International Appl. No. PCT/US2013/046346, dated Sep. 25, 2013.
International Search Report issued in International Appl. No. PCT/US2013/046346, dated Sep. 25, 2013.
Owen Fletcher, The Future of Agriculture May Be Up, The Wall Street Journal, Oct. 15, 2012, <http://online.wsj.com/article/SB10000872396390443855804577602960672985508.html>, 7 pages.
Vertical Farming Technology <http://www.terraspheresystems.com>, accessed Apr. 21, 2015.
Martha Irvine, In a Chicago suburb, an indoor farm goes 'mega', <http://bigstory.ap.org/article/chicago-suburb-indoor-farm-goes-mega>, Mar. 28, 2013, 8 pages.
Microfarms and bioreactors in modular systems, <http://www.algaeindustrymagazine.com/scalable-algae-microfarms-part-5/>, Jan. 6, 2013, 10 pages.
J.P. Bitog et al., Application of computational fluid dynamics for modeling and designing photobioreactors for microalgae production: A review, Computers and Electronics in Agriculture, vol. 76, Issue 2, May 2011, pp. 131-147.
Francesca L. Crowe et al., Risk of hospitalization or death from ischemic heart disease among British vegetarians and nonvegetarians: results from the EPIC-Oxford cohort study, Am J Clin Nutr, vol. 97, No. 3, Mar. 2013, pp. 597-603.
M. Dominique Ashen, Vegetarian Diets in Cardiovascular Prevention; Curr Treat Options Cardiovas Med., vol. 15, Issue 6, Aug. 9, 2013, pp. 735-745.
Tao Huang et al., Cardiovascular Disease Mortality and Cancer Incidence in Vegetarians: A Meta-Analysis and Systemic Review, Ann Nutr Metab, vol. 60, No. 4, Jun. 2012, pp. 233-240.
ScienceDaily, "Vegetarianism can reduce risk of heart disease by up to a third", <http://www.ox.ac.uk/media/news_stories/2013/130130.html>, Jan. 30, 2013, 2 pages.
Claire T. McEvoy et al., Vegetarian diets, low-meat diets and health: a review: Cambridge Journals—Public Health Nutrition, vol. 15, Issue 12, Dec. 2012, pp. 2287-2294.

Xue Chen et al., "Lumostatic Strategy for Microalgae Cultivation Utilizing Image Analysis and Chlorophyll Content as Design Parameters, Bioreource Technology," vol. 102, No. 10, Feb. 15, 2011, pp. 6005-6012.
Ivo Havlik et al., "Monitoring of Microalgal Cultivations with On-line, Flow-Through Microscopy," Algal Research, vol. 2, No. 3, Apr. 26, 2013, pp. 253-257.
Kanhaiya Kumar et al., "Use of Image Analysis Tool for the Development of Light Distribution Pattern Inside the Photobioreactor for the Algal Cultivation," Bioreseouce Technology, vol. 143, Jun. 3, 2013, pp. 88-95.
J.M. Sandnes et al., "Real-time Monitoring and Automatic Density Control of Large-Scale Microalgal Cultures Using Near Infrared (NIR) Optical Density Sensors, Journal of Biotechnology," vol. 122, No. 2, Mar. 23, 2006, pp. 209-215.
Miguel V. Córdoba-Matson et al., "Evaluation of Isochrysis Galbana (clone T-ISO) Cell Numbers By Digital Image Analysis of Color Intensity," Journal of Applied Phycology, vol. 22, No. 4, Sep. 19, 2009, pp. 427-434.
Arne Bluma et al., "In-situ Imaging Sensors for Bioprocess Monitoring: State of the Art," Analytical and Bioanalytical Chemistry, vol. 398, No. 6, Sep. 12, 2010, pp. 2429-2438.
Ivo Havlik et al., "Online Monitoring of Large Cultivations of Microalgae and Cyanobacteria," Trends in Biotechnology, vol. 31, No. 7, May 23, 2013, pp. 406-414.
International Search Report issued in International Appl. No. PCT/IB2015/000398, dated Oct. 28, 2015.
Written Opinion of the International Searching Authority issued in International Appl. No. PCT/IB2015/000398, dated Sep. 11, 2015.
Matthias Eberius, "Observation Parameters of the Duckweed Growth Inhibition Test Frond Number—Total Frond Area—Dry weight", LemnaTec, Mar. 14, 2001, 2 pages.
Matthias Eberius, "Observation Parameters in the Duckweed Growth Inhibition Test", LemnaTec, Mar. 14, 2011, 2 pages.
J. Sánchez et al., "A Virtual Laboratory for Tubular Photobioreactors for Outdoor Microalgae Culture", 10th IFAC Symposium Advances in Control Education, The International Federation of Automatic Control, Aug. 28-30, 2013 Sheffield, UK, pp. 297-302.
Silks Hemming et al., "Rapport GTB-1221 Algenteeltsystemen voor de tuinbouw—Integratie", 2012, URL:http://library.wur.nl/WebQuery/wurpubs/fulltext/249619 [retrieved on Sep. 29, 2017].
Communication Pursuant to Rule 164(2)(b) and Article 94(3)EPC issued in European Application No. 15718577.8, dated Oct. 20, 2017, 11 pages.
Fong Qiu: "Algae Architecture", Jul. 9, 2013 (Jul. 9, 2013) URL: https://repository.tudelft.nl/i slandora/object/uuid:b0b6e05d-49d8-4cc0-9e28-f510b0a8b215/datastream/OBJ/download [retrieved on Sep. 28, 2017].
Committee on the Sustainable Development of Algal Biofuels et al: "Sustainable Development of Algal Biofuels in the United States", Sustainable Development of Algal Biofuels in the United States, Dec. 18, 2012 (Dec. 18, 2012), XURL: https://download.nap.edu/cart/download.cgi ?record_i d=13437 [retrieved on Sep. 29, 2017].
Arbib Zouhayr et al. : "Long Term Outdoor Operation of a Tubular Airlift Pilot Photobioreactor and a High Rate Algal Pond as Tertiary Treatment of Urban Wastewater", Ecological Engineering, Elsevier, Amsterdam, NL, vol. 52, Jan. 30, 2013 (Jan. 30, 2013), pp. 143-153.
Rouke Bosma et al., "AlgaePARC Exploring Scale-up Challenges in Microalgae Mass Production", ALGAE Workshop, Nov. 16, 2012, Nov. 16, 2012 (1012-11-16), URL: http://www.umb.no/statisk/forsiden/algeworkshopnovl2/bosma.pdf [retrieved on Sep. 29, 2017].
Slegers P.M. et al., "Scenario Analysis of Large Scale Algae Production in Tubular Photobioreactors", Applied Energy, Elsevier Science Publishers, GB, vol. 105, Feb. 9, 2013 (Feb. 9, 2013), pp. 395-406.

* cited by examiner

1400

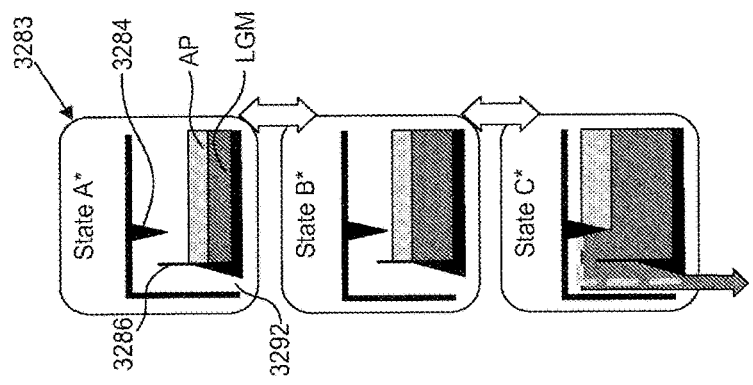
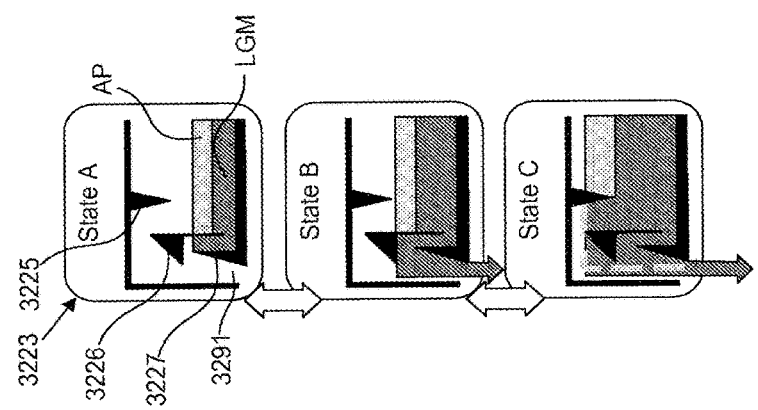
FIG. 33B

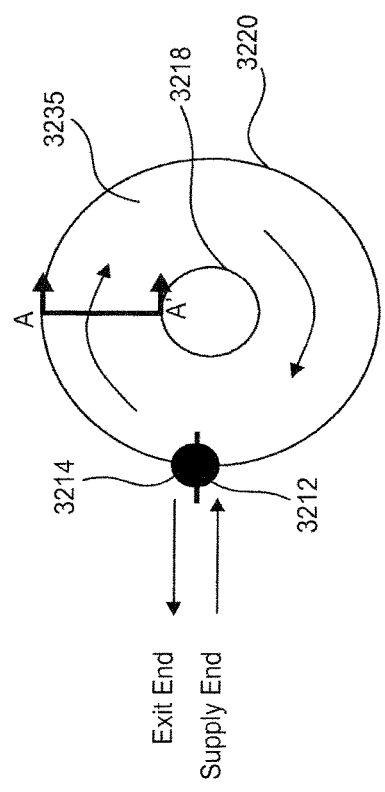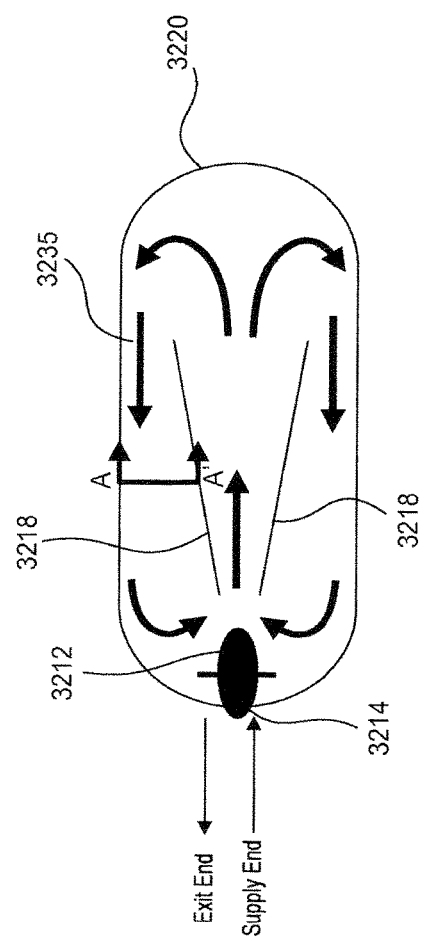
FIG. 35C
FIG. 35D

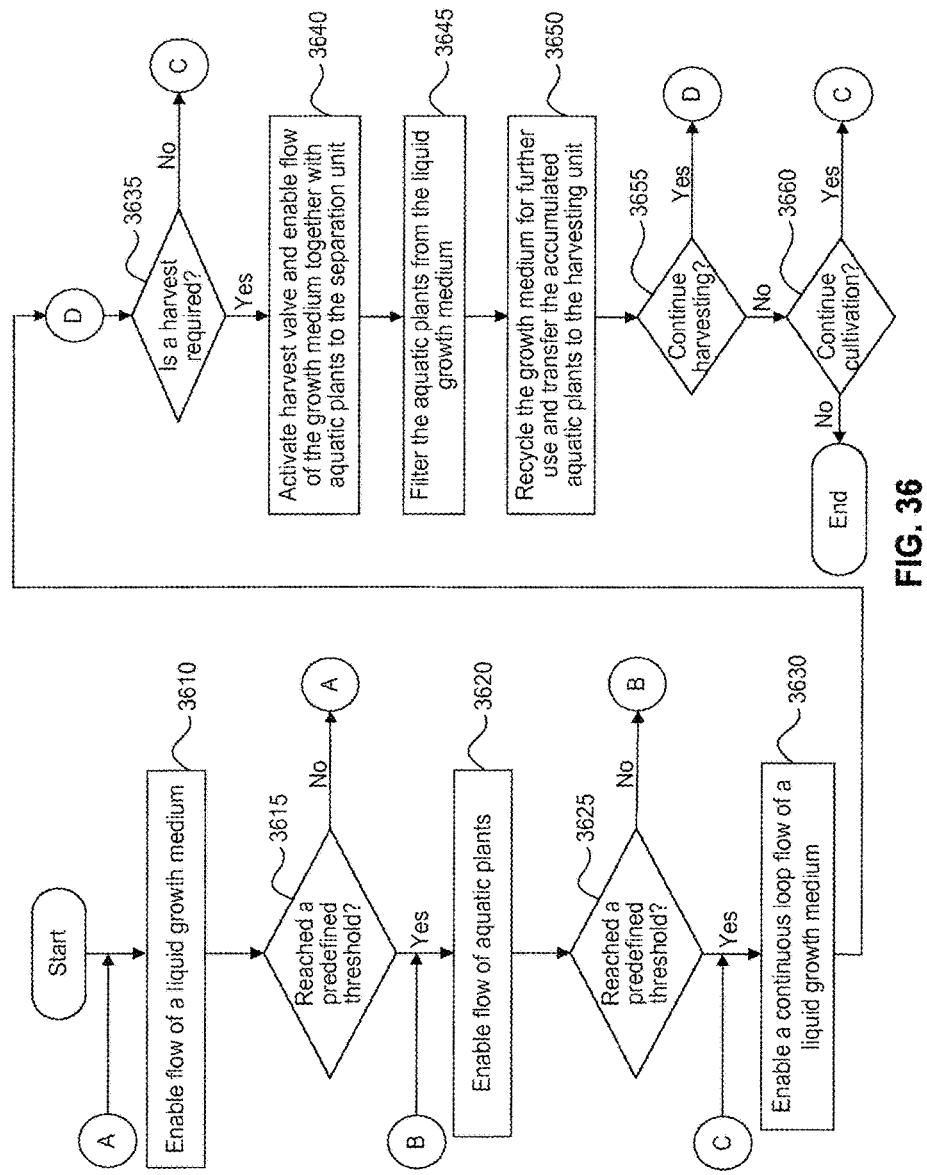

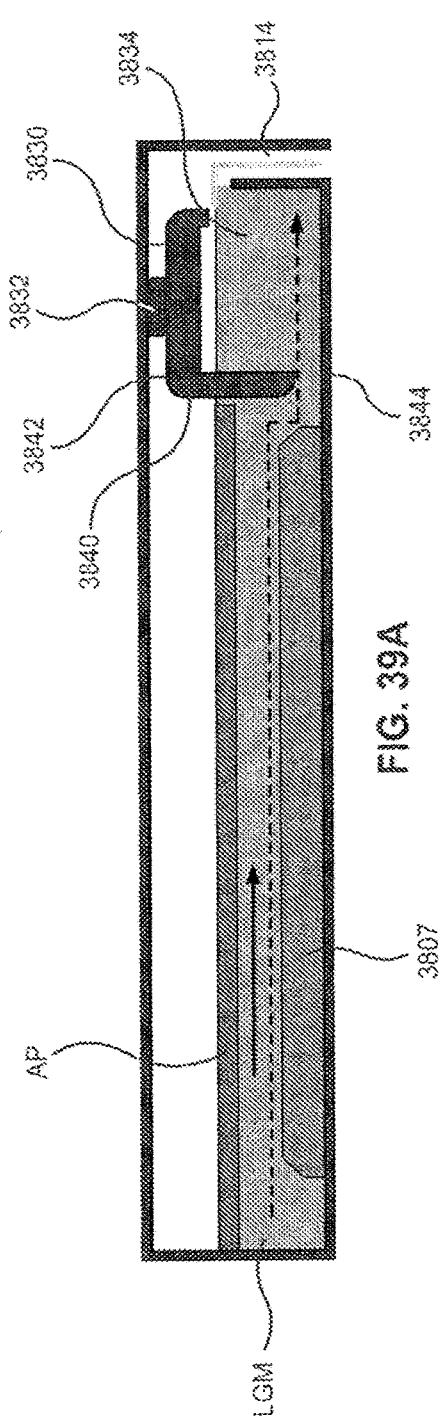
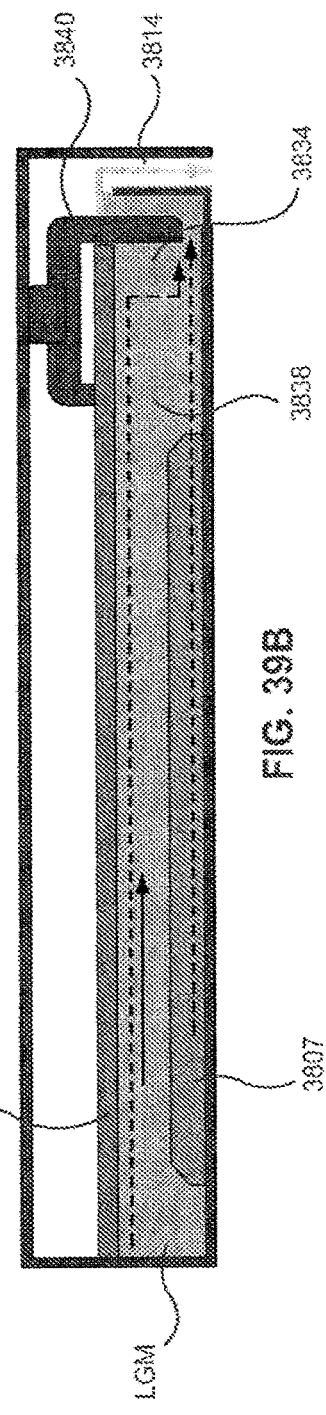

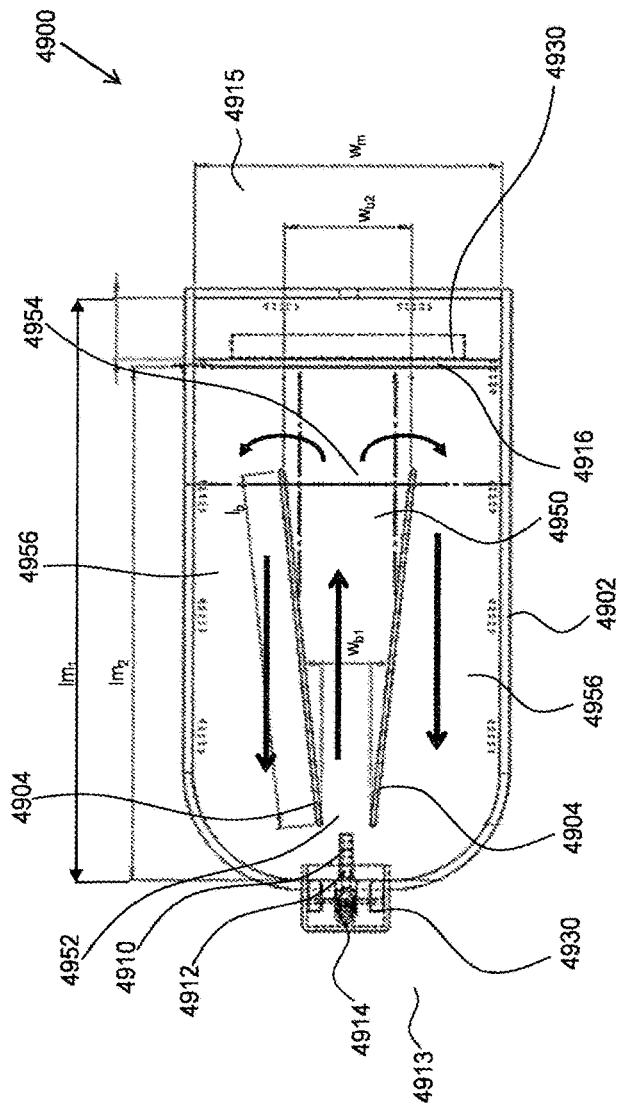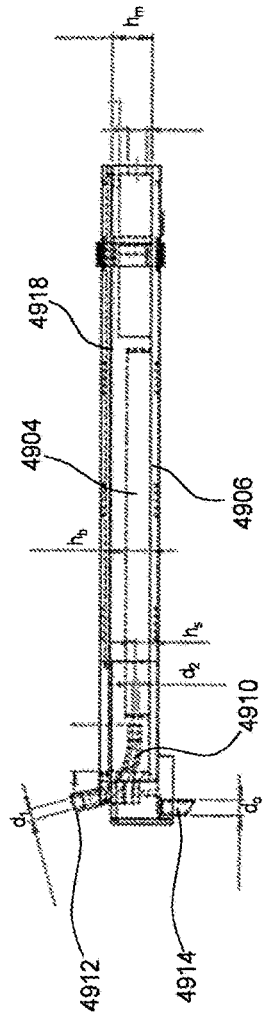
FIG. 49A
FIG. 49B

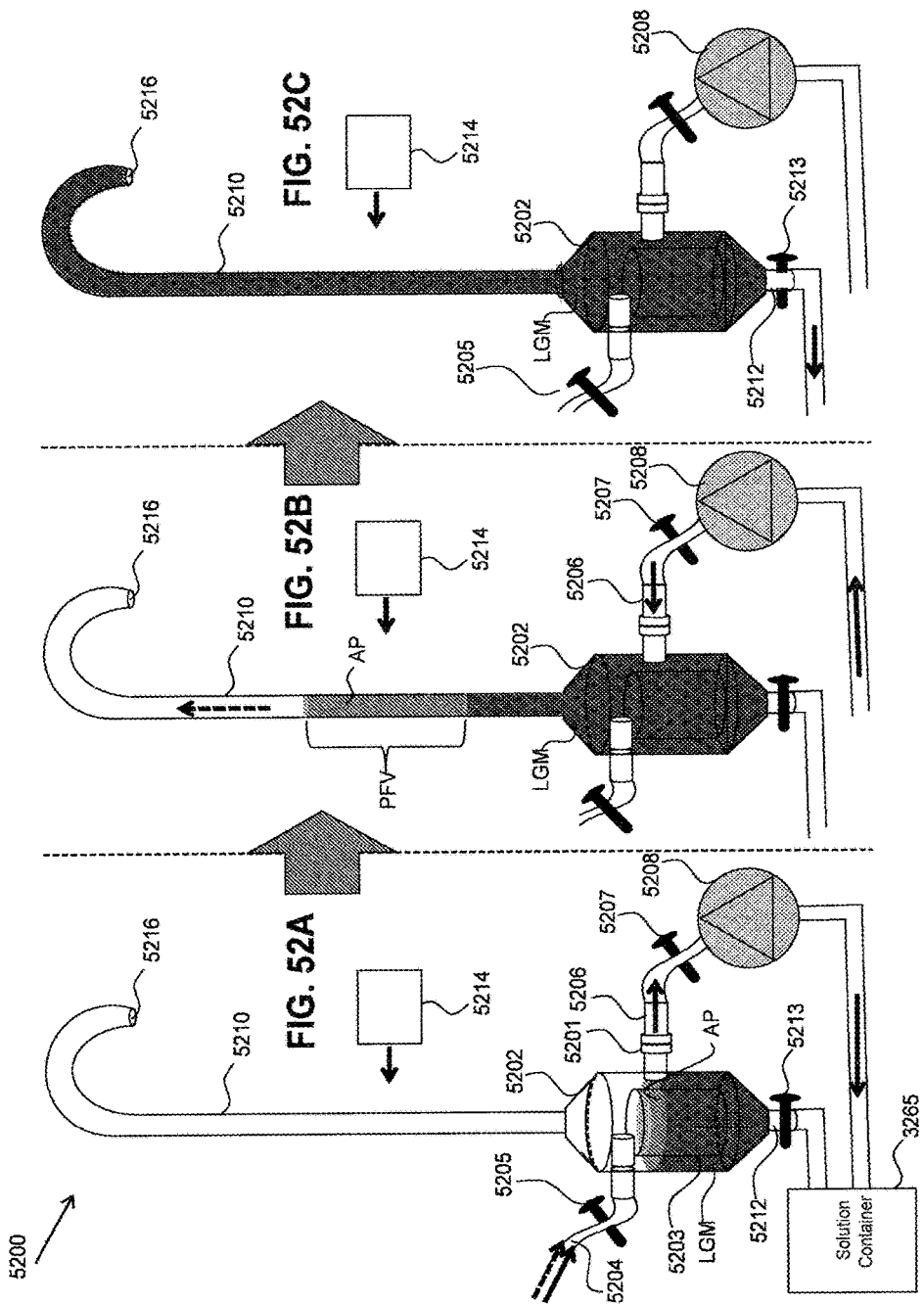

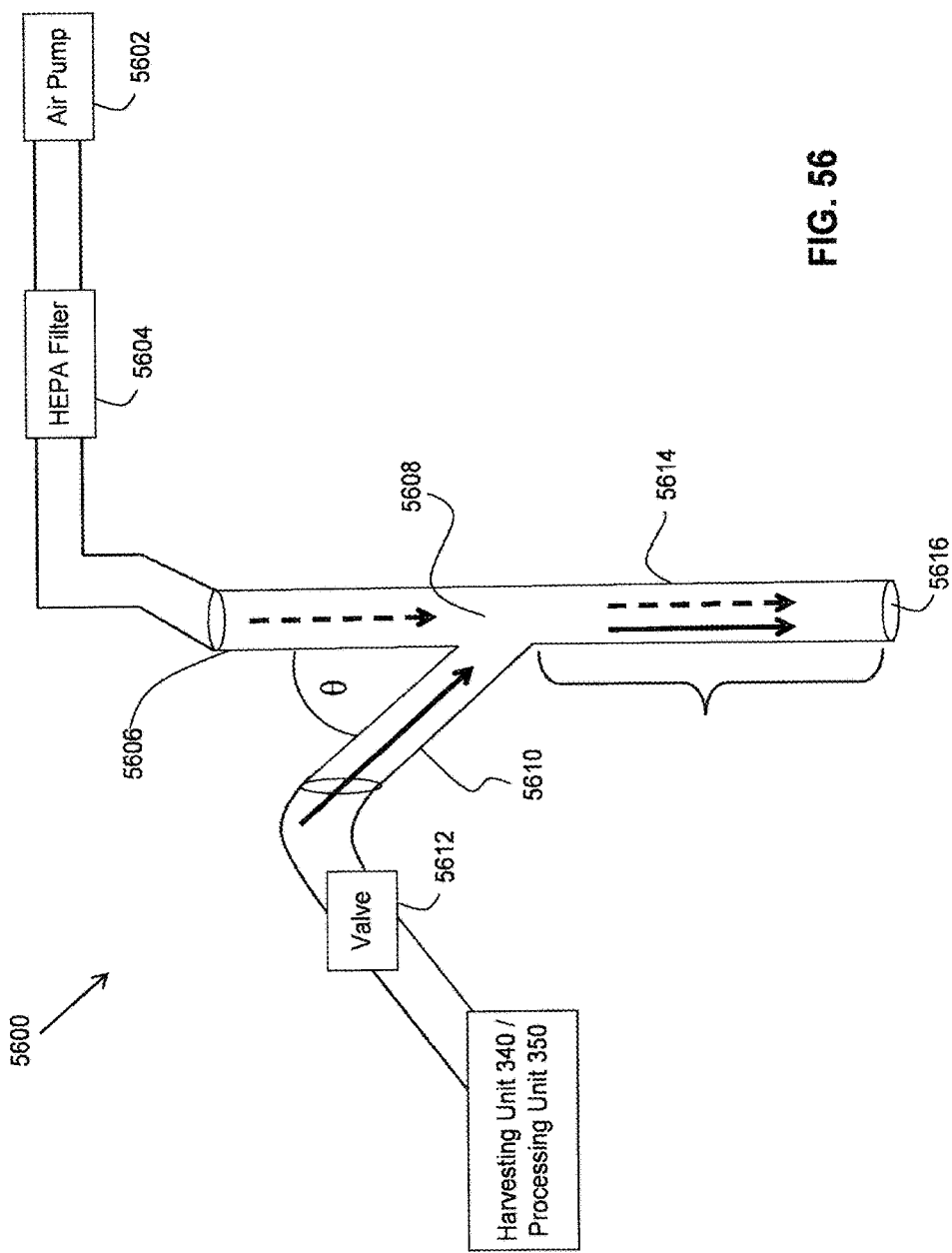

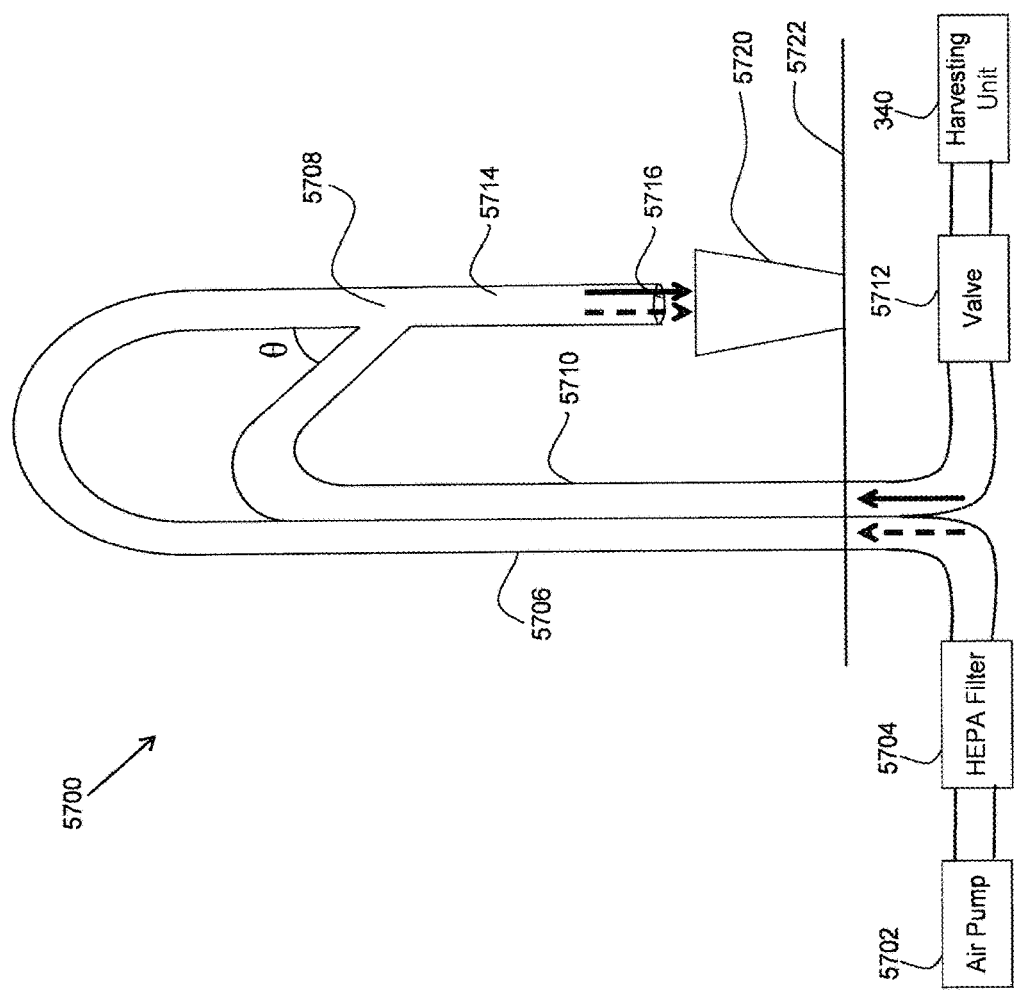

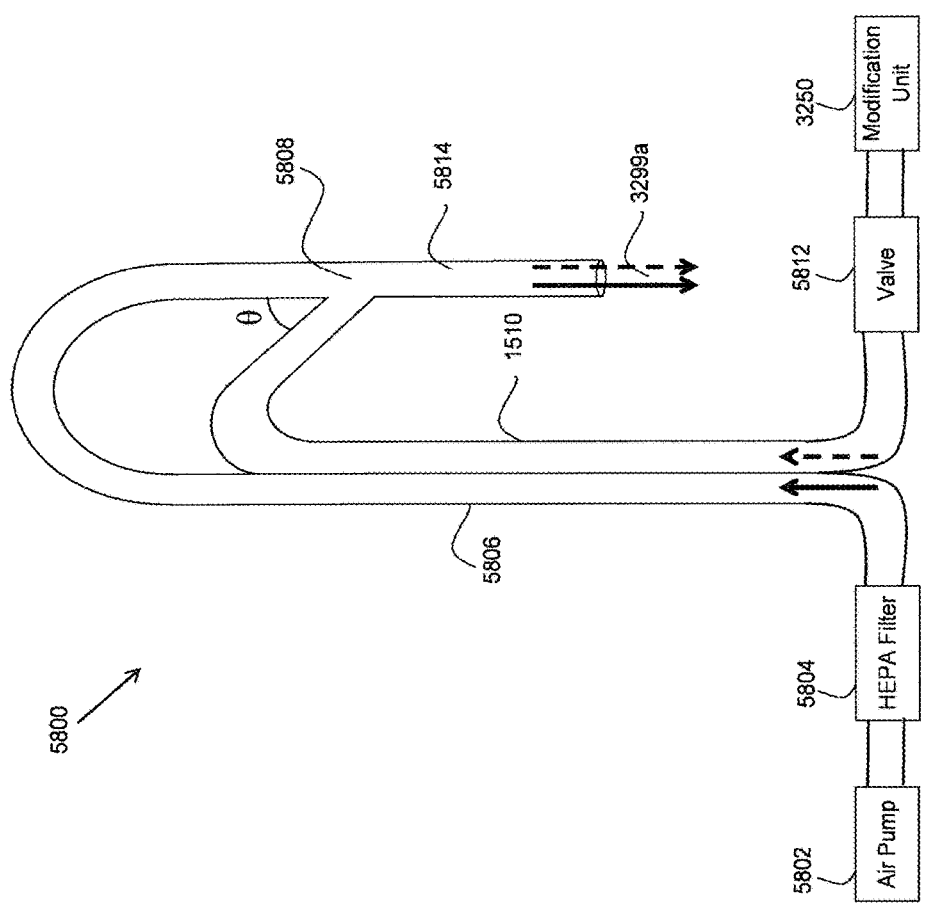

SYSTEMS AND METHODS FOR CULTIVATING AND DISTRIBUTING AQUATIC ORGANISMS

CROSS-REFERENCE TO RELATED APPLICATIONS

This application is a continuation of U.S. application Ser. No. 14/635,949, filed on Mar. 2, 2015, which is incorporated herein in its entirety by reference thereto. This application claims priority to the following U.S. Provisional Applications via U.S. application Ser. No. 14/635,949, each of which is incorporated herein in its entirety by reference thereto:

U.S. Provisional App. No. 61/947,787, filed on Mar. 4, 2014;

U.S. Provisional App. No. 62/036,509, filed on Aug. 12, 2014; and

U.S. Provisional App. No. 62/096,269, filed Dec. 23, 2014.

BACKGROUND OF THE INVENTION

Field of the Invention

Embodiments of the inventions generally relate to systems and methods for cultivating and distributing an aquatic organism. In particular, embodiments relate to monitoring and controlling the cultivation of an aquatic plant culture and the distribution of the aquatic plant culture.

Background Art

The global rise of non-infectious diseases chronic and degenerative diseases, such as cardiovascular diseases, type II diabetes, asthma, cancer, dementias, hypertension, osteoporosis, attention deficit disorder (ADD) and attention deficit hyperactivity disorder (ADHD) may be directly linked to unhealthy diets resulting from a high consumption of processed foods with low nutritious qualities. Research indicates that vegetarian based diets along with a reduced consumption of processed foods can lower the occurrence of cardio vascular diseases and cancer. The following references are examples of such research, each of which is incorporated herein in its entirety by reference thereto:
1) Francesca L Crowe et al., Risk of hospitalization or death from ischemic heart disease among British vegetarians and nonvegetarians: results from the EPIC-Oxford cohort study; 2013; Am J Clin Nutr March 2013.
2) Dominique Ashen M. Vegetarian Diets in Cardiovascular Prevention; Curr Treat Options Cardiovasc Med. 2013 Aug. 9.
3) Tao Huang et al., Cardiovascular Disease Mortality and Cancer Incidence in Vegetarians: A Meta-Analysis and Systematic Review; Ann Nutr Metab 2012; 60:233-240.
4) University of Oxford, Vegetarianism can reduce risk of heart disease by up to a third; Science Daily, 30 Jan. 2013.
5) Claire T McEvoy et al., Vegetarian diets, low-meat diets and health: a review; Cambridge Journals—Public Health Nutrition/Volume 15/Issue 12/December 2012, pp 2287-2294.

As such, there is an increasing desire for more nutritious foods. This has led to the rapid global development of the health and wellness foods market, which reached $200B by 2011 and is forecasted to grow at a 5% CAGR over the next years to come. However, this segment continues to operate through the agro-food non-sustainable practices and its supply chain inefficiencies. Almost 33% of the food grown for human consumption is lost today, 65% for fruits & vegetables. And the agri-food industry is expected to account for 50% of the global greenhouse gas emission by 2030. Furthermore, although this segment aims to promote healthier food, it eventually supplies "engineered" food that the majority of the consumers does not trust and/or cannot afford on a daily base. As Todd Runestad, Editor-In-Chief of *Functional Ingredients Magazine* summarized it: "Consumers understand the inherent healthiness of fruits and vegetables, so if you can just put them in a convenient and tasty delivery system, you're on your way." Aquatic edible plants are attractive vegetables because they are convenient, tasty, and an excellent source of protein, dietary fibers, essential minerals (dietary chemical elements), key vitamins, and other phytochemicals (e.g. antioxidants) needed for a healthy diet. Thus, cultivating aquatic plants and the distribution of these aquatic plants to consumers are fields of interest.

BRIEF SUMMARY OF THE INVENTION

Some embodiments include a method for monitoring a culture of aquatic plants in a bioreactor. The method includes performing an analysis of at least one image of the culture. The analysis may include receiving the at least one image of the culture of aquatic plants from at least one image sensor disposed in the bioreactor and performing an image processing technique on the at least one image to determine at least one physical characteristic of the culture and performing an analysis to determine at least one state of the culture. In some embodiments, the method includes adjusting at least one growing condition based on one or more of the at least one determined physical characteristic and the at least one determined state.

In some embodiments, the growing condition is adjusted based on the at least one determined physical characteristic and the at least one determined state.

In some embodiments, the at least one characteristic is determined based on at least one physical parameter of the aquatic plant culture. The at least one physical parameter can be at least one of: the surface area of the aquatic plants, the density of the aquatic plants, the amount of light absorbed by the aquatic plants, the wavelength of light reflected from the surface of the aquatic plants, the wavelength of light which is transmitted through the aquatic plants, and the distribution of the wavelengths in the reflected or transmitted light.

In some embodiments, the method includes storing in a database a time stamp of when the at least one image is received together with the at least one parameter of the aquatic plant culture.

In some embodiments, the method includes determining the at least one state by monitoring changes in the at least one physical characteristic over time.

In some embodiments, the at least one physical characteristic is at least one of: a shape of an aquatic plant, a size of an aquatic plant, a pigment of an aquatic plant, a texture of an aquatic plant, or a transparency of an aquatic plant.

In some embodiments, the at least one state is at least one of: a healthy culture, a contaminated culture, a growth phase of the culture, a selective nutrients profile, a growth rate of the culture, a stressed culture, a biomass density, a mortality rate, a dead culture, a dying culture, and a viability of the aquatic plants' growth.

In some embodiments, the growth phase of the culture is one of a lag phase, an exponential phase, a stationary phase, a death phase, and any intermediate phase.

In some embodiments the culture of aquatic plants is selected from at least one of: *Spirodela, Landoltia, Lemna, Wolffiella,* and *Wolffia.*

In some embodiments, the method includes storing in a database at least one of: the at least one image, the at least one physical characteristic, and the at least one state.

In some embodiments, the at least one growing condition includes at least one of: a light level, light spectrum, light interval, temperature, fertilizer elements level, water level, vapor pressure, humidity, pH, ion concentration, oxygen concentration, $CO_2$ level, culture density, air flow, growth solution flow, and culture flow.

In some embodiments, the method includes operating at least one valve in response to determining at least one characteristic or the at least one state.

In some embodiments the method is executed by one or more processors. In some embodiments the culture is disposed in the bioreactor. In some embodiments the method is performed by a server in communication with a control unit. In some embodiments the method is performed by a control unit.

In some embodiments, the at least one state of the culture of aquatic plants is determined based on the developmental stage of individual aquatic plants within the aquatic plant culture. In some embodiments, the developmental stage of the individual aquatic plants is determined based on the at least one characteristic. In some embodiments, the developmental stage of the individual aquatic plants is determined by at least one of: the presence of a connection area between a mother plant and a daughter plant and the absence of a connection area between a mother plant and a daughter plant.

Some embodiments include a system for monitoring a culture of aquatic plants. The system includes a processor in communication with at least one image sensor disposed in a bioreactor and a memory in communication with the processor, containing instructions executed by the processor. The processor is configured to receive at least one image of the culture of aquatic plants from at least one image sensor disposed in the bioreactor, perform image processing on the at least one image to determine at least one physical characteristic of the aquatic plant culture, perform an analysis to determine at least one state of the culture, and control operation of the bioreactor based on one or more of: the determination of the at least one physical characteristic and the determination of the at least one state.

In some embodiments, the processor is configured to monitor the changes in the at least one characteristic by using at least one mathematical model.

In some embodiments, the processor is in communication with the bioreactor via a server over a network. In some embodiments, the processor is located in a control unit within the bioreactor.

In some embodiments, the bioreactor includes at least one input unit for receiving an aquatic organism used as a starter material for an aquatic plant culture, at least one growing unit for growing the aquatic plant culture, at least one harvesting unit for harvesting the aquatic plant culture, and at least one output unit for providing a consumable derived from the aquatic plant culture.

In some embodiments, the processor is further configured to control the bioreactor by adjusting at least one growing condition.

Some embodiments include a bioreactor for growing an aquatic plant culture. The bioreactor includes at least one input unit for receiving an aquatic organism used as a starter material for an aquatic plant culture, at least one growing unit for growing the aquatic plant culture, at least one harvesting unit for harvesting the aquatic plant culture, at least one output unit for providing a consumable derived from the aquatic plant culture, and a control unit. The control unit is configured receive an image from an imaging system disposed in the bioreactor, the imaging system including at least one image sensor, determine at least one characteristic related to the aquatic plant culture by performing at least one image processing technique on the at least one image, and control the operation of the at least one bioreactor units based on the determination of the at least one characteristic.

In some embodiments, the bioreactor includes a modification unit for altering the aquatic plant culture in terms of ingredient content and a customization unit for customizing the consumable provided to an end user.

In some embodiments, the imaging system includes a plurality of light sources. In some embodiments, the plurality of light sources illuminate the aquatic plant culture with various forms of light having different wavelengths or different illumination intensities. In some embodiments, the imaging system is configured to collect light reflected off the culture of aquatic plants and light transmitted through the culture of aquatic plants. In some embodiments, the imaging system includes at least one light source positioned above the aquatic plant culture and at least one light source positioned below the aquatic plant culture.

Some embodiments include a computer program product with a non-transitory computer readable medium having computer program logic recorded thereon. When the computer program logic is executed by one or more processors of a server computer system it causes the server computer system to receive at least one image of a culture of aquatic plants from at least one image sensor disposed in a bioreactor; perform image processing on the at least one image to determine at least one physical characteristic of the aquatic plant culture; and control operation of the at least one bioreactor based on the determination of the at least one physical characteristic.

Some embodiments include an apparatus for growing aquatic plants in a controlled and compact environment, the apparatus including a stack of modules, the stack of modules including a plurality of vertically stacked individual modules, each individual module designed to contain the aquatic plants and a liquid growth medium. At least one first valve in communication with at least one individual module, the at least one first valve enabling the flow of at least one of: a predetermined volume of the aquatic plants and a predetermined volume the liquid growth medium. A first vertical raceway in communication with the at least one first valve and connected to the plurality of vertically stacked individual modules, the first vertical raceway enabling the flow of at least one of: the predetermined volume of liquid growth medium and the predetermined volume of aquatic plants from a higher individual module in the stack of modules to a lower individual module in the stack of modules.

In some embodiments, the first valve is a static valve.

In some embodiments, the apparatus includes at least one second valve in communication with at least one individual module, the at least one second valve being in communication with a second vertical raceway and being configured to harvest a predetermined volume of aquatic plants.

In some embodiments, the second vertical raceway is connected to a separation unit. In some embodiments, the second vertical raceway is connected to a harvesting unit.

In some embodiments, the first vertical raceway comprises a plurality of interconnected sub-channels and each of the plurality of interconnected sub-channels is in communication with at least one first valve.

In some embodiments, the at least one first valve includes at least one baffle. In some embodiments, the at least one second valve includes at least one baffle.

In some embodiments, each individual module is a horizontal raceway configured to grow the culture of aquatic plants.

In some embodiments, each individual module in the stack of modules includes at least one first valve. In some embodiments, each individual module in the stack of modules includes at least one second valve.

In some embodiments, the apparatus also includes a modification unit in communication with the stack of modules.

In some embodiments, the at least one second valve is a dynamic valve.

In some embodiments, the apparatus also includes a storage unit connected to the modification unit for storage of recycled liquid growth medium.

In some embodiments, the modification unit is preforms at least one of: sterilization, disinfection, essential salts dissolving, fertilizer dissolving, aeration, a PH adjustment, and a temperature adjustment.

In some embodiments, the apparatus includes at least one of: at least one light source, at least one air flow source, at least one inlet to receive air flow, and at least one outlet to release excess pressure.

In some embodiments, the apparatus includes a control unit, the control unit being configured to control the flow of the predetermined volume of the aquatic plants and the predetermined volume of the liquid growth medium. In some embodiments, the control unit is configured to control the flow of the predetermined volume of the aquatic plants and the predetermined volume of the liquid growth medium by controlling the flow liquid growth medium into a single individual module in the plurality of vertically stacked individual modules.

In some embodiments, the apparatus includes a biomass quantification unit configured to perform in-line measurements of plant floating volume (PFV) on the aquatic plants.

Some embodiments are directed towards a cartridge for distributing an aquatic plant culture including a body having a plurality of sealed capsules where at least one of the sealed capsules contains an aquatic plant culture in a preservation medium and at least one of the sealed capsules contains a fertilizer stock solution.

In some embodiments, the aquatic plant culture is selected from the group consisting of: *Spirodela, Landoltia, Lemna, Wolffiella,* and *Wolffia*. In some embodiments, the aquatic plant culture is in a predetermined life stage. In some embodiments, the predetermined life stage is a spring life stage. In some embodiments, the predetermined life stage is a winter life stage.

In some embodiments, the cartridge includes an identification label. In some embodiments, the identification label includes at least one of: a barcode, a radio-frequency identification (RFID) chip, and a quick response code.

In some embodiments, the identification label includes coded information related to the cartridge and the coded information includes information related to at least one of: the contents of one or more sealed capsules, the type of aquatic plant culture contained within at least one of the sealed capsules, the type of fertilizer stock solution contained within at least one of the sealed capsules, the date the capsules were sealed, the type of preservation medium, optimum growing conditions for the type of aquatic plant culture contained within at least one of the sealed capsules, the location where the capsules were sealed, a SKU number, and a fertilizer stock solution protocol matching the aquatic plant culture contained within the capsules.

In some embodiments, the identification label includes coded information and the coded information includes authentication information related to the source of the cartridge.

In some embodiments, the cartridge incudes a sensor. In some embodiments, the sensor includes at least one of: a temperature sensor, a pressure sensor, an oxygen sensor, a light sensor, and a pH sensor.

In some embodiments, the preservation medium is liquid. In some embodiments, the preservation medium is a gel.

In some embodiments, the fertilizer stock solution includes at least one macro- or micro-element including, for example, nitrogen, phosphorous, iron, potassium, sulfur, calcium, magnesium, zinc, compounds containing at least one macro- or micro-element, and combinations thereof. In some embodiments, the fertilizer stock solution is a certified organic fertilizer solution.

In some embodiments, the aquatic plant culture is a seasoned aquatic plant culture.

Some embodiments are directed towards a bioreactor including an input unit configured to receive a cartridge containing an aquatic plant culture, the input unit including an extractor configured to remove the aquatic plant culture from the cartridge; an incubation unit for receiving the aquatic plant culture from the input unit; a growing unit for growing the aquatic plant culture; a harvesting unit for harvesting the aquatic plant culture; and a control unit. The control unit may be configured to read an identification label associated with the cartridge received at the input unit to obtain cartridge identification information and send the cartridge identification information to a server.

In some embodiments, the bioreactor also includes a memory and the control unit is further configured to store the cartridge identification information in the memory.

In some embodiments, the server comprises a database for storing the cartridge identification information.

In some embodiments, the control unit is further configured to record a time stamp of when the aquatic plant culture is removed from the cartridge and send the time stamp to the server. In some embodiments, the server is configured to track the distribution of the cartridge based on the cartridge identification information and the time stamp.

In some embodiments, the server is configured to perform at least one of the following actions based on the cartridge identification information and the recorded time stamp: (a) request a new cartridge shipment for the bioreactor; (b) adjust a shipment date for a subsequent cartridge shipment; (c) adjust the aquatic plant culture in a cartridge for a subsequent cartridge shipment; (d) customize the contents of a cartridge to be sent to a specific location; (e) send a status report for the bioreactor to a central processing location; (f) adjust the growth conditions in another bioreactor; (g) adjust a preservation medium for a subsequent cartridge shipment; (h) adjust a fertilizer stock solution for a subsequent cartridge shipment; and (i) adjust the harvesting schedule in another bioreactor.

In some embodiments, adjusting the harvesting schedule in the another bioreactor changes a life stage at which another aquatic plant culture is harvested and packaged into another cartridge. In some embodiments, adjusting the harvesting schedule in another bioreactor changes the time within a life stage at which another aquatic plant culture is harvested and packaged into another cartridge.

In some embodiments, the control unit is further configured to receive an image from an imaging system disposed in the bioreactor, the imaging system comprising at least one image sensor configured to image the aquatic plant culture in at least one of the cartridge and the incubation unit; determine at least one characteristic related to the aquatic plant culture; and send the at least one characteristic related to the aquatic plant culture to the server.

In some embodiments, the server is configured to perform at least one of the following actions based on the determination of a characteristic of the aquatic plant culture: (a) request a new cartridge shipment for the bioreactor; (b) adjust a shipment date for a subsequent cartridge shipment; (c) adjust the aquatic plant culture in a cartridge for a subsequent cartridge shipment; (d) customize the contents of a cartridge to be sent to a specific location; (e) send a status report for the bioreactor to a central processing location; (f) adjust the growth conditions in another bioreactor; (g) adjust a preservation medium for a subsequent cartridge shipment; (h) adjust a fertilizer stock solution for a subsequent cartridge shipment; (i) adjust the harvesting schedule in another bioreactor; and (j) adjust one or more substances housed within a cartridge for a subsequent cartridge shipment.

Some embodiments are directed towards a system for growing an aquatic plant culture including a server and a bioreactor in communication with the server. The bioreactor may include an input unit configured to receive a cartridge containing a culture of aquatic plants, the input unit comprising an extractor configured to remove the aquatic plant culture from the cartridge; an incubation unit for receiving the aquatic plant culture from the input unit; a growing unit for growing the aquatic plant culture; a harvesting unit for harvesting the aquatic plant culture; and a control unit. The control unit may be configured to read an identification label associated with the cartridge received at the input unit to obtain cartridge identification information and send the cartridge identification information to the server.

Some embodiments are directed towards a method of distributing an aquatic plant culture including growing an aquatic plant culture; harvesting a portion of the aquatic plant culture when the aquatic plant culture is in a predetermined life stage; packaging the portion of the aquatic plant culture and a preservation medium in a sealed capsule of a cartridge; and distributing the cartridge to a remote location, the remote location determined based on one or more of: a need for the portion of the aquatic plant culture, a distribution time required to send the cartridge to the remote location, and the predetermined life stage of the portion of the aquatic plant culture.

In some embodiments, growing the aquatic plant culture comprises maturing the aquatic plant culture through an entire life cycle before harvesting.

In some embodiments, the method also includes packaging at least one fertilizer stock solution in another sealed capsule of the cartridge. In some embodiments, the type of the fertilizer stock solution is determined based on the species of the aquatic plant culture.

In some embodiments, the type of preservation medium is determined based on at least one of the species of the aquatic plant culture and the predetermined nature life stage of the portion of the aquatic plant culture.

In some embodiments, the aquatic plant culture is grown in a bioreactor.

Some embodiments are directed towards a distribution system for distributing an aquatic plant culture including a source bioreactor for growing an aquatic plant culture; a point-of-use bioreactor for growing a portion of the aquatic plant culture received from the source bioreactor; and a server in communication with the source bioreactor and the point-of-use bioreactor. The server may be configured to coordinate the distribution of the portion of the aquatic plant culture from the source bioreactor to the point-of-use bioreactor based on one or more of: a need for the portion of the aquatic plant culture, a distribution time required to send the cartridge to the point-of-use bioreactor, and a life stage of the portion of the aquatic plant culture.

BRIEF DESCRIPTION OF THE DRAWINGS/FIGURES

Figure 17A:
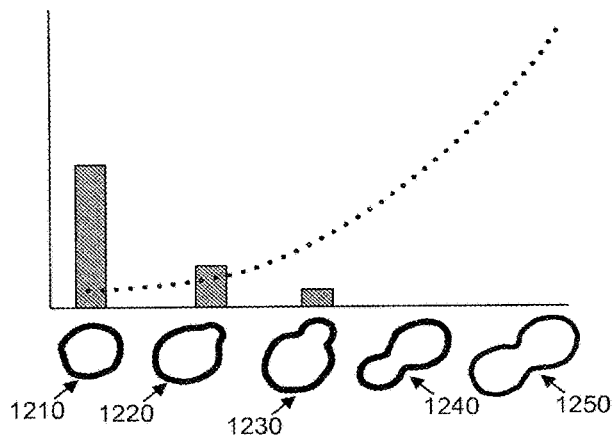
Figure 17B:
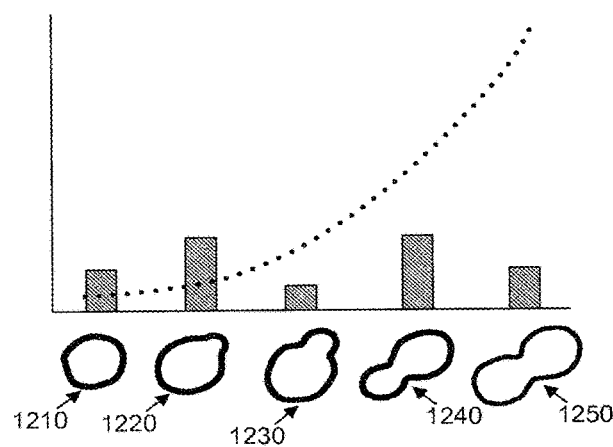
Figure 17C:
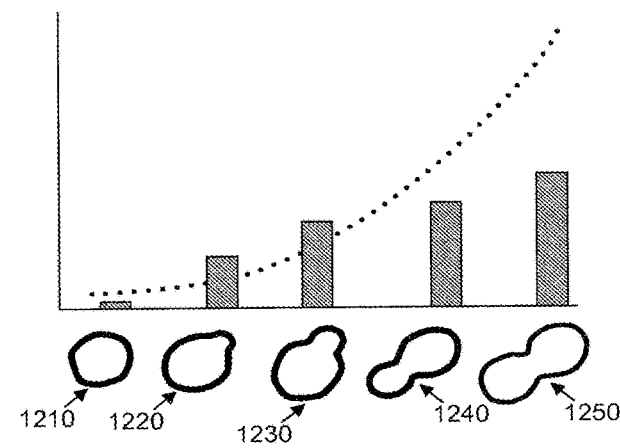

FIGS. 17A-17C show distribution graphs for various phases of growth for a culture of aquatic plants. FIG. 17A shows a distribution graph for early growth (lag phase). FIG. 17B shows a distribution graph for a transition to high rate growth (exponential phase). FIG. 17C shows a distribution graph for high rate growth (exponential phase).

Figure 18:
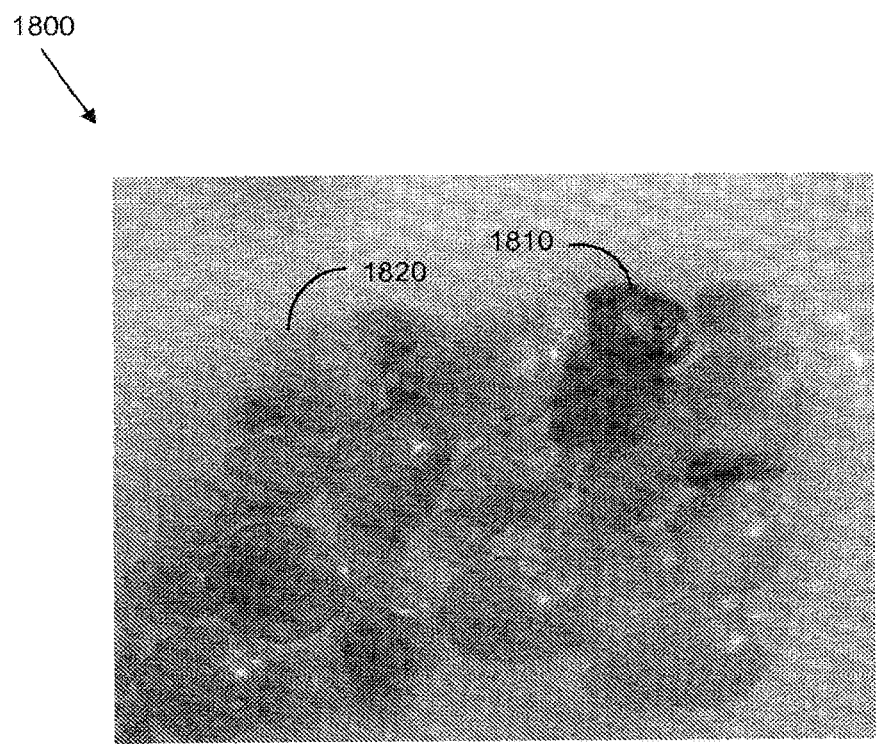

FIG. 18 is an image of a contaminated culture of aquatic plants according to an embodiment.

Figure 19A:
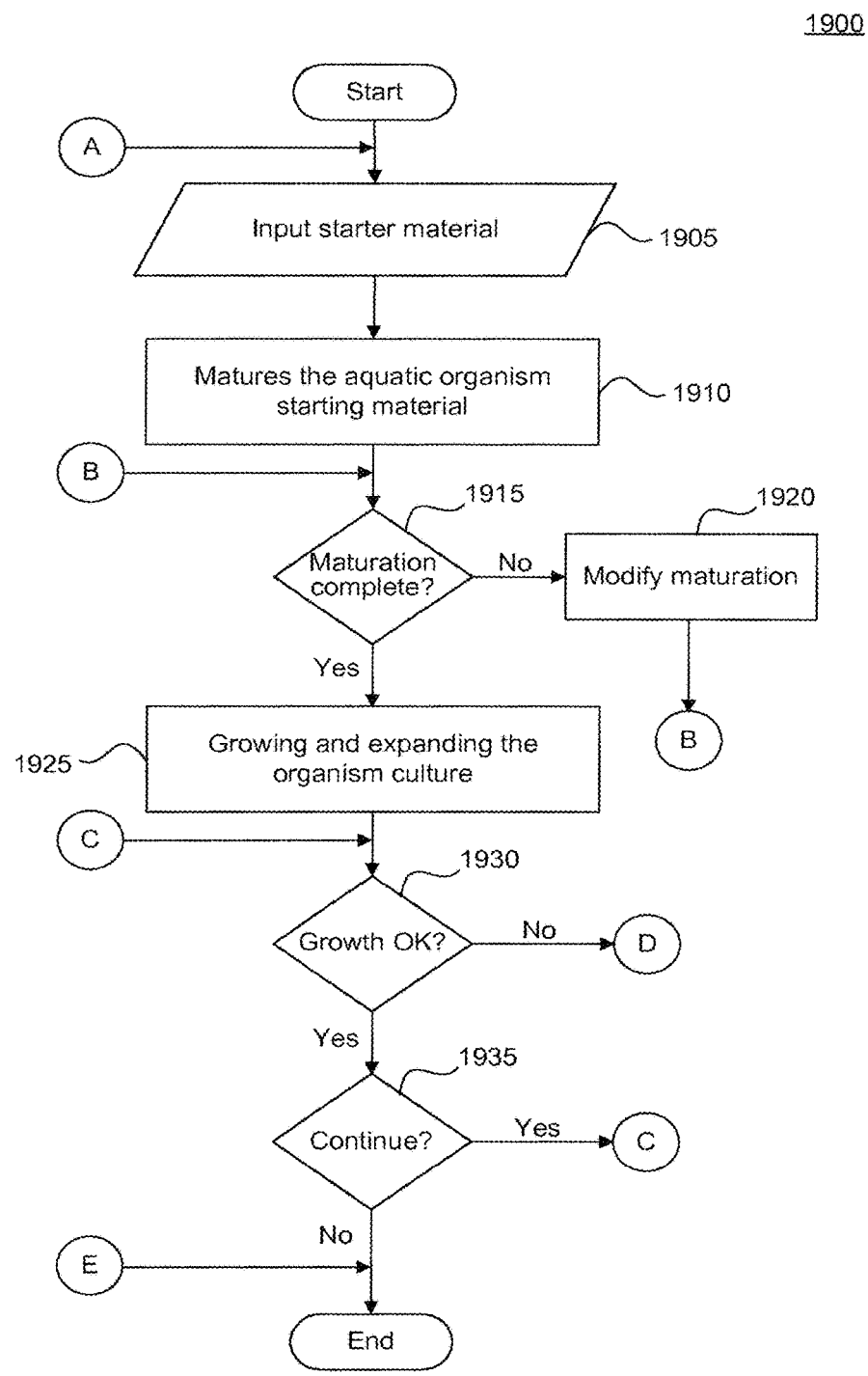
Figure 19B:
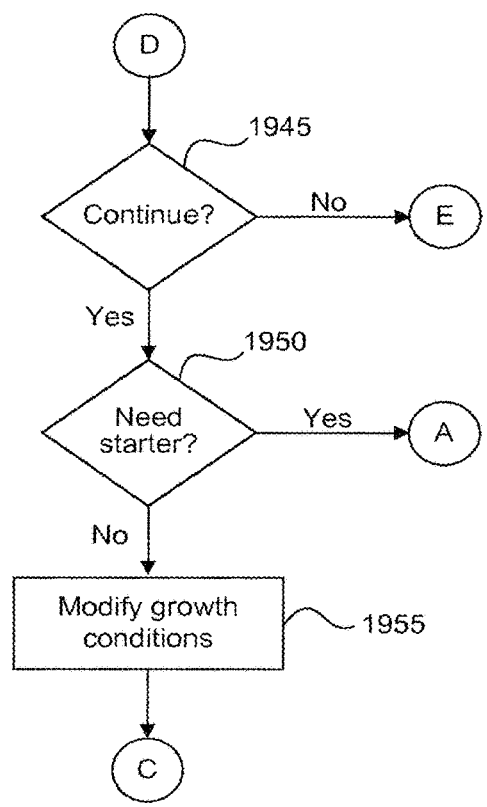

FIGS. 19A-19B is a flowchart describing the operation of growing an aquatic culture according to an embodiment.

Figure 20A:
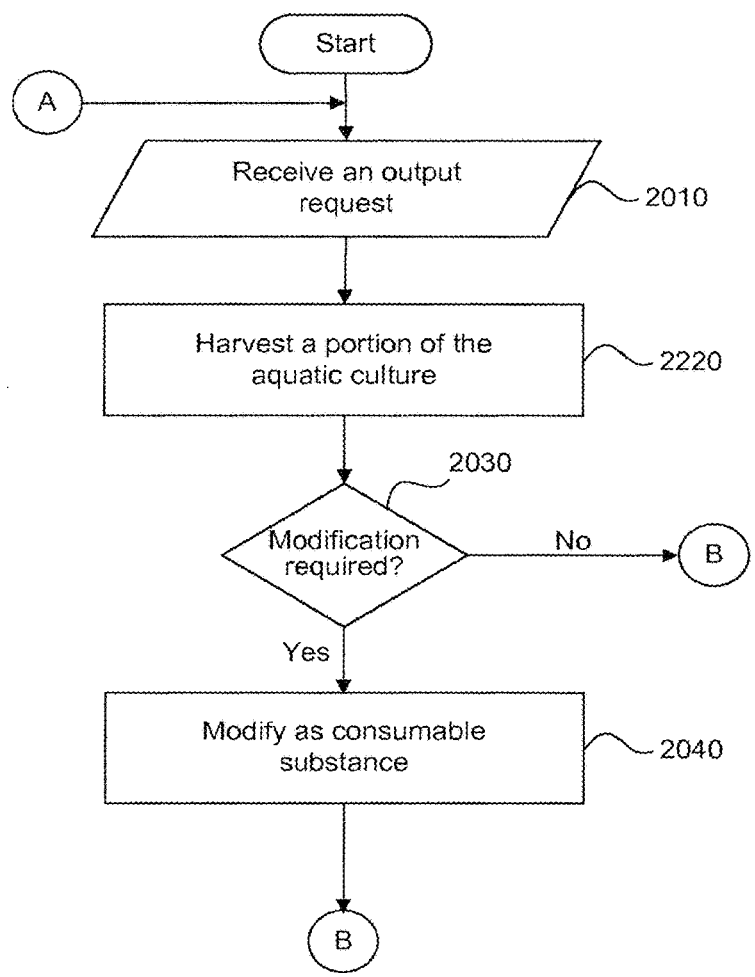
Figure 20B:
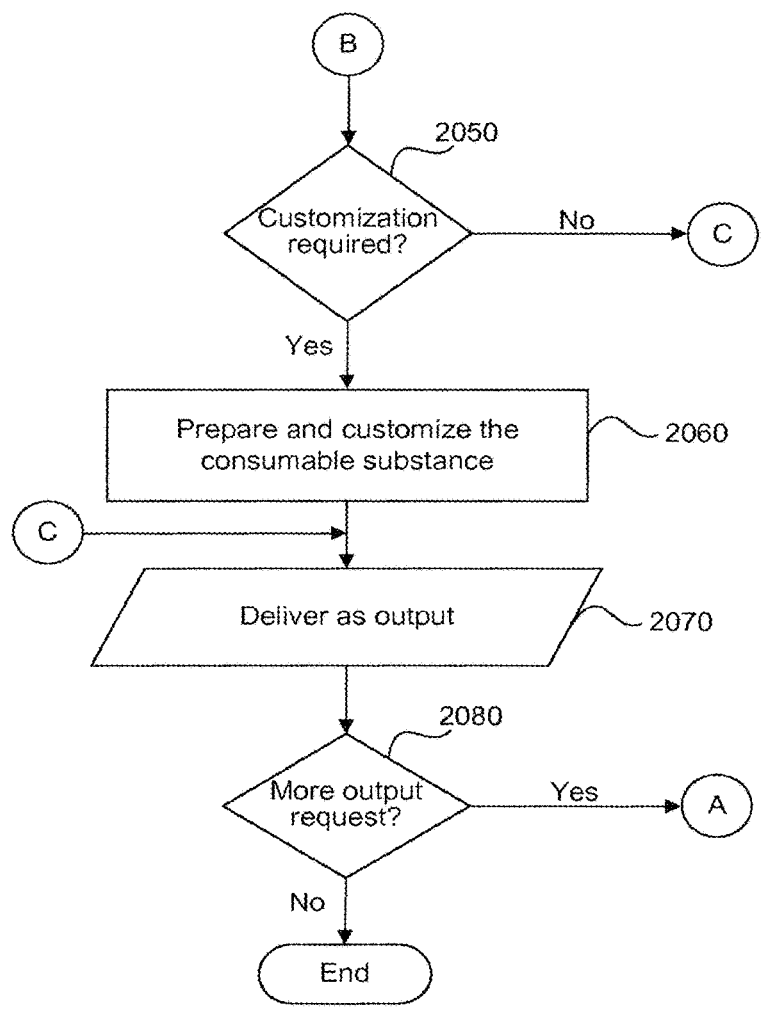

FIGS. 20A-20B is a flowchart describing the operation of delivering an output of consumable substance according to an embodiment.

Figure 21:
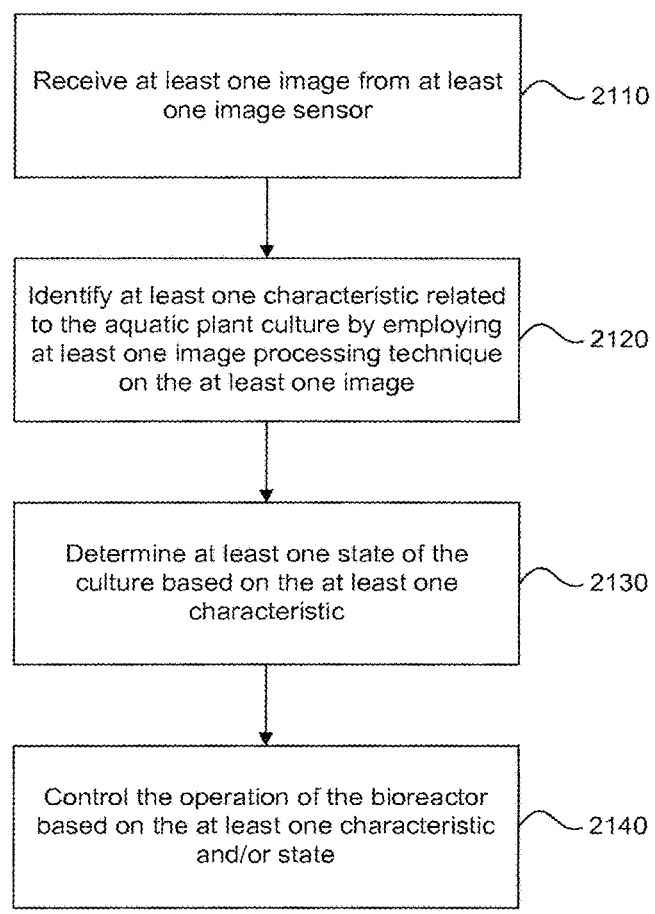

FIG. 21 is a flow chart describing the operation of adjusting a growing condition in a bioreactor according to an embodiment.

Figure 22:
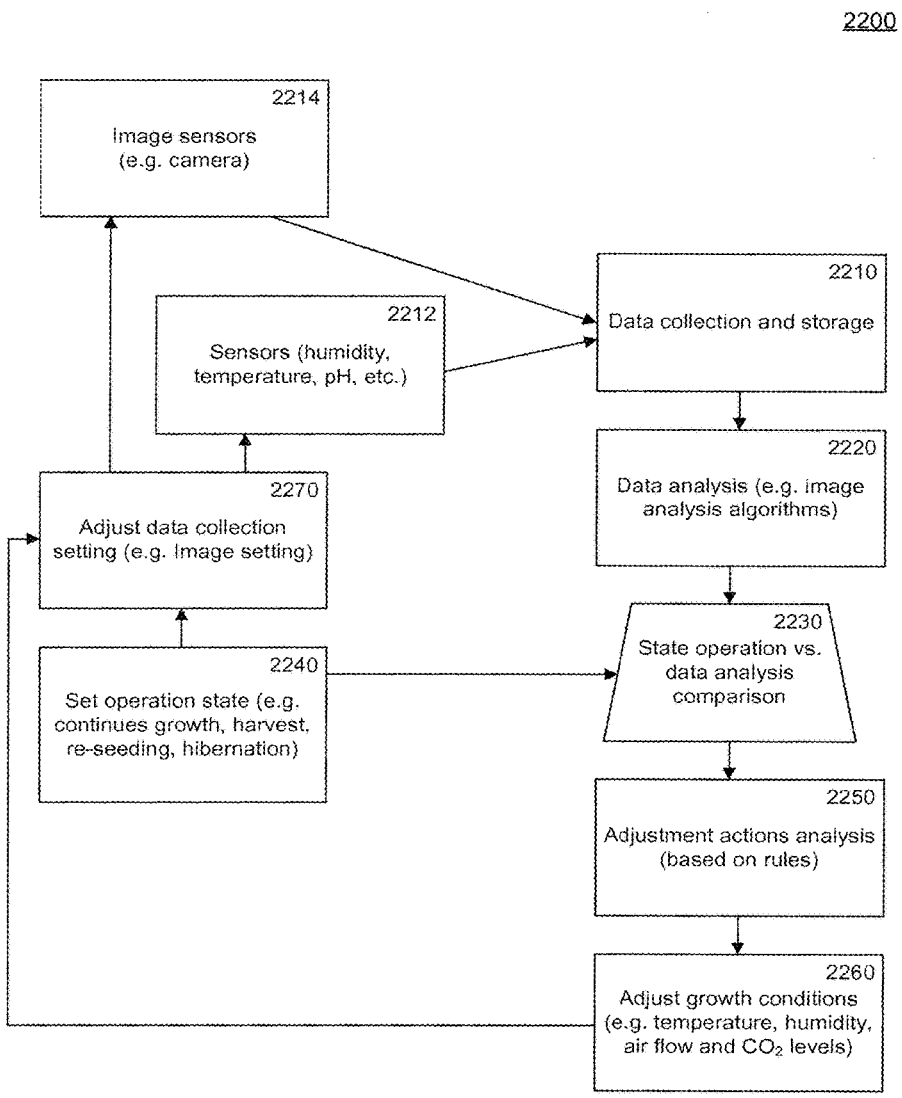

FIG. 22 is a schematic block diagram illustrating the operation of a system according to an embodiment.

Figure 23:
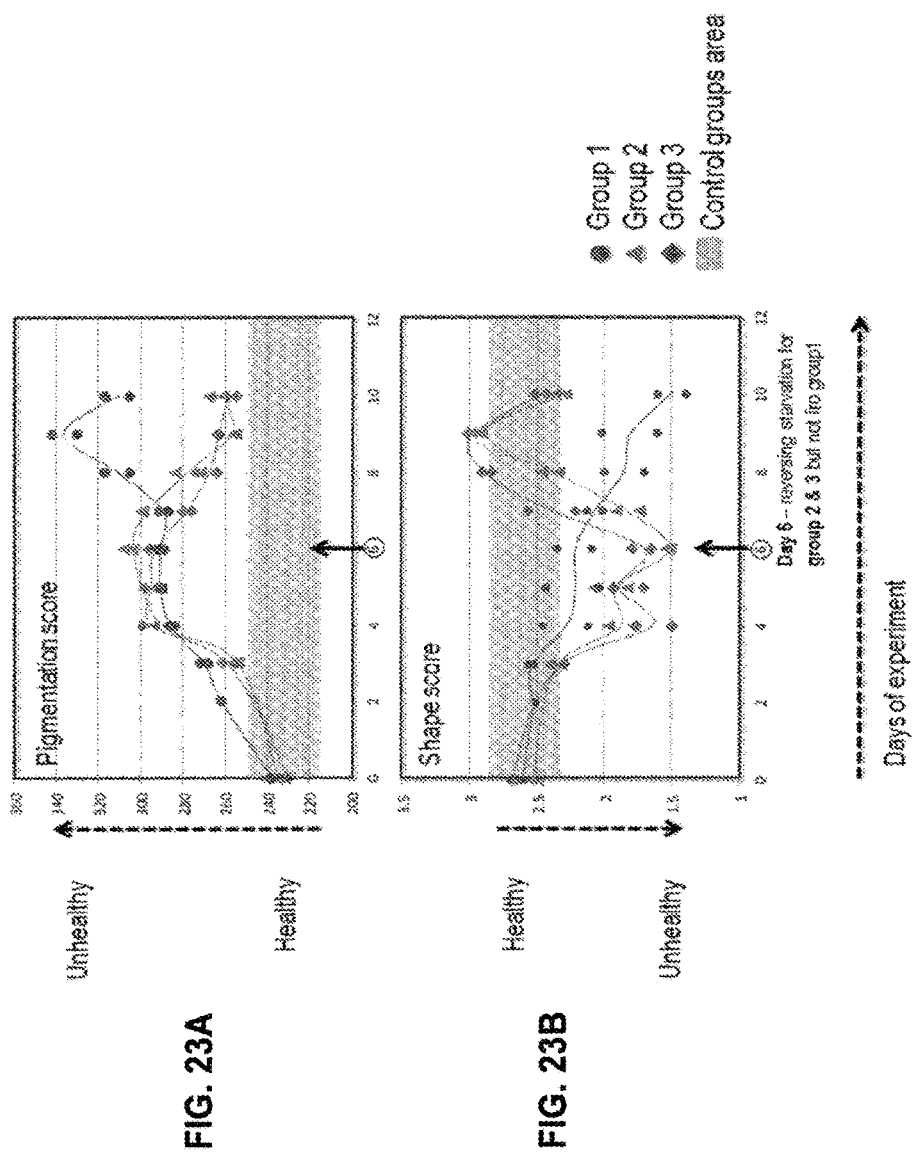

FIGS. 23A-23B are graphs illustrating exemplary results of an image processing technique performed on a culture of aquatic plants according to an embodiment.

Figure 24:
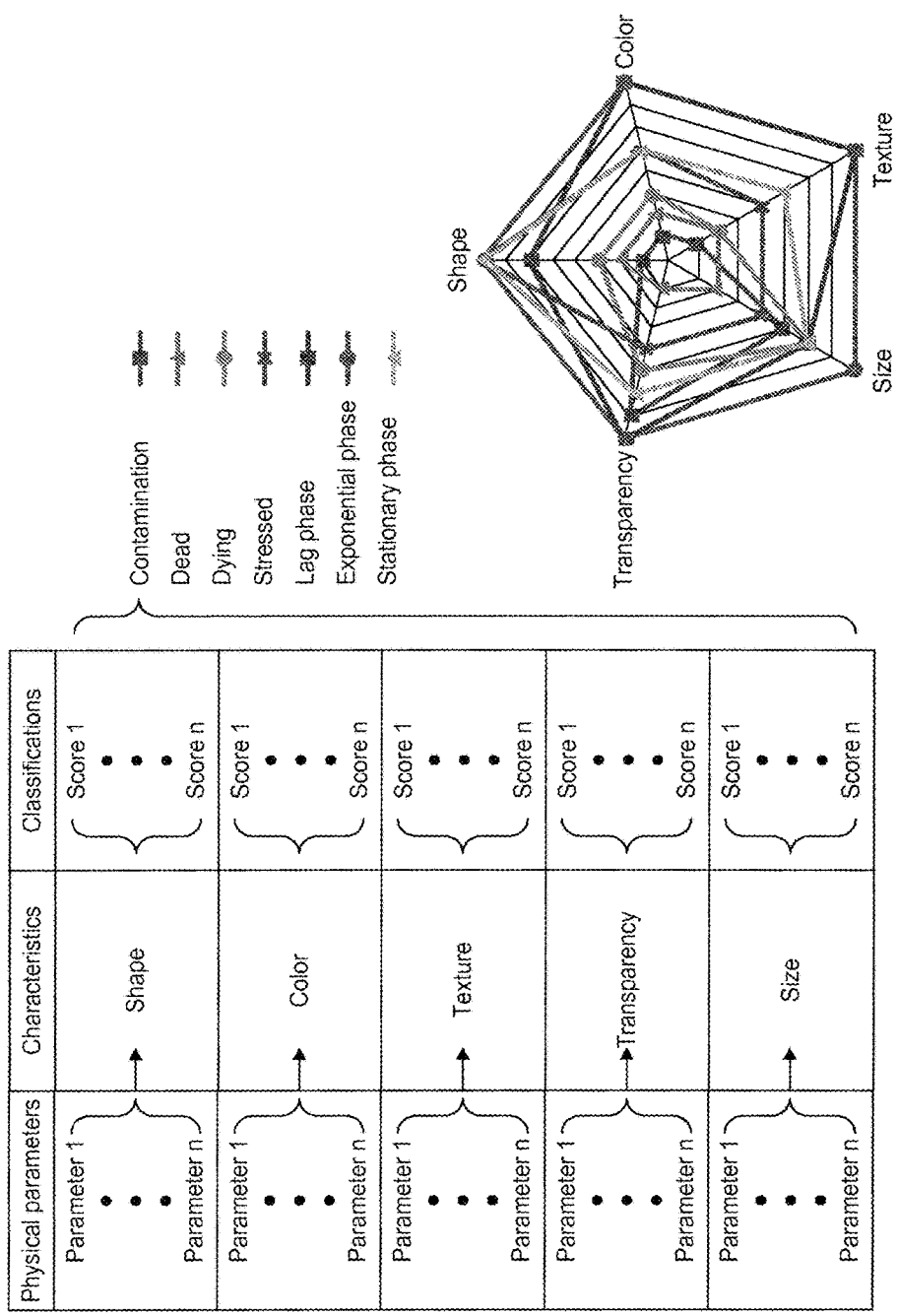

FIG. 24 is a representation of a method for processing an image according to an embodiment.

Figure 25A:
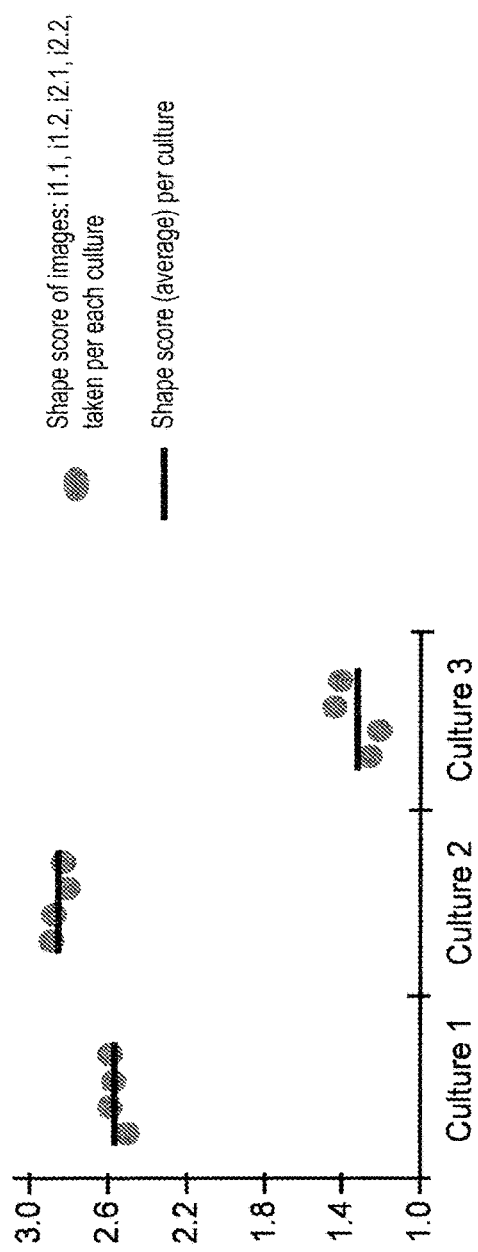
Figure 25B:
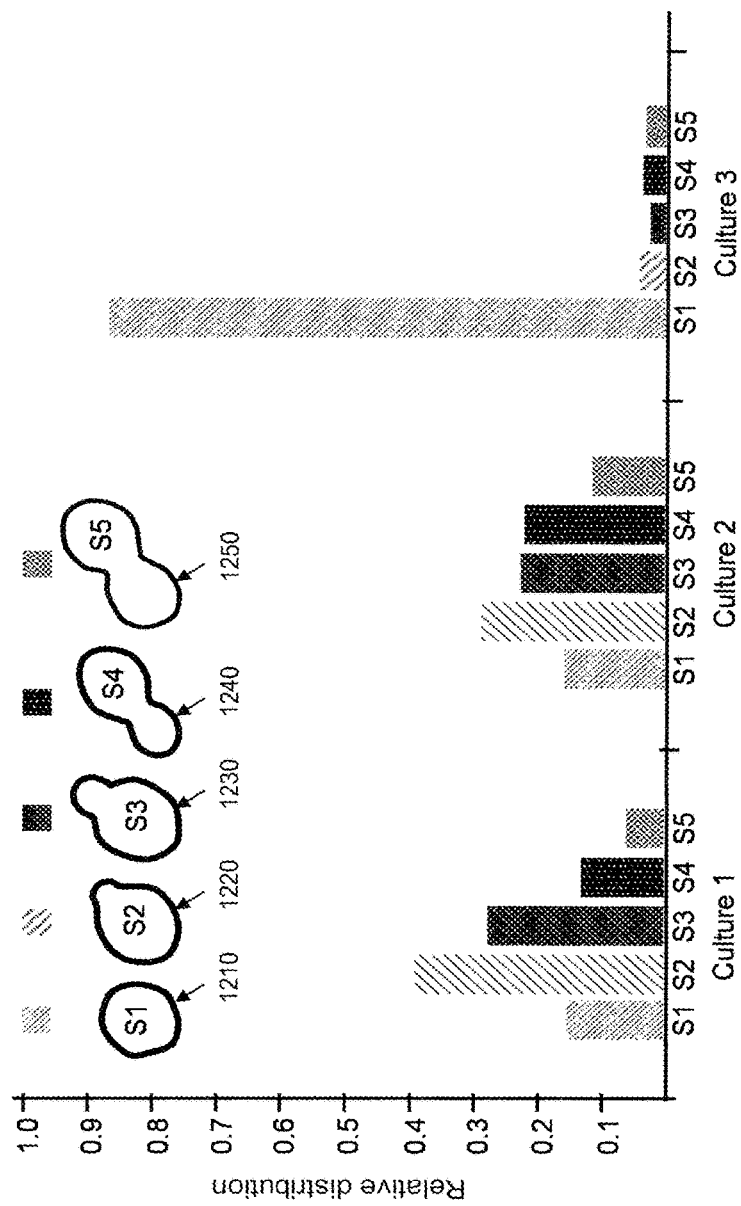

FIGS. 25A-25B are graphs illustrating exemplary results of a method for processing an image according to an embodiment.

Figure 26:
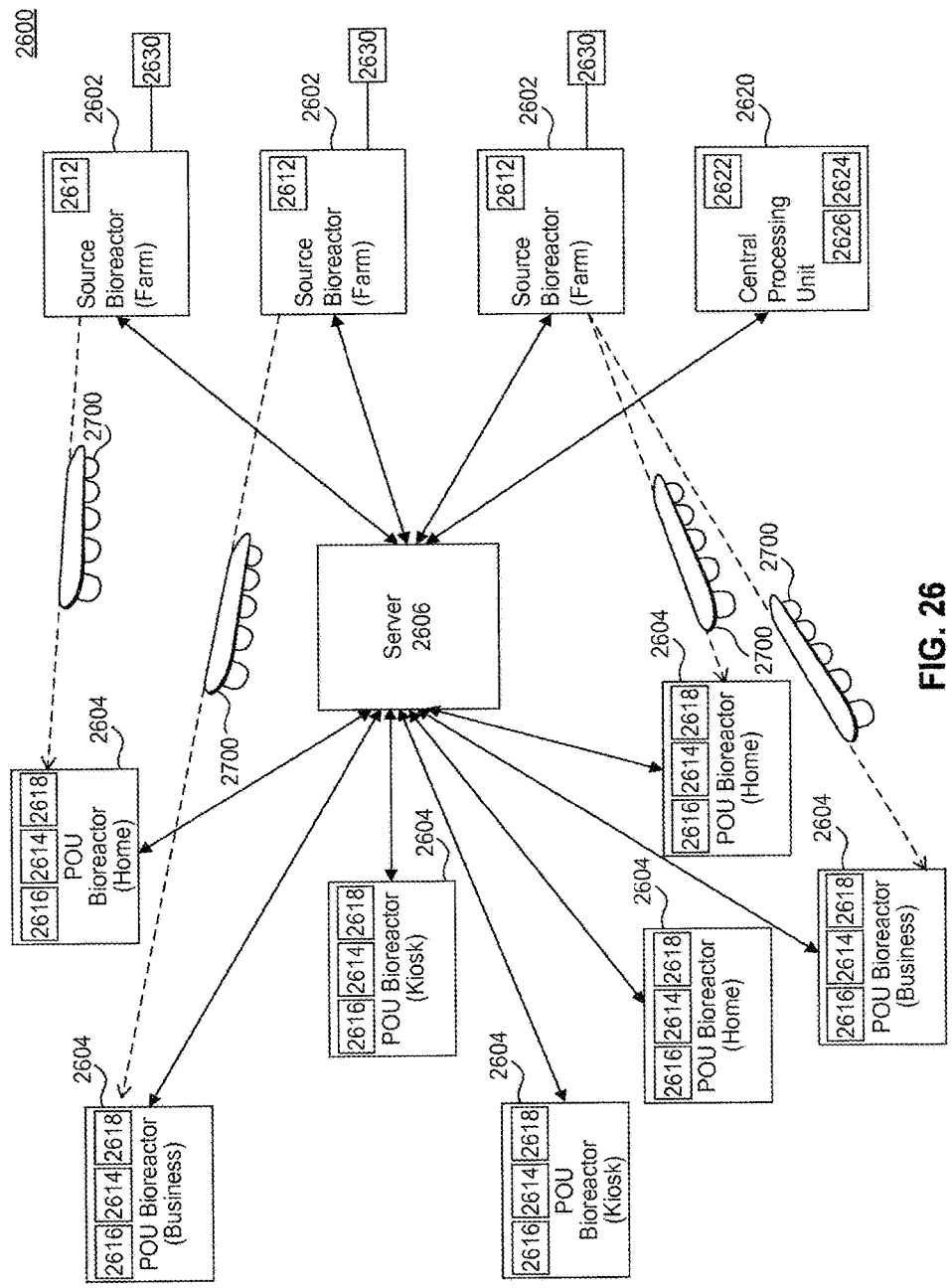

FIG. 26 is a schematic block diagram of a distribution system for aquatic plant cultures according to an embodiment.

Figure 27:
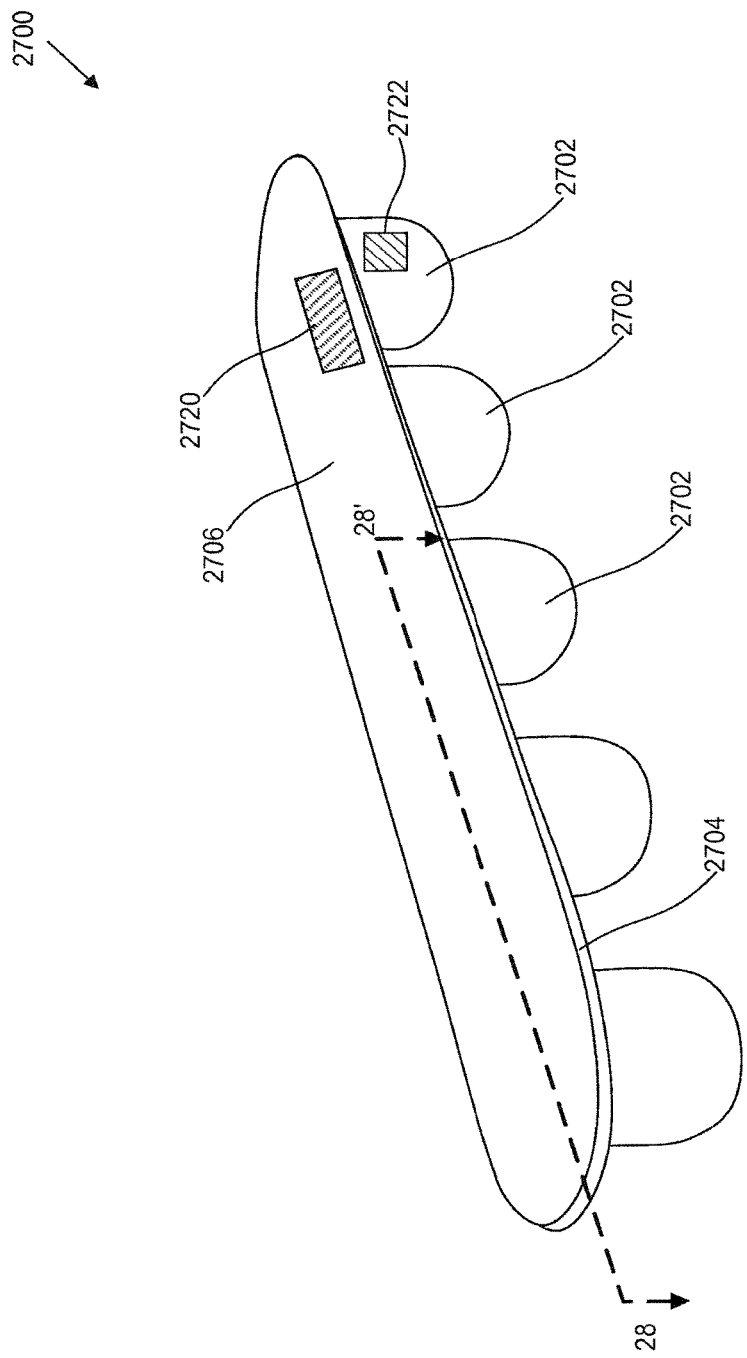

FIG. 27 is a perspective view of a cartridge for distributing aquatic plant cultures according to an embodiment.

Figure 28:
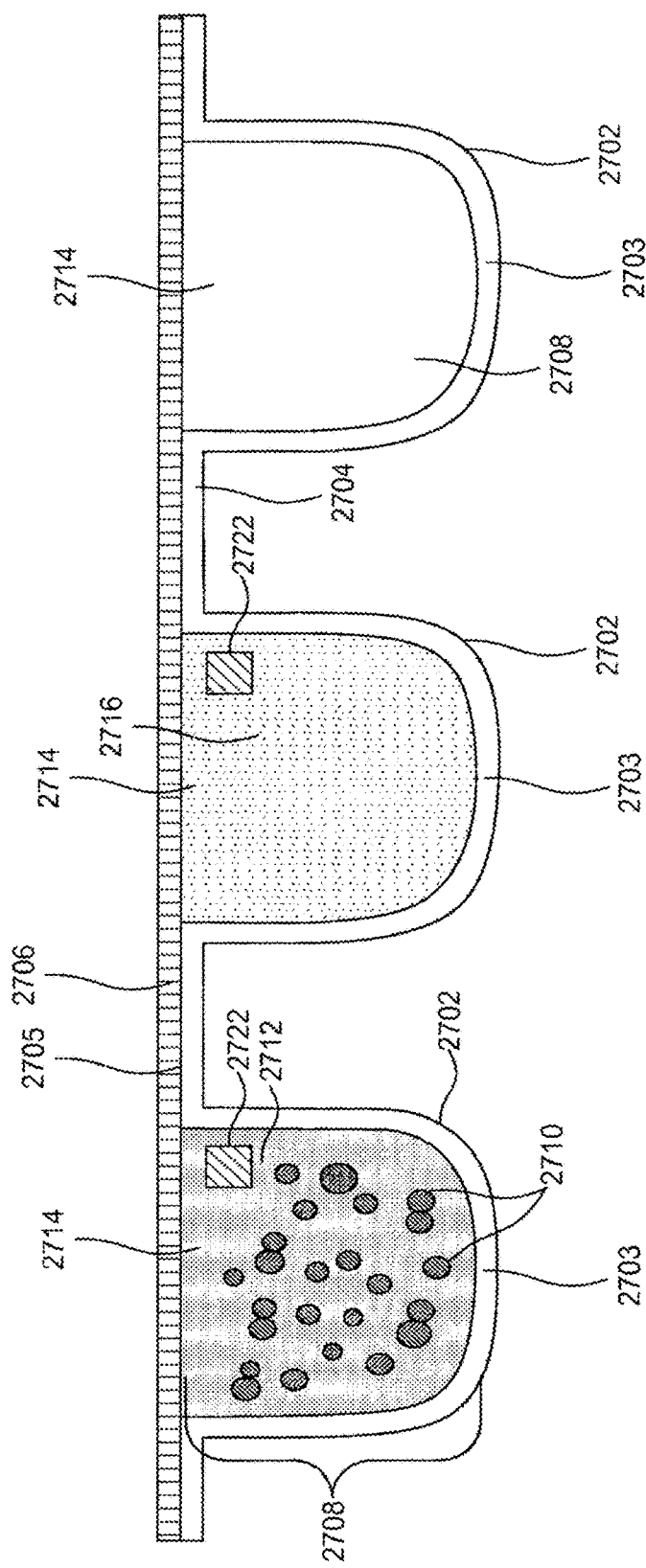

FIG. 28 is a cross-section of the cartridge in FIG. 27 along the line 28-28' in FIG. 27 according to an embodiment.

Figure 29:
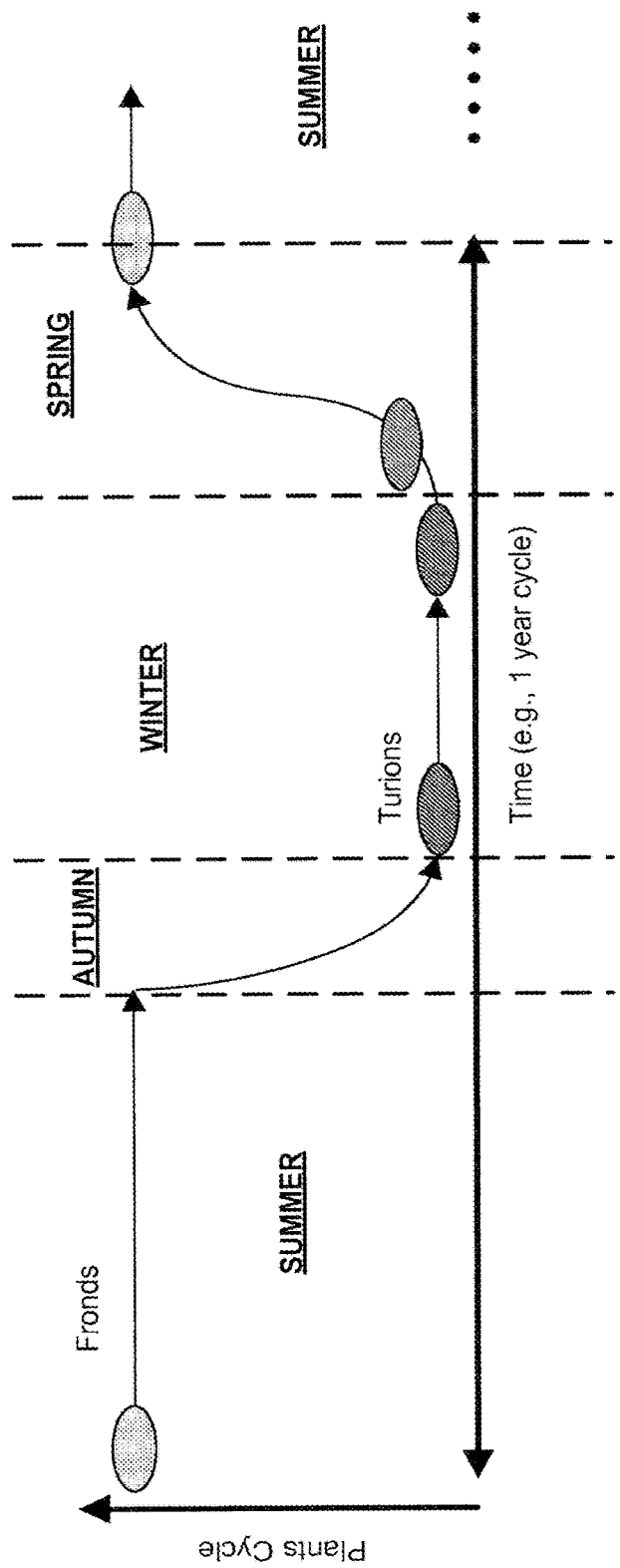

FIG. 29 is schematic of a life cycle for an aquatic plant culture according to an embodiment.

Figure 30A:
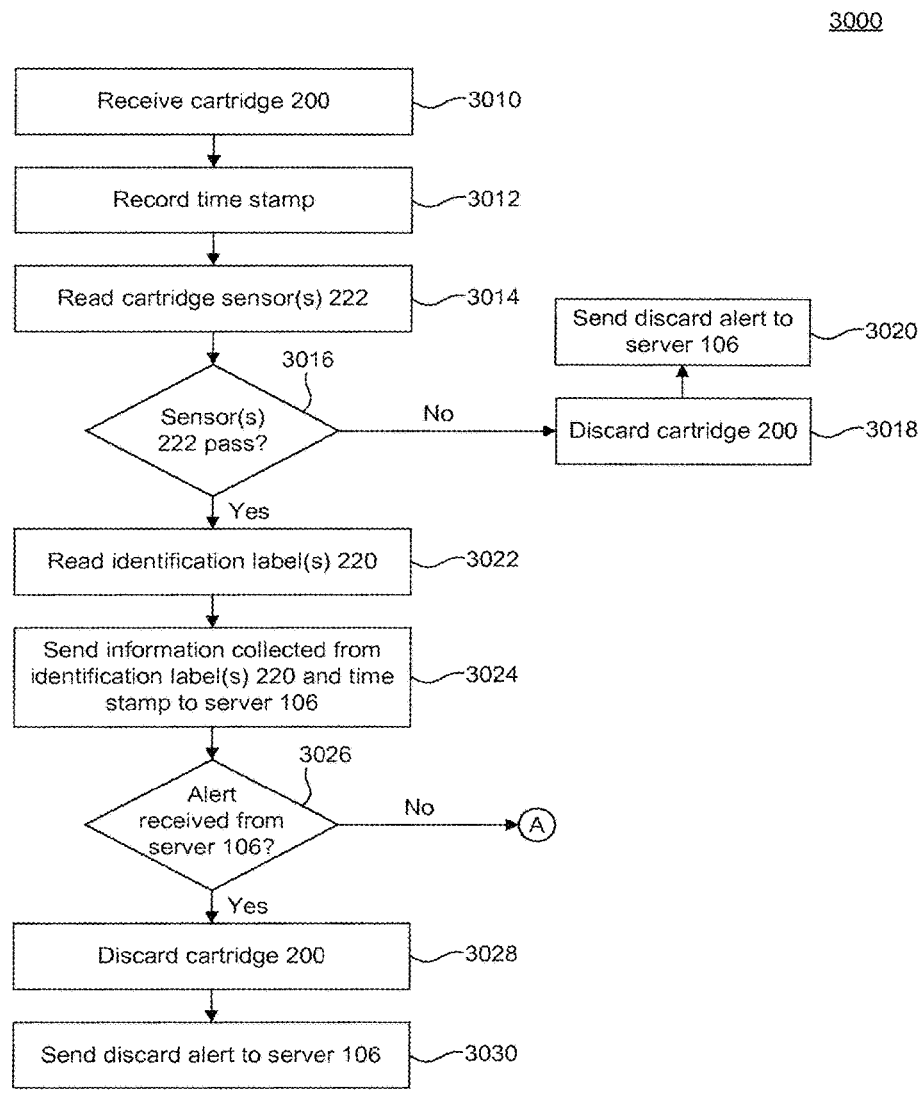
Figure 30B:
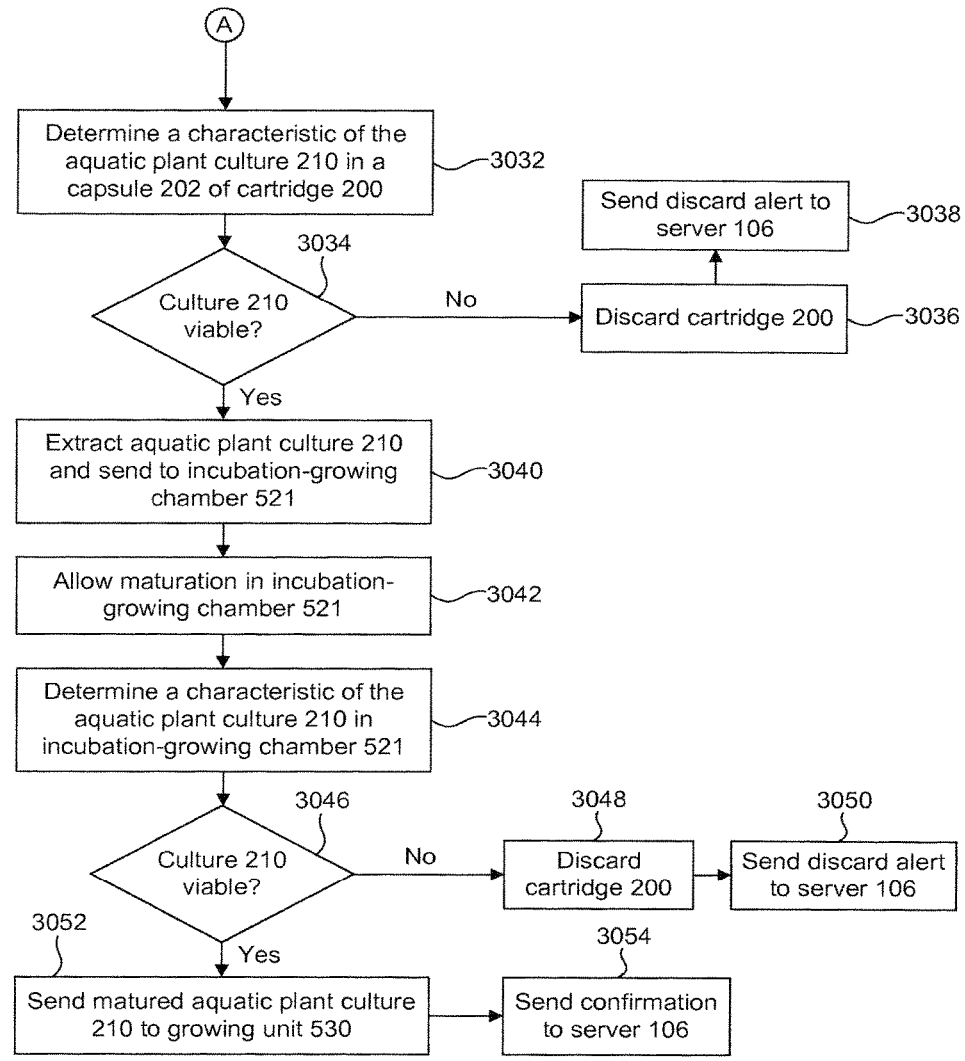

FIGS. 30A-30B show a flow chart illustrating an initialization process according to an embodiment.

Figure 31:
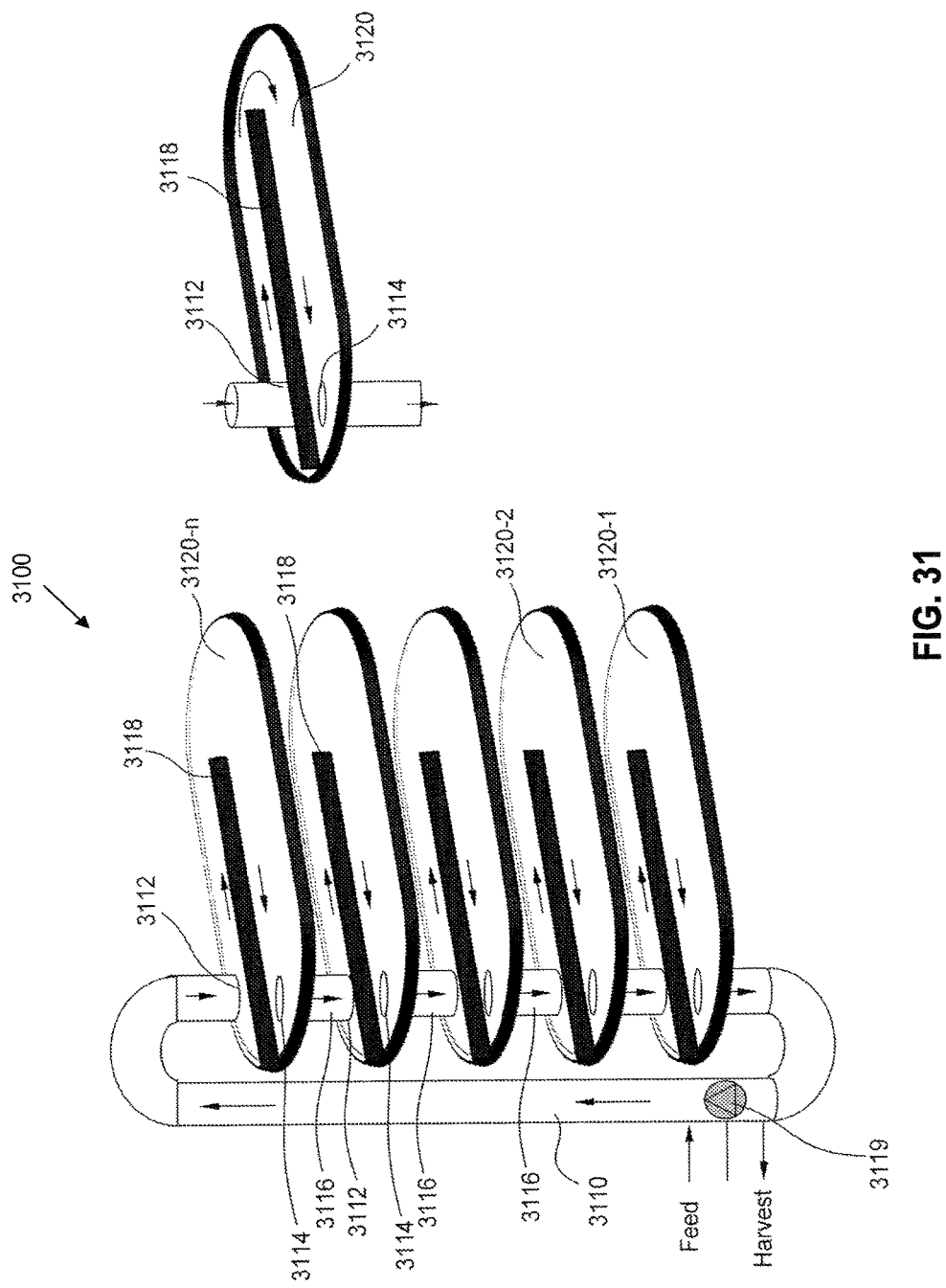

FIG. 31 is a growing apparatus having a plurality of stacked modules according to an embodiment.

Figure 32:
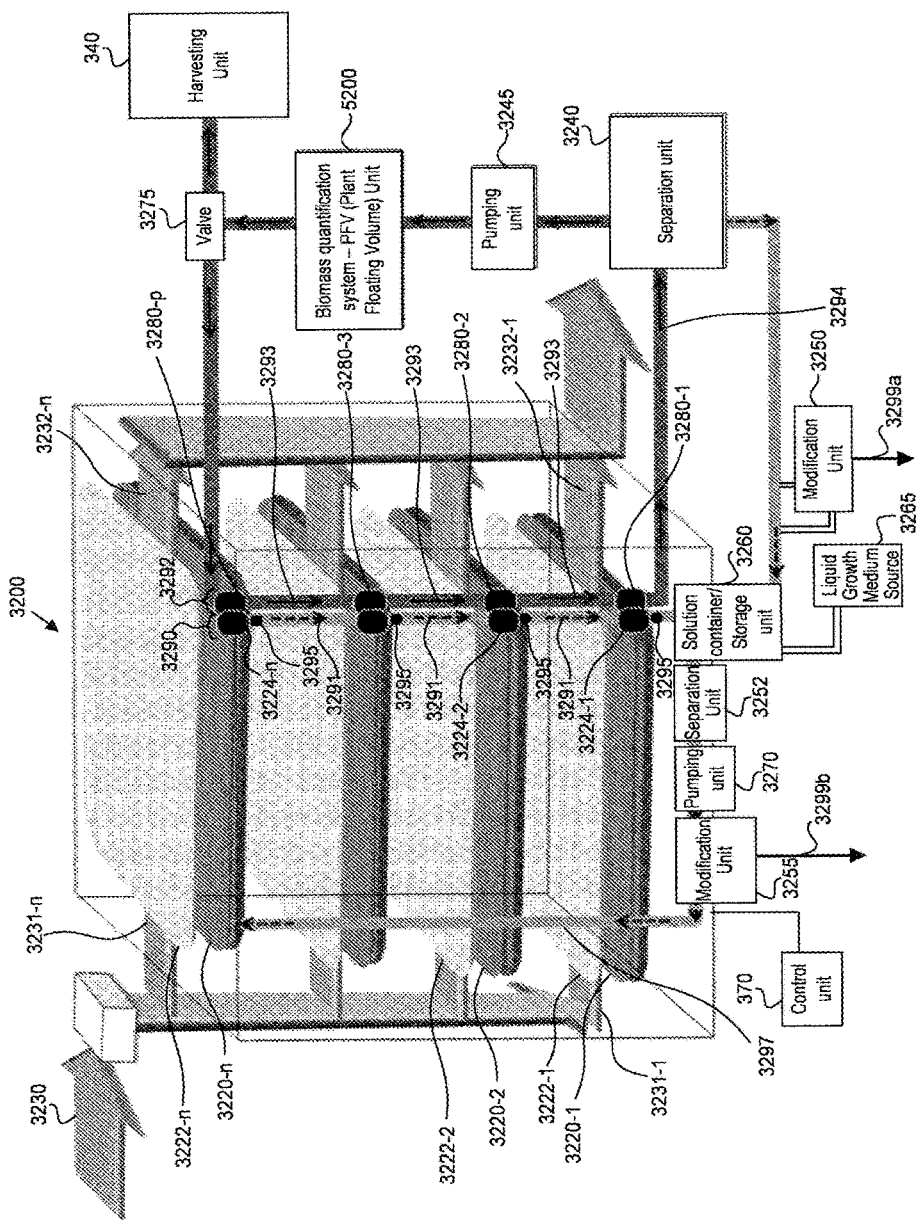

FIG. 32 is a growing apparatus having a plurality of stacked modules according to an embodiment.

Figure 33A:
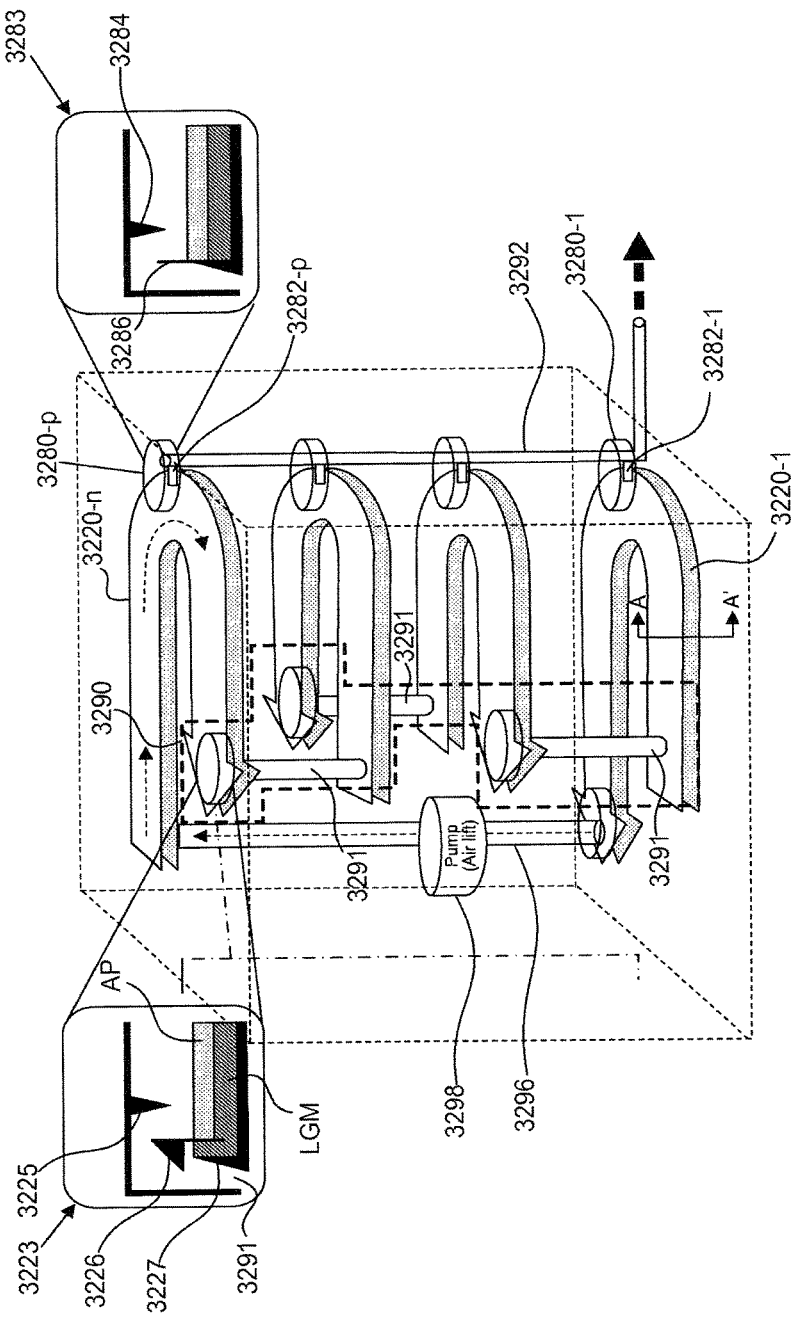

FIG. 33A is a growing apparatus having a plurality of stacked modules according to an embodiment. FIG. 33B is a schematic illustrating the operation of the valves in FIG. 33A according to an embodiment.

Figure 34:
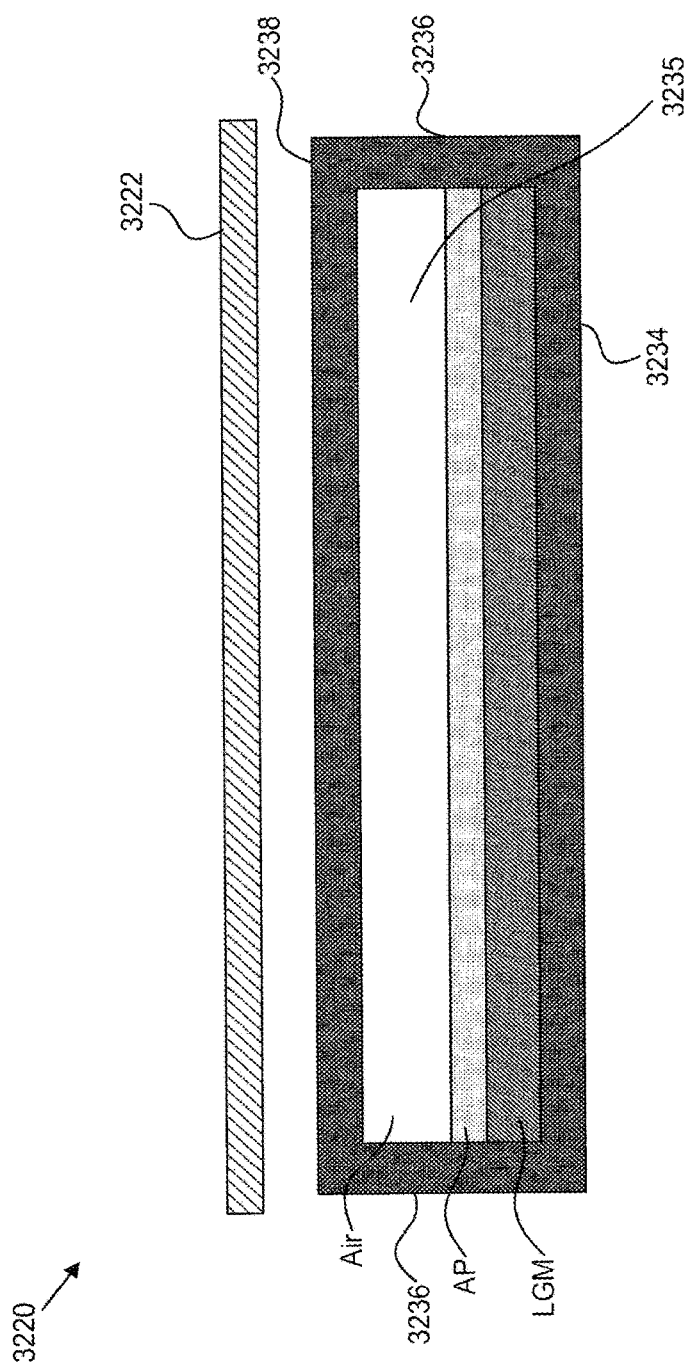

FIG. 34 is a cross-sectional view of a module along line A-A' in FIGS. 33A, 35A, 35B, 35C, and 35D.

Figure 35A:
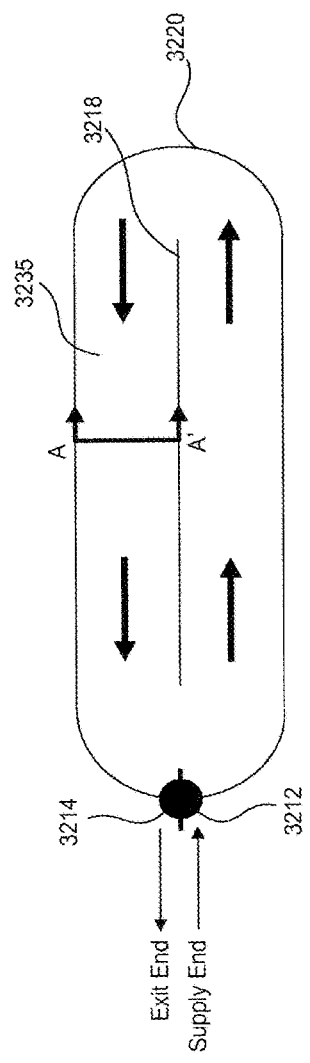
Figure 35B:
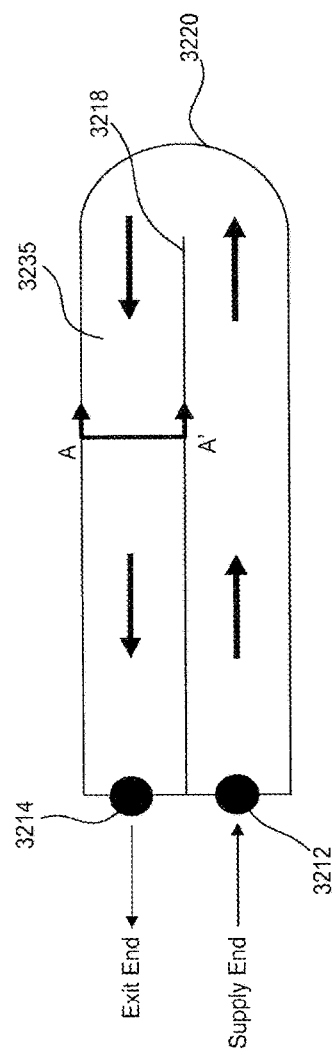

FIG. 35A is a module according to an embodiment. FIG. 35B is a module according to an embodiment. FIG. 35C is a module according to an embodiment. FIG. 35D is a module according to an embodiment.

FIG. 36 is a flowchart describing an operation for growing and harvesting aquatic plants according to an embodiment.

Figure 37:
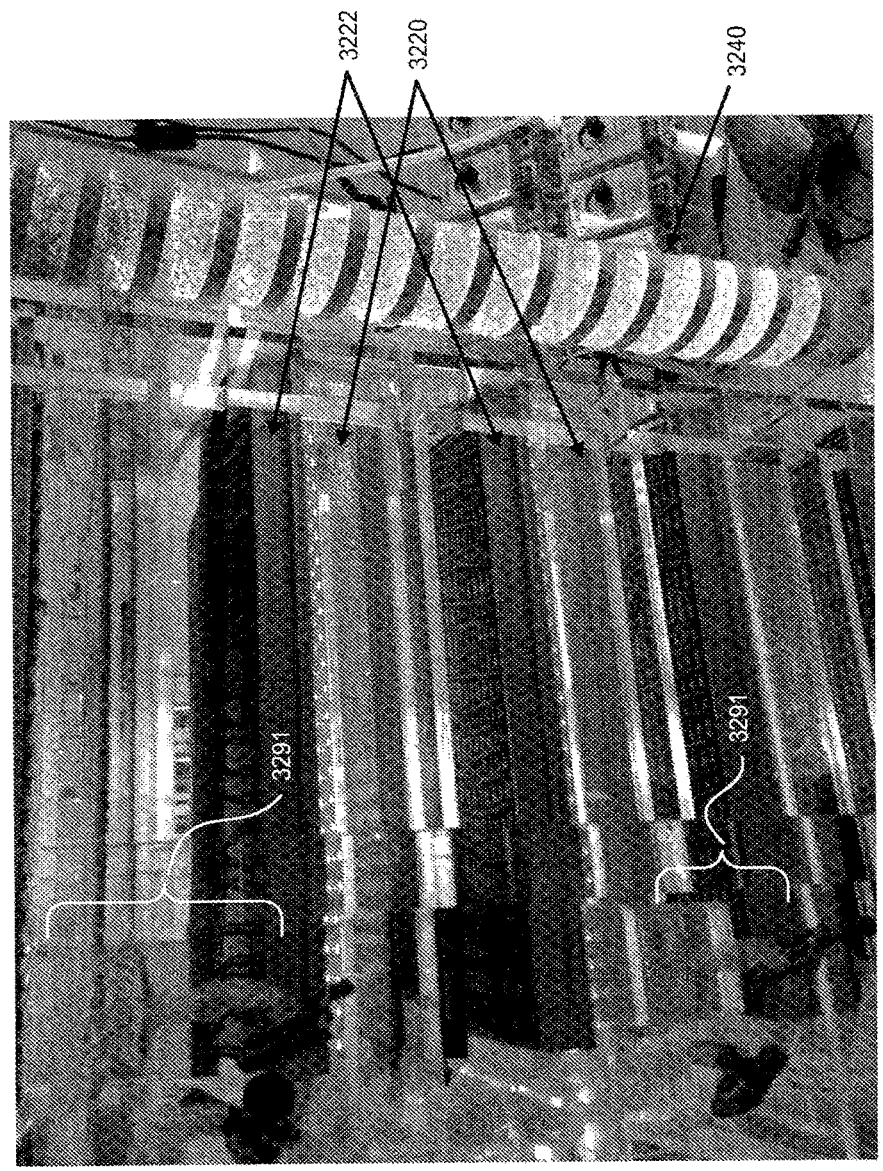

FIG. 37 is an exemplary image of a bioreactor system according to an embodiment.

Figure 38:
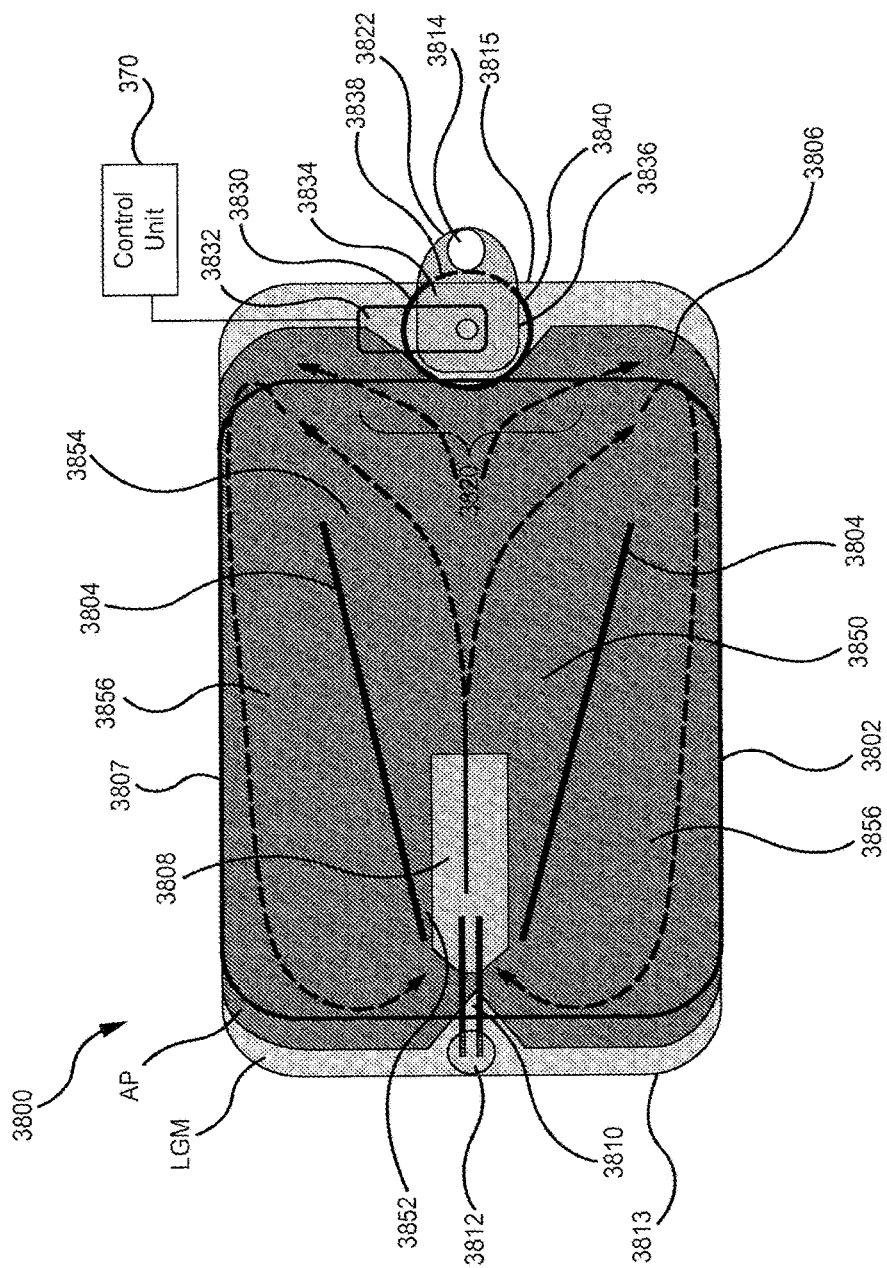

FIG. 38 is an aerial view of a module according to an embodiment.

FIGS. 39A-39B are cross-sectional views of the module in FIG. 38 showing the operation of a valve according to one embodiment.

Figure 40:
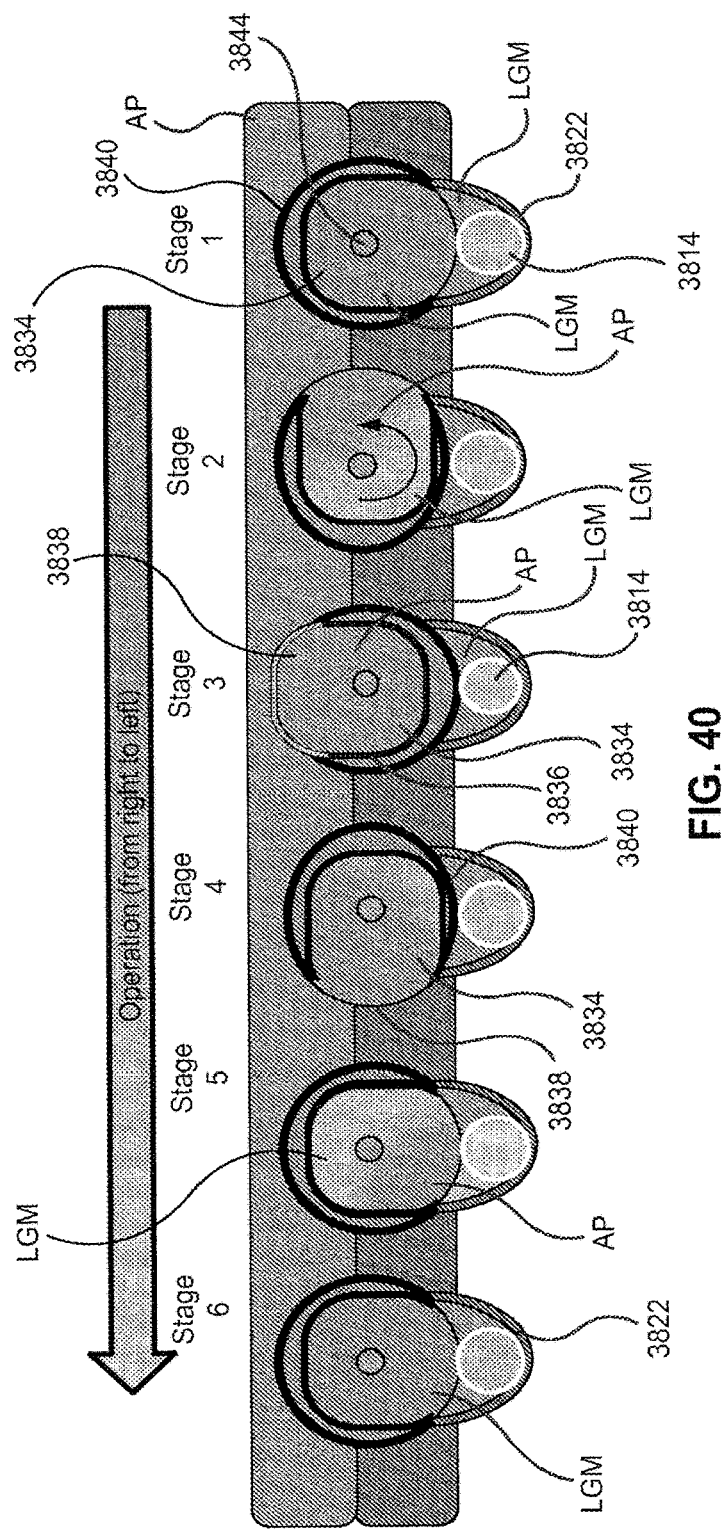

FIG. 40 illustrates the operation of a valve according to an embodiment.

Figure 41:
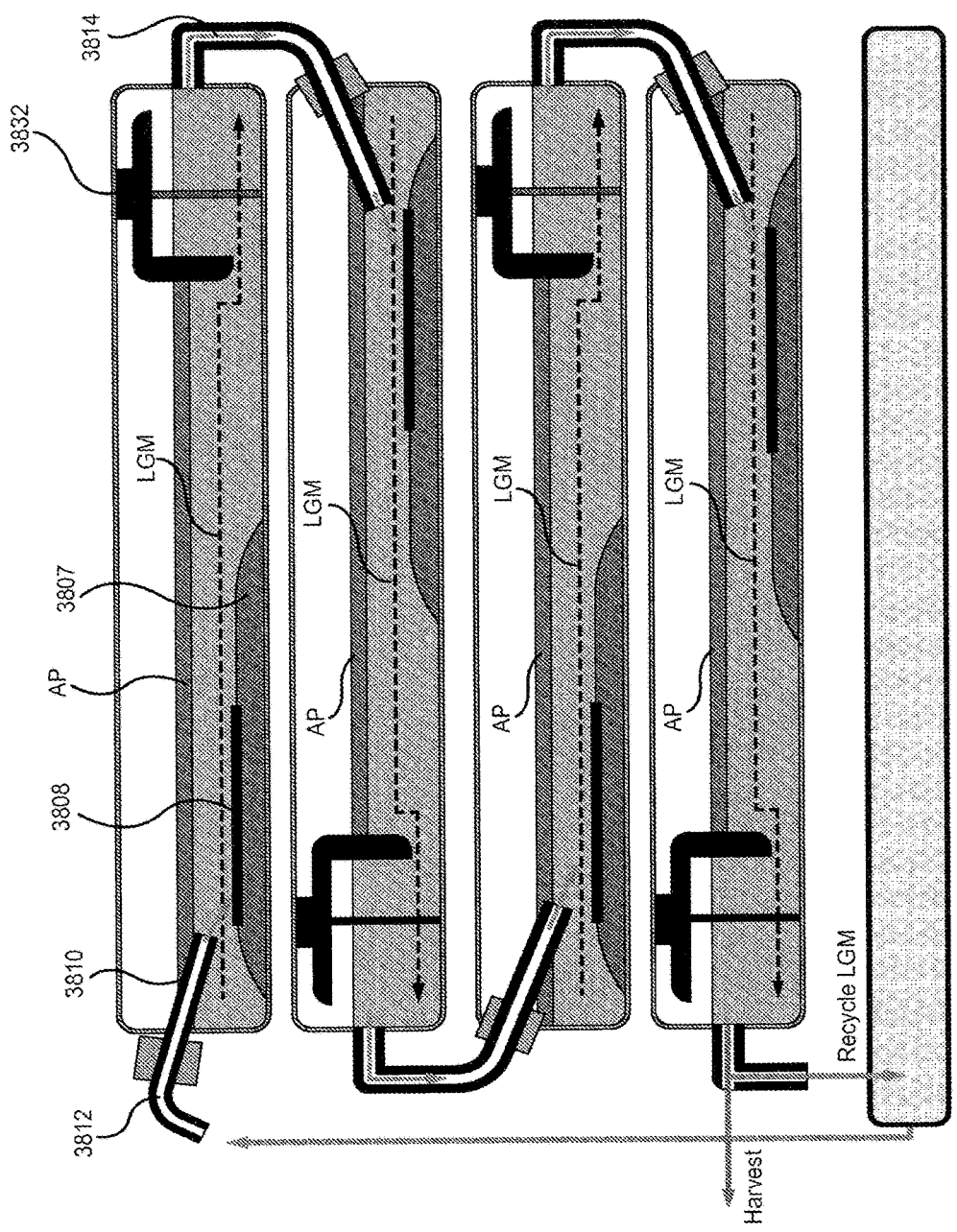

FIG. 41 is a cross-sectional view of a plurality of stacked modules according to an embodiment.

Figure 42:
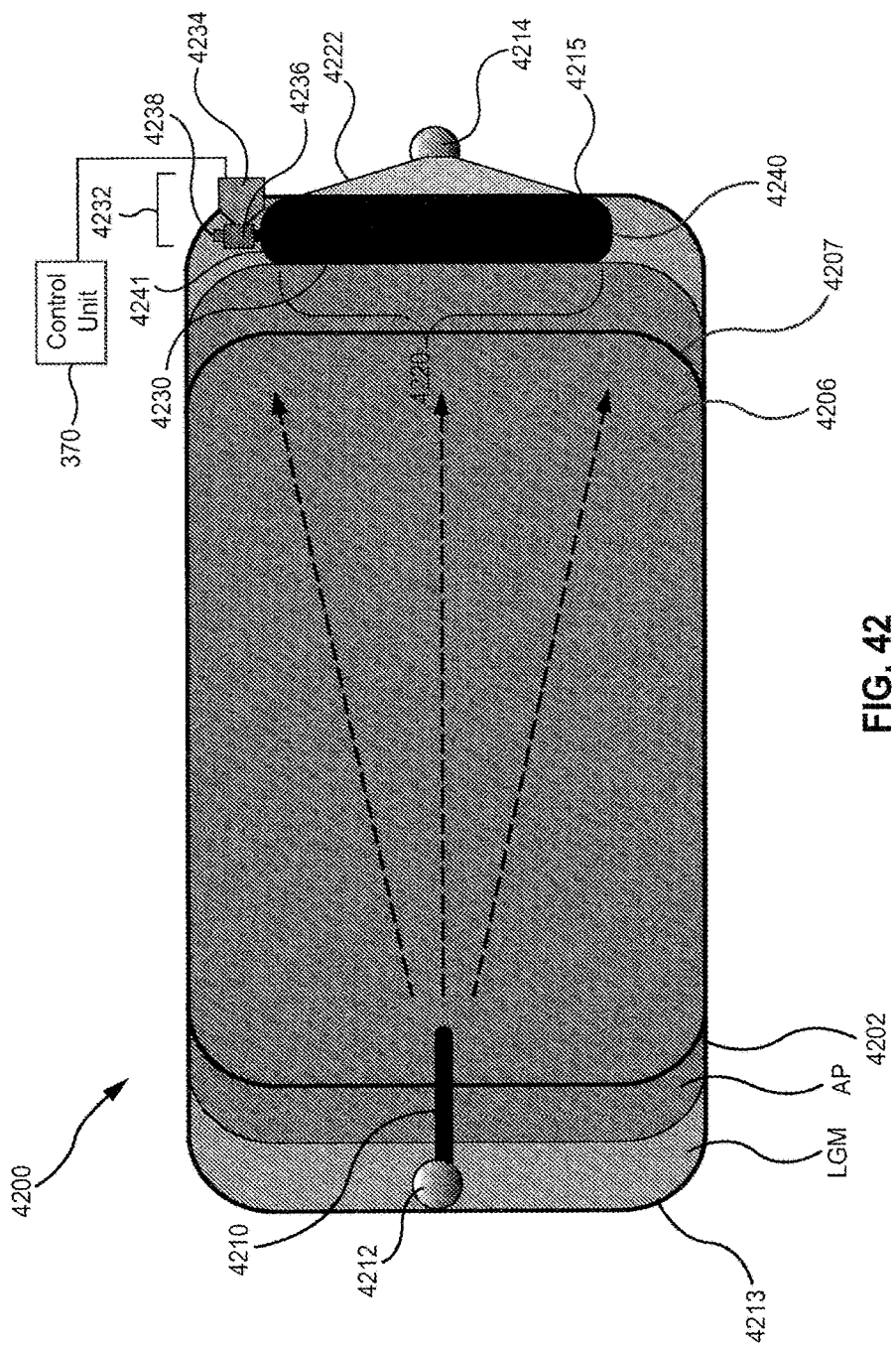

FIG. 42 is an aerial view of a module according to an embodiment.

Figure 43:
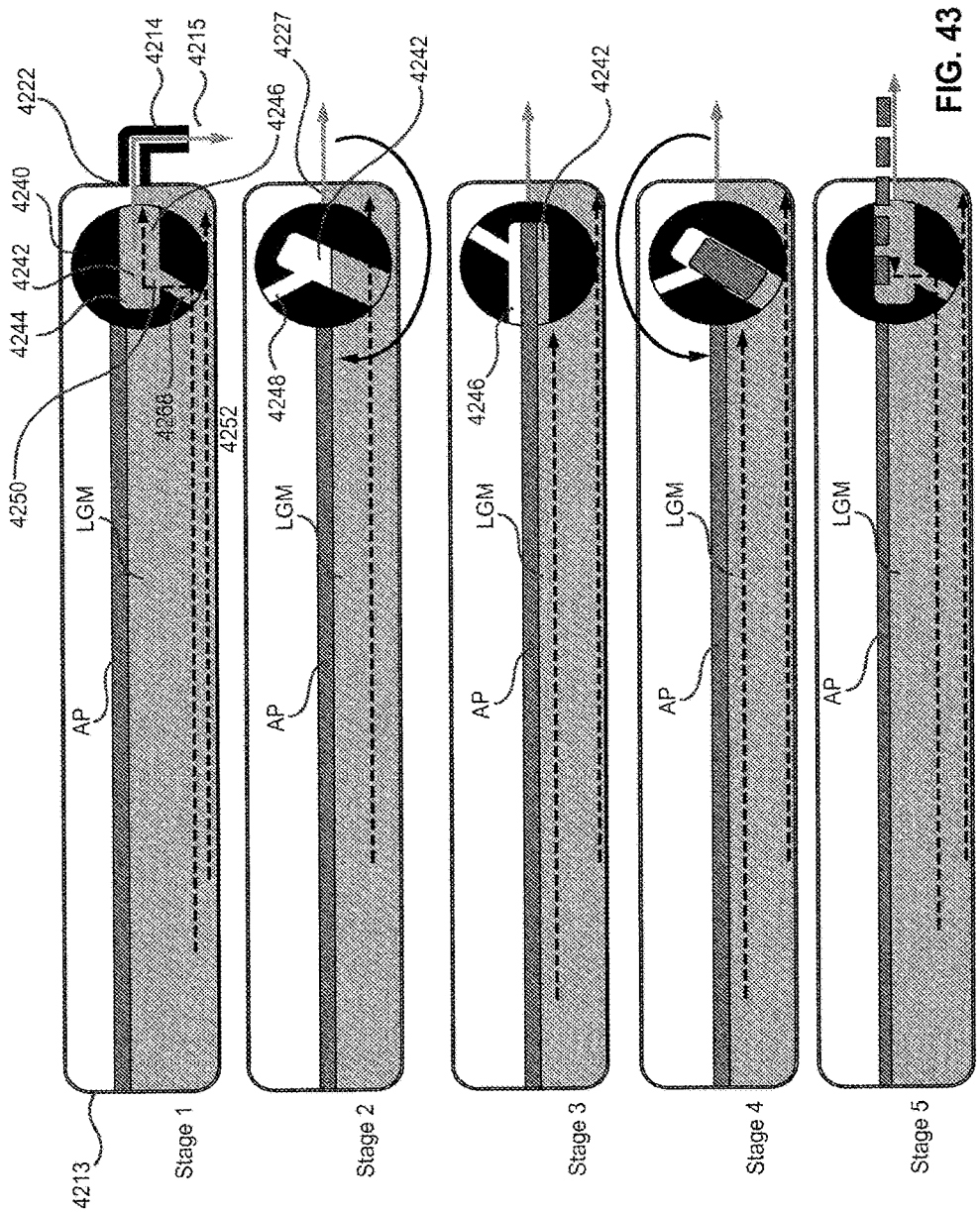

FIG. 43 shows cross-sectional views of the module in FIG. 42 illustrating the operation of a valve according to an embodiment.

Figure 44:
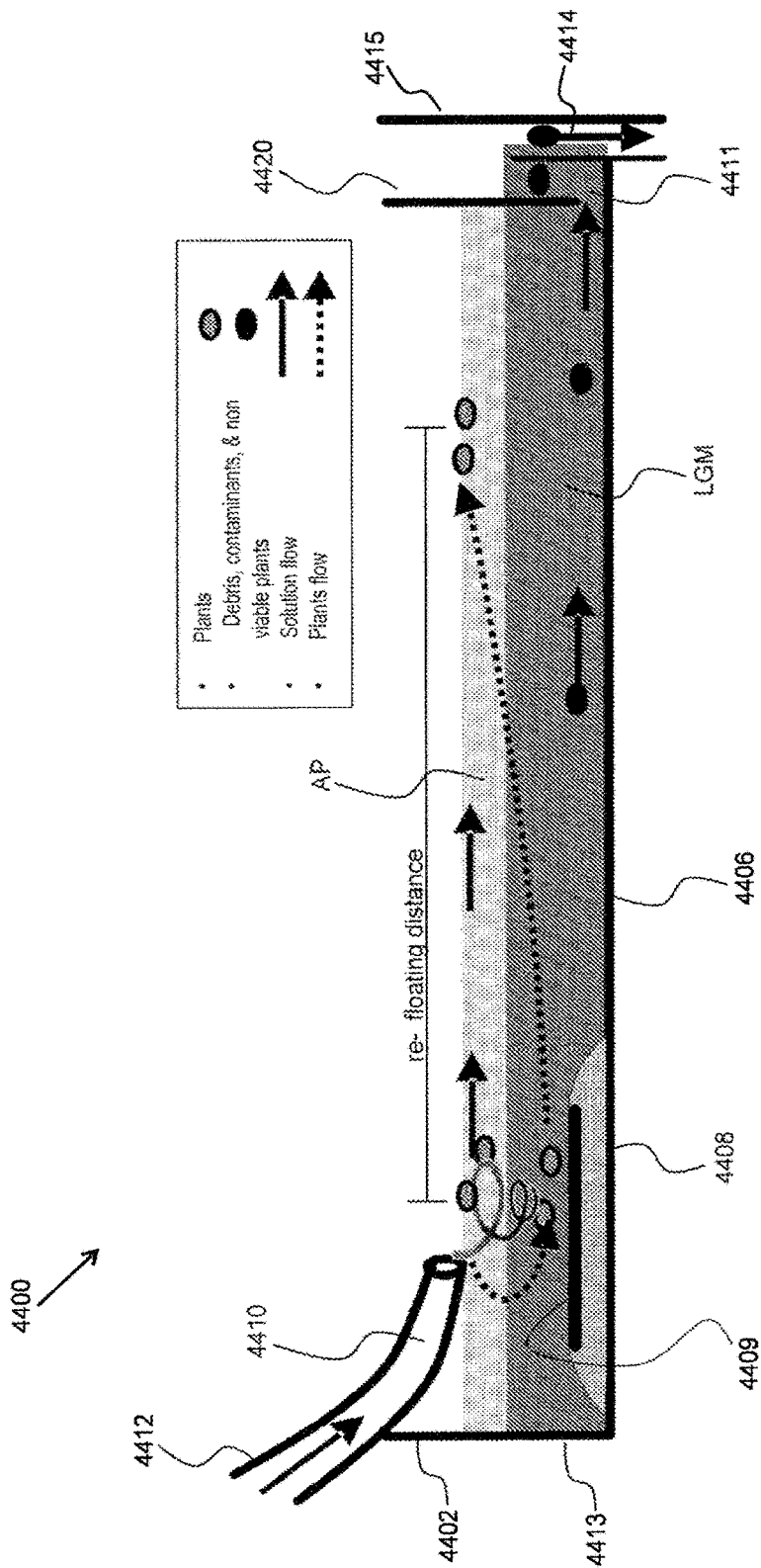

FIG. 44 is a cross-sectional view of a module according to an embodiment.

Figure 45:
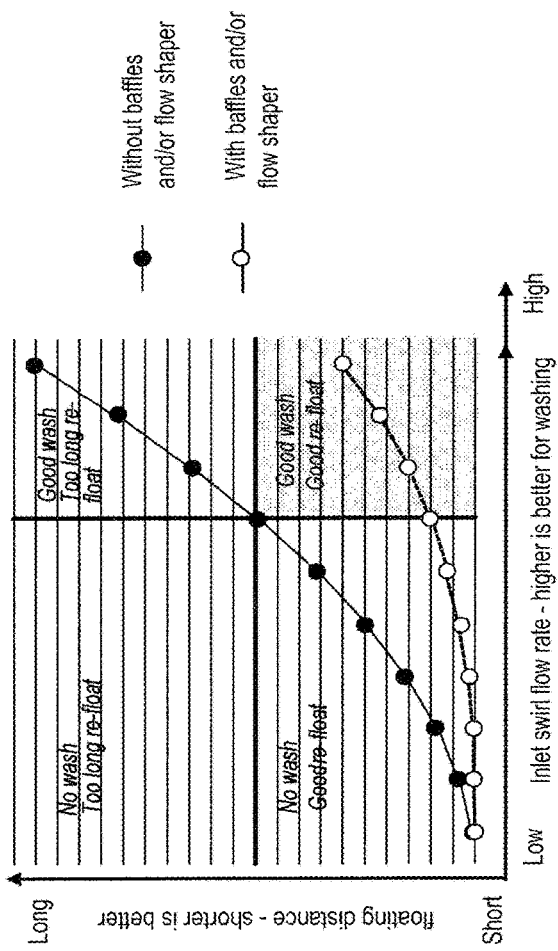

FIG. 45 is a graph illustrating re-floating distance.

Figure 46:
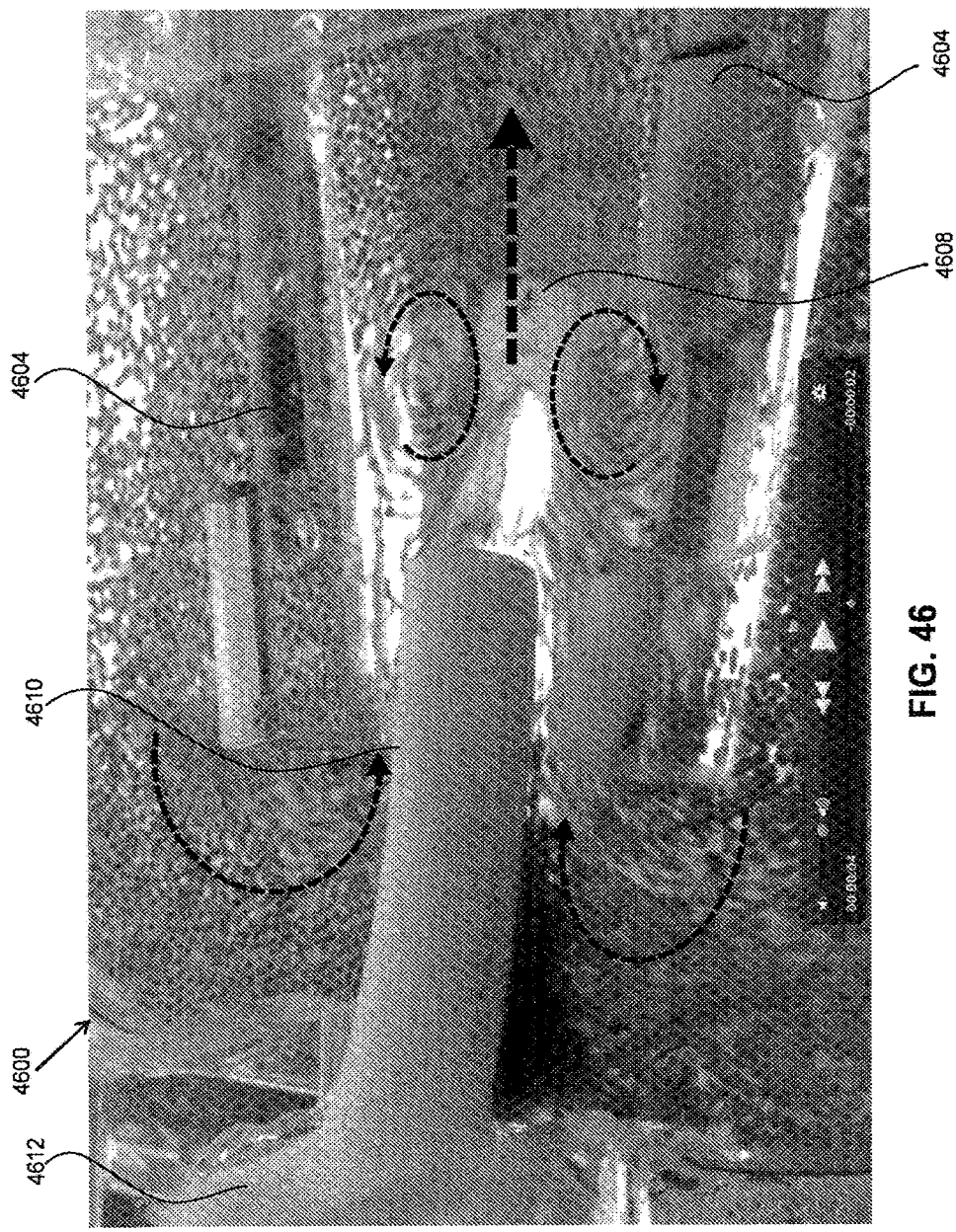

FIG. 46 is an exemplary image of a module according to an embodiment.

Figure 47A:
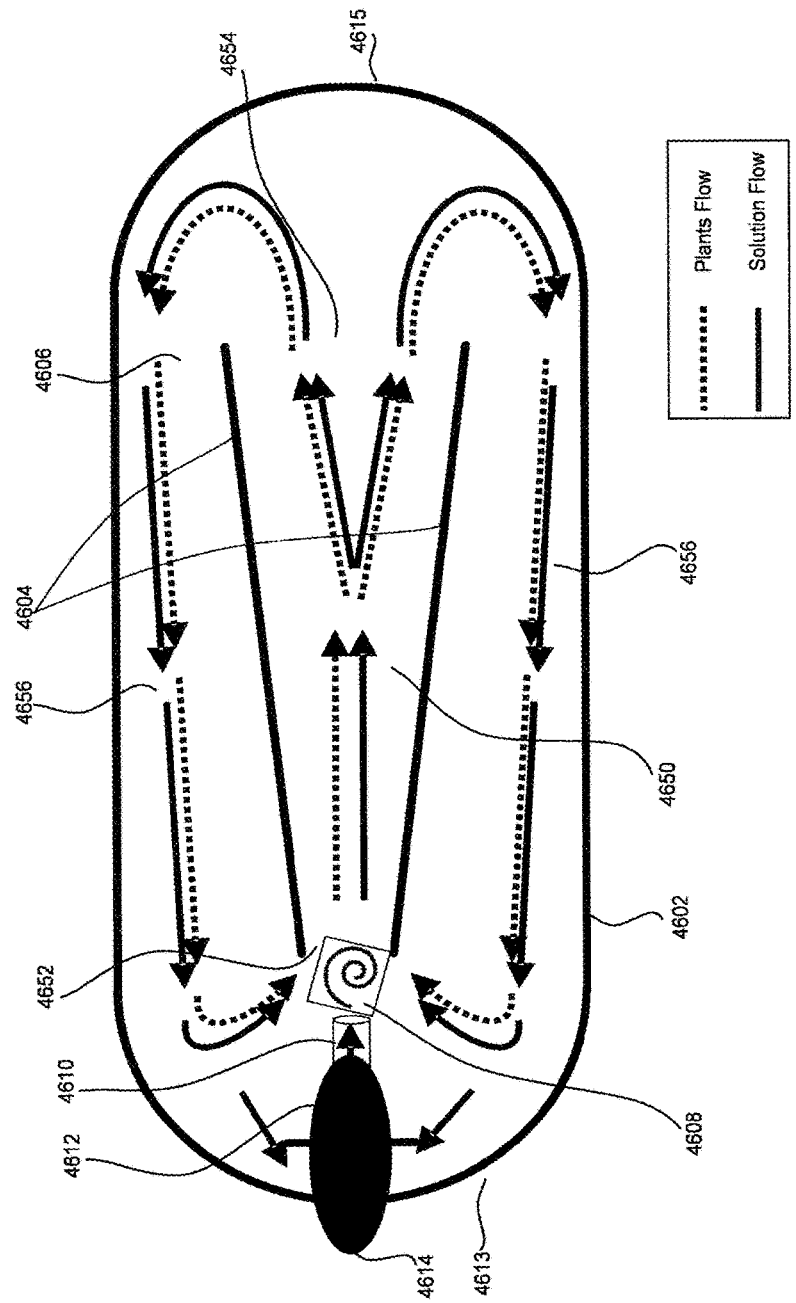
Figure 47B:
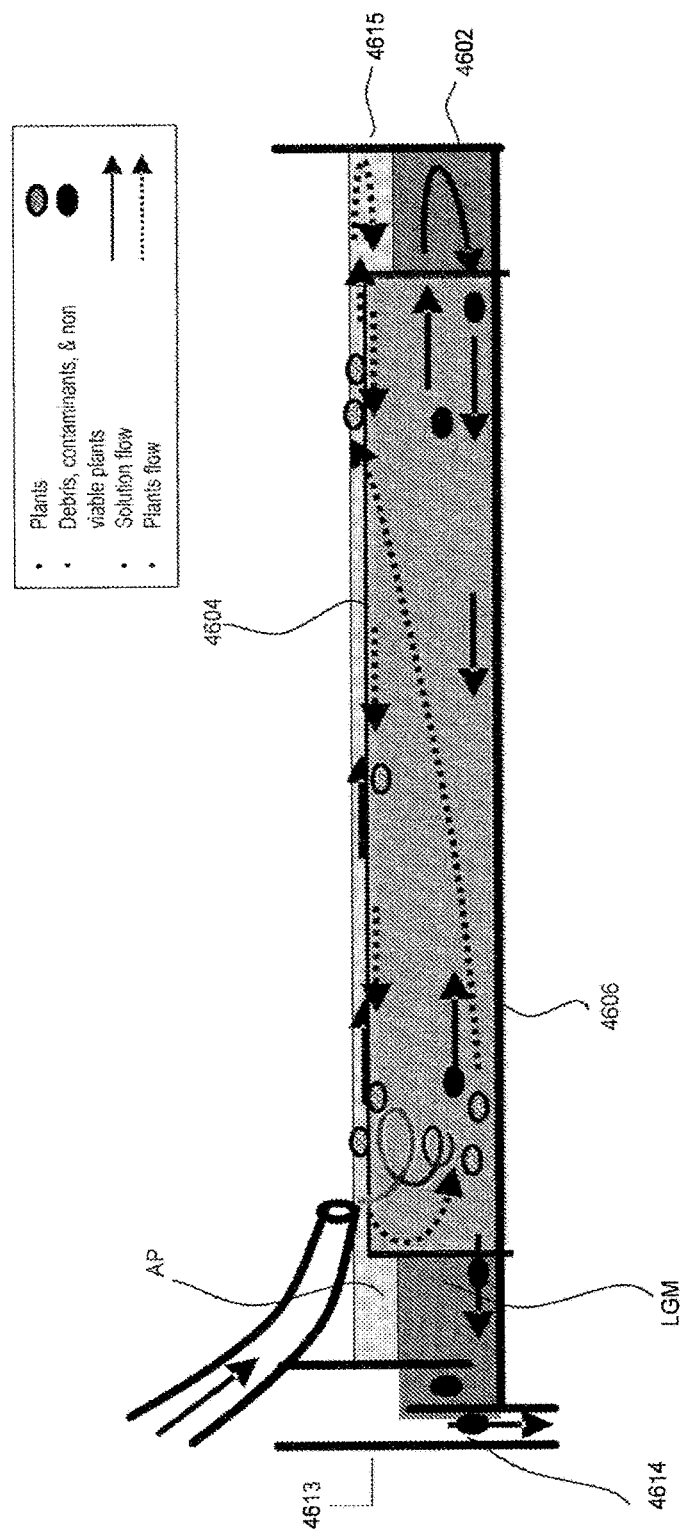

FIG. 47A is an aerial view of a module according to an embodiment. FIG. 47B is a cross-sectional view of the module in FIG. 47A.

Figure 48A:
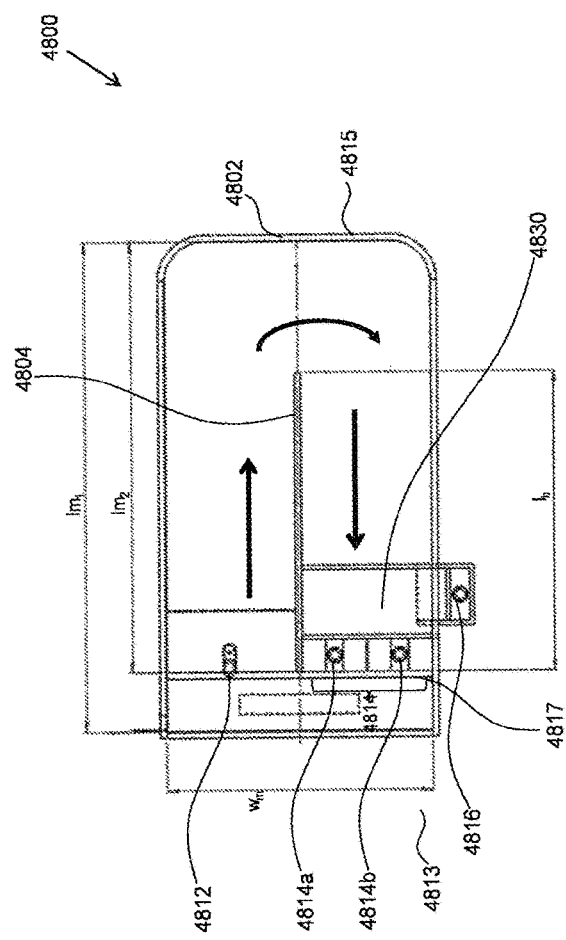
Figure 48B:
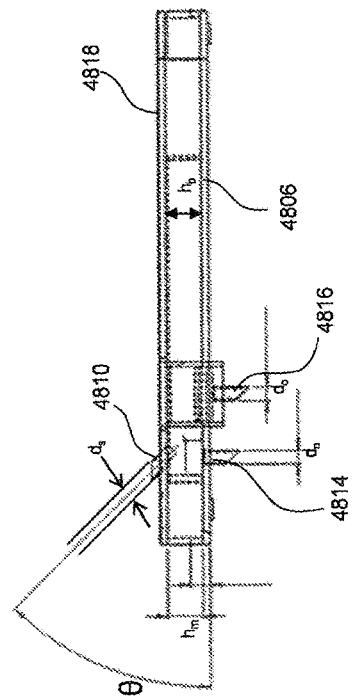

FIG. 48A is an aerial view of a module according to an embodiment. FIG. 48B is a cross-sectional view of the module in FIG. 48A.

FIG. 49A is an aerial view of a module according to an embodiment. FIG. 49B is a cross-sectional view of the module in FIG. 49A.

Figure 50:
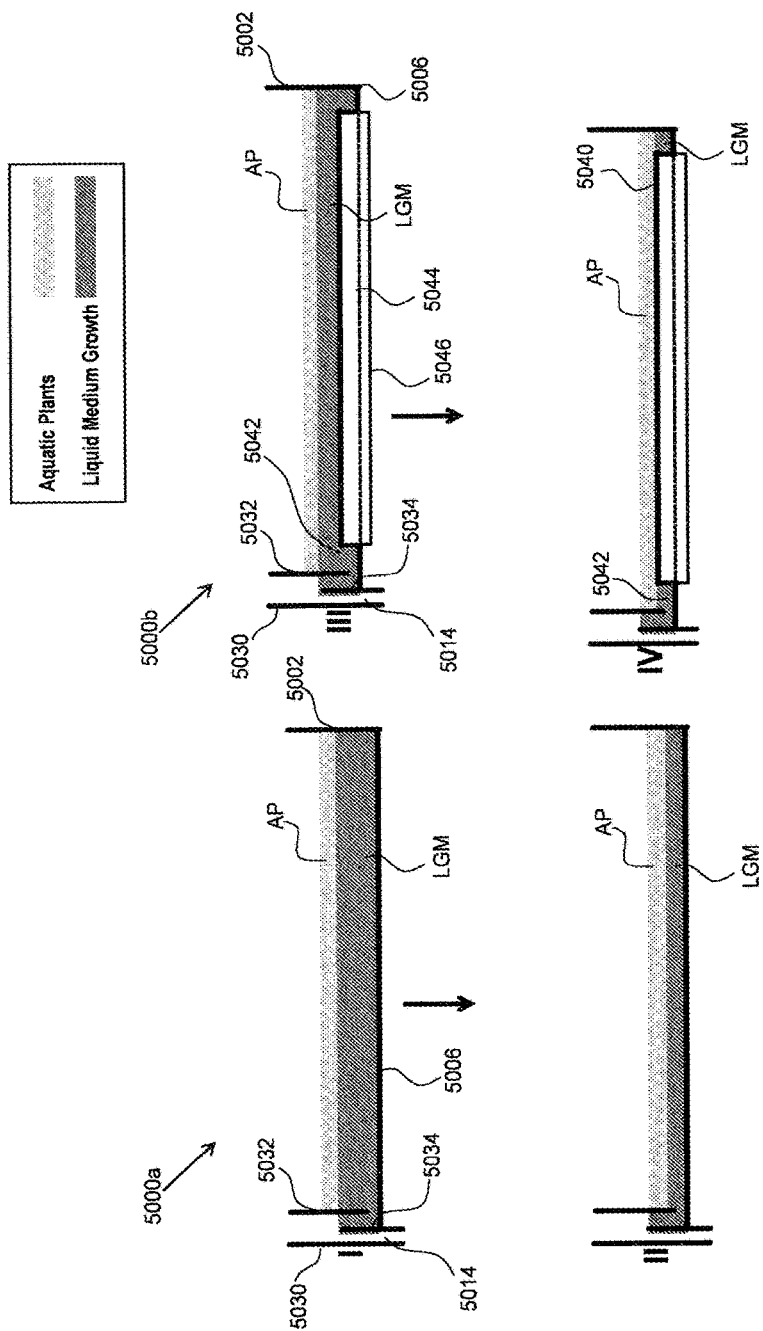

FIG. 50 is a comparison between modules illustrating a ramped floor according to an embodiment.

Figures 51A, 51B:
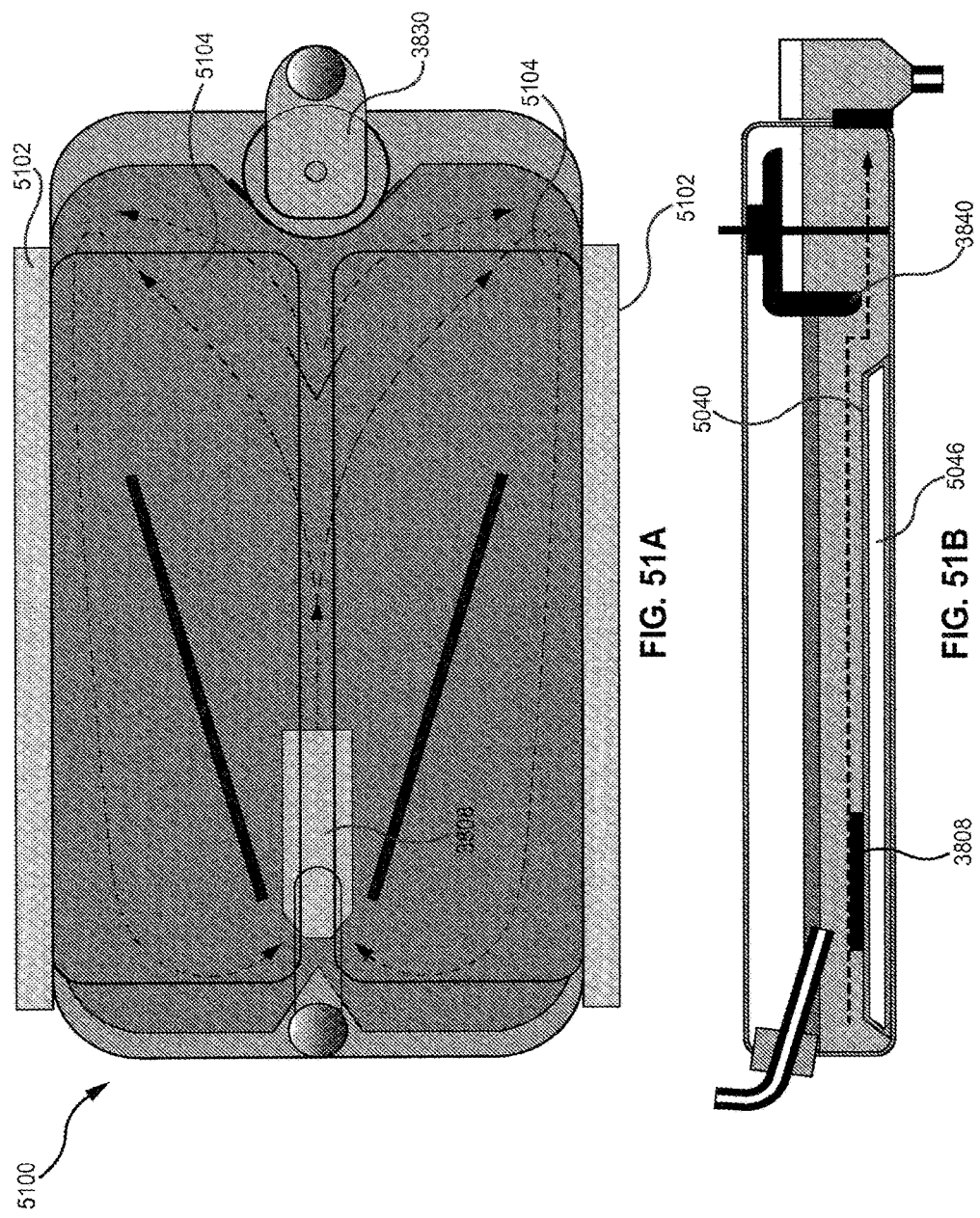

FIG. 51A is an aerial view of a module according to an embodiment. FIG. 51B is a cross-sectional view of the module in FIG. 51A.

FIGS. 52A-52C illustrate a biomass harvesting and quantification unit according to an embodiment and the operation thereof.

Figure 53:
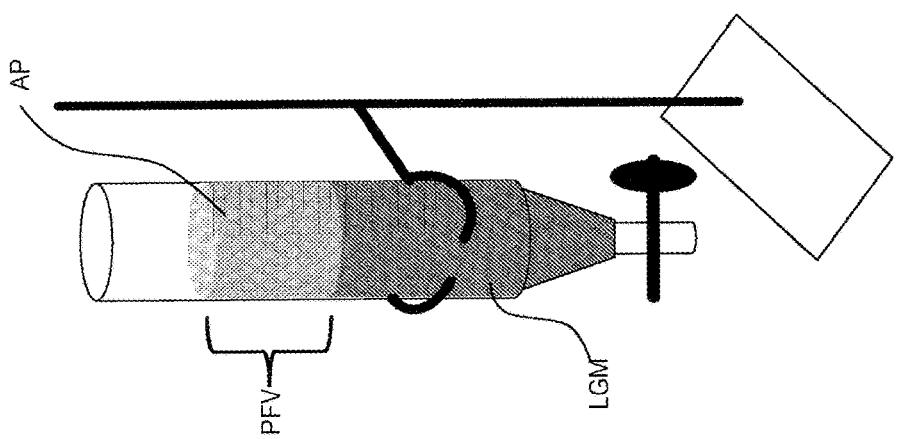

FIG. 53 is a schematic depicting the measurement of PFV.

Figure 54:
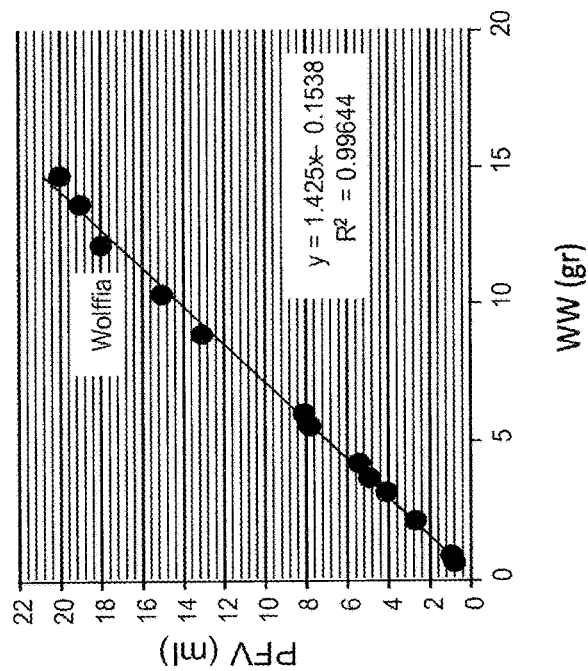

FIG. 54 is a graph illustrating the relationship between PFV and WW according to an embodiment.

Figures 55A, 55B:
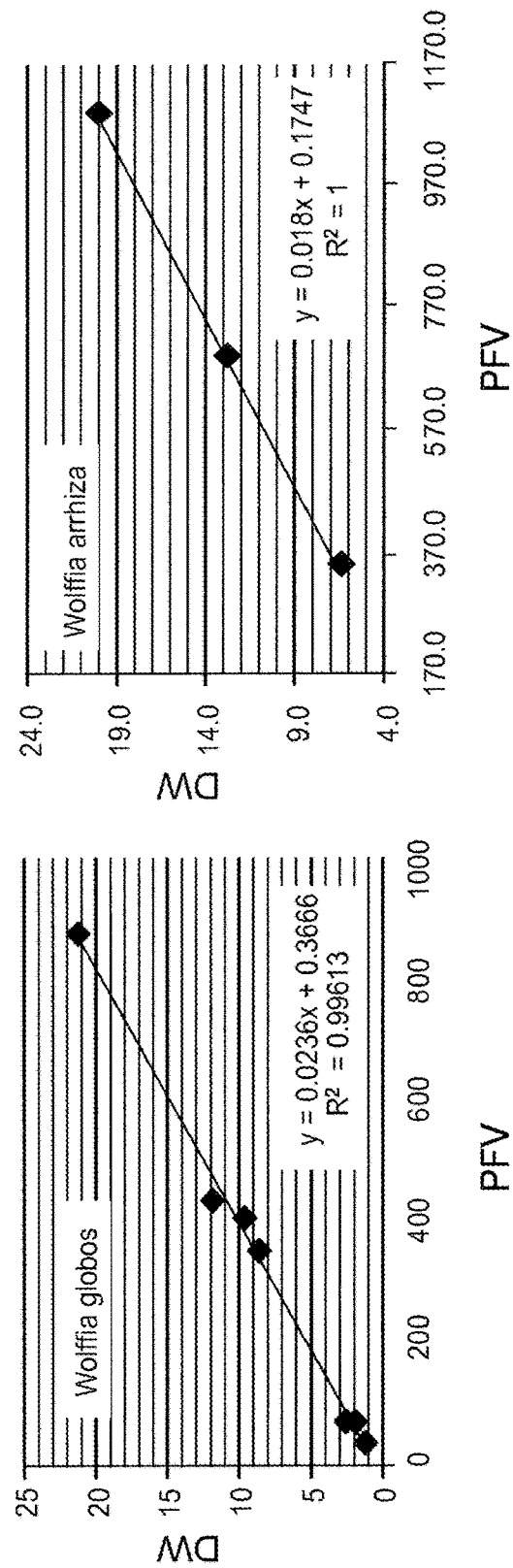

FIGS. 55A-55B are graphs illustrating the relationship between PFV and DW according to various embodiments.

FIG. 56 is a sterilization unit according to an embodiment.

FIG. 57 is a sterilization unit according to an embodiment.

FIG. 58 is a sterilization unit according to an embodiment.

Figure 59:
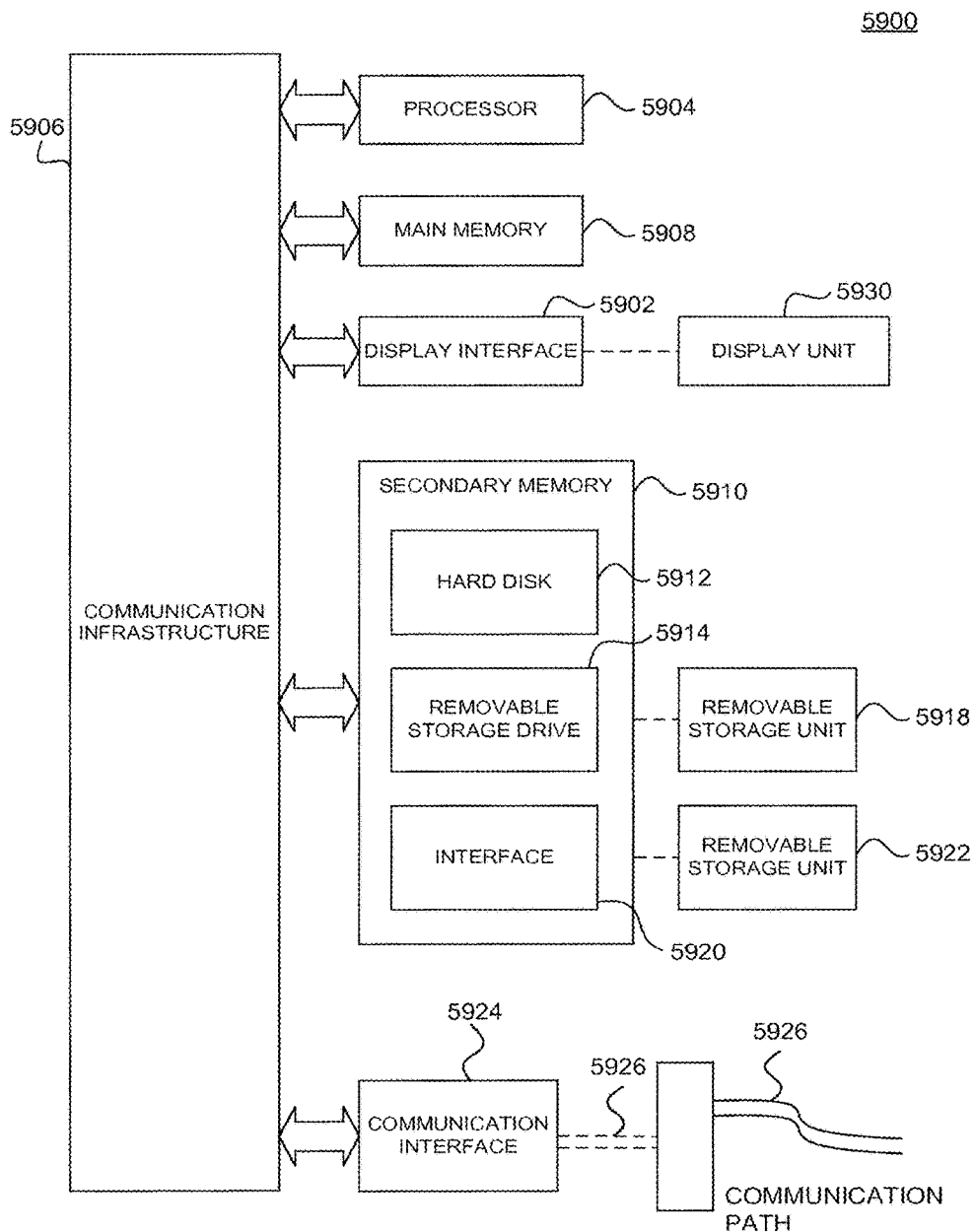

FIG. 59 is a schematic block diagram of an exemplary computer system in which embodiments may be implemented.

DETAILED DESCRIPTION OF THE INVENTION

The present inventions will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present inventions. Other suitable modifications and adaptations of the variety of conditions and parameters normally encountered in the field, and which would be apparent to those skilled in the art, are within the spirit and scope of the inventions.

As used herein the term "aquatic organism" includes all biological organisms living or growing in, on, or near the water such as, but not limited to, fish, molluscs, crustaceans, echinoderms, other invertebrates and their lifestages, as well as aquatic (e.g., marine and fresh water) plants. Types of aquatic plants include, but are not limited to, algae, *Spirodela, Landoltia, Lemna, Wolffiella, Wolffia*, and the like. While embodiments described herein may refer to "aquatic plants," "an aquatic plant culture," or "culture of aquatic plants" any of the embodiments descried herein may be used to grow, culture, harvest, etc. any type of "aquatic organism."

The convenience, taste, and high nutrient valve of aquatic organisms, such as aquatic plants, makes cultivating and distribution of aquatic organisms desirable. However, during cultivation, an aquatic plant culture is typically subject to various time consuming analyses, performed under the direction of an expert trying to detect the state of the culture. Hence there is a need to provide quicker, simpler, and more efficient ways to determine parameters related to aquatic plant growth, thus increasing control, efficiency, and performance, while minimizing the need for human involvement. Moreover, there is a need for monitoring the culture for early detection of stressful conditions and invaders that will allow for continuous adjustment and optimization of conditions related to the growth of the culture, thus increasing the safety, quality, and yield volume of the harvest.

One common way to monitor the growth is by analyzing samples extracted from the culture at predefined intervals. This involves trained personal, the use of specific modalities, tools, and equipment within a laboratory facility. For example, these days, microscopic analyses are usually performed by an expert in the field to determine morphological features of the culture. Moreover, the microscopic observations are used to identify the existence of bio-contaminants (e.g., bacteria, algae, fungi) and/or selective nutrients that may be found in the culture (e.g., antioxidants, dietary chemical elements, proteins, etc.). However, such analyses are time consuming and expensive, which limits their frequent use in common practice.

Moreover, these analyses are performed by different tests specific for selected parameters, and lack the power of an integrated multi-parameter analysis. For example, organism counting may be used to monitor the growth of the culture over time, for example, by determining a biomass density, growth acceleration, growth slowdown, growth phase (e.g., lag, exponential, stationary), mortality rate, etc. However, even state of the art counter modalities provide only one parameter without the ability to detect early transitions and without the ability to suggest related factors and trends.

Thus, there is a need for a system, which may include real-time, continuous, on-site testing, with a possibility for automated and autonomous implementation, and with a possibility for Wi-Fi communication and remote control. These features will facilitate accurate and highly potent real-time culture management and performance optimization.

A horizontal raceway, also known as a flow-through system, is an artificial channel used in aquaculture to culture aquatic organisms, for example, fish, algae, and aquatic plants such as, *Spirodela, Landoltia, Lemna, Wolffiella, Wolffia*, and the like. The traditional horizontal raceway typically includes a continuous circuit flow system used for mixing the aquatic organisms while increasing aeration and homogenizing nourishment ingredients. The continuous circuit flow is used to provide a required level of liquid growth medium, which allows the aquatic organisms to be cultured at high densities within the raceway.

Figure 1A:
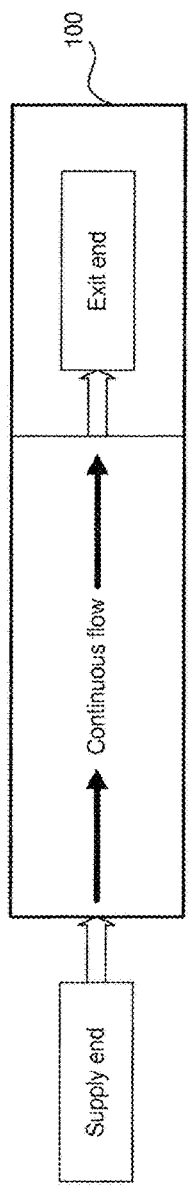
FIGS. 1A-1D are illustrations of horizontal raceways.
Figure 1B:
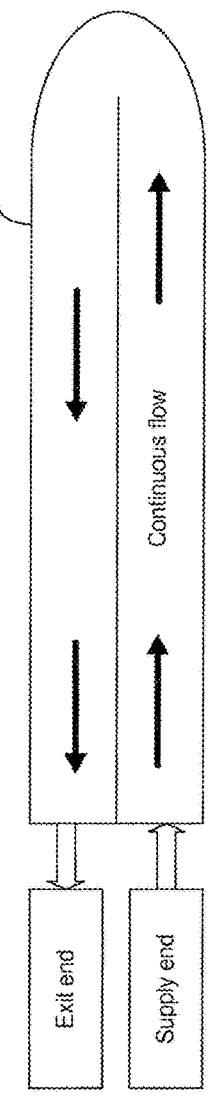
Figure 1C:
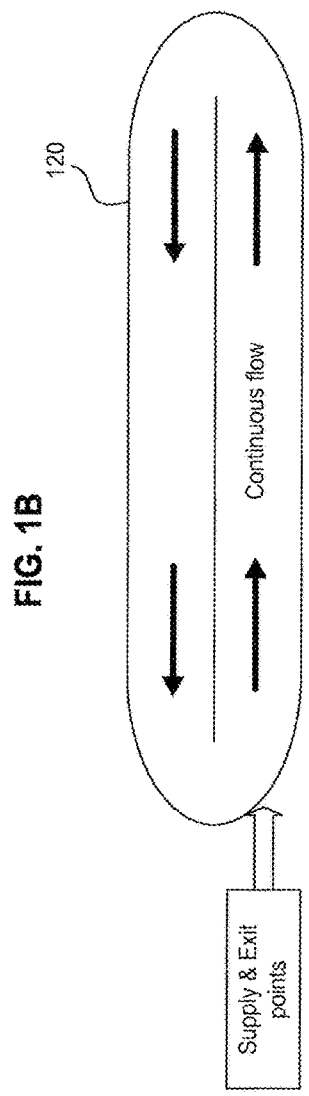
Figure 1D:
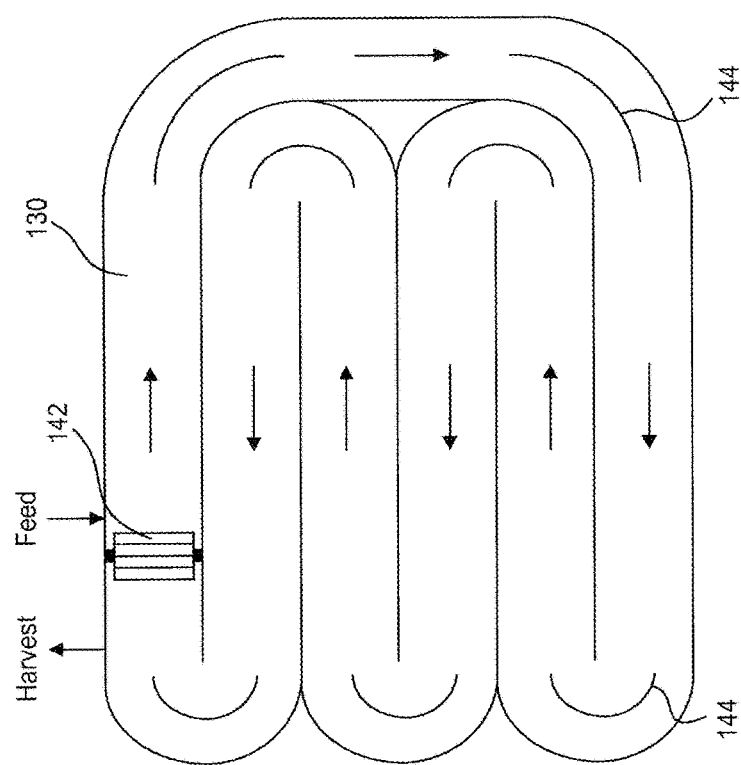
Figure 2:
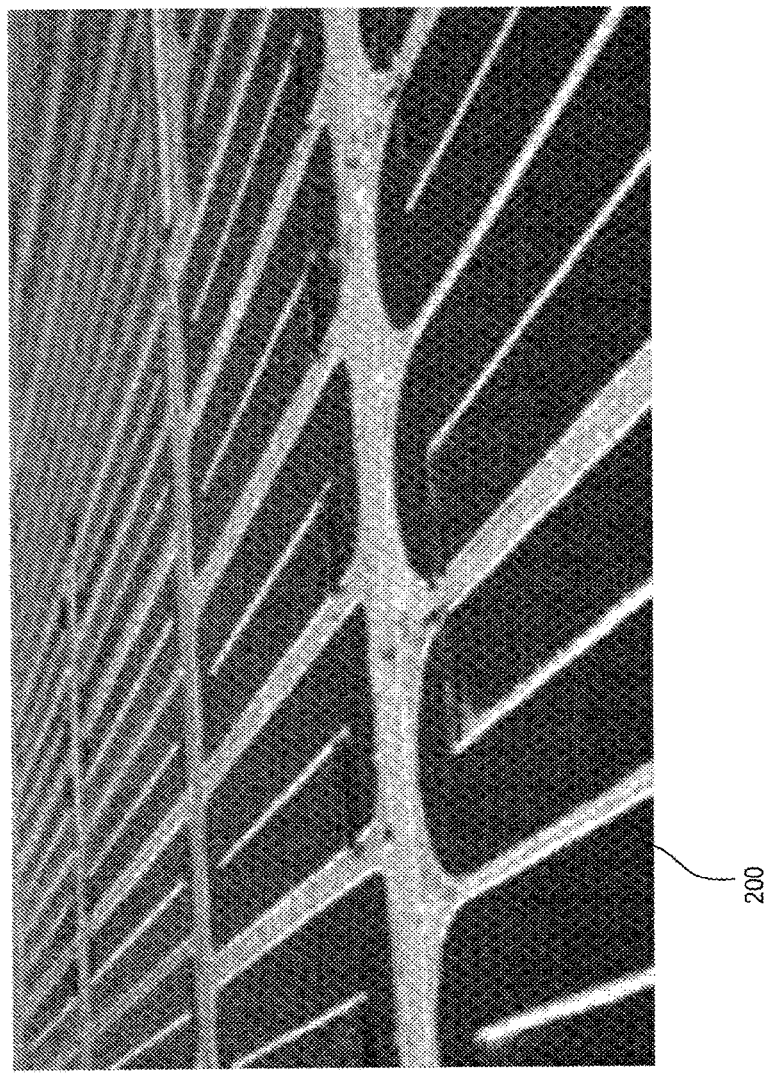
FIG. 2 is an aerial image of an aquaculture farm for growing aquatic plans.

As shown in FIG. 1A, a horizontal raceway 100 may be found in the form of a rectangular channel containing a current flowing liquid, for example, water, flowing from a supply end to an exit end. In the aquaculture industry, in order to create a large mass of aquatic organisms, the aquatic organisms may be cultured in a double horizontal raceway. The double horizontal raceway may be found in a form of an ellipse containing a circuit water flow from a supply end to an exit end (shown as 110 in reference to FIG. 1B) or in a closed ellipse with a continuous circuit flow having supply and end points located at any point on the ellipse (shown as 120 in FIG. 1C and 200 in FIG. 2). Some horizontal raceways may include a continuous meandering channel (shown as 130 in FIG. 1D). Some horizontal raceways, for example horizontal raceway 130, may include a paddle wheel 142 and one or more baffles 144. Horizontal raceways facilitate the culturing of large amounts of aquatic organisms over a large culture area from single points of feeding, monitoring, and harvesting.

The nature of the horizontal raceway, as currently implemented in the art, has various limitations. As exemplified in FIG. 2, while a horizontal raceway structure permits the growth of a large mass of aquatic organisms, it requires a large, flat, and open surface area. Furthermore, aquaculture operations using conventional horizontal raceway configurations may be costly. For example, the loading and discharging of large volumes of water solution and harvested biomass can be a costly operation. Large horizontal raceways may also require complex cleaning systems, sensitive control systems, etc. Moreover, high costs for the required infrastructure and construction of large ponds may also be a burden for the aquaculture industry.

A conventional aquaculture farm may be equipped with a plurality of control units, which separately control individual horizontal raceway channels. In such a configuration the growth of the aquatic organisms may be inconsistent within the aquaculture farm depending on the growth conditions provided to each horizontal raceway channel. Inconsistent growth may result in an inhomogeneous final product of aquatic organisms produced by the aquaculture farm.

As such efficient control of the environment needed for optimal growth of aquatic plants is of interest. Moreover, a compact and cost effective system for growing the aquatic plants is of interest.

Often times an aquatic organism, such as an aquatic plant culture, is dependent on its ecosystem (e.g., amount of light, temperature, natural nutrients, etc.) for proper growth and sustainability. Any time an aquatic plant culture is removed from its optimal ecosystem, it may be subject to deterioration, contamination, or death. As such, the transportation and/or distribution of an aquatic plant culture in an environment that does not mimic its optimal ecosystem is a sensitive operation that needs to be properly controlled to ensure aquatic plants are delivered to their destination in a viable state.

For example, an aquatic plant culture should be protected from harmful conditions (such as high temperature) during transportation. Additionally, the packing and distribution of an aquatic plant culture should ensure that a user receives a viable culture that is suitable for his or her needs. In the event that a non-viable culture is received by a user, a cause and solution for the delivery of a non-viable culture should be identified to prevent recurrence.

Additionally, it may be preferable to package and transport an aquatic plant culture in a way that minimizes transportation and distribution costs. For example, if an aquatic plant culture can be transported at ambient temperature (e.g., in the range of 18° C. to 25° C.), costs associated with regulating the temperature of the culture during transportation can be reduced. Furthermore, if an aquatic plant culture remains viable within a shipping container for an extended period of time (e.g., approximately one week or more), costs associated with expedited shipping can be reduced.

Moreover, monitoring and controlling of a distribution of cartridges based on information received from one or more components within the distribution system may increase the efficiency of distributing the cartridges, and may facilitate quick identification and rectification of any problems within the distribution system.

Embodiments of the present inventions described herein, or elements thereof, facilitate efficient monitoring, cultivation, harvesting, and/or distribution of aquatic organisms, such as an aquatic plant culture, as well as other objectives.

In some embodiments, systems and methods for continuous monitoring of aquatic plant growth, for example, an aquatic culture of *Wolffia* are provided. These systems and methods may facilitate early detection of characteristics associated with an aquatic plant culture. The system may receive at least one image of a culture of aquatic plants. And the system may adjust an image acquisition set-up (e.g. image sensor, optics, and light) per requested detection. A culture of aquatic plants can include one or more aquatic plants or a combination of different types of aquatic plants. The system may identify at least one parameter of a plurality of parameters related to at least one characteristic of the aquatic plants by employing at least one image processing technique on each image of the culture.

The image processing technique may include, but is not limited to, a technique executed by a processor using an algorithm to recognize various parameters associated with the aquatic plants found in a received image. For example, the algorithm may be a shape or color recognition algorithm that is capable of determining the color and shape of the aquatic plants by analyzing light reflected by and transmitted through a culture of aquatic plants. The computer algorithm may include a process for scoring a number of characteristics for an aquatic plant culture. The computer algorithm may also include an algorithm for comparing a received image with reference data related to parameters and/or characteristics from stored images, including but not limited to, baseline images, reference images previously collected from the same culture, and/or reference images previously collected from a different culture stored in a database to determine a growth phase and/or current state of the aquatic plants.

The identified parameters may include, but are not limed to, the surface area of the aquatic plants, the density of the aquatic plants, the amount of light absorbed by the aquatic plants, the wavelength of light reflected from the surface of the aquatic plants, the wavelength of light that is transmitted through the aquatic plants, and the distribution of the wavelengths in the reflected or transmitted light. The system may then determine at least one characteristic of the culture based on the parameters. The characteristics of the aquatic plants may include, but are not limited to, a shape of the aquatic plant, a size of the aquatic plant, a pigment (color) of the aquatic plant, a texture of the aquatic plant, or a transparency of the aquatic plant. The system may then classify and score the aquatic culture based on the parameters related to at least one characteristic to determine a state of the aquatic culture. The state of the aquatic culture may be, but is not limited to a biomass density, a growth acceleration rate, a growth slowdown rate, a healthy culture, a contaminated culture, a stressed culture, a dead culture, a dying culture, selective macronutrients or micronutrients concentration/profile, a growth phase of the culture, a morality rate, etc. A stressed culture may indicate a lack of at least one fertilizer element, extreme light or temperature conditions, or poor pH conditions. Furthermore, the system may be configured to identify contamination events and levels, which may occur as a result of an invasion of the culture and growth by bacteria, algae, fungi, etc.

The systems and methods for continuous monitoring of aquatic plant growth may be used to cultivate individual aquatic plants cultures or a plurality of aquatic plant cultures. The systems and methods may continuously monitor one or more aquatic plant cultures within one or more bioreactors. And data collected from a bioreactor (e.g., data collected from performing an image processing technique) may be used to efficiently control the monitoring and growth of one or more aquatic plant cultures in one or more bioreactors. Moreover, data collected from a bioreactor may be used to facilitate distribution of one or more aquatic plant cultures.

Figure 3:
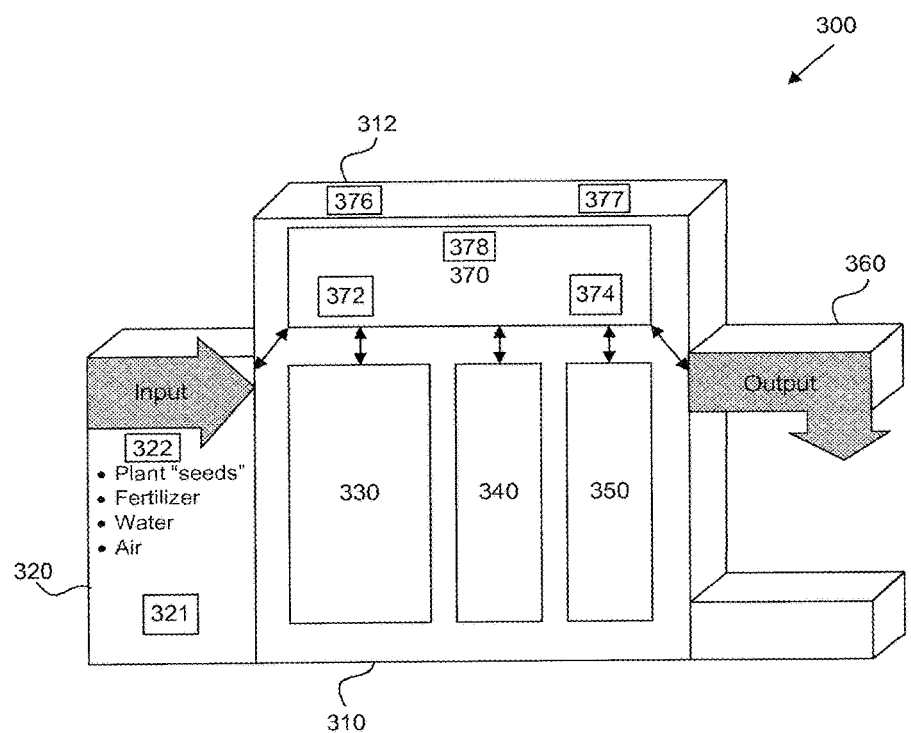
FIG. 3 is a schematic block diagram of a bioreactor system according to an embodiment.

FIG. 3 shows a system 300 for cultivating, harvesting, and outputting a culture of aquatic plants according to an embodiment. System 300 includes a bioreactor 310. Bioreactor 310 may have one or more growing units 330 adapted to grow one or more aquatic plants in the system, one or more harvesting units 340 adapted to harvest one or more aquatic plants in the system, and one or more processing units 350 adapted to modify and/or customize one or more aquatic plants harvested from the one or more harvesting units 340. A control unit 370 may be configured to control one or more operations of system 300.

System 300 may also include an input unit 320 adapted to receive an aquatic organism used as a starter material or organism (e.g., an aquatic plant culture in a predetermined life stage), fertilizers, water, and air. The aquatic organism starter material may be, for example, but not by way of limitation, a plant from the Lemnaceae family (Duckweed), especially, from the *Spirodela, Landoltia, Lemna, Wolffiella* and *Wolffia* genera, edible micro and macro-algae. In another embodiment starter materials of aquatic organisms that are not necessarily edible are used. The starter material may be in various development states and forms, for example, but not by way of limitation, in a pre-matured or matured plant form, in attenuated form, in dormant form, in etiolated form, and/or in seed form System 300 may also include one or more output units 360 adapted to supply the aquatic plant and/or a culture conditioned medium as, for example, a foodstuff, a medicinal substance, a cosmetic substance, a chemical substance, or other useful products. In some embodiments, output unit 360 may output an aquatic plant culture in an unaltered form (e.g., at a source bioreactor 2602 for packaging and distribution or at a POU bioreactor 2604 for consumption as discussed below).

In some embodiments, there are two consecutive steps performed in input unit 320: an acceptance step and an incubation step. The acceptance step includes receiving the starter material from the delivery package (e.g. a capsule/cartridge, such as capsules 2702 of cartridge 2700) into an incubation-growing chamber 321 while keeping and grading sterile conditions. The incubation step includes the time and conditions necessary to allow the starter material to mature prior to being transferred to growing unit 330. The incubation-growing chamber 321 may include one or more sensors, for example sensors 372 and image sensors 374, which can deliver data to control unit 370 in order to: (1) ensure a safe/contamination free state for the new batch, and (2) to ensure that the started material reaches an acceptable maturation state. In some embodiments, keeping these two steps within input unit 320, rather than including them in growing unit 330, may allow for the simple and quick replacement of a new culture in the event of an error related to the new culture.

Input unit 320 may include an extractor 322 for accessing one or more capsules/cartridges (e.g., capsules 2702 or cartridges 2700) and extracting one or more aquatic plant cultures and fertilizer stock solutions from the capsules/cartridges. Extractor 322 may include any suitable mechanism for accessing and extracting one or more aquatic plant cultures and/or fertilizer stock solutions. In some embodiments, extractor 322 may include a pipetting type device with a piercing end for accessing and extracting one or more aquatic plant cultures and/or fertilizer stock solutions. In some embodiments, extractor 322 may include a vacuum device for extracting one or more plant cultures and/or fertilizer stock solutions. In some embodiments, extractor 322 may include a vacuum device for extracting one or more plant cultures and/or fertilizer stock solutions. In some embodiments, extractor may include a movable mechanical device (e.g., a mechanical arm) for moving between different positions (e.g., from an extraction position for extracting an aquatic plant and/or fertilizer to a dispensing position of dispensing the aquatic plant and/or fertilizer into an incubation unit or growing unit. In some embodiments, extractor 322 may include a washing unit for washing out the contents of one or more capsules. In operation, control unit 370 may read and store information located on labels and/or sensor (e.g., identification labels 2720 and/or cartridge sensors 2722), for example in a memory 378 of bioreactor 310. In some embodiments, the reading and storage of information may be performed while a capsule/cartridge is located in input unit 320. Additionally, control unit 370 may record a time stamp of when a capsule/cartridge is received by input unit 320 and/or when one or more capsules of a cartridge are accessed by extractor 322.

Control unit 370 may be configured to control the operation of each unit (320, 330, 340, 350, 360) and monitor system 300 in real-time by collecting data from sensors 372 (372-1 through 372-n) and image sensors 374 (374-1 through 374-n). Control unit 370 may be configured to monitor and adjust the growing conditions in each of the units using sensors 372 and/or 374. "Real-time" as used herein may include delays inherent to transmission technology, delays designed to optimize resources, and other inherent or desirable delays that would be apparent to one of skill in the art. In some embodiments, some or all of these transmissions may be delayed from real time, or may occur after completion of specific operations.

Sensors 372 can include, but are not limited to, temperature sensors, humidity sensors, pH sensors, $CO_2$ sensors, light sensors, flow sensors, fluid level sensors, etc. Image sensors 374 may be cameras adapted to provide at least one image of the culture of aquatic plants. Control unit 370 may be configured to monitor and analyze data collected from sensors 372 and/or 374 and control culture conditions, the process flow, and operation of units 320, 330, 340, 350, and 360 based on the data collected from sensors 372 and/or 374. In some embodiments, bioreactor 310 is a self-contained unit that includes input unit 320, growing unit 330, harvesting unit 340, processing unit 350, output unit 360, and control unit 370 within a single housing 312.

In some embodiments, as shown, for example, in FIG. 3, bioreactor 310 is a self-contained bioreactor 310 having an on-board control unit 370. In some embodiments, control unit 370 may be in communication with a network for collecting, storing, and/or processing information related to operating bioreactor 310. In such embodiments, the network may include a device, such as a server, for collecting, storing, and/or processing information related to operating a plurality of bioreactors.

Figure 4:
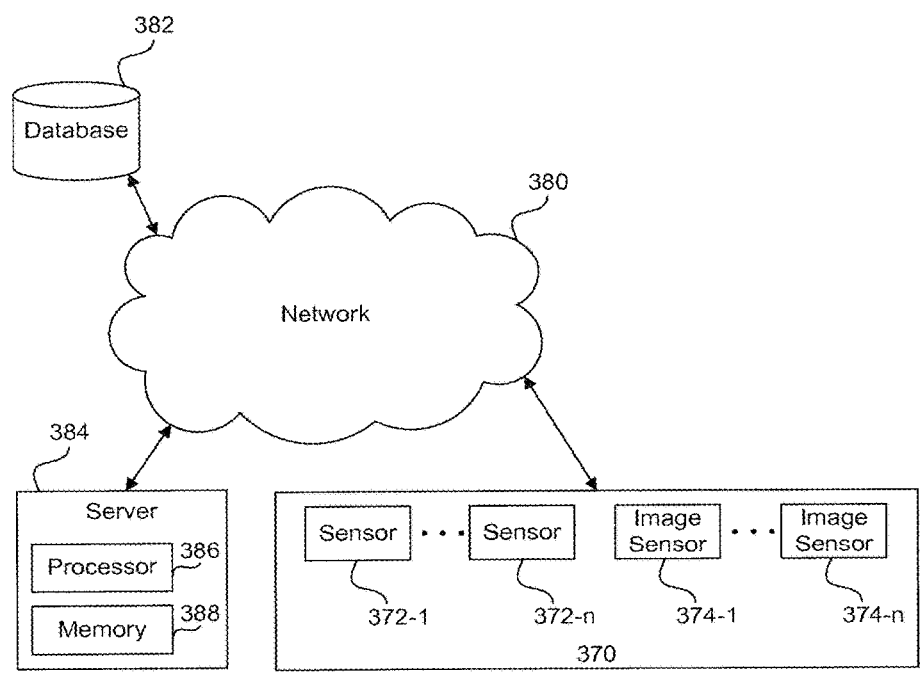
FIG. 4 is a schematic block diagram of a network in communication with a bioreactor control unit according to an embodiment.

In some embodiments, control unit 370 is adapted to collect and process data/parameters related to the detection of characteristics associated with an aquatic plant culture. In some embodiments, control unit 370 may be in communication with a network 380 for collecting, storing, analyzing, and/or processing data related to the detection of characteristics associated with an aquatic plant culture. FIG. 4 is an exemplary and non-limiting schematic diagram of network 380 for collecting, storing, analyzing, and/or processing data related to detection of characteristics associated with a culture of aquatic plants. Network 380 can be a local area network (LAN), a wide area network (WAN), a metro area network (MAN), the worldwide web (WWW), the Internet, implemented as wired and/or wireless networks, and any combinations thereof. Network 380 may receive and/or collect data from sensors 372 and 374 connected to control unit 370 and communicatively connected to network 380.

Each image sensor 374 may be adapted to provide at least one image of an aquatic plant culture. Such culture may include, but is not limited to, a species of *Spirodela*, *Landoltia*, *Lemna*, *Wolffiella*, *Wolffia*, and the like, or a combination of thereof. A database 382 may be communicatively connected to the network 380. Database 382 may be used to maintain information to be used for detection of characteristics related to the aquatic plant culture.

Network 380 includes a server 384. Server 384 may include a processor 386 and a memory 388. Memory 388 contains instructions executed by the processor 386. Server 384 may receive at least one image of the culture of aquatic plants, for example, from at least one image sensor 374. In response to receiving an image, server 384 may be configured to identify at least one parameter of a plurality of parameters related to a characteristic of the aquatic plants by employing at least one image processing technique on each image received. And, in turn, server 384 may determine one or more characteristics of the aquatic plant culture. The plurality of characteristics may include, but are not limited to, morphological features (e.g., shape, size), color features (e.g., one or more aquatic plants' pigments), a texture of the aquatic plants, a transparency level of the aquatic plants, etc. For example, server 384 may be configured to identify one or more individual aquatic plants and/or one or more aquatic plants found in different reproduction stages (e.g., different stages of growth). The aquatic plants may be found in different sizes, which may be measured by server 384 based on their surface area. Moreover, server 384 may be configured to identify aquatic plants with different textures, for example, a smooth texture, or a texture with dotted areas. These and other various non-limiting embodiments of the image processing techniques are described herein.

In some embodiments, the color of the aquatic plants may be determined by the pigments of elements, such as, carotenoids and/or chlorophylls and/or flavenoids found in the aquatic plants. The aquatic plants' pigments may be determined based on their density, reflected light wavelengths and their absorption spectrum. For example, carotenoids with approximate absorbance of about 420 nm to about 480 nm may have an orange pigment. As another example, typical chlorophylls have a green pigment that can be identified by approximate absorbance maxima of between about 430 nm and about 662 nm when it comes to chlorophyll a, while chlorophyll b has approximate maxima between about 453 nm and about 642 nm. A healthy or unhealthy aquatic plant color may be determined by the amount and distribution of the colors of the aquatic plant's pigments. An unhealthy aquatic plant's colors are colors out of a healthy scheme, for a given aquatic plant culture. For example, a healthy color scheme may result in a hue of green and yellow tones.

In some embodiments, server 384 may be configured to determine a number of aquatic plants found in the culture and a number of aquatic plants with the same color tones and/or scheme, shape, etc. found in the culture. In some embodiments, each identified parameter is saved in database 382 in an entry that also includes a time stamp of when a respective image is received. In some embodiments, server 384 may be configured to store a determined characteristic and/or state, such as a determined growth phase, in database 382 along with a time stamp. Database 382 may serve as a log containing some or all of the information, including the image, identified parameters, and determined characteristics and states, along with time stamps for monitoring an aquatic plant culture over time.

Server 384 may also be configured to analyze the parameters, characteristics, and their time stamps as recorded in database 382 to determine at least one state of the aquatic culture. The state may be, a growth acceleration rate, a growth slowdown rate, stress level, mortality level and/or rate, and so on. Each state may be determined by evaluating changes in the identified parameters and/or characteristics over time. For example, server 384 may use at least one mathematical model to determine a biomass density of the culture. Furthermore, server 384 may be configured to facilitate early detection of contaminants by identifying changes in one or more of the pigments, the texture, and the morphological features of the aquatic plants. Contamination may occur as a result of an invasion of living elements such as bacteria, algae, fungi, and the like, or as a result of a chemical contamination by one or more elements or substances. It should be noted that in a case of contamination, the pigments of the aquatic plants may change, for example, from a hue of yellow and green tones to a hue of red and brown tones. In addition, the morphological appearance of the aquatic plants may change due to the presence of contaminating elements or substances, for example, one or more aquatic plants may have an unsmooth texture and/or a distorted shape. In addition, foreign bodies and foreign shapes, which are different from the aquatic plants' typical shapes, can be detected as contamination elements.

In some embodiments, each parameter of an aquatic plant culture may be saved in database 382 in an entry that also includes a time stamp of when a respective image is received and/or taken. In some embodiments, server 384 may be configured to store a determined characteristic and/or state, such as a determined growth phase, in database 382 along with a time stamp. As such, database 382 may serve as a log containing some or all of the information, including the image, identified parameters, and determined characteristics and states, along with time stamps for monitoring an aquatic plant culture over time.

In some embodiments, server 384 may be configured to generate a selective nutrients profile of, for example, antioxidants, proteins, dietary chemical elements, etc. found in the aquatic plants. Moreover, server 384 may be configured to determine a growth phase of the culture (e.g., lag phase, exponential phase, stationary phase, death phase, and any intermediate phase).

During the lag phase of the growth cycle, the aquatic plants are maturing and not yet able to vegetatively propagate. In the lag phase a significant portion of the aquatic plants are found as individual aquatic plants with a low transparency level. Moreover, the distribution of the colors of the aquatic plants' pigments in the lag phase may be more green than yellow due to the active pigments (e.g., chlorophylls) found in the aquatic plants. The exponential phase is the period when the individual aquatic plants are vegetatively propagating.

In the exponential phase most of the aquatic plants are connected to one or more aquatic plants (because of a mother-daughter pairing after a daughter plant sprouts from a mother plant). The transparency level of the aquatic plants is usually relatively low and their total pigment is usually significantly green. During the exponential phase the number of mother-daughter pairs at different maturation states may be measured (e.g., using one or more image processing techniques discussed herein). The growth rate in this phase depends on the growth conditions, which affect the frequency of aquatic plant reproduction and the probability of both mother and daughter aquatic plants surviving.

The stationary phase is the period in which a growth rate and a death rate are equal. The culture may contain aquatic plants that are connected to each other (mother-daughter pairs) at different maturation stages, and healthy aquatic plants that are found as individuals, all with healthy green pigmentation. In addition, a high number of unhealthy/dead aquatic plants may be detected via their bright yellow pigmentation and a relatively high transparency level. The number of new aquatic plants created during stationary phase is limited by growth factors, such as the depletion of an essential nutrient and/or the secretion of a contact inhibitory factor. As a result, the rate of aquatic plants growth may match the rate of aquatic plants death.

The death phase is the period when the aquatic plants are under lethal stress (e.g., run out of nutrients). Most of the aquatic plants in the death phase are found as individuals with bright yellow pigmentation and a relatively high transparency level. At the death phase, the distribution of the colors of the aquatic plants' pigments may be more yellow than green because of a drastic reduction in the content of active pigment molecules (e.g. chlorophylls).

Different growth phases may be classified by different shapes, colors, and the like. In some embodiments, server 384 may be configured to store for future use in database 382, for example, at least one image of the culture, the determined characteristics, the growth phase of the culture, and other related data, along with a time stamp of when that data was received.

While FIG. 4 shows a network for collecting, storing, and analyzing data from sensors 372 and 374, control unit 370 may include all the necessary components, such as a processor and memory, to perform the collecting, storing, and analyzing absent a network. In such an embodiment, bioreactor 310 may comprise a stand-alone unit adapted to operate in the absence of a network. In some embodiments, a stand-alone bioreactor may function as the "server" for any number of other bioreactors. In other words, a stand-alone bioreactor may be a supervisory bioreactor that receives data collected by sensors 372/374 of other bioreactors, as well as data collected by its sensors 372/374.

Figure 5:
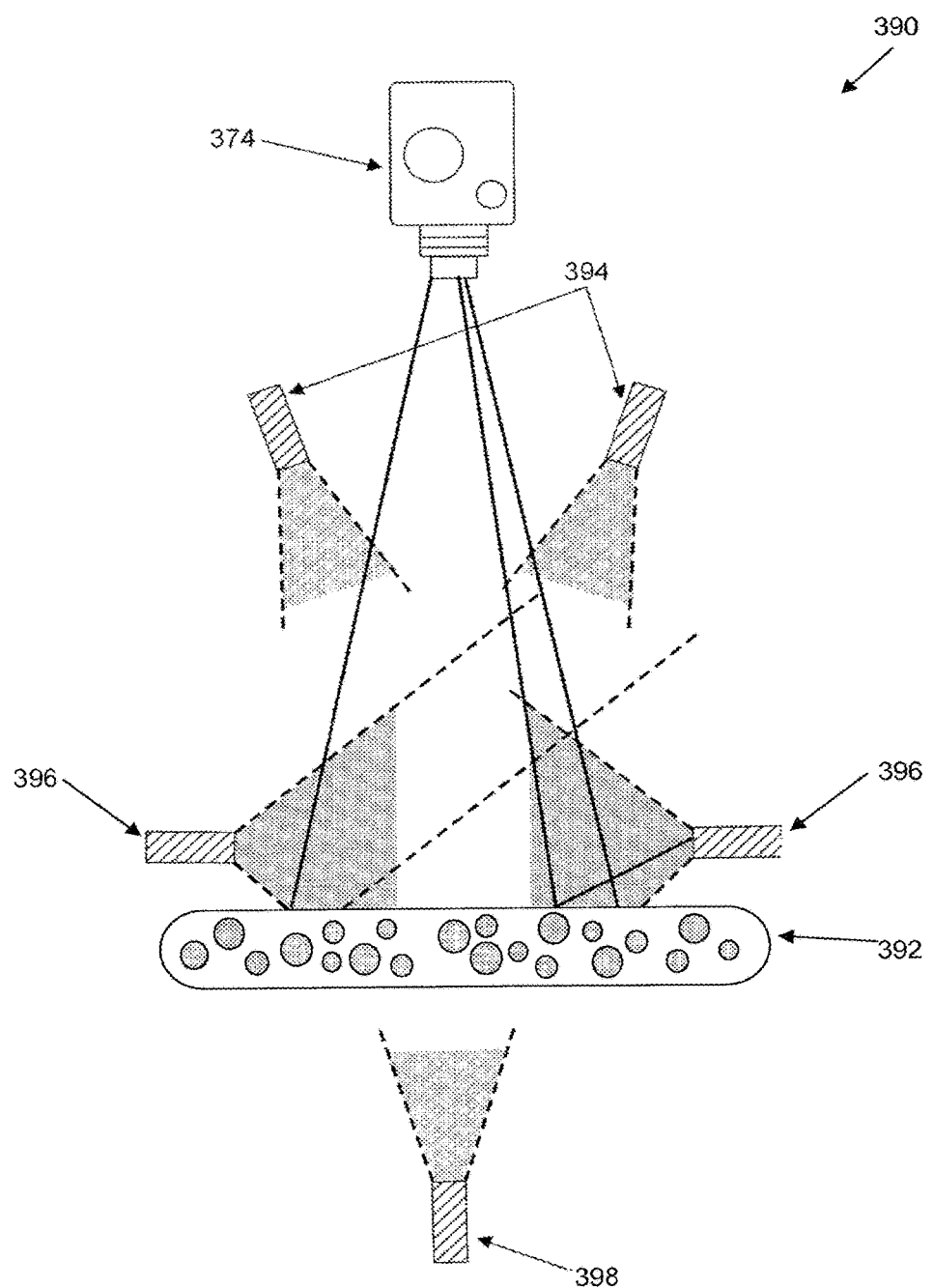
FIG. 5 is an imaging system according to an embodiment.

FIG. 5 shows an imaging system 390 for collecting multi-perspective and multi-wavelength images of an aquatic plant culture 392 within bioreactor 310 according to an embodiment. Imaging system 390 may include at least one image sensor 374, such as, but not limited to, a camera that collects light reflected by and/or transmitted through culture 392. Various light sources may be positioned around culture 392 for illuminating culture 392 with various forms of light with different wavelengths and different illumination intensities. For example, bright-field light sources 394 and dark-field light sources 396 may produce light that is reflected off of culture 392 and collected by image sensor 374. Also, transmitted light source 398 may produce light that is collected by image sensor 374 after it has passed through culture 392. Each image collected can be taken by applying one or more light source, each set to illuminate at a desired intensity, as defined by control unit 370.

Figure 6A:
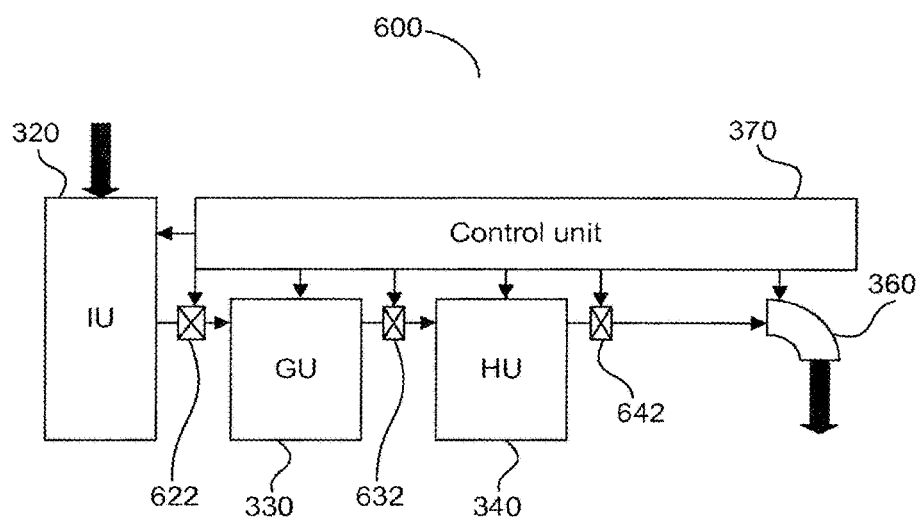
FIG. 6A is a schematic block diagram of a bioreactor system according to an embodiment.

FIG. 6A is an exemplary and non-limiting schematic diagram of a system 600 according to an embodiment. System 600 includes a bioreactor having four operation units: one or more input units (IU) 320, one or more growing units (GU) 330, one or more harvesting units (HU) 340, and one or more output units 360. Output unit(s) 360 may deliver a harvested portion of an aquatic organism, or a culture conditioned medium, to be used as, for example, foodstuff or a cosmetic substance. Output unit 360 may include at least one nozzle for dispensing foodstuff or a cosmetic substance.

Units 320, 330, 340 and 360 may be subsystems, each comprised of one or more compartments, and the operation of each of the units may be controlled by control unit 370. In some embodiments, control unit 370 may control a series of valves 622, 632 and 642 that allow for the delivery of an aquatic organism from one operation unit to another. In some embodiments, one or more of the valves are unidirectional and allow the delivery of content from a first unit to a second unit, for example, from growing unit 330 to harvesting unit 340. In some embodiments, one or more of the valves are bidirectional and allow the delivery of content from a first unit to a second unit and from the second unit to the first unit (e.g., allowing delivery of content from growing unit 330 to harvesting unit 340 as well as from harvesting unit 340 to unit growing unit 330). The direction of flow through the valves may be controlled by control unit 370.

In operation, an aquatic organism used as a starter material (e.g., an aquatic plant culture in a predetermined life stage) may be inserted into input unit 320. In input unit 320, the starter material enters via a contamination free procedure and may then be fertilized and exposed to light in a controlled and monitored way to stimulate maturation to a cultivation state. The monitoring and control of the process may be monitored and/or controlled by control unit 370.

Control unit 370 may perform a plurality of physiological, chemical and physical measurements that relate to ensuring a contamination free state, organism viability, growth rate, growth cycle and culture health conditions, as well as environmental growth conditions, such as temperature, ion concentration, $O_2$ and $CO_2$ concentration, light intensity, and more. In some embodiments, the image may be an image of an aquatic plant culture present in incubation-growing chamber 321. In some embodiments, the image may be an image of an aquatic plant culture present in a cartridge received by input unit 320 (e.g., an aquatic plant culture contained within a capsule 2702 in cartridge 2700). In such embodiments, the viability of an aquatic plant culture (e.g., a contamination state of the aquatic plant culture) may be determined before the culture is introduced into incubation-growing chamber 321, thereby reducing the possibility of contaminating incubation-growing chamber 321.

Once the aquatic plant culture has matured in incubation-growing chamber 321 and control unit 370 confirms that no contamination is present, the matured and contamination free aquatic plant culture may be transferred to growing unit 330, for example, via valve 622. Growing unit 330 may facilitate the growth of the aquatic plant culture by providing and preserving (bio-mimicking) the aquatic plant culture' optimal native environmental conditions, including continued monitoring and adjustments of growth conditions to meet safety, quantity, and quality specifications. The optimal native environmental conditions may be defined and provided as physical conditions (such as light and temperature level and timing, water flow rate, air flow and pressure, and organism dynamic concentrations), chemical conditions of the growth substrate (such as potential hydrogen, Ion concentration, fertilizer compounds, dissolved $CO_2$ and air composition), and physiological conditions (such as organism morphology, size, and color patterns). Control unit 370 may monitor these environmental conditions by collecting data from sensors 372 and image sensors 374. Additionally, control unit 370 may continuously monitor, adjust and optimize these environmental conditions in real-time.

When a harvesting operation is required the aquatic plant culture may be transferred to harvesting unit 340, for example via valve 632. Harvesting unit 340 may harvest of at least a portion of the aquatic plant culture. The harvested culture may be cleaned to meet output criteria, such as food grade criteria, and may then be transferred to one or more output units 360, for example, via valve 642, and may be supplied as foodstuff or a cosmetic substance to the user through the one or more output units 360. The monitoring and control of the whole harvest process, from valve 632 to output unit 360, may be controlled by control unit 370. In some embodiments, the harvest process may include the collection of conditioned growth media or substrate from growing unit 330, which may include components secreted from the culture, in combination or without the aquatic plant culture itself.

Figure 6B:
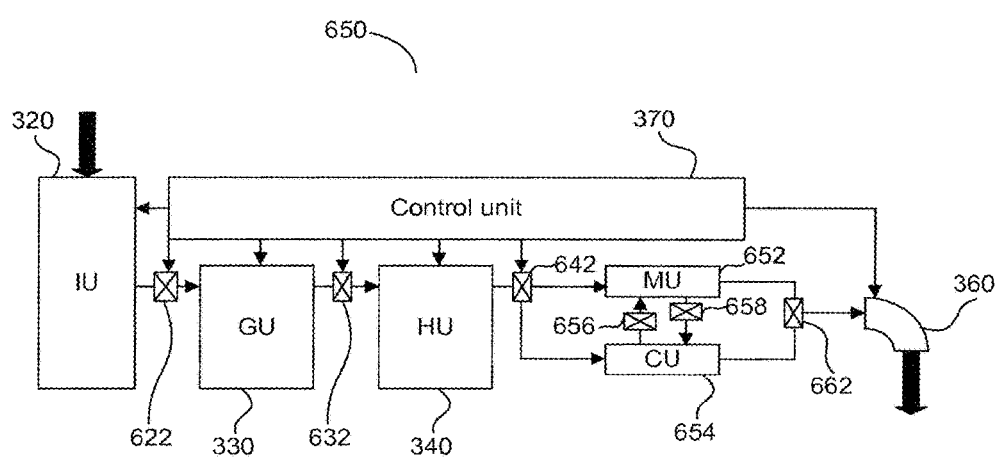
FIG. 6B is a schematic block diagram of a bioreactor system according to an embodiment.

FIG. 6B is an exemplary and non-limiting schematic diagram of a system 650 including a bioreactor according to another embodiment showing the details of processing unit 350. In this embodiment the harvested culture is transferred from harvesting unit 340 through valve 642 to a modification unit (MU) 652, to a customization unit (CU) 654, or both in parallel or a bidirectional sequential order. The culture may be transferred from customization unit 654 to modification unit 652 through a valve 656 or from modification unit 652 to customization unit 654 through a valve 658. In some embodiments, the transfer of the harvested culture to modification unit 652 and/or customization unit 654 in parallel or a bidirectional sequential order may be performed under the control of control unit 370. In some embodiments, the transfer may be performed manually.

Control unit 370 may control the operations of modification unit 652 and customization unit 654. Modification unit 652 may include one or more compartments. Modification unit 652 may be configured to alter of the outputted foodstuff or cosmetic substance in terms of ingredients content. This may be accomplished by changing selected growth condition factors, or a combination of changes in different factors that may cause or induce a modification. These factors may include light intensity level and/or spectrum, substrate or air temperature, air gas mix, fertilizer mix changes, or any combination of these or other factors at different time intervals and lengths. In some embodiments, the modification may include purification and concentration of bioactive components from the organism and/or the conditioned media or substrate. The harvested culture may then be transferred through a valve 662 and supplied as foodstuff or a cosmetic substance to the user through the one or more output units 360.

Customization unit 654 may include one unit, separate subsystems or any combination thereof and may include one or more compartments. In customization unit 654, the harvested culture of the aquatic organism may be treated as a fresh output following a cleaning step with no additional processing or may go through one or more physical changes according to a user's preferences, such as but not limited to, grounding and/or squeezing fresh foodstuff into a liquid product, drying it to a pre-defined level ranging from 95%-5% water, turning it into a paste at desired viscosity level, or grinding it to a powder. These changes may include various flavoring procedures or ingredient add-ons to reach a required outcome for further use or consumption. The harvested culture of the aquatic organism may then be transferred through valve 662 and supplied as foodstuff or a cosmetic substance to the user through the one or more output units 360. In some embodiments, the harvested culture of the aquatic organism can be transferred through both modification unit 652 and customization unit 654 through valve 662 and then supplied as foodstuff or a cosmetic substance to the user through the one or more output units 360.

The use of a plurality of parallel units in each of the stages of the systems 300, 600, or 650 facilitates the creation of multiple and/or different foodstuffs or cosmetic products and may facilitate mixing of different productions of foodstuffs and/or cosmetic substances. For example, if there are two compartments in input unit 320, it is possible to provide starter materials of two different organisms that may be grown separately in two separate compartments in growing unit 330 and then mixed into a single foodstuff in harvesting unit 340. Alternatively, if harvesting unit 340 includes of a plurality of compartments, control unit 370 may control the production so that the content of the compartments in growing unit 330 are transferred into separate compartments of harvesting unit 340.

In some embodiments, bioreactor 310 may include a display 376 for displaying information to a user (e.g., a liquid crystal display (LCD) or a light emitting diode (LED) display). Bioreactor 310 may also include a user interface 377 (e.g., a keyboard, buttons, or a touch screen (which may or may not be integrated into display 376)) for receiving commands from a user. Control unit 370 may be configured to control display 376 and receive commands from user interface 377. Display 376 and user interface 377 may allow a user to control various aspects of bioreactor 310. For example, display 376 and user interface 377 may allow a user to order new cartridges (e.g., cartridges 2700), contact customer service, review messages from a server (e.g., server 384 or 2606). As a non-limiting example, display 376 and user interface 377 may allow a user to review order confirmations for sending new starter material to bioreactor 310 (e.g., a new cartridge 2700) and/or signal bioreactor 310 to dispense an aquatic plant culture from output unit 360. Display 376 may also display one or more operating statuses of bioreactor 310, for example, but not limited to, the temperature within bioreactor 310, the volume of aquatic plants within bioreactor 310, the network connection status of bioreactor 310 (i.e., whether or not bioreactor 310 is currently in communication with a server), and an error status for bioreactor 310.

Figure 7:
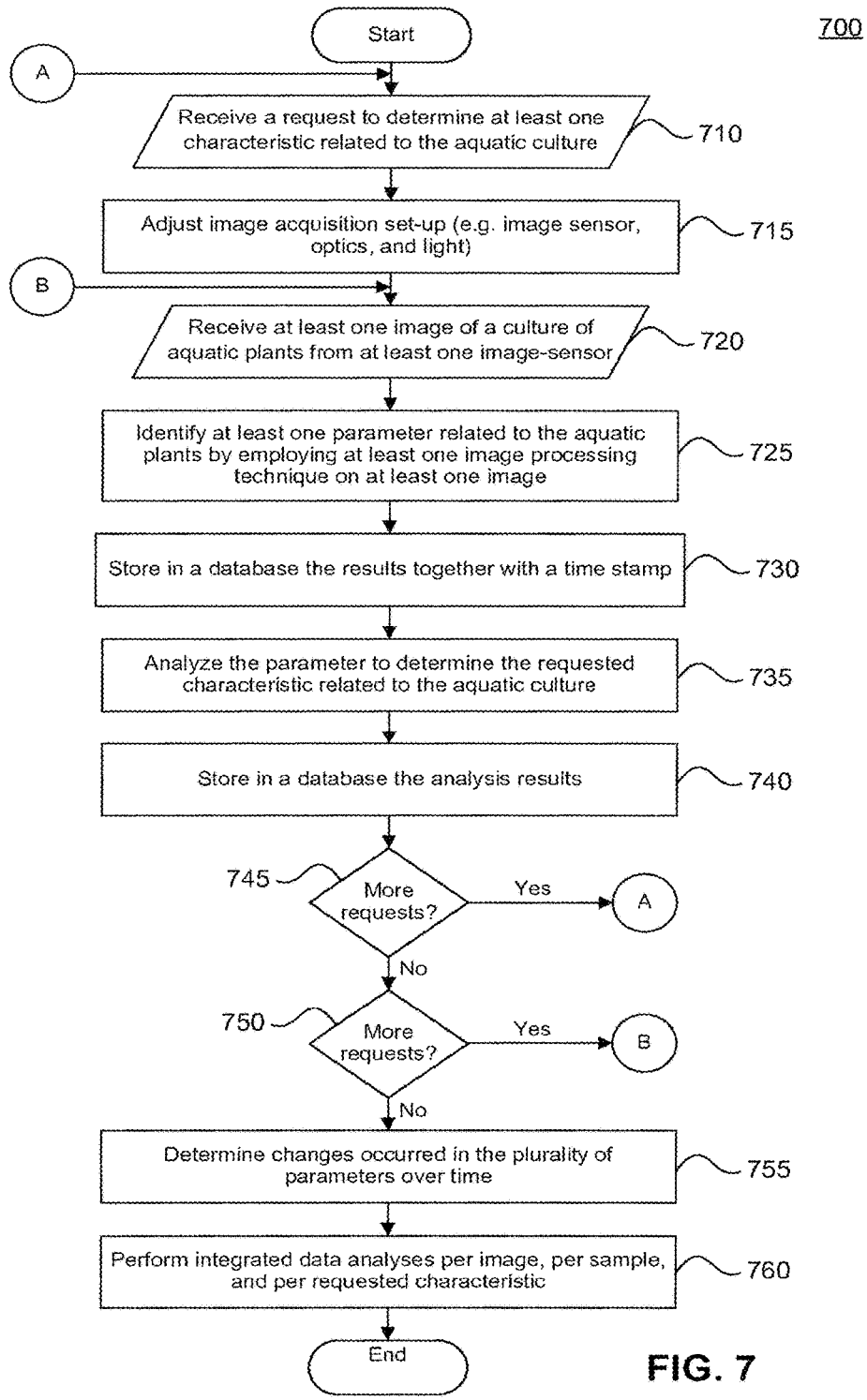
FIG. 7 is a flow chart describing the operation of determining at least one characteristic related to an aquatic culture according to an embodiment.

Operation of monitoring at least one characteristic related to a culture of aquatic plants according to one embodiment will now be described in reference to FIG. 7, which shows an exemplary and non-limiting flow chart 700. According to one embodiment, the operation includes monitoring at least one of a shape, color, texture, transparency, or size of aquatic plants within the aquatic plant culture. In 710, the method starts when server 384 receives a request to determine at least one characteristic related the aquatic plant culture. In 715, server 384 may adjust the imaging equipment, for example, image sensors 374, and prepare for acquiring an image. In 720, server 384 may receive at least one image of the culture, for example, from at least one image sensor 374. In 725, server 384 may identify at least one parameter of a plurality of parameters related to the aquatic plants by employing at least one image processing technique on the at least one image. In 730, server 384 may store the identified parameter(s) along with the results of the image processing technique within database 382 together with a time stamp.

In 735, server 384 may analyze the results related to the identified parameters to determine at least one characteristic related to the aquatic plant culture. Then, in 740, server 384 may store the characteristic(s) in database 382. Server 384 may then determine if there are additional requests in 745. If there is an additional request, server 384 may begin the process over again at 710. If there is not an additional request, server 384 may check if there are any additional images that need to be processed in 750. If there are additional images that need to be processed, server 384 may return to 720. If there are no additional images to be processed, server 384 may proceed to 755. In 755, server 384 may determine changes that have occurred in the parameter(s) over time. Finally, in 760, server 384 may preform integrated data analysis per image, per sample, and per requested characteristic to determine a state of the aquatic plant culture.

The integrated data analysis may be, but is not limited to, an image processing technique that compares a received image with reference data related to parameters and characteristics from stored images, including but not limited to, baseline images, reference images previously collected from the same culture, and/or reference images previously collected from a different culture stored in a database to determine a characteristic of the aquatic plants. The integrated data analysis may also include scoring the requested characteristic(s) (as described below with reference to FIGS. 24-25B, for example) and comparing the scores for each characteristic with previous scores, reference scores, and/or baseline scores.

Figure 8:
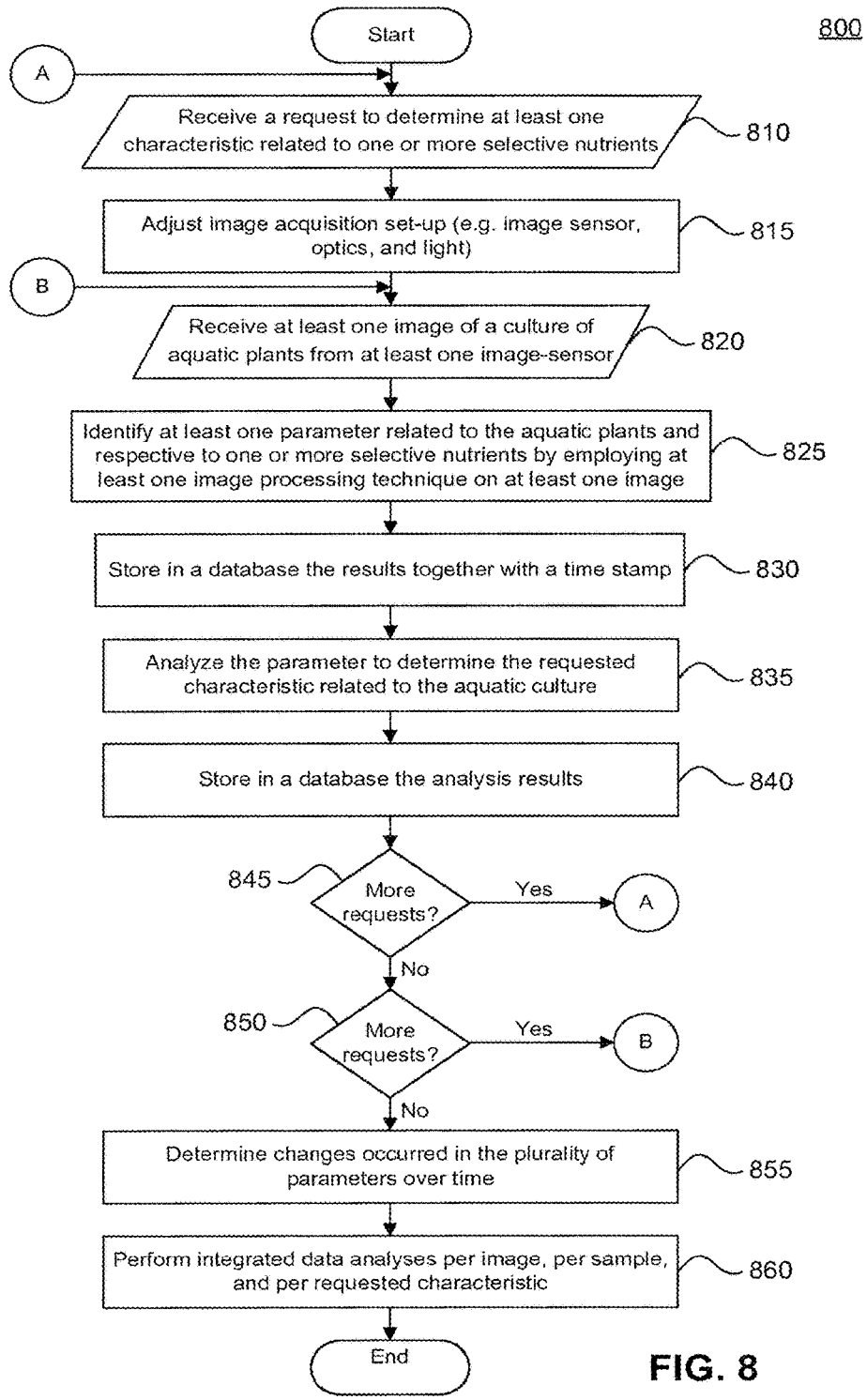
FIG. 8 is a flowchart describing the operation of determining a selective nutrients profile according to an embodiment.

Operation of monitoring one or more selective nutrient levels found in a culture of aquatic plants according to one embodiment will now be described in reference to FIG. 8, which shows an exemplary and non-limiting flowchart 800. According to one embodiment, the operation includes monitoring the levels or concentrations of, for example, antioxidants, proteins, dietary chemical elements, etc. that may be found in the culture aquatic plants. In some embodiments, a selective nutrient concentration may be determined based on, for example, chlorophyll levels or carotenoid levels. In 810, the method starts when server 384 receives a request to determine at least one characteristic related to one or more selective nutrients levels in the culture. In some embodiments, server 384 may receive a request to monitor a specific characteristic related to one or more selective nutrients in the culture of aquatic plants. In 815, server 384 may adjust the imaging equipment, for example, image sensors 374, and prepare for acquiring an image. In 820, server 384 may receive at least one image of the culture, for example, from at least one image sensor 374. In 825, server 384 may identify at least one parameter of a plurality of parameters related to the aquatic plants and related to one or more selective nutrients by employing at least one image processing technique on the at least one image. Specifically, parameters related to pigment molecules (e.g. chlorophylls), which are found in the aquatic plants, may be identified. In some embodiments, server 384 may be configured to determine a light absorption of pigment molecules by projecting light on the culture, for example, in an approximate wavelength of about 520-570 nm in the visible spectrum in case of chlorophylls detection. Chlorophyll causes the aquatic plants to be seen in green color, and thus, a chlorophyll deficiency will cause the aquatic plant to appear less green and more yellow. In some embodiments, server 384 may be configured to use at least one mathematical model to determine the concentration of pigment molecules (e.g., chlorophylls in the culture).

In 830, server 384 may store the identified parameter(s) along with the results of the image processing technique within database 382 together with a time stamp. In 835, server 384 may analyze the at least one parameter to determine the requested characteristic related to one or more selective nutrients of the aquatic plant culture. Then, in 840, server 384 may store the characteristic(s) in database 382. Server 384 may then determine if there are additional requests in 845. If there is an additional request, server 384 may begin the process over again at 810. If there is not an additional request, server 384 may check if there are any additional images that need to be processed in 850. If there are additional images that need to be processed, server 384 may return to 820. If there are no additional images to be processed server 384 may proceed to 855. In 855, server 384 may determine changes that have occurred in the parameter(s) over time. Finally, in 860, server 384 may preform integrated data analysis per image, per sample, and per requested characteristic to determine at least a selective nutrients profile of the aquatic plant culture.

The integrated data analysis may be, but is not limited to, an image processing technique that compares a received image with reference data related to parameters and characteristics from stored images, including but not limited to, baseline images, reference images previously collected from the same culture, and/or reference images previously collected from a different culture stored in a database to determine one or more selective nutrient levels found in a culture of aquatic plants. The integrated data analysis may also include scoring the requested characteristic(s) (as described below with reference to FIGS. 24-25B, for example) and comparing the scores for each characteristic with previous scores, reference scores, and/or baseline scores.

In some embodiments, server 384, in 855, may be configured to retrieve information stored in database 382 to evaluate changes that occurred in pigment molecule levels. This may be used to determine a stress rate in the culture. In such an embodiment, a decrease in pigments molecule levels (e.g., chlorophyll level) over time may imply an increase in a culture's stress level. In other words, an increase in the level of stress in the culture may be reflected in a reduction of the green pigmentation intensity in the culture and in an appearance of a light yellow tone respective thereto. In some embodiments, server 384 may be configured to generate a profile of selective nutrients found in the culture, for example, by determining the concentration of magnesium that is found in the chlorophylls.

Figure 9:
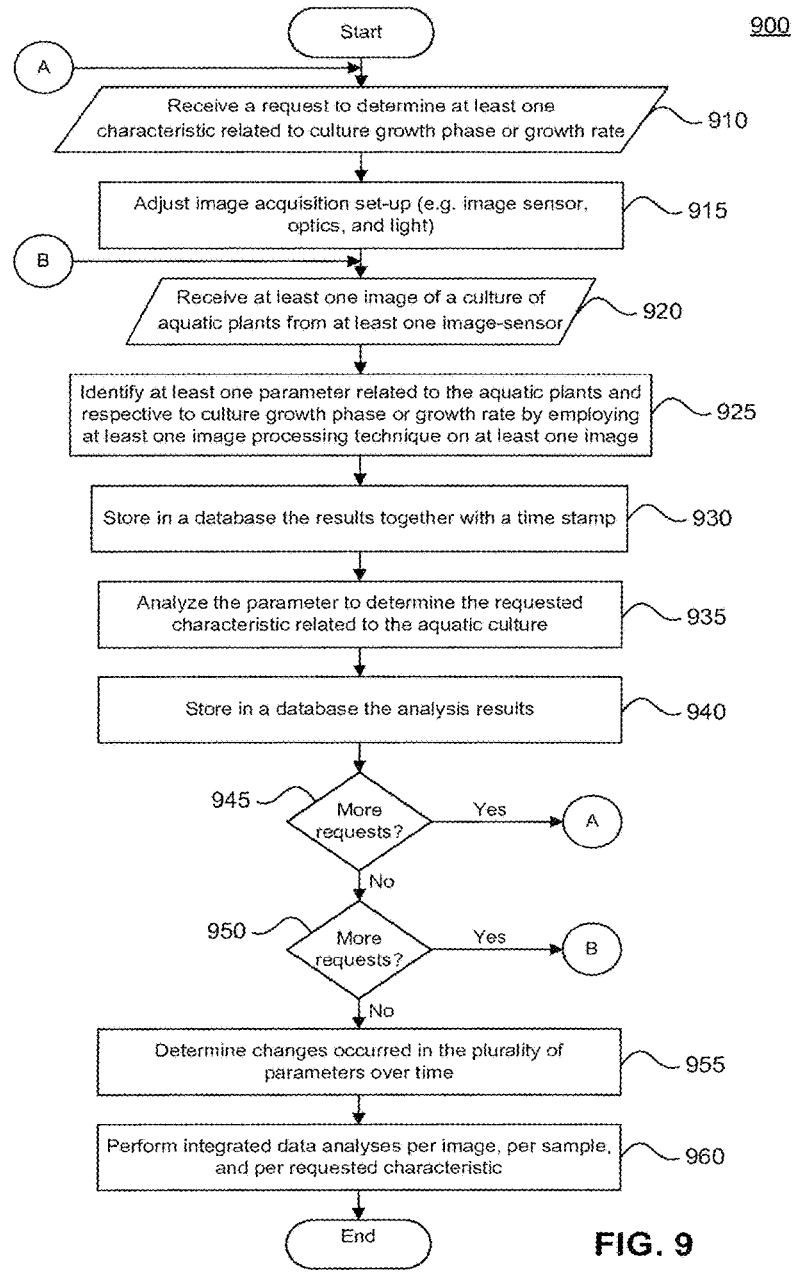
FIG. 9 is a flowchart describing the operation of determining a growth phase or growth rate of a culture of aquatic plants according to an embodiment.

Operation of determining a growth phase or a growth rate of a culture of aquatic plants according to one embodiment will now be described with reference to FIG. 9, which shows an exemplary and non-limiting flowchart 900. In 910, the method starts when server 384 receives a request to determine at least one characteristic related to the growth phase or a growth rate of the culture of aquatic plants, for example, *Wolffia* growth. In 915, server 384 may adjust the imaging equipment, for example, image sensors 374, and prepare for acquiring an image. In 920, server 384 may receive at least one image of the culture, for example, from at least one image sensor 374.

In 925, server 384 may identify at least one parameter related to the aquatic plants and related to the culture's growth phase or growth rate by employing at least one image processing technique on the at least one image. In some embodiments, server 384 may be configured to identify parameters related to, for example, at least one of the shape, the size, the texture, the transparency level, the pigments (color), etc. of the aquatic plants. Moreover, server 384 may be configured to identify a number of aquatic plants found with the same shape, size, color, etc. In some embodiments, the analyses are performed at equal intervals for consistency purposes, however, in other embodiments, different strategies may be employed. In 930, server 384 may store the identified parameter(s) along with the results of the image processing technique within database 382 together with a time stamp. In step 935, server 384 may analyze the at least one parameter to determine the requested characteristic related to the growth phase or growth rate of aquatic plant culture. Then, in 940, server 384 may store the characteristic(s) in database 382. In some embodiments, server 384 may be configured to store a determined characteristic, such as a determined growth rate, in database 382 along with a time stamp. In some embodiments, database 382 may serve as a log containing some or all of the information, including the image, identified parameters, and determined characteristics, along with time stamps for monitoring an aquatic plant culture over time.

Server 384 may then determine if there are additional requests in 945. If there is an additional request, server 384 may begin the process over again at 910. If there is not an additional request, server 384 may check if there are any additional images that need to be processed in 950. If there are additional images that need to be processed, server 384 may return to 920. If there are no additional images to be processed server 384 may proceed to 955. In 955, server 384 may evaluate changes that occurred in the identified parameters over time to determine the growth rate and/or growth phase. Finally, in 960, server 384 may preform integrated data analysis per image, per sample, and per requested characteristic to determine at least one of a growth phase or growth rate of the aquatic plant culture.

The integrated data analysis may be, but is not limited to, an image processing technique that compares a received image with reference data related to parameters and characteristics from stored images, including but not limited to, baseline images, reference images previously collected from the same culture, and/or reference images previously collected from a different culture stored in a database to determine the growth phase and/or growth rate of a culture of aquatic plants. The integrated data analysis may also include scoring the requested characteristic(s) (as described below with reference to FIGS. 24-25B, for example) and comparing the scores for each characteristic with previous scores, reference scores, and/or baseline scores.

Figure 12A:
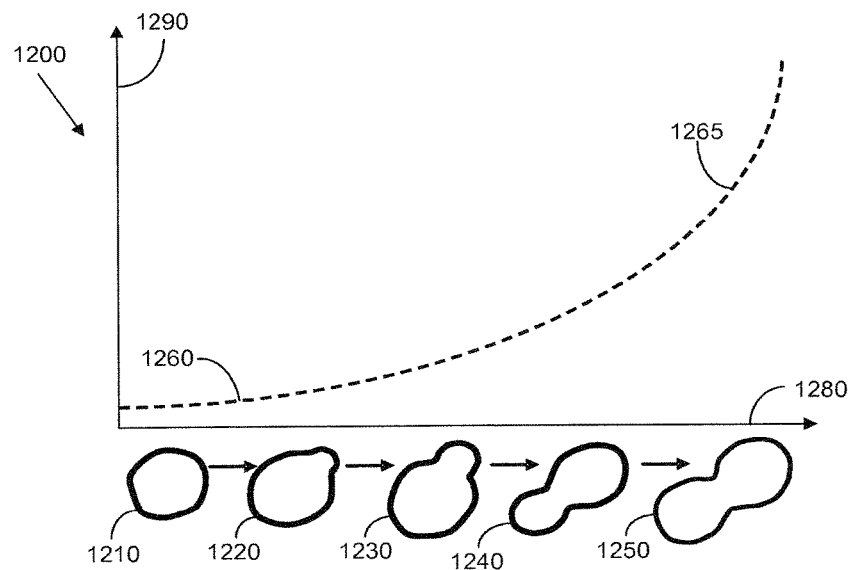
FIGS. 12A-12B show histograms describing the growth of a culture of aquatic plants according to an embodiment.

As a non-limiting example, server 384 may be configured to estimate the changes that occurred over time in the number of aquatic plants found in different vegetative reproduction stages respective of their shape as described below with respect to FIG. 12A. Moreover, server 384 may be, alternatively or further, configured to estimate the changes that occurred over time for a particular parameter (e.g., the density of chlorophyll, which is related to the intensity of a green pigment). Intense green pigment may indicate healthy aquatic plants; so when the level of the green pigment decreases, it may indicate that the culture is found in a stress state, which may indicate a growth slowdown. Server 384 may be configured to use, for example, at least one mathematical model to determine the growth rate related to a number of vegetative reproduction events that occur per a culture portion and per a time unit. When the number of vegetative reproduction events per a culture portion and per a time unit increases, it is likely an indication that there is an increase in the growth rate of the culture.

When most of the aquatic plants are connected to one or more aquatic plants (mother-daughter pairs or mother-daughter colonies of 3-5 plants) and their respective pigment is intense green, this may imply that the culture is found in an exponential growth phase. In a case where the daughter aquatic plants have less chlorophyll than their mothers, this may indicate a stress condition. The pigment of the daughter aquatic plants in such a case will have a brighter green tone. When most of the aquatic plants are found as individual aquatic plants, their pigment is more yellow then green, and their transparency level is high, this may imply that the culture is found in an unhealthy state or even found in a death phase. In some embodiments, server 384 may be configured to determine the existence of contaminants by identifying, for example, an abnormal shape of aquatic plants together with existence of an abnormal pigment (e.g., a pigment that is not found in a hue of green to yellow), a non-typical texture of the aquatic plants, etc.

Figure 12B:
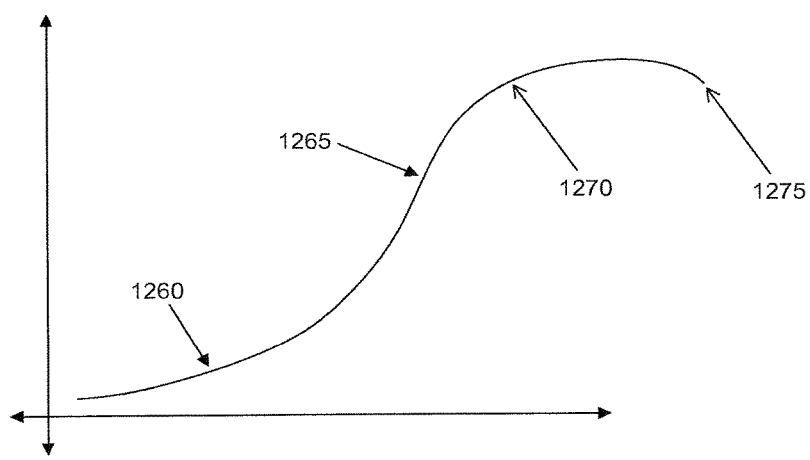

In some embodiments, server 384 may be configured to retrieve the parameters that are identified at several points in time respective of a plurality of images. Server 384 may further be configured to use such parameters to generate a histogram describing the growth phases of the culture. For example, as shown in FIG. 12B, the growth phases of the culture may include a lag phase 1260, an exponential phase 1265, a stationary phase 1270, and death phase 1275.

In some embodiments, server 384 may be configured to determine a stress state, and/or whether stress exists, by evaluating changes that occurred in the identified parameters related to the characteristic(s) over time, for example, changes in the shape, the size, the pigment (color), the texture, the transparency level, etc. of an aquatic plant. An increased number of aquatic plants with different abnormalities, such as aquatic plants with unhealthy pigment (e.g., a pigment that is not found in a hue of the intense green pigmentation), aquatic plants with a reduced size, aquatic plants with an increased transparency, aquatic plants with distorted texture or shape, etc. may imply an increased stress level. In some embodiments, server 384 may be configured to use at least one mathematical model to determine a number of abnormal aquatic plants that occur per a time unit.

Figure 10:
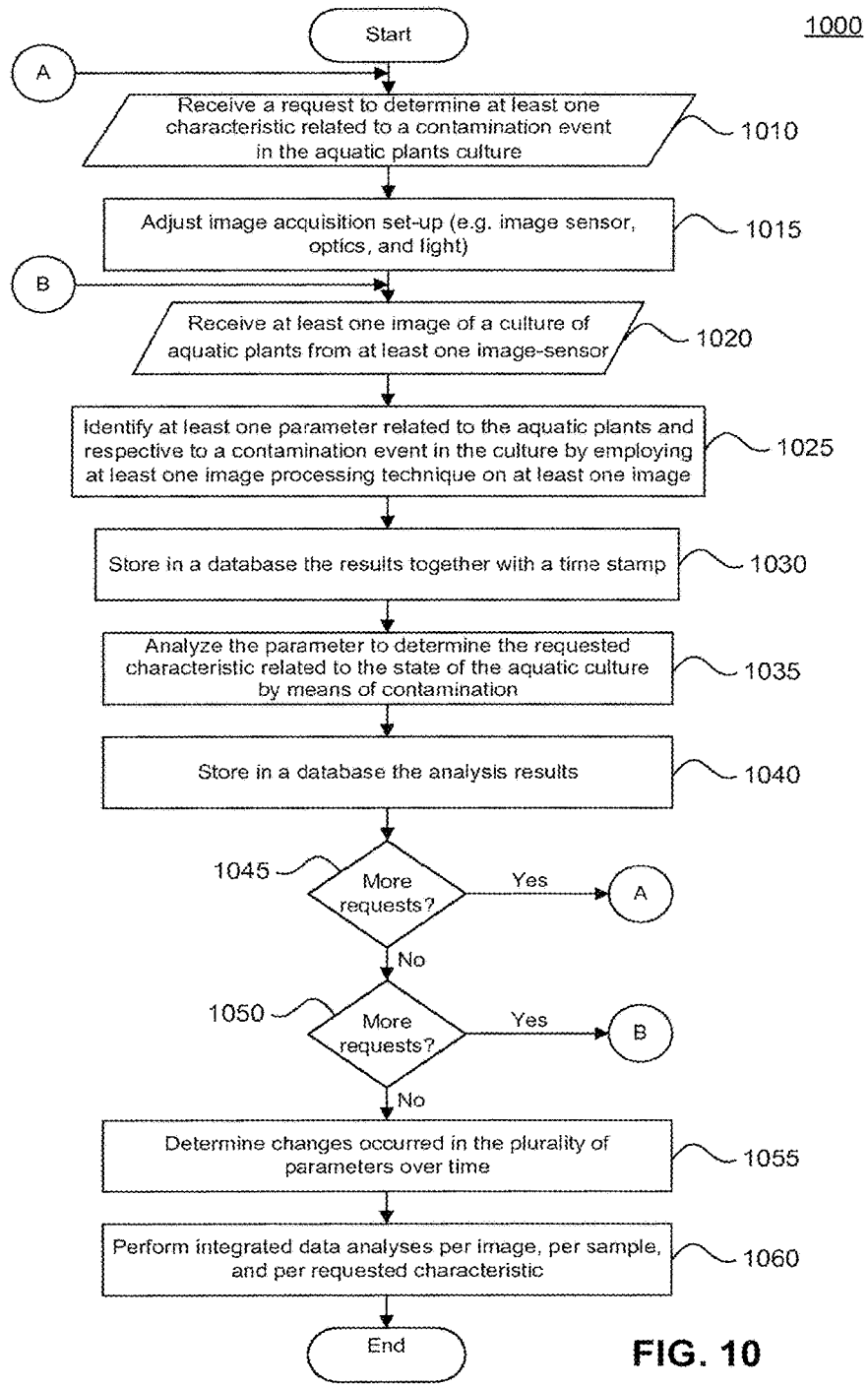
FIG. 10 is a flowchart describing the detection of contamination events in a culture of aquatic plants according to an embodiment.

Operation of detecting contamination events in a culture of aquatic plants according to one embodiment will now be described with reference to FIG. 10, which shows an exemplary and non-limiting flowchart 1000. In 1010, the method starts when server 384 receives a request to determine at least one characteristic related to a contamination event in the culture of aquatic plants. Contamination may occur because of, for example, invasion of bacteria, algae, fungi, and the like. In 1015, server 384 may adjust the imaging equipment, for example, image sensors 374, and prepare for acquiring an image. In 1020, server 384 may receive at least one image of the culture, for example, from at least one image sensor 374. In 1025, server 384 may identify at least one parameter related to the aquatic plants and related to a contamination event in the culture by employing at least one image processing technique on the at least one image. In 1030, server 384 may store the identified parameter(s) along with the results of the image processing technique within database 382 together with a time stamp.

In 1035, server 384 may analyze the parameter(s) to determine the requested characteristic related to a contamination state in the aquatic plant. For example, server 384 may be configured to identify the distribution of the colors in the aquatic plants' pigments by projecting a combination of basic colors on the culture with specific wavelengths. In response, the culture will reflect light at different wavelengths, depending on one or more elements that are found in each aquatic plant. The reflected light wavelengths may be analyzed to determine characteristics, i.e. color, associated with each element in an aquatic plant. For example, the reflected light of chlorophyll is green with an approximate wavelength of about 520-570 nm, which is in the visible spectrum.

In addition, server 384 may be configured to analyze the light rays that pass through a surface of the aquatic plants. This may be used to identify the shape and/or the size of the aquatic plants. Reflected light rays would imply the existence of an aquatic plant at a certain location, however passing of light would imply that there is no aquatic plant at that location. Furthermore, server 384 may be configured to identify aquatic plants with abnormal texture by, for example, comparing an image received from the image sensor 374 to at least one image of aquatic plants with normal texture found in database 382.

In 1040, server 384 may store the characteristic(s) in database 382. Server 384 may then determine if there are additional requests in 1045. If there is an additional request, server 384 may begin the process over again at 1010. If there is not an additional request, server 384 may check if there are any additional images that need to be processed in 1050. If there are additional images that need to be processed, server 384 may return to 1020. If there are no additional images to be processed server 384 may proceed to 1055. In 1055, server 384 may determine changes that occurred in the parameter(s) over time.

Typically, in a case of contamination, the pigment of the aquatic plants changes, for example, from a hue of yellow and green to a hue of red and brown. In addition the morphological appearance of the aquatic plants may change as a result of, for example, bacteria, algae, fungi, and the like that may be found in the culture or as a result of a chemical contamination. The morphological change may be expressed, for example, in an unsmooth texture and/or a distorted surface of one or more aquatic plants. In some embodiments, server 384 may be configured to identify the distorted surface by identifying changes in the light rays passing through the aquatic plants. In some embodiments, server 384 may store in database 382 a time stamp of when the image is received together with the identified parameters. In some embodiments, server 384 may be configured to store a determined characteristic, such as a contamination event characteristic, in database 382 along with a time stamp. In some embodiments, database 382 may serve as a log containing some or all of the information including, the image, identified parameters, and determined characteristics, along with time stamps for monitoring an aquatic plant culture over time.

Finally, in 1060, server 384 may preform integrated data analysis per image, per sample, and per requested characteristic to determine if the aquatic plant culture is contaminated. The integrated data analysis may be, but is not limited to, an image processing technique that compares a received image with reference data related to parameters and characteristics from stored images, including but not limited to, baseline images, reference images previously collected from the same culture, and/or reference images previously collected from a different culture stored in a database to determine if the aquatic plant culture is contaminated. The integrated data analysis may also include scoring the requested characteristic(s) (as described below with reference to FIGS. 24-25B, for example) and comparing the scores for each characteristic with previous scores, reference scores, and/or baseline scores.

If server 384 determines that the culture is contaminated, server 384 may first determine the level of contamination. If server 384 determines that the contamination is "low level" contamination, server 384 may perform anti-contamination measures. Anti-contamination measures include, but are not limited to, UV cycles, wash cycles, increasing the pH of the culture, altering the growth medium of the culture, and altering the light or temperature conditions. Following the performance of anti-contamination measures, server 384 may monitor the culture's response and the contamination status in real-time, for example, by employing the method described in FIG. 10. If server 384 determines that the contamination has been eliminated, server 384 may revert to standard operating conditions and continue growing the culture. If server 384 determines that the contamination cannot be eliminated, server 384 may lock output unit 360 and may send an alter report to a user and/or to a control center.

Figure 11:
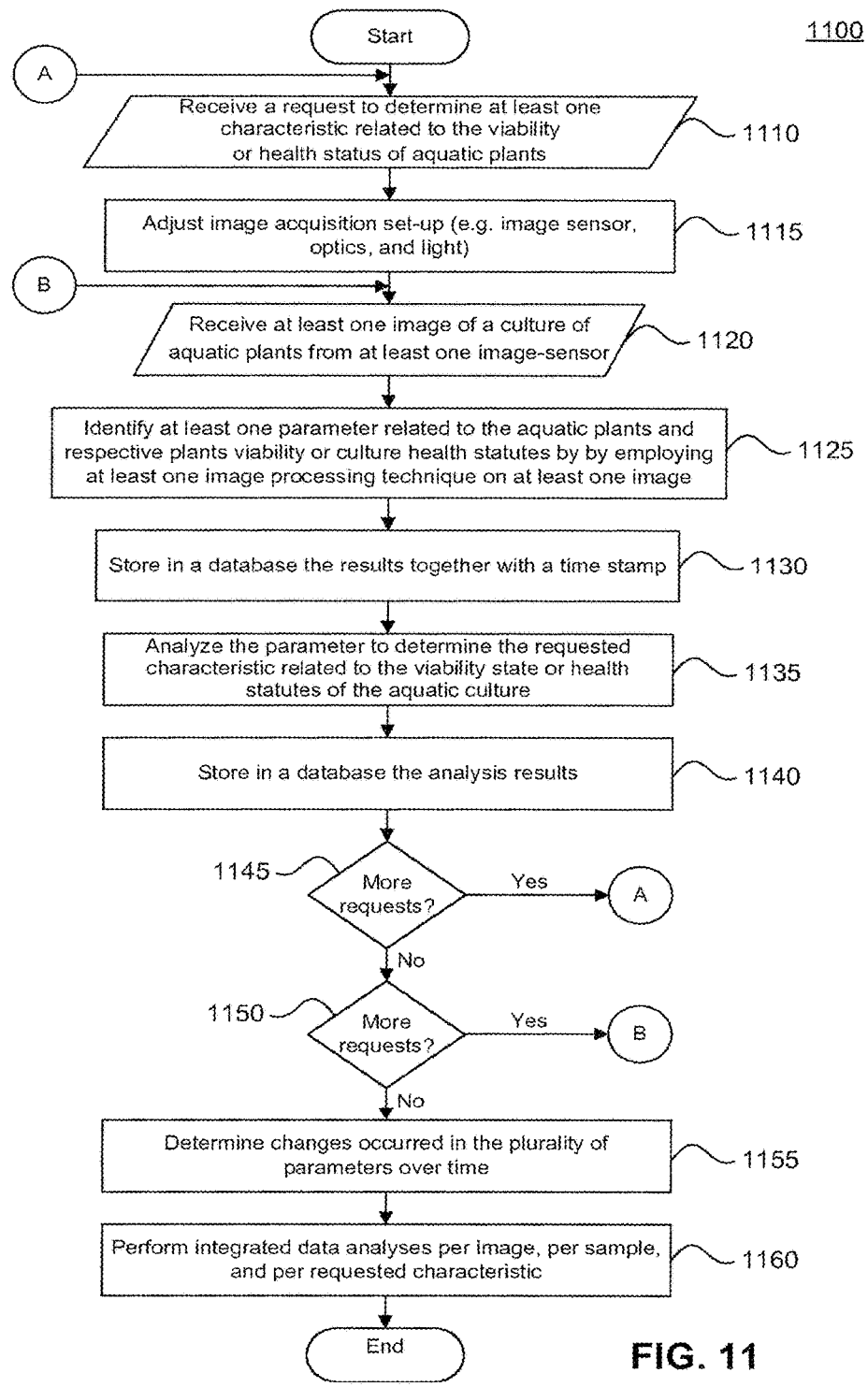
FIG. 11 is a flowchart describing the operation of determining a viability state or health statues of aquatic plants growth according to an embodiment.

Operation of determining a viability or health status of a culture of aquatic plants' growth according to one embodiment will now be described in reference to FIG. 11, which shows an exemplary and non-limiting flowchart 1100. In 1110, the method starts when server 384 receives a request to determine at least one characteristic related to the viability or health status of a culture of aquatic plants, for example, *Wolffia* growth. In 1115, server 384 may adjust the imaging equipment, for example, image sensors 374, and prepare for acquiring an image. In 1120, server 384 may receive at least one image of the culture, for example, from at least one image sensor 374. In 1125, server 384 may identify at least one parameter related to the aquatic plants and related to the plants' viability or culture health status by employing at least one image processing technique on the at least one image. In 1130, server 384 may store the identified parameter(s) along with the results of the image processing technique within database 382 together with a time stamp. In 1135, server 384 may analyze the parameter(s) to determine the requested characteristic related to the viability or health of the aquatic plant.

For example, server 384 may instruct imaging system 390 to project light at different wavelengths and/or illumination levels on the culture. In turn, imaging system 390 captures the reflected light in an image. Then server 384 may analyze the image in terms of different wavelength and illumination conditions. In some embodiments, server 384 may be configured to identify the distribution of the pigmentation in the aquatic plants' image. For example, but without limitation, server 384 may be configured to identify light rays passing through a surface of an aquatic plant, which will change according to changes in the surface of the aquatic plant. Moreover, server 384 may be configured to identify one or more morphological features, for example, the shape and/or the size of the aquatic plants. In some embodiments, server 384 may be configured to identify, for example a shape of a single circle, which represents an individual aquatic plant, two or more circles of aquatic plants connected to each other, which represents a mother-daughter pair found in vegetative reproduction, etc. Furthermore, the size of the aquatic plants may be measured by server 384 in accordance with their surface area.

Additionally, server 384 may be configured to identify the texture and/or the transparency levels of the aquatic plants. In general, the transparency level of a material describes the relative ability of the material to allow the passage of light rays through the material, or reflect rays of light off the material. In order to determine the level of transparency of an aquatic plant, server 384 may be configured to measure, for example, the light rays passing through the aquatic plant. Moreover, in order to identify the texture of an aquatic plant, server 384 may be configured to analyze the received image by comparing it to images that are stored in database 382. Aquatic plants generally have areas with a smooth or a dotted texture at a defined distribution. Therefore, in some embodiments, when server 384 identifies aquatic plants containing different textures distributions, other texture types, and/or high a level of transparency server 384 may be configured to consider them as unhealthy aquatic plants.

Moreover, in some embodiments, server 384 may be configured to identify the number of the aquatic plants found with the same pigments, shape, texture, etc.

Server 384 may be configured to determine the density of the culture of aquatic plants, for example, by evaluating a change in the intensity of light passing through the aquatic plants. Alternatively, server 384 may be configured to use at least one mathematical model to measure the mass of aquatic plants found in a given volume.

In 1140, server 384 may store the characteristic(s) in database 382. A time stamp may be stored along with the characteristic(s) in 1140. Server 384 may then determine if there are additional requests in 1145. If there is an additional request, server 384 may begin the process over again at 1110. If there is not an additional request, server 384 may check if there are any additional images that need to be processed in 1150. If there are additional images that need to be processed, server 384 may return to 1120. If there are no additional images to be processed, server 384 may proceed to 1155. In 1155, server 384 may determine changes that occurred in the parameter(s) over time.

Finally, in 1160 server 384 may perform integrated data analysis per image, per sample, and per requested characteristic to determine the viability or health of the culture based on the parameters identified in 1125 and one or more characteristics related to the aquatic plant growth cycle. For example, in some embodiments, a vegetative reproduction is characterized by aquatic plants which are connected to each other. Moreover, a death phase may be characterized by aquatic plants with a lack of a green pigment and high transparency level. Furthermore, healthy aquatic plants may be characterized by, for example, a strong green pigment. The existence of pigment that is not green or yellow may indicate the existence of contamination. And a connection between at least two aquatic plants may imply a mother-daughter relationship.

The integrated data analysis performed in 1160 may be, but is not limited to, an image processing technique that compares a received image with reference data related to parameters and characteristics from stored images, including but not limited to, baseline images, reference images previously collected from the same culture, and/or reference images previously collected from a different culture stored in a database to determine the viability or health status of a culture of aquatic plants. The integrated data analysis may also include scoring the requested characteristic(s) (as described below with reference to FIGS. 24-25B, for example) and comparing the scores for each characteristic with previous scores, reference scores, and/or baseline scores.

The operations described in FIGS. 7-11 may be integrated in whole or in part. Moreover, while the operations in FIGS. 7-11 have been described with respect to a network having a server and a database it will be appreciated that control unit 370 could contain all the necessary components to perform the operations in FIGS. 7-11 in the absence of a network. In such an embodiment, bioreactor 310 may comprise a stand-alone unit adapted to operate in the absent of a network. In addition, in some embodiments, control unit 370 may be understood to include server 384 and database 382. Additionally, it will be appreciated that any operation discussed herein as being performed by control unit 370 could, in whole or in part, be performed by server 384.

Operation of monitoring the growth of a culture overtime will now be described with reference to FIG. 12A, which is a histogram 1200 generated for a culture of aquatic plants according to one embodiment. A plurality of parameters that are identified at several points in time related to a plurality of images may be retrieved from database 382. In some embodiments, server 384 may evaluate the changes that occurred in the shape of the aquatic plants over time. Server 384 may also be configured to count the number of aquatic plants found having a certain shape at each point in time. The aquatic plants may be found, for example, as an individual aquatic plant 1210, a mother aquatic plant connected to a small circular shape of a baby daughter aquatic plant 1220, a mother aquatic plant connected to a more developed circular shape of a young daughter aquatic plant 1230, a mother aquatic plant connected to an almost fully developed circular shape of a grown daughter aquatic plant 1240, and two aquatic plants (a mother aquatic plant with a mature daughter with similar size connected to each other) 1250.

By identifying the aquatic plants' shape and quantifying the number of aquatic plants having the same shape per each shape, server 384 is capable of determining the growth phase of the culture. For example, when most of the aquatic plants are found as individual aquatic plants 1210 (as shown, for example, in FIG. 14), server 384 may determine that the culture is found in lag phase 1260. When server 384 identifies aquatic plants with a variety of shapes 1210 through 1250, at a typical ratio as demonstrated in FIG. 17C, server 384 may determine that the culture is found in exponential phase 1265. By way of a non-limiting example, server 384 may be configured to identify a majority of aquatic plants as individual aquatic plants 1210 having a high level of transparency and having more yellow pigment then green pigment. In this example, the culture may be identified as a culture that is in death phase, e.g. stage 1275 in FIG. 12B.

Server 384 may be configured to generate histogram 1200 of aquatic plant biomass accumulation over time respective of their shape. In FIG. 12A, the X axis 1280 represents a time line and the Y axis 1290 represents the natural logarithm (ln) function of the aquatic plants biomass accumulation. In some embodiments, server 384 may also evaluate the changes that occur in the pigment of the aquatic plants and their transparency level to determine the growth phases of the culture.

Figure 13:
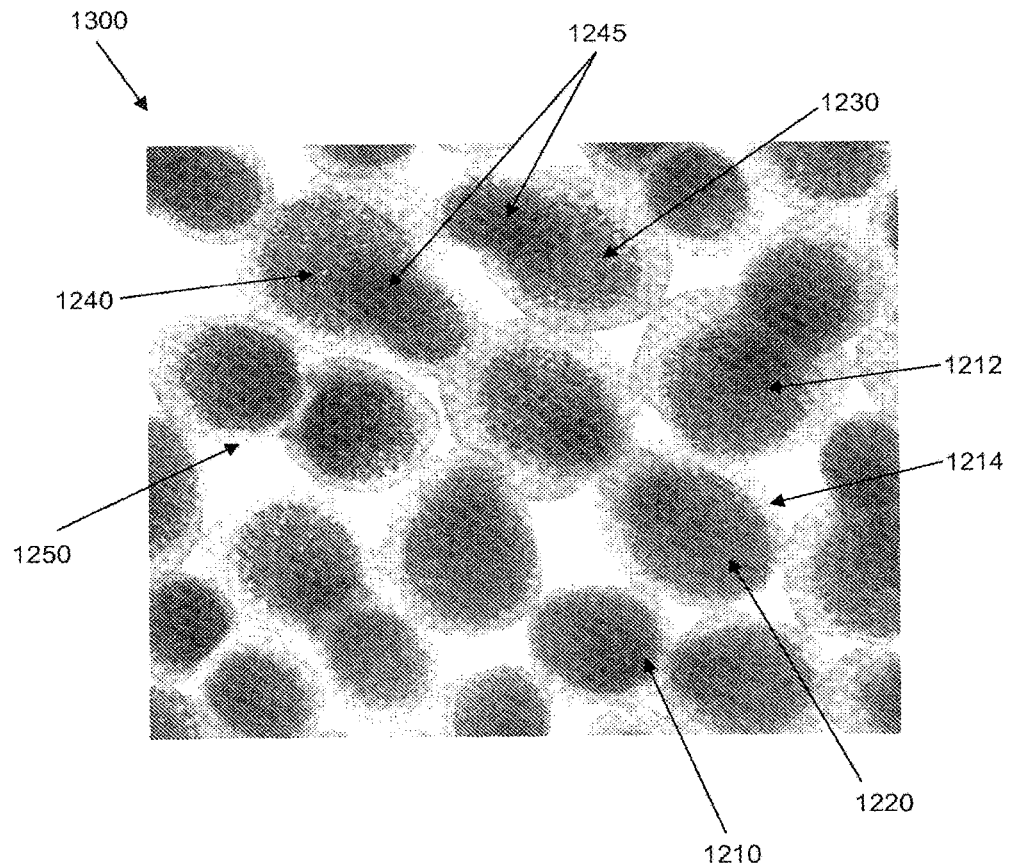
FIG. 13 is an image of aquatic plants in various stages of development.

FIG. 13 shows an exemplary image 1300 collected by imaging system 390. Image 1300 contains aquatic plants at various stages of development including an individual aquatic plant 1210, a mother aquatic plant connected to a small circular shape of a baby daughter aquatic plant 1220, a mother aquatic plant connected to a more developed circular shape of a young daughter aquatic plant 1230, a mother aquatic plant connected to an almost fully developed circular shape of a grown daughter aquatic plant 1240, and two aquatic plants (a mother aquatic plant with a mature daughter with similar size) connected to each other 1250. FIG. 13 also shows dense chlorophyll with dotted texture areas, like area 1212, which may be used by control unit 370 to classify a healthy culture of aquatic plants. Outer regions with smooth texture and bright color 1214 of the aquatic plants may be used by control unit 370 to classify the color and texture of the aquatic plants. Furthermore, connection areas 1245 between mother and daughter plants can be identified by control unit 370. Connection areas 1245 are typically the darkest green areas and can be used by control unit 370 to determine the growth phase the aquatic plant culture. For example, a high number of connection areas 1245 would indicate that the culture is currently in exponential phase 1265.

Figure 14:
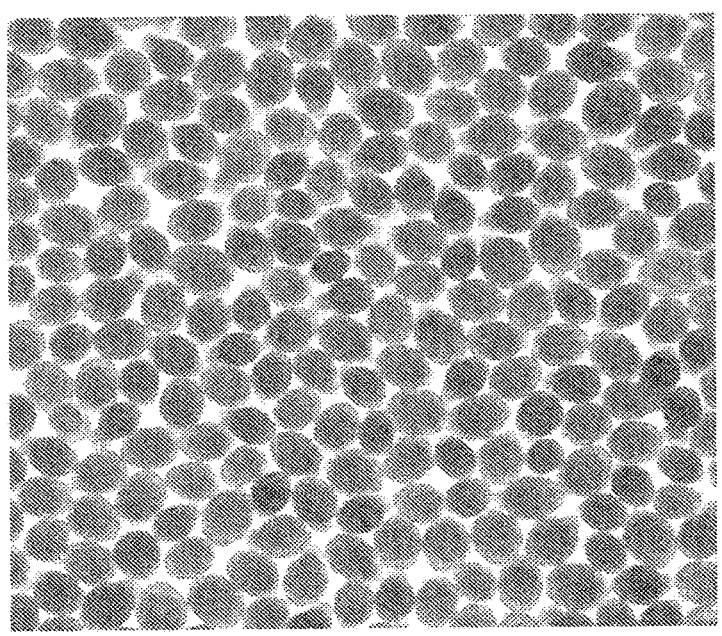
FIG. 14 is an image of a healthy culture of aquatic plants found in the lag phase according to an embodiment.

FIG. 14 shows another exemplary image 1400 collected by imaging system 390 showing a healthy culture of aquatic plants found in lag phase 1260. During operation, image 1400 of the culture may be received by server 384 from an image sensor 374. Image 1400 may be analyzed by at least one image processing technique to identify characteristics related to the aquatic plants. For example, by projecting light on the culture in an approximate wavelength of about 520-570 nm in the visible spectrum, and capturing an image using an image sensor 374, the culture is found to have significant green pigment, which stands for healthy aquatic plants. Moreover, most of the aquatic plants are found as individuals 1210 with a low level of transparency. In this case, server 384 may determine that the culture found is in lag phase 1260 based upon identification of these characteristics.

Figure 15:
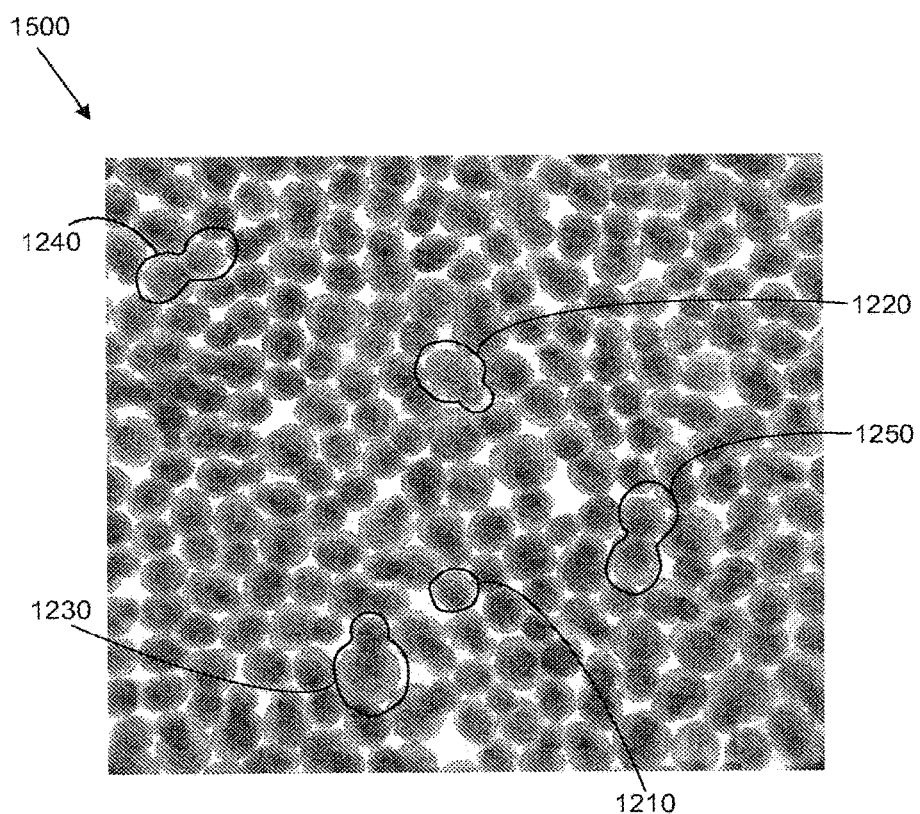
FIG. 15 is an image of a healthy culture of aquatic plants found in the exponential phase according to an embodiment.

FIG. 15 shows an exemplary image 1500 collected by imaging system 390 showing a healthy culture of aquatic plants found in exponential phase 1265. During operation, image 1500 of the culture may be received by the server 384 from an image sensor 374. The image may be analyzed by at least one image processing technique to identify characteristics related to the aquatic plants. For example, by projecting light on the culture in an approximate wavelength of about 520-570 nm in the visible spectrum, and capturing an image by an image sensor 374, the culture is found to have a significant green pigment, which stands for healthy aquatic plants. Moreover, when analyzing the culture, server 384 may be configured to identify aquatic plants with different shapes with low a level of transparency. According to image 1500, the culture contains a plurality of mother aquatic plants found as individual aquatic plants 1210, a plurality of mother aquatic plants connected to a small circular shape of a baby daughter aquatic plant 1220, a plurality of mother aquatic plants connected to a more developed circular shape of a young daughter aquatic plant 1230, a plurality of mother aquatic plants connected to an almost fully developed circular shape of a grown daughter aquatic plant 1240, a plurality of mother aquatic plants connected to a mature daughter 1250. In this case, based upon identification of these characteristics and their typical relative distribution, server 384 may be determine that the culture found is in exponential phase 1265.

Figure 16:
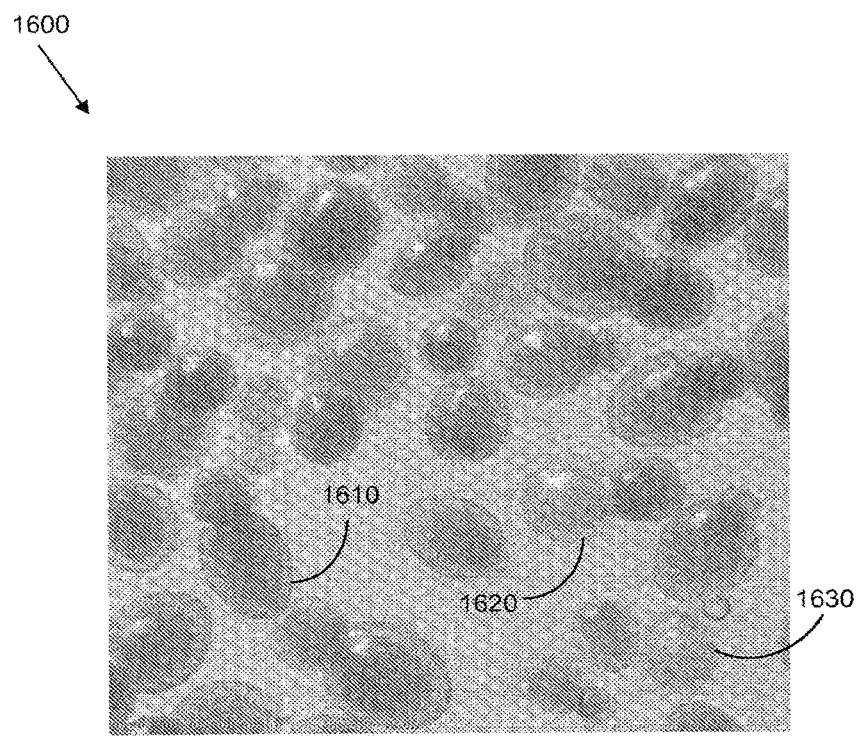
FIG. 16 is an image of a healthy culture of aquatic plants found in the stationary phase according to an embodiment.

FIG. 16 shows an exemplary image 1600 collected by imaging system 390 showing a healthy culture of aquatic plants found in stationary phase 1270. During operation, image 1600 of the culture may be received by server 384 from an image sensor 374. The image may be analyzed by at least one image processing technique to identify characteristics related to the aquatic plants. For example, by projecting light on the culture, and capturing an image using an image sensor 374, server 384 may be configured to identify the distribution of green and yellow colors of the aquatic plants' pigments. Moreover, server 384 may be configured to determine that different aquatic plans have a different level of transparency based upon analyzing the light rays passing through the aquatic plants.

According to image 1600, the culture contains healthy aquatic plants, for example, aquatic plant 1610, and unhealthy/dying aquatic plants, for example, aquatic plant 1620. Healthy aquatic plant 1610 is identified due to the distribution and intensity of the green pigmentation. The light reflected off of healthy aquatic plant 1610 will be more green than yellow due to the presence of active pigments molecules (e.g., chlorophylls). Unhealthy/dying aquatic plant colors are identified due to light yellow pigmentation that is out of the healthy scheme. In this case, unhealthy/ dying aquatic plant 1620 appears more yellow than green, indicating a lack of active pigment molecules (e.g., chlorophylls). The presence of inactive pigment molecules occurs when the aquatic plant dies. Moreover, server 384 may be configured to identify the transparency level of the aquatic plants. The transparency level of unhealthy/dying aquatic plant 1620 is high compared to the transparency level of healthy aquatic plant 1610. In this case, based upon identification of these characteristics, server 384 may determine that the culture is found in the death phase. In contrast, the detection of a relatively small number of dying individual plants and/or relatively small number of mother-daughter pairs, in which the mother (the larger plant) is detected as a dying plant 1620, may indicate a healthy culture with normal senescence rate of individual plants 1630. In this case, server 384 may determine that the culture is found in the stationary phase.

FIGS. 17A-C illustrate the transition of a culture from lag phase 1260 to exponential phase 1265 according to an exemplary embodiment of system 300 in use. FIG. 17A shows the distribution of various aquatic plant cells according to their development at the beginning of lag phase 1260. At the beginning of lag phase 1260 there are a large number of individual plants 1210 and no mature mother/daughter plants 1250. As the culture begins to grow, as shown in FIG. 17B, the distribution changes. Finally, as shown in FIG. 17C, when the culture reaches a high growth phase (exponential phase 1265) the number of mature mother/daughter plants 1250 is highest. Control unit 370 may be configured to use the change in distribution of aquatic plants in various stages of development over time to monitor and control the growing conditions for the aquatic plant culture.

For example, under continuous standard growth conditions, the culture should be in an exponential phase, generating biomass at high rate. Control unit 370 may continuously monitor the growth phase to assure exponential phase by adjusting growing conditions at real-time, e.g. light intensity, temperature, fertilizers elements in the growth medium, pH, and water cycle. In addition, a request to harvest a portion of the culture may be provided according to the culture's growth phase, preferably only in exponential phase. In addition, upon a request to slow the culture growth rate because of, for example, a decrease in an output demanded, the culture growth conditions may be altered, e.g. by a reduction in light intensity, resulting in the transition from exponential phase towards lag phase. Control unit 370 may monitor this transition to assure the desired result by adjusting the conditions in real-time until the desired results are reached. Similar control will occur following a request to increase biomass generation rate.

FIG. 18 shows an exemplary image 1800 collected by imaging system 390 showing an image 1800 of a contaminated culture of aquatic plants. During operation, image 1800 of the culture may be received by server 384 from an image sensor 374. Image 1800 may be analyzed by at least one image processing technique to identify, for example, the pigmentation, the texture, and the morphological features of the aquatic plants. In some embodiments, aquatic plants with unhealthy colors are identified in the culture, for example, aquatic plant 1810. In general, the unhealthy aquatic plant's colors are defined as colors out of the healthy scheme for a particular culture. The healthy pigmentation scheme may include a distribution of tones in the green and yellow scales of colors. In contrast, the distribution of colors for unhealthy aquatic plants may be in the red to brown scale. The culture in image 1800 contains normal aquatic plants, for example, aquatic plant 1820 having a normal shape of a mother aquatic plant connected to a small circular shape of a baby daughter aquatic plant (as described above with respect of FIG. 12A) and aquatic plans with abnormal morphological appearance, for example, aquatic plant 1810. Server 384 may therefore determine that the culture in image 1800 is contaminated upon identification of these characteristics.

Operation of growing aquatic organisms according to an embodiment will now be described with reference to FIGS. 19A-B, which show an exemplary and non-limiting flowchart 1900. In 1905 an aquatic organism starter material is inserted into the system through input unit 320, where it is prepared to enter the growing unit 330. At this stage the user may be able to select different materials (plant species) using the same system or mixing species to meet different nutritional or functional needs. In 1910, the aquatic organism matures through input unit 320. In 1915, it is checked whether the maturation of the starter culture of the aquatic organism is satisfactory based on an array of standard physiological, chemical and physical measurements that can be digitally read by control unit 370, and if so, execution continues with 1925; otherwise, execution continues with 1920. In 1920, the maturation process is modified and controlled by control unit 370 and execution continues with 1915. In 1925 the culture grows and expands continuously under the supervision of control unit 370. In 1930 it is checked whether the growing culture meets an array of defined physiological, chemical and physical criteria that are measured by control unit 370, and if so, execution continues with 1935. Otherwise execution continues with 1945. In 1935, it is checked whether to continue growing the culture and if so, execution continues with 1930; otherwise execution terminates and the culture is harvested. In 1945 it is checked whether to continue growing the culture and if so, execution continues with 1950; otherwise execution terminates. If an error occurs, control unit 370 may generate a status alert report notifying a technical support team who may continue to operate the growing operation manually. If the technical support team or a different user requests termination of the growing operation, control unit 370 may discard the culture while continuing to output other, already completely matured cultures, via harvesting and output processes. Alternatively, following a user request for termination, the user can manually discard the culture via drainage valves.

In 1950 it is checked, based on defined criteria, if a new starter is needed and if so, execution continues with 1905; otherwise, execution continues with 1955 in which the growth conditions are modified and then execution continues with 1930.

Operation of delivering an output of a consumable substance to a user according to an embodiment will now be described with reference to FIGS. 20A-B, which show an exemplary and non-limiting flowchart 2000. In 2010, an output is requested via control unit 370. In 2020, a portion of the culture is harvested. In 2030 it is checked whether a modification of the culture is required, and if so execution continues with 2040; otherwise, execution continues with 2050. In 2040 the culture is modified (e.g., in modification unit 652) as a consumable substance such as foodstuff or an efficient cosmetic substance to meet expected user preferences. In 2050 it is checked whether a customization of the culture is required and if so execution continues with 2060; otherwise, execution continues with 2070. In 2060 the culture is customized (e.g., in customization unit 654) according to user preferences that are transmitted via control unit 370 (e.g., via display 376 and/or user interface 377). In 2070 the consumable substance is delivered through the one or more output units (e.g., output units 360). In 2080 it is checked whether there is an additional output request, and if so execution continues with 2010; otherwise execution terminates.

The operation of growing the aquatic organism as described in FIGS. 19A-B and the operation of delivering an output of a consumable substance as described in FIGS. 20A-B may be integrated in whole or in part. Furthermore, in some embodiments, a self-contained production apparatus may be provided that is capable of providing a plurality of stages for automatically providing controlled growth of a starter material into product substances.

While the operations in FIGS. 19A-20B have been described with respect to a network having a server and a database it will be appreciated that control unit 370 could contain all the necessary components to perform the operations in FIGS. 19A-20B in the absence of a network. In such an embodiment, bioreactor 310 may comprise a stand-alone unit adapted to operate in the absent of a network.

Operation of controlling bioreactor 310 based on at least one image processing technique will now be described with reference to FIG. 21, which shows an exemplary and non-limiting flowchart 2100. In step 2110 control unit 370 receives at least one image from at least one image sensor 374. Control unit 370 then performs an image processing technique based on at least one parameter related to the aquatic plant to determine at least one characteristic related to the aquatic plant in 2120. The at least one parameter may be, but is not limed to, the surface area of the aquatic plants, the density of the aquatic plants, the amount of light absorbed by the aquatic plants, the wavelength of light reflected from the surface of the aquatic plants, the wavelength of light which is transmitted through the aquatic plants, and the distribution of the wavelengths in the reflected or transmitted light. And the at least one characteristic can include, but is not limited to, a shape of the aquatic plant, a size of the aquatic plant, a pigment (color) of the aquatic plant, a texture of the aquatic plant, or a transparency of the aquatic plant.

In step 2130, control unit 370 determines at least one state of the culture based on the determined characteristic(s). In 2130, the determined state may be, but is not limited to, a healthy culture, a contaminated culture, a dead culture, a dying culture, biomass density, mortality rate, growth phase of the culture, selective nutrients profile, growth rate of the culture, and viability of the culture. In step 2140 control unit 370 controls the operation of the bioreactor based on the at least one characteristic and/or state of the aquatic plant determined by the image processing technique.

In some embodiments, control unit 370 may be configured to adjust at least one growing condition. The at least one growing condition can include, but is not limited to, a light level, a light spectrum, a light interval, temperature, a fertilizer element level, water level, vapor pressure, humidity, pH, ion concentration, oxygen concentration, $CO_2$ level, culture density, air flow, growth solution flow, and culture flow. In some embodiments, control unit 370 may be configured to control at least one valve, 622, 632, 642, 656, 658, or 662 based on the at least one characteristic and/or state. In some embodiments, control unit 370 may be configured to control at least one request for a specific modification or customization process based on the at least one characteristic and/or state. In some embodiments, control unit 370 may be configured to control a request for at least one input based on the at least one characteristic and/or state. In some embodiments, control unit 370 may be configured to control at least one system-error state based on the at least one characteristic and/or state.

Operation of analyzing and modifying culture conditions within bioreactor 310 based on data collected from sensors 372 and image sensors 374 according to an embodiment will now be described with reference to FIG. 22, which illustrates an exemplary and non-limiting flowchart 2200. In step 2210 control unit 370 collects data from sensors 372 and image sensors 374. Control unit 370 may adjust the settings and collection criteria for sensors 372 and images sensors 374 based on the operation state of bioreactor 310 determined in step 2240. Data collected from sensors 372 may include, for example, a light level, temperature, fertilizer level, water level, vapor pressure, humidity, pH, ion concentration, oxygen concentration, $CO_2$ level, culture density, culture flow, and other suitable culture data. Images sensors 374, which may include, for example one or more cameras, may collect continuous and real-time images of an aquatic plant culture. In step 2220 control unit 370 performs an image processing technique to determine at least one characteristic of the aquatic plant culture. The at least one characteristic can include, for example, a shape of the aquatic plant, a size of the aquatic plant, a pigment (color) of the aquatic plant, a texture of the aquatic plant, or a transparency of the aquatic plant. For example, in some embodiments, in step 2220 control unit 370 may determine the viability of the aquatic plant culture as described above with reference to FIG. 11. Furthermore, as described above with reference to FIGS. 9 and 10, for example, control unit 370 may also determine the growth rate of the aquatic plant culture and/or if contamination is present in the culture.

In step 2230 control unit receives the set operation state of bioreactor provided in step 2240 and compares the set operation state to the characteristic(s) determined in step 2230. For example, control unit 370 may be configured to determine which stage of growth a culture is currently in (ex. re-seeding, hibernation, harvesting) and compares that to the characteristic(s) of the aquatic plant culture determined in step 2230. In step 2250, based on the operation state and the characteristic(s) determined in step 2220, control unit 370 determines if the growing conditions within bioreactor 310 need to be changed and outputs a required action or protocol for adjusting growing conditions in step 2260. For example, control unit 370 may be configured to adjust the light level, temperature, fertilizer, water level, ventilation (humidity and $CO_2$ level), culture density and culture flow within bioreactor 310. In some embodiments where they are present, control unit 370 may be configured to operate valves 622, 632, 642, 656, 658, and 662 based on the collected and analyzed data. For example, using the data from sensors 372 and 374, control unit 370 may be configured to move an aquatic plant culture to harvesting unit 340 after the culture has reached a stationary phase 1270 in growing unit 330. Furthermore, using the data from sensors 372 and 374, control unit 370 may be configured to optimize the growing conditions within bioreactor 310 thereby ensuring a high yield of aquatic plants while maintaining and guarding their food-grade quality. If control unit 370 determines that the growing conditions of a culture are already optimized control unit 370 may be configured to take no action. Additionally, based on the adjustments made to the growth conditions made in step 2260, control unit 370 may adjust the data collection settings (i.e. the image collection settings for imaging system 390) in step 2270.

The operation of an exemplary image processing technique used in steps 2220 through 2260 to determine characteristic(s) of an aquatic plant culture and adjust the growing conditions within bioreactor 310 according to one embodiment will now be described in reference to FIGS. 23A, 23B, and 24.

As illustrated in FIG. 24, control unit 370 may be configured to analyze one or more parameters related to a characteristic (e.g. shape, color, texture, transparency, size) of individual aquatic plants within an aquatic plant culture. Control unit 370 may be configured to instruct imaging system 390 to take a plurality of images of the same aquatic culture and score each image (e.g. four images as discussed in FIGS. 25A-B). Based the characteristics of the individual aquatic plants within the aquatic plant culture, each image of the aquatic plant culture is scored (i.e. score 1 through score n). As a non-limiting example, an image showing a large number of individual healthy green plants may be given a high score for color, while an image showing a large number of unhealthy individual bright yellow plants may be given a low score for color. Control unit 370 may analyze any number of individual plants within each image taken of the culture to determine the score for each characteristic. For example, control unit 370 may determine the shape score for an aquatic culture by averaging the shape scores for each image that was taken of the culture (e.g. 4 images) as discussed below in reference to FIGS. 25A-B. Based on the scores for each image of the aquatic plant culture, control unit 370 integrates, e.g. via vector mathematics, the specific score for each characteristic and determines the state of the culture (e.g. healthy (in lag, exponential or stationary phase), unhealthy, stressed, dying, dead, or contaminated).

The hexagon graph in FIG. 24 is an example of typical scores for cultures in different states. For example, a dead culture receives low scores for each characteristic, and therefore is shown having points located near the center of the hexagonal graph in FIG. 24. In contrast, a culture in exponential phase receives high scores and is shown having points located near the exterior of the hexagon graph. In some embodiments, control unit 370 may compare the scores for each culture to previously collected data and/or hexagon graphs to determine the state of the different cultures.

FIGS. 23A and 23B illustrate how control unit 370 is capable of altering the growing conditions within bioreactor 310 after preforming an image processing technique on a culture of aquatic plants within bioreactor 310. The y-axis in both figures represents the relative healthiness of an aquatic plant culture and the x-axis represents time (in days). In both FIGS. 23A and 23B, an aquatic plant culture was starved under 3 different conditions (groups 1, 2, & 3) for 6 days. Images of two culture samples for each group were taken every 24 hours, and analyzed using an image processing technique (algorithm) described herein. Selective physical parameters of individual plants and/or the culture as a whole were measured and then mathematical and statistical methods were applied to provide classification scores for the shape and pigmentation (color) characteristics. As shown in FIGS. 23A and 23B, the scores for both shape and pigmentation (color) characteristics reflected a progressive transition from a healthy status to a severely unhealthy status by day 6. After day 6, control unit 370 was allowed to reverse the starvation conditions by causing a physical change in the culture medium (i.e. adjusting growing conditions) of groups 2 & 3, but not of group 1, which was kept as a control under its starvation conditions. Images of two culture samples, of each group, were further taken every 24 hours till day 10, and analyzed using an image-processing technique (algorithm) described herein.

The analyses results revealed that cultures of both groups 2 & 3 responded positively to the changes in their growth conditions demonstrating a reverse pattern to a healthy status. In contrast, the health status of group 1 continued to decay. For comparison, images were also taken from control groups and analyzed using an image-processing technique (algorithm) described herein. FIGS. 23A and 23B both illustrate that control unit 370 is capable of detecting an unhealthy culture (e.g. a stressed or dying culture) and altering growing conditions within bioreactor 310 in order to produce healthy aquatic plants and optimize output. Furthermore, FIGS. 23A and 23B both illustrate that control unit 370 is capable of optimizing the growing conditions for relatively healthy aquatic plants. For example, if control unit 370 detects that the color of an aquatic plant culture is shifting from mostly green to more yellow, control unit 370 may adjust the growing conditions within bioreactor to ensure that the aquatic culture does not being to die.

The operation of an exemplary image processing technique used to determine the shape score a culture of aquatic plants will now be described with reference to FIGS. 25A and 25B. First, control unit 370 instructs imaging system to take four images of three different cultures (cultures 1, 2, and 3). Control unit 370 may instruct imaging system 390 to take a desired number of images for each culture. In some embodiments, imaging system 390 may take less than four images of an aquatic plant culture. In some embodiments, imaging system 390 may take more than four images of an aquatic plant culture.

After collecting images, control unit 370 may identify at least one parameter related to the shape of a number of individual aquatic plants within each image taken of each culture. In some embodiments, the number of individual aquatic plants may be, but is not limited to, at least 500 aquatic plants. Based on the at least one identified parameter related to the shape, control unit 370 may be configured to determine the number of aquatic plants in each culture having the same shape (i.e. shapes 1210 through 1250). FIG. 25B shows an exemplary bar graph showing the relative distribution of aquatic plants having the same shape in cultures 1, 2, and 3. The exemplary graph in FIG. 25B includes the individual aquatic plants from all four images taken of each aquatic plant culture.

Each bar (S1 through S5) represents the number of relative counts for a specific shape. For example, bar S1 for culture 1 represents the relative number of individual aquatic plants having a shape corresponding to an individual aquatic plant 1210 within the culture. The relative counts for each shape within a culture (S1 through Sn) and the shape variant number (Sn") for a culture can be expressed as follows:

Relative counts of a specific shape (S1 . . . Sn) per culture:
S1=[AVG of S1 (i1.1) . . . S1 (in.n')]
S2=[AVG of S2 (i1.1) . . . S2 (in.n')]
S3=[AVG of S3 (i1.1) . . . S3 (in.n')]

Shape variant number (Sn") for a culture:
Sn"=[AVG of Sn" (i1.1) . . . Sn"(in.n')]

where:
"S" means shape
"i" means image;
n is an integer representing the culture sampling number (ex. 1-2);
n' is an integer representing the number of an image taken (ex. 1-2) for each culture sampling (e.g. after sample stirring); and
n" is an integer representing the shape variant number.

The matrix below illustrates an exemplary numbering scheme for images (i1.1, i1.2, etc.) taken of an aquatic plant culture at specific time points.

$$\begin{matrix} i1.1 & i1.2 & \ldots & i1.n' \\ i2.1 & i2.2 & & i2.n' \\ \vdots & & & \vdots \\ in.1 & in.2 & \ldots & in.n' \end{matrix}$$

Based on the relative counts for each shape in each image taken of an aquatic plant culture, control unit 370 is configured to score each image. As shown in FIG. 25A, the score for each image taken (e.g. four images) may be averaged by control unit 370 to produce the final shape score for each aquatic plant culture 1 through 3. The shape score for each individual image (i1.1, i1.2, i2.1, i2.2, etc.) may be expressed using the following formula:

Image shape score=$[a_{S1}(X_{S1})+a_{S2}(X_{S2})+a_{S3}(X_{S3})+\ldots a_{Sn}(X_{Sn})]/(X_{S1}+X_{S2}+X_{S3}+\ldots X_{Sn})$ where:
XS1 ... XSn=Counts (X) of a defined shape (S1 ... Sn)
aS1 ... aS n=Shape factor (a) defined per shape (S1 ... Sn)

FIG. 25A shows the shape score for each image taken and the average shape score for three cultures where each culture was sampled twice and two images were taken per sample (four images total). In the example shown in FIG. 25A, culture 3 received the lowest shape score. The low shape score for culture 3 stems from the large amount of individual aquatic plants 1210 present within the culture (see FIG. 25B). The large number of individual plants in culture 3 may indicate that the culture is in lag phase or death phase. In contrast, culture 2 received the highest shape score. As shown in FIG. 25B, culture 2 has the highest relative amount of plants having shape 1240 (a mother aquatic plant with a per-mature daughter with smaller size connected to each other) and 1250 (a mother aquatic plant with a mature daughter with similar size connected to each other). This may indicate that culture 2 is in exponential phase. While FIG. 25A shows results from cultures sampled twice with two images per sample, a culture can be sampled any number of times and each sampling can include any number of images.

It should be noted that a low shape score does not necessarily mean that a culture is dying, dead, stressed, etc. As shown in FIG. 24, a culture in lag phase does not receive an exceptionally high shape score. As such, control unit 370 may be configured to score each characteristic of a culture before it determines the culture's state and adjusts a growth condition accordingly. Control unit 370 may be configured to score other characteristics, e.g. the color, texture, transparency, and size, of each aquatic plant culture in a similar fashion to the way it scored shape as described above. In some embodiments, control unit 370 may score each characteristic of an aquatic plant culture and compare the scores with baseline or reference scores (e.g., scores taken at a pervious time) stored in database 382. The comparison with baseline or reference scores may allow control unit 370 to determine the current state of an aquatic plant culture.

A control unit (e.g., control unit 370) and/or server (e.g., server 384) may be used to collect data (e.g. sensor data from sensors 372 or image data from sensors 374) for one or more bioreactors. This data may be monitored and/or processed (e.g., via an image processing technique discussed herein) to control the operation of one or more bioreactors. In some embodiments, the monitored and/or processed data may be used to coordinate a distribution system for one or more aquatic plant cultures. The distributions system may be used to distribute one or more aquatic plant cultures to individuals (e.g., customers) across the globe.

FIG. 26 shows a schematic of a distribution system 2600 for distributing an aquatic organism, such an aquatic plant culture, according to an embodiment. Distribution system 2600 may include one or more source bioreactors 2602 and one or more point-of-use (POU) bioreactors 2604. Source bioreactors 2602 may include one or more of the components of bioreactor systems 300, 600, and/or 650 discussed herein. In some embodiments, source bioreactors 2602 may include all the components of bioreactor system 300 and/or bioreactors systems 600 and 650. POU bioreactors 2604 may also include one or more of the components of bioreactor systems 300, 600, and/or 650. In some embodiments, POU bioreactors 2604 may include all the components of bioreactor system 300 and/or bioreactors systems 600 and 650. As illustrated in FIG. 26, both source bioreactors 2602 and POU bioreactors 2604 are in communication with a server 2606 via a network. Server 2606 may be the same as or similar to server 384 and the network may be the same as or similar to network 380. And server 2606 may be configured to perform one or more the operations of server 384.

Server 2606 may be configured to process information received by source bioreactors 2602 and POU bioreactors 2604 and use the information to monitor and coordinate the distribution of cartridges 2700 containing aquatic plant cultures from source bioreactors 2602 to POU bioreactors 2604 (discussed below in detail). Server 2606 may also use the information exchanged over the network to adjust various factors (e.g., growing and/or harvesting conditions at source bioreactors 2602) in order to optimize the growth of aquatic plant cultures in source bioreactors 2602 and/or POU bioreactors 2604. Additionally, server 2606 may use the information to optimize the distribution of cartridges 2700 (e.g., distribution times and distributions schedules). Details regarding the types of information that may be exchanged over server 2606 and the actions server 2606 may take in response to receiving and processing the exchanged information are discussed below in more detail.

FIG. 27 shows a cartridge 2700 for containing an aquatic plant culture 2710 according to an embodiment. Cartridge 2700 may be used to transport aquatic plant culture 2710 from one location to another (e.g., from a source bioreactor 2602 to a POU bioreactor 2604) and protect aquatic plant culture 2710 during transportation. Cartridge 2700 may include a plurality of capsules 2702 coupled together via a body 2704. Cartridge 2700 may have any number of capsules 2702 and capsules 2702 may be any suitable size or shape. Each capsule 2702 may contain an aquatic plant culture 2710 in a preservation medium 2712 or a fertilizer stock solution 2716. In some embodiments, more than one capsule 2702 in cartridge 2700 may contain an aquatic plant culture 2710 in a preservation medium 2712. In some embodiments, more than one capsule 2702 in cartridge 2700 may contain a fertilizer stock solution 2716 corresponding to an aquatic plant culture 2710 contained in a different capsule 2702 of cartridge 2700. An opening 2714 of each capsule 2702 may be sealed by a seal 2706. In some embodiments, a single seal 2706 may seal all the capsules 2702 of a cartridge 2700. In some embodiments, individual capsules 2702 may be sealed with individual seals 2706.

FIG. 28 shows a cross-section of cartridge 2700 along line 28-28' in FIG. 27. As shown in FIG. 28, each capsule 2702 includes a side wall 2703 defining an interior volume 2708 for holding aquatic plant culture 2710 in preservation medium 2712 or for holding fertilizer stock solution 2716. In some embodiments, side wall 2703 may comprise an impermeable material (i.e., a material that does not allow air or water to pass through it). In some embodiments, the impermeable material may be a metal, such as, but not limited to, aluminum. In some embodiments, the impermeable material may be a food grade plastic, such as, but not limited to, polyethylene, polypropylene, polyethylene terephthalate, polystyrene, or polycarbonate. In some embodiments, side wall 2703 may comprise an opaque material (e.g., aluminum or an opaque plastic). In some embodiments, side wall 2703 may comprise a non-opaque material that is coated with an opaque coating, such as, but not limited to, a paint or a laminate. In some embodiments, side wall 2703 may comprise a high strength material such that capsule 2702 will retain its shape during transportation. For example, the high strength material may resist deformation due to cartridge 2700 being dropped or heavy objects being placed on top of cartridge 2700 during transportation. Resistance to deformation may protect aquatic plant culture 2710 from being subject to high pressure caused by a reduction of interior volume 2708 and reduce the possibility of side wall 2703 being punctured during transportation.

In some embodiments, all or a portion of side wall 2703 may comprise a gas permeable material that allows the transfer of gases (e.g., oxygen and carbon dioxide) between aquatic plant culture 2710 and the environment surrounding cartridge 2700. In some embodiments, only the portion of side wall 2703 defining the capsule(s) 2702 that holds aquatic plant culture(s) 2710 may be composed, in whole or in part, of a gas permeable material. In some embodiments, the gas permeable material may be silicone. In embodiments including a gas permeable side wall material, all or a portion of side wall 2703 may be coated with a material that allows the transfer of gases, but also protects cartridge 2700 from damage (e.g., scratching, puncturing, or denting). In some embodiments, side wall 2703 may include a structural layer coated with a gas permeable material (e.g., silicone) to allow the transfer of gases between aquatic plant culture 2710 and the environment surrounding cartridge 2700. In such embodiments, the structural layer may comprise a porous material, such as but not limited to a porous material made of a food grade plastic. The structural layer may protect aquatic plant culture 2710 while the gas permeable material allows the transfer of gases.

In some embodiments, all or a portion of side wall 2703 may comprise a non-opaque and gas permeable material. In some embodiments, only the portion of side wall 2703 defining the capsule(s) 2702 that holds aquatic plant culture(s) 2710 may be composed, in whole or in part, of a gas permeable and non-opaque material. In some embodiments, the gas permeable material may be non-opaque silicone. In embodiments including a non-opaque gas permeable side wall material, all or a portion of side wall 2703 may be coated with a material that allows the transfer of gases and light, but also protects cartridge 2700 from damage (e.g., scratching, puncturing, or denting). In some embodiments, side wall 2703 may include a non-opaque structural layer coated with a non-opaque gas permeable material (e.g., silicone) to allow the transfer of gases between aquatic plant culture 2710 and the environment surrounding cartridge 2700. In such embodiments, the structural layer may comprise a porous material, such as but not limited to a porous material made of a food grade plastic. The structural material may protect aquatic plant culture 2710 while the gas permeable material allows the transfer of gases.

In some embodiments, side walls 2703 and body 2704 are single integral piece. In other words, side wall 2703 may be integrally formed with body 2704 during manufacturing. In some embodiments, side walls 2703 and body 2704 may be separate pieces that are attached using, for example, an adhesive or welding. In some embodiments, side walls 2703 and body 2704 may formed of the same material. In some embodiments, side walls 2703 and body 2704 may be formed of different materials. In some embodiments, all or a portion of the exterior surface of cartridge 2700 may be coated with an anti-microbial coating.

In some embodiments, seal 2706 may comprise an impermeable material, such as, but not limited to, an aluminum foil (with or without polymeric film layers), rubber, polyethylene, polystyrene, polyurethane, or polycarbonate. In some embodiments, seal 2706 may be composed of the same material as body 2704 and/or capsules 2702. Seal 2706 may seal with a top wall 2705 of body 2704 to prevent one or more of light, air, and liquid from entering capsule(s) 2702 though opening(s) 2714 of capsule(s) 2702. In some embodiments, seal 2706 may be sealed with top wall 2705 using, for example, an adhesive, a weld, or a heat seal.

In some embodiments, all or a portion of seal 2706 may comprise a non-opaque and/or gas permeable material that allows the transfer of gases (e.g., oxygen and carbon dioxide) between aquatic plant culture 2710 and the environment surrounding cartridge 2700. In some embodiments, seal 2706 may be made of silicone. In embodiments including a seal 2706 that is gas permeable, all or a portion of seal 2706 wall may be coated with a material that allows the transfer of gases, but also protects seal 2706 from damage (e.g., scratching, puncturing, or denting).

Aquatic plant culture 2710 contained within capsule(s) may include any species of aquatic plant, including, but not limited to, *Spirodela, Landoltia, Lemna, Wolffiella*, and *Wolffia*. Aquatic plant culture 2710 may be sealed within capsule 2702 in a predetermined life stage. The predetermined life stage may be a summer, spring, fall, or winter life stage, as discussed below with reference to FIG. 29.

Preservation medium 2712 may be a liquid or a gel. In some embodiments, the gel may be an agar based gel. In some embodiments, preservation medium 2712 may include a dissolved carbon. The dissolved carbon may be, but is not limited to, a sugar such as glucose, sucrose, fructose, and a combination thereof. In such embodiments, dissolved carbon in preservation medium 2712 provides aquatic plant culture 2710 with nutrients during distribution. When contained in capsule 2702, aquatic plant culture 2710 consumes the dissolved carbon to generate energy needed to survive in cartridge 2700 during distribution of cartridge 2700. In embodiments where side wall 2703 surrounding aquatic plant culture 2710 is made of an impermeable and/or opaque material, aquatic plant culture 2710 will need the dissolved carbon to survive because photosynthesis (the aquatic plant culture's natural energy generating process) will be prevented by the material of side wall 2703.

Aquatic plant culture 2710 will consume oxygen and generate carbon dioxide inside capsule 2702 while converting the dissolved carbon in preservation medium 2712 into energy. An aquatic plant culture housed in a capsule 2702 made of, in whole or in part, a gas permeable material may allow the aquatic plant culture to survive longer in cartridge 2700, compared to a capsule 2702 composed solely of an impermeable material. The gas permeable material will allow carbon dioxide within capsule 2702 to be replaced with oxygen from the environment surrounding cartridge 2700, thereby preventing an anaerobic condition within capsule 2702, which is harmful to the aquatic plant culture.

In some embodiments, preservation medium 2712 may not include a dissolved carbon. In such embodiments, all or a portion of side wall 2703 surrounding aquatic plant culture 2710 may be made of a non-opaque and gas preamble material. In such embodiments, the non-opaque gas permeable material will allow photosynthesis to occur by allowing aquatic plant culture 2710 to receive light and carbon dioxide from the environment surrounding cartridge 2700. The gas permeable material will also allow oxygen, created during photosynthesis, to escape cartridge 2700. Allowing photosynthesis to occur while aquatic plant culture 2710 is within cartridge 2700 may allow aquatic plant culture 2710 to slowly mature during distribution of cartridge 2700, rather than only providing aquatic plant culture 2710 with nutrients (i.e., dissolved carbon) to keep it alive. Slow maturation of aquatic plant culture 2710 during distribution may facilitate rapid recovery and growth of aquatic plant culture 2710 when it is received at a bioreactor (e.g., at a POU bioreactor 2604). In some embodiments, an aquatic plant culture 2710 may slowly mature within a capsule 2702 of cartridge 2700 for 2-3 weeks. But the time may be extended depending on temperature. Decreasing the temperature of the aquatic plant culture will decrease the maturation rate of the aquatic plant culture, thus decreasing the amount of energy needed to survive. In some embodiments, preservation medium 2712 may include a dissolved carbon and all or a portion of side wall 2703 surrounding aquatic plant culture 2710 may be made of a non-opaque and gas preamble material.

In some embodiments, cartridges 2700 may be used for long term storage of aquatic plant cultures. For example, aquatic plant cultures in winter phase may be stored at low temperatures (e.g., 2° C.-8° C.) for at least 3 months. The low temperature facilitates long term storage by decreasing the maturation and development of the aquatic plant cultures, thereby decreasing the energy required to survive. In other words, the low temperature may keep the aquatic plant culture in the dormant winter stage for an extended period of time. Capsules made of the impermeable, gas permeable, and/or non-opaque materials discussed above with regards to capsules 2702 may be used to house aquatic plant cultures for an extended period of time. And during long term storage, the aquatic plant cultures may survive by converting dissolved carbon in a preservation medium into energy and/or via photosynthesis. In some embodiments, the long term storage of aquatic plant cultures serves as a biobank of viable aquatic plant cultures capable of being introduced into a bioreactor for maturation, growth, and harvesting.

Fertilizer stock solution 2716 contained in one or more capsules 2702 may include one or more macro- or micro-elements including, but not limited to, nitrogen, phosphorous, iron, potassium, sulfur, calcium, magnesium, zinc, compounds containing at least one of these elements, and combinations thereof. Fertilizer stock solution 2716 may be packaged in capsules 2702 in any suitable form. In some embodiments, fertilizer stock solution 2716 may be a liquid or semi-solid. In some embodiments, fertilizer stock solution 2716 may be a solid such as, but not limited to, a powder or a granulated solid. In some embodiments, fertilizer stock solution 2716 may be a specific blend of fertilizer elements designed for a specific species of aquatic plant culture 2710. In some embodiments, fertilizer stock solution 2716 may be a certified organic fertilizer solution. In some embodiments, different capsules 2702 of cartridge 2700 contain different types of fertilizer stock solutions 2716 that are extracted and utilized at a POU bioreactor 2604 according to a protocol for optimizing the growing conditions for an aquatic plant culture 2710. The fertilizer stock solution protocol may be instructions related to the types and amounts of fertilizer stock solution(s) 2716 and the timing for fertilizer stock solution 2716 dosages within a POU bioreactor 2604. In some embodiments, the protocol may be included in the cartridge identification information on an identification label 2720 (see FIG. 27) associated with a cartridge 2700.

In some embodiments, a cartridge 2700 may include fertilizer stock solutions 2716 only, which may be transferred to stock fertilizer containers associated with a bioreactor system. In such embodiments, a fertilizer medium may be prepared in the system (e.g., by mixing the components of the fertilizer medium) from the stock fertilizer solution containers and transferred to a location within a bioreactor system (e.g., incubation-growing chamber 321). The control unit associated with a bioreactor system (e.g., control unit 2612 or control unit 2614) may control the preparation and transfer of the fertilizer medium.

In some embodiments, one or more capsules 2702 may contain other substances, including, but not limited to, cleaning agents and additives. A cleaning agent may be provided for cleaning a POU bioreactor 2604. In some embodiments, a cartridge 2700 may contain only cleaning agents for cleaning a POU bioreactor 2604. Instructions for the cleaning process and the utilization of the cleaning agent(s) may be provided on identification label 2720 and executed by control unit 2614. Instructions related to the additives (e.g., amount and timing of doses) may also be provided on identification label 2720 and executed by control unit 2614.

Cartridge 2700 may include one or more identification labels 2720 with cartridge identification information located thereon. Identification label(s) 2720 may be, but are not limited to, a barcode, a radio-frequency identification (RFID) chip, and a quick response (QR) code. Identification label(s) 2720 may be located anywhere on cartridge 2700. In some embodiments, identification label(s) 2720 may be located on the exterior or interior surface of a side wall 2703. In some embodiments, identification label(s) 2720 may be located on body 2704 or seal 2706. The identification label(s) 2720 may include coded cartridge identification information related to a cartridge 2700. In some embodiments, the identification label(s) 2720 may additionally or alternatively include non-coded information, such as dates or descriptive symbols. In some embodiments, identification labels 2720 may not be located on cartridge 2700, but may be provided separately (e.g., on a receipt or information pamphlet distributed along with a cartridge 2700).

Identification label(s) 2720 may include cartridge identification information (coded or non-coded) related one or more of the following aspects of a cartridge 2700: (i) the contents of one or more sealed capsules 2702 (e.g., whether a capsule 2702 contains an aquatic plant culture 2710 or a fertilizer stock solution 2716), (ii) the type (e.g., species) of aquatic plant culture 2710 contained within at least one of the sealed capsules 2702, (iii) the type of fertilizer stock solution 2716 contained within at least one of the sealed capsules 2702, (iv) the date the capsules 2702 were sealed, (v) the type of preservation medium 2712 contained within at least one of the sealed capsules 2702, (vi) the optimum growing conditions for the type of aquatic plant culture 2710 contained within at least one of the sealed capsules 2702, (vii) the location where the capsules 2702 were sealed (e.g., the source bioreactor 2602 from which the aquatic plant culture originated), (viii) a SKU (stock keeping unit) number, and (ix) a fertilizer stock solution protocol for an aquatic plant culture 2710 contained within at least one of the sealed capsules 2702.

In some embodiments, identification label(s) 2720 include coded information that includes authentication information related to the source of cartridge 2700. The authentication information may be used to indicate whether or not a cartridge 2700 is a valid cartridge sent from an approved entity. In other words, the authentication information may be used to prevent the use of counterfeit cartridges that may be harmful to a POU bioreactor 2604. A cartridge lacking the appropriate authentication information may indicate that the cartridge is a counterfeit cartridge manufactured or distributed by a non-approved entity, which may contain a diseased aquatic plant culture and/or be made with unacceptable materials (e.g., harmful plastics). A diseased aquatic plant culture may contaminate the entire POU bioreactor 2604 and require extensive cleaning and sterilization before the POU bioreactor 2604 can be put back into use. And cartridges 2700 made with unacceptable materials may result in a contaminated aquatic plant culture being introduced into the POU bioreactor 2604, which would also require extensive cleaning and sterilization before the POU bioreactor 2604 can be put back into use. If a cartridge 2700 lacks the appropriate authentication information, a control unit 2614 of a POU bioreactor 2604 may discard (or reject) that cartridge 2700.

Each item of cartridge identification information located on identification labels 2720 may be utilized by at least a control unit 2614 of a POU bioreactor 2604 and server 2606 within distribution system 2600. Control unit 2614 may be configured to control the operation of a POU bioreactor 2604 based on the cartridge identification information. Server 2606 may be configured to track and coordinate the distribution of cartridges 2700 and/or control the operation of a POU bioreactor 2604 using the cartridge identification information.

As shown in FIGS. 27 and 28, cartridge 2700 may include one or more cartridge sensors 2722. Cartridge sensors 2722 may sense a physical or chemical condition related to cartridge 2700 and/or the environment surrounding cartridge 2700. In some embodiments, one or more cartridge sensors 2722 are located within one or more capsules 2702 (e.g., on the interior surface of a side wall 2703 as shown in FIG. 28) for sensing a condition within capsules 2702. In some embodiments, one or more cartridge sensors 2722 may be located on an external surface of cartridge 2700. For example, on the exterior surface of side wall 2703 (see, e.g., FIG. 27) or on seal 2706. Cartridge sensors 2722 may be optical or electrical sensors. Cartridge sensors 2722 may be, but are not limited to, temperature sensors, pressure sensors, oxygen sensors, light sensors, and pH sensors. Cartridge sensors 2722 may indicate, either visually or electronically, a physical or chemical condition that may be harmful to an aquatic plant culture 2710 contained with cartridge 2700.

For example, a temperature sensor may indicate if a threshold maximum or minimum temperature has been reached during distribution of cartridge 2700. The threshold maximum temperature may be greater than or equal to 28° C. The threshold minimum temperature be less than or equal to 2° C. The temperature sensor may indicate that the maximum or minimum threshold temperature has been reached, for example, by changing color or by electronically storing an indication thereof. In some embodiments, temperature sensor may indicate whether or not the maximum or minimum temperature was reached and sustained for a certain amount of time. As another example, an oxygen sensor located within a capsule 2702 may indicate an increase in oxygen within capsule 2702 during distribution, thus indicating that the seal for that capsule 2702 has been compromised. The oxygen sensor may indicate a change in oxygen levels either optically or electronically. The electrical or optical signal from cartridge sensors 2722 may be read by a reader 2618 located in the input unit of a POU bioreactor 2604. If a cartridge sensor 2722 indicates a harmful condition, control unit 2614 of a POU bioreactor 2604 may discard (or reject) that cartridge 2700.

In some embodiments, cartridge sensor(s) 2722 may be configured to store changes in a condition during distribution of cartridge 2700. For example, a temperature cartridge sensor 2722 may record of log of temperatures that cartridge 2700 experienced during distribution. As such, cartridge sensor(s) 2722 may create a log of the conditions experienced during a cartridge's distribution trip.

An aquatic plant culture, such as *Spirodela, Landoltia, Lemna, Wolffiella*, and *Wolffia*, has a natural life cycle having four natural life stages. These natural life stages, which are depicted in FIG. 29, are a summer life stage, an autumn life stage, a winter life stage, and a spring life stage. In nature, an aquatic plant culture may move through these four life stages over the course of year. An aquatic plant culture behaves in specific manner during each life stage. And different species of aquatic plant cultures may behave differently from others.

In the "summer life stage" or "vegetative stage" a substantial amount of the aquatic plants in an aquatic plant culture are "frond" plants. Fronds are leafy plants that float on the top of an aqueous body, such as a pond or a lake. An aquatic plant culture may be deemed to be in summer life stage when the rate of production of new frond daughter plants is approximately equal to the rate of death of frond mother plants (e.g., when the aquatic plant culture has reached maximum density within a system). The summer life stage is an aquatic plant culture's fully developed stage. In this stage, the aquatic plant culture may grow at a relatively constant rate and contains a large amount of nutrients, e.g., protein. The frond plants float on top of the aqueous body so that they can absorb large amounts of sunlight for photosynthesis. The large volume of floating frond plants during summer life stage allows the aquatic plant culture to dominate over other organisms within an aqueous body by depriving other organisms of light and oxygen required for growth. The duration of the summer life stage will depend on the environment surrounding the aquatic plant culture (e.g., ecological conductions such as the amount of sunlight, dissolved nutrients, and the water temperature).

When ecological conditions warrant, the aquatic plant culture will transition from summer life stage to "autumn life stage." In autumn life stage, the frond plants may transition to "turions." Turions are a dormant form of the aquatic plants, which may be referred to as "winter buds," "overwinter buds," or "sinkers." The culture transitions from frond plants to turion plants when mother frond plants receive a natural signal, based on ecological conditions, to produce a turion as its next daughter plant. During autumn stage, turion daughter plants are produced and may sink while the frond mother plants will float till they die. A turion plant is different from a frond plant in various ways. For example, the protein in the frond plants is replaced with starch in the turions. The starch provides an energy storage that will enable the turions to survive, transition back to fronds, and float when the environmental conditions improve. An aquatic plant culture may be deemed to be in autumn life stage when the production rate of new frond daughter plants is less than the production rate of turion daughter plants. The duration of the autumn life stage will depend on the environment surrounding the aquatic plant culture (e.g., ecological conditions such as the amount of sunlight, dissolved nutrients, and the water temperature). Additionally, for some species and/or some geographical areas of aquatic plant cultures, the summer fronds will not transition to turions that sink, but to turions that will remain floaters in a form having very slow growth.

In "winter life stage," almost all of the plants within an aquatic plant culture may be turions and remain dormant, usually at the bottom of an aqueous body. The duration of winter life stage will depend on the environment surrounding the aquatic plant culture (e.g., ecological conductions such as the amount of sunlight and the water temperature). Some aquatic plant cultures may not transition from the turion dormant form, and will continue to produce, yet at a very low rate, new daughter frond plants during winter life stage.

When ecological conditions warrant (e.g., when days become longer (more sunlight) and the temperature rises), the dormant turion plants will begin to transition to frond plants and re-float to the surface of an aqueous body. The transition from turion plants to frond plants is called "pre-spring life stage." During "spring life stage," there is a large amount of growth as the plants transitioned to fronds begin producing new daughter frond plants at a very high rate. An aquatic plant culture may be deemed to be in spring life stage when the rate of production of new frond daughter plants is greater than the rate of death of mother frond plants. For example, the spring growth rate for an aquatic plant culture may result in the biomass of the aquatic plant culture doubling every 48 hours. This high production rate of new frond daughter plants continues until the aquatic plant culture reaches summer life stage. The duration of spring life stage will depend on the environment surrounding the aquatic plant culture (e.g., ecological conditions such as the amount of sunlight, dissolved nutrients, and the water temperature).

In nature, a culture of aquatic plants typically repeats this four stage life cycle on an annual basis. The ecological conditions (e.g., amount of sunlight, dissolved molecules, and temperature) surrounding the aquatic plant culture may dictate the transition between the different life stages. Different species of aquatic plants at different geographical locations may have different life cycle patterns and/or life stage durations. Also, the behavior an aquatic plant culture may be highly related to the geographical area and the climate conditions in which the aquatic plant culture is growing. For example, in areas where there is not a very cold winter, the turions may not sink to the bottom of the aqueous body and spring life stage may last longer.

In a bioreactor, the ecological conditions, and therefore the life stage of an aquatic plant culture, can be controlled by biomimicking the natural ecological conditions for each life stage of an aquatic plant culture. For example, a control unit (e.g., control unit 370 in FIG. 3) may control one or more ecological conditions, thus controlling the life stage of an aquatic plant culture. These ecological conditions may include, but are not limited to, physical conditions (such as light and temperature level and timing, water flow rate, air flow and pressure, and organism dynamic concentrations), and chemical conditions of the growth substrate (such as potential hydrogen, Ion concentration, fertilizer compounds, dissolved $CO_2$ and air composition). Accordingly, a bioreactor may be used to cultivate an aquatic plant culture in a specific and predetermined life stage. In some embodiments, a bioreactor may be used to cultivate an aquatic plant culture through different subsequent life stages or a full life cycle. Moreover, a bioreactor may be used to harvest an aquatic plant culture in a specific and predetermined life stage. It should be noted that the natural ecological conditions for a given species may be different from other species. In some embodiments, a control unit of a bioreactor may be configured to adjust growing conditions within the bioreactor based on the species of aquatic plant culture being grown in that bioreactor.

Returning now to distribution system 2600 for distributing an aquatic plant culture illustrated in FIG. 26. A source bioreactor 2602, and specifically a control unit 2612 of source bioreactor 2602, may be configured to grow large amounts of an aquatic plant culture for an extended period of time (e.g., a plurality of years). Source bioreactor 2602 may be configured to allow an aquatic plant culture to move through each life stage (i.e., summer, autumn, winter, and spring) by controlling the ecological conditions of the aquatic plant culture growing within source bioreactor 102. Control unit 2612 may be the same as or similar to control unit 370 discussed above. And may control unit 2612 may be configured to perform one or more the operations of control unit 370 discussed above. Control unit 2612 may be configured to send information related to the operation of a source bioreactor 2602 to server 2606. The information related to the operation of source bioreactor 2602 may be, but is not limited to, a harvesting schedule, the specie(s) of aquatic plant cultures begin grown by the source bioreactor 2602, the operating status of the source bioreactor (e.g., fully operational or out-of-service), and the volume of aquatic plants available for harvesting.

In contrast to source bioreactors 2602, a POU bioreactor 2604, and specifically control unit 2614 of POU bioreactor 2604, may be configured to grow relatively small batches of an aquatic plant culture in a specific life stage or specific set of life stages. For example, a POU bioreactor 2604 may be configured to continuously mimic the spring condition of a given aquatic plant culture so as to continuously grow that culture in spring life stage. Control unit 2614 may be the same as or similar to control unit 370 discussed above. And control unit 2614 may be configured to perform one or more the operations of control unit 370 discussed above. POU bioreactors 2604 may be designed for commercial or home use. For example, POU bioreactors 2604 may be designed for use in the kitchen of a home or in a restaurant. As another example, POU bioreactors 2604 may be designed as a kiosk or self-serving unit for use in restaurants, office buildings, or public areas (e.g., malls or shopping centers). In some embodiments, POU bioreactors 2604 may grow aquatic plant cultures through all four life stages.

In some embodiments, POU bioreactors 2604 constantly output (via, e.g., output unit 360) aquatic plants in a spring life stage when the nutrient content of the aquatic plants is high. Since the spring life stage of an aquatic plant culture may not be able to be indefinitely sustained and because aquatic plants will be harvested and consumed at POU bioreactors 2604, new batches of aquatic plant cultures (e.g., sealed in capsules 2702 of cartridges 2700) need to be supplied to POU bioreactors 2604 on a regular basis to ensure that POU bioreactors 2604 have aquatic plants with a high nutrient content ready for harvesting. In some embodiments, POU bioreactors 2604 may be supplied with new aquatic plant cultures on a bi-weekly or monthly basis.

Server 2606 in communication with source bioreactors 2602 and POU bioreactors 2604 may facilitate the constant supply of new batches of aquatic plant cultures from source bioreactors 2602 to POU bioreactors 2604. Server 2606 may use information collected from source bioreactors 2602 and POU bioreactors 2604 to monitor the operation of the bioreactors. Server 2606 may also track the distribution of cartridges 2700 containing aquatic plant cultures 2710 sealed in capsules 2702 using information located on identification labels 2720 associated with cartridges 2700. Server 2606 may use the information collected from source bioreactors 2602, POU bioreactors 2604, and the information on identification labels 2720 associated with cartridges 2700 to track the distribution of cartridges 2700 and adjust one or more operations within distribution system 2600 (e.g., shipment dates, growth conditions in a source bioreactor 2602, harvesting date/time for a source bioreactor 2602, etc.) as discussed below in detail. Server 2606 may track the distribution of cartridges 2700 and adjust one or more operations within distribution system 2600 to ensure that each POU bioreactor 2604 consistently receives new and viable batches of aquatic plant cultures in sealed in cartridges 2700 in a timely and efficient manner.

A constant and reliable supply of viable aquatic plant cultures within distribution system 2600 may be accomplished by offsetting the life cycles of the aquatic plant cultures growing in different source bioreactors 2602. Cycle setting may be performed by stimulating (or initiating) selected cycle stage plants to develop to the next cycle stage plants. For example, stimulating summer life stage or spring life stage fronds to transition to winter life stage plants, or stimulating winter life stage plants to transition to early spring life stage plants. A whole life cycle duration may be a year, shorter than a year or longer. And offsetting between source bioreactors 2602 may be dependent on the duration of the whole applied life cycle. The life cycles may be offset from each other such that, at any given time, an aquatic plant culture in specific life stage is available for harvesting. For example, if the whole life cycle duration is a year and distribution system 2600 contains four source bioreactors 2602, the life cycle of the aquatic plant cultures growing within the growing units 330 of different source bioreactors 2602 may be offset from each other by approximately 3 months.

Table 1 illustrates the respective life stages for the aquatic plant cultures in each of the four source bioreactors 2602 in such a distribution system. For simplicity, the exemplary time periods for each life stage in Table 1 are three months. But, the time periods may be shorter or longer depending on ecological conditions in each source bioreactor 2602 and/or the number of source bioreactors 2602 within a given distribution system. Additionally, each life stage does not necessary last for the same amount of time. For example, the winter stage for each source bioreactor 2602 may be shortened (e.g., via control unit 370 altering the ecological/growth conditions within each source bioreactor 2602) to approximately a 2-3 weeks while the other life stages are extended in time. This will result in more aquatic plants being in spring stage. And in embodiments where it is desirable to harvest and package aquatic plant cultures in spring stage, this will result more aquatic plants being ready for harvesting at a given time.

TABLE 1

Exemplary Life Stages For Aquatic Plant Cultures in Different Source Bioreactors. Spring life stage fronds may be harvested and packaged from bioreactor 1 during October-December; from bioreactor 2 during January-March; from bioreactor 3 during April-June; and from bioreactor 4 during July-September

|  | Summer | Autumn | Winter | Spring |
| --- | --- | --- | --- | --- |
| Source Bioreactor #1 | January-March | April-June | July-September | October-December |
| Source Bioreactor #2 | April-June | July-September | October-December | January-March |
| Source Bioreactor #3 | July-September | October-December | January-March | April-June |
| Source Bioreactor #4 | October-December | January-March | April-June | July-September |

As shown Table 1, regardless of which month of the year it is, an aquatic plant culture in each life stage is available for harvesting from one of the four source bioreactors 2602. For example, if it is desirable to harvest and package an aquatic plant culture in the spring life stage, source bioreactor #1 is available for harvesting in October through December, source bioreactor #2 is available for harvesting in January through March, source bioreactor #3 is available for harvesting in April through June, and source bioreactor #4 is available for harvesting in July through September.

The offsetting of source bioreactors 2602 and the control of the life stages within each bioreactor facilitates the planning and implementation of distributing aquatic plant cultures to various locations (e.g., various POU bioreactors 2604). In some embodiments, server 2606 may receive information related to the current life stage for the aquatic plant culture(s) in each source bioreactor 2602. Server 2606 may use this information to facilitate efficient distribution of an aquatic plant cultures sealed in cartridges 2700.

While multiple source bioreactors 2602 have been described as having offset growth stages of aquatic plant cultures, a single source bioreactor 2602 may include a plurality of growing units (e.g., growing units 330) for growing aquatic plant cultures with offset life stages. For example, a source bioreactor 2602 may include four growing units 330 with aquatic plant cultures having life stages offset as described in Table 1. In such an embodiment, control unit 2612 may control the ecological conditions in each growing unit 330 to control the life stage of the aquatic plant culture in each growing unit 330. Additionally, while four source bioreactors 2602 have been described, distribution system 2600 may include any number of source bioreactors 2602 (with any number of growing units 330) for growing aquatic plant cultures with life stages that coincide or are offset. As a non-limiting example, distribution system 2600 may include 12 source bioreactors 2602, each growing an aquatic plant culture in a life stage that is offset by one month relative to the other bioreactors (i.e., the life cycles for the 12 aquatic plant cultures are offset sequentially by one month). Server 2606 may track the life stages of aquatic plants in each source bioreactor 2602 and/or growing unit 330 and may adjust the life stages accordingly.

In some embodiments, source bioreactors 2602 within distribution system 2600 may grow aquatic plant cultures through a full life cycle with each culture having shifted cycle initiation times. In some embodiments, an aquatic plant culture's whole life cycle duration may be a year, shorter than a year, or longer. In some embodiments, the life cycle of different aquatic plant cultures within distribution system 2600 may be offset by initiating specific life cycles at different times. For example, a cycle initiation step may be performed by stimulating summer life stage or spring life stage fronds to transition to winter life stage, or by stimulating winter life stage plants to transition to spring life stage plants. Shifting initiation time between source bioreactors 2602 may be dependent on the duration of the whole applied life cycle in order to ensure that at any given time one or more source bioreactors 2602 generates aquatic plants suitable to be harvested and packaged. Cycle initiations may be performed under the control of server 2606 and/or control unit 2612.

As a non-limiting example, distribution system 2600 may include 12 source bioreactors 2602 and the initiation step in each source bioreactor 2602 may be performed in subsequent intervals separated by a month. If the duration of the whole life cycle applied is a year, and every month (i.e., January-December) early spring life stage aquatic plants need to be harvested and packaged, the initiation step may be performed by stimulating winter life stage plants to transition to early spring life stage fronds at specific times within each source bioreactor 2602 separated by a month. For example, a first source bioreactor 2602 may be initiated in January, a second source bioreactor 2602 may be initiated in February, a third source bioreactor may be initiated in March, and so on. Thus in the next January, early spring life stage frond plants can be harvested from the first source bioreactor 2602, in the next February early spring life stage frond plants can be harvested from the second source bioreactor, and so on.

When an aquatic plant culture reaches a predetermined life stage in a source bioreactor 2602, that aquatic plant culture may be harvested, divided into portions, and packaged for distribution. An output unit of source bioreactor 2602 (e.g., output unit 360) may output a quantity of aquatic plant culture to be packaged into a shipping container (e.g., into capsule 2702 of cartridge 2700). In some embodiments, the output unit of source bioreactor 2602 may include a sterilization unit (e.g., sterilization units 5600 or 5700).

Source bioreactors 2602 may be configured to harvest an aquatic plant culture in any life stage and may harvest either frond or turion plants. In some embodiments, as shown in FIG. 26, source bioreactor 2602 may include a labeling unit 2630 for placing identification label(s) 2720 and/or cartridge sensor(s) 2722 on cartridges 2700. In some embodiments, labeling unit 2630 may be a separate unit in communication with one or more source bioreactors 2602. Control unit 2612 may be configured to control labeling unit 2630 or communicate with a control unit of labeling unit 2630. Control unit 2612 may be configured to send the cartridge identification information located on identification label(s) 2720 to server 2606 after a cartridge 2700 has been labeled.

The predetermined life stage in which an aquatic plant culture is harvested and packaged may be based on at least a need for the aquatic plant culture and the distribution time required to send a cartridge 2700 containing the harvested aquatic plant culture to a certain location. In some embodiments, the determination of which life stage an aquatic plant culture should be harvested at is determined based on information collected by server 2606. In some embodiments, server 2606 may control or instruct the harvesting of an aquatic plant culture in a predetermined life stage from one or more source bioreactors 2602 and/or growing units 330.

As an exemplary embodiment, an aquatic plant culture may be harvested and packaged into capsule 2702 in spring life stage. When packaged in spring life stage, the aquatic plant culture may be packaged in a capsule 2702 designed to preserve the aquatic plant culture in spring life stage and at the same time within spring life stage that it was when packaged into capsule 2702. In other words, the spring life stage will be locked in time and the characteristics of the aquatic plant culture 2710 will not be altered while in capsule 2702. Therefore, when the aquatic plant culture is received at a POU bioreactor 2604, it will behave as if it never left the source bioreactor 2602. In some embodiments, the aquatic plant culture may be packaged in a capsule 2702 designed to facilitate slow maturation of the aquatic plant culture in the spring life stage during distribution.

When received by a POU bioreactor 2604, the aquatic plant culture will resume (or continue) its spring life stage in the growing unit (e.g., growing unit 330) of POU bioreactor 2604. As such, nutrient dense frond plants will quickly grow and become available for harvesting and/or consumption at POU bioreactors 2604. In some embodiments, an aquatic plant culture in spring life stage may be suitably preserved (or allowed to slowly mature) in preservation medium 2712 for 1-2 weeks. But it may be longer. The ability of preservation medium 2712 to preserve (or facilitate slow maturation of) an aquatic plant culture may be dependent on the type and amount of preservation medium packaged with a capsule 2702.

As other exemplary embodiment, an aquatic plant culture may be harvested and packaged into a capsule 2702 in winter life stage. In some embodiments, when packaged in winter life stage, the aquatic plant culture may be packaged in a capsule 2702 designed to preserve the aquatic plant culture in winter life stage. In some embodiments, the aquatic plant culture may be packaged in a capsule 2702 designed to facilitate slow maturation of the aquatic plant culture. Therefore, when the aquatic plant culture is received at a POU bioreactor 2604, it will resume (or continue) its winter life stage in POU bioreactor 2604 and transition into spring life stage at the appropriate time (e.g., under the control of control unit 2614). In some embodiments, an aquatic plant culture in winter life stage may be suitably preserved (or allowed to slowly mature) in preservation medium 2712 for 1-3 weeks. A packaged aquatic plant culture in winter life stage may survive longer, relative to a culture in spring life stage, because the plant culture is in a naturally dormant life stage. In winter life stage, the aquatic plant culture may consume less nutrients, and thus may be capable of surviving for an extended period of time within preservation medium, when compared to an aquatic plant culture in spring life stage. The preservation or slow maturation of an aquatic plant culture in winter stage may be longer than 1-3 weeks. The ability of preservation medium 2712 to preserve (or facilitate slow maturation of) an aquatic plant culture may be dependent on the type and amount of preservation medium packaged with a capsule 2702.

In some embodiments, an aquatic plant culture may be harvested and packaged at a specific time during a predetermined life stage. For example, an aquatic plant culture may be harvested and packaged in the first two weeks of its spring life stage. An aquatic plant culture harvested and packaged at this time will behave like it has just entered spring life stage when it is introduced into a POU bioreactor 2604. This makes the spring life stage, which rapidly produces nutrient dense fronds plants quickly available for harvesting and/or consumption at POU bioreactors 2604. As another example, an aquatic plant culture may be harvested and packaged in its winter life stage. An aquatic plant culture harvested and packaged at this time may take some time to transition into spring life stage in POU bioreactors 2604 (when compared to a culture harvested in spring life stage), but it may survive longer in preservation medium 2712. This may allow the culture to have a longer shelf life, and thus storage time, and allow it to be distributed over longer distances. While specific harvesting and packaging times have been discussed above, aquatic plant cultures growing within source bioreactors 2602 may be harvested at any time depending on one more factors. Server 2606 may control, monitor, and adjust harvesting and packaging times for aquatic plant cultures growing within source bioreactors 2602 in distribution system 2600 based on information received from source bioreactors 2602 and POU bioreactors 2604.

In some embodiments, only "seasoned" aquatic plant cultures may be harvested and packaged for distribution. A "seasoned" aquatic plant culture means a culture of aquatic plants that has already matured through an entire life cycle in a bioreactor (i.e. progressed through at least one spring life stage, at least one summer life stage, at least one autumn life stage, and at least one winter life stage). For example, if a source bioreactor 2602 begins growing an aquatic plant culture in spring life stage on Jan. 1, 2014, and it takes a year for the aquatic plant culture to progress though all four life stages, that aquatic plant culture will be "seasoned" as of Jan. 1, 2015. As such, the seasoned aquatic plant culture will first be available for harvesting on Jan. 1, 2015. As other example, if a source bioreactor 102 begins growing an aquatic plant culture in winter life stage on Apr. 1, 2014, and it takes a year for the aquatic plant culture to progress through all four life stages, that aquatic plant culture will be "seasoned" as of Apr. 1, 2015. Individual plants within an aquatic plant culture are deemed to be seasoned if the culture that produces the individual plant is deemed to be seasoned. For example, if a new individual aquatic plant develops within an aquatic plant culture that has been growing for three years (e.g., passed through three spring, summer, autumn, and winter stages), the new individual aquatic plant is considered to be "seasoned" because it was produced by a "seasoned" aquatic plant culture.

Harvesting seasoned aquatic plant cultures may help to ensure quality control. The viability and sustainably of an aquatic plant culture may be higher for a seasoned aquatic plant culture since it has shown its ability to sustain viability for at least one life cycle. Furthermore, a seasoned aquatic plant culture may be optimized (e.g., for shipping or growing in POU bioreactor 2604) by controlling the growing conditions of the aquatic plant culture within a source bioreactor 2602 throughout its first life cycle. Moreover, it is less likely that any contamination and/or unhealthy plants would be present in a seasoned aquatic plant culture. Contamination may be identified and removed from the culture during its first life cycle and unhealthy plants may be nursed to health or removed from the culture during its first life cycle (e.g., under control of control unit 2612). Moreover, harvesting seasoned aquatic plant cultures may help to synchronize the offsetting of bioreactors to ensure a constant and reliable supply of viable aquatic plant cultures to be packaged.

When a portion of an aquatic plant culture is harvested and packaged in a capsule 2702 of a cartridge 2700, one or more fertilizer stock solutions 2716 may be packaged in other capsules 2702 of cartridge 2700. The type of fertilizer stock solutions 2716 may be selected based on the species of aquatic plant culture 2710. In some embodiments, different types of fertilizer stock solutions 2716 may be packaged into different capsules 2702 of a cartridge 2700. Information related to the type and amount of fertilizer stock solution(s) 2716 packaged within one or more capsules 2702 may be included in the information located on identification label 2720 associated with a cartridge 2700. Control unit 2614 of a POU bioreactor 2604 may use this information to appropriately fertilize the aquatic plant culture once it is received by the POU bioreactor 2604.

Identification label 2720 may also include information related to the type and/or amount of preservation medium 2712 packaged with aquatic plant culture 2710 within a capsule 2702. In some embodiments, multiple capsules 2702 of a cartridge 2700 may contain separate aquatic plant cultures 2710, which may be the same or different species. Once the appropriate aquatic plant culture(s) 2710, preservation medium(s) 2712, and fertilizer stock solution(s) 2716 are packaged within a cartridge 2700, cartridge 2700 may be labeled with identification label 2720.

As depicted in FIG. 26, once the appropriate aquatic plant culture(s) 2710, preservation medium(s) 2712, and fertilizer stock solution(s) 2716 are packaged within a cartridge 2700 and cartridge 2700 is labeled with identification label 2720, cartridge 2700 may be distributed to a specific location and/or specific POU bioreactor 2604. The distribution of individual cartridges 2700 may depend on at least one of the following factors: (1) a need for an aquatic plant culture, (2) the distribution time required to send the cartridge a location, and (3) the predetermined life stage of the portion of the aquatic plant culture packaged within cartridge 2700. Server 2606 may be configured to distribute cartridges 2700 to specific locations and/or specific POU bioreactors 2604 based on at least the above factors. In some embodiments, server 2606 may be configured to automatically distribute cartridges 2700 to specific locations and/or specific POU bioreactors 2604 based on at least the above factors.

After arriving at its destination, cartridge 2700 may be placed into the input unit (e.g., input unit 320) of a POU bioreactor 2604. Once received in input unit 320, POU bioreactor 2604, and specifically control unit 2614 of POU bioreactor 2604, may perform an initialization processes for cartridge 2700 and the aquatic plant culture(s) contained therein. The initialization process may include one or more of the following steps: reading identification label(s) 2720, recording a time stamp of when cartridge 2700 is received by POU bioreactor 2604, reading cartridge sensor(s) 2722, taking an image of the aquatic plant culture(s) contained with a capsule 2702, sending the aquatic plant culture(s) to an incubation unit (e.g., incubation-growing chamber 321), taking an image of the aquatic plant culture(s) in the incubation unit, and preforming an image processing technique on the images collected to determine at least one characteristic of the aquatic plant culture(s).

Control unit 2614 may include a scanner 2616 configured to read coded information on identification label 2720. Scanner 2616 may be, but is not limited to, a barcode scanner, an RFID sensor, and a QR code scanner. Scanner 2616 may be located within the input unit of a POU bioreactor 2604 and/or may be accessible from the exterior of POU bioreactor 2604 so that a user can manually operate scanner 2616. Control unit 2614 may be configured to receive, process, and/or store all the information collected during the initialization process. Control unit 2614 may further be configured to send the information collected during the initialization process to server 2606.

FIGS. 30A and 30B show an initialization process 3000 according to an embodiment. In step 3010 a cartridge 2700 is received in an input unit (e.g., input unit 320) of a POU bioreactor 2604. When cartridge 2700 is received, control unit 2614 may record a time stamp of when the cartridge 2700 was received in step 3012. In some embodiments, the input unit of POU bioreactor 2604 may also include a sterilization chamber for sterilizing cartridge 2700 received in the input unit. The sterilization chamber may sterilize cartridge 2700 using any suitable sterilization process, including, but not limited to, UV irradiation methods, ozone ($O_3$) sterilizing/disinfecting methods, and the like.

After the time stamp is recorded in step 3012, cartridge sensor(s) 2722 associated with cartridge 2700 are read by control unit 2614 in step 3014. Control unit 2614 may include a reader 2618 configured to read cartridge sensor(s) 2722. Reader 2618 may be, but is not limited to, an optical sensor (e.g., for reading a color indicator on a cartridge sensor 2722), an RFID sensor (e.g., for reading information from a RFID chip of a cartridge sensor 2722), an electrical sensor (e.g., for contacting and reading electrical information stored on a cartridge sensor 2722), etc. In step 3016 control unit 2614 determines whether or not the information obtained from cartridge sensor(s) 2722 indicates a problem with cartridge 2700 (i.e., whether or not the information obtained from cartridge sensors passes). For example, if a temperature cartridge sensor 2722 indicates that a cartridge 2700 has been subjected to excessive heat, control unit 2614 may determine that cartridge 2700 is problematic. If one or more cartridge sensors 2722 show a problem with cartridge 2700, control unit 2614 may discard (or reject) cartridge 2700 in step 3018 and alert server 2606 of the problem with cartridge 2700 in step 3020. If cartridge 2700 is discarded or rejected in step 3018, control unit 2614 may terminate the initialization process and wait for a new cartridge 2700 to be inserted into the input unit of POU bioreactor 2604.

If control unit 2614 determines that the information obtained from cartridge sensor(s) 2722 in step 3016 passes, then control unit 2614 may be configured to read and collect cartridge identification information from identification label(s) 2720 associated with cartridge 2700 using scanner 2616 in step 3022. In embodiments, where identification label(s) 2720 are not located on cartridge 2700, control unit 2614 may signal a user (e.g., via display 376) to scan the identification label(s) 2720 using scanner 2616. Additionally, a user may input cartridge identification information using user interface 377. After reading and collecting cartridge identification information from identification label(s) 2720, control unit 2614 may be configured to store the information (e.g., in memory 378) and/or send the at least some of the cartridge identification information to server 2606 in step 3024. Control unit 2614 may also send the time stamp of when cartridge 2700 was received in the input unit to server 2606 in step 3024. Once received by server 2606, server 2606 may be configured store the information (e.g., in memory 388) and/or process the information (e.g., using processor 386).

After sending the information in step 3024, control unit 2614 may wait for server 2606 to respond with a message indicating that it is safe to proceed with the initialization process or with an alert that is it not safe to proceed. If an alert is received, control unit 2614 may discard (or reject) cartridge 2700 in step 3028 and alert server 2606 that cartridge 2700 was discarded in step 3030. If cartridge 2700 is discarded or rejected in step 3028, control unit 2614 may terminate the initialization process and wait for a new cartridge 2700 to be inserted into the input unit of POU bioreactor 2604. If a message indicating that is safe to proceed is received in step 3026, initialization process may proceed to step 3032. In some embodiments, control unit 2614 itself may make the determination of whether or not to discard cartridge 2700 in step 3026, but regardless, control unit 2614 may send the cartridge identification information and time stamp to server 2606 in step 3024 and the discard alert to server in step 3030.

Steps 3016 and 3026 will reject problematic cartridges 2700 (e.g., cartridges that may be contaminated or that may not have viable aquatic plant cultures based on information received from identification label(s) 2720 and cartridge sensor(s) 2722). These steps may serve to protect a POU bioreactor 2604 from handling potentially contaminated or non-viable aquatic plant cultures, which may result in the need for extensive cleaning and sterilization before POU bioreactor 2604 can be put back into use. In other words, steps 3016 and 3026 act as an initial screening process for cartridges 2700 and ensure that only cartridges 2700 containing safe and healthy aquatic plant cultures are opened and extracted in the input units of POU bioreactors 2604.

In step 3032, extractor 322 may access one or more capsules 2702 of cartridge 2700 and control unit 2614 may image an aquatic plant culture 2710 contained in one or more of capsules 2702. In response to receiving an image, control unit 2614 may be configured to identify at least one parameter of a plurality of parameters related to a characteristic of the aquatic plants by employing at least one image processing technique on each image received. And, in turn, control unit 2614 may determine one or more characteristics of aquatic plant culture 2710. The plurality of characteristics may include, but are not limited to, morphological features (i.e. shape, size), color features (one or more aquatic plants' pigments), a texture of the aquatic plants, a transparency level of the aquatic plants, etc. In some embodiments, control unit 2614 may identify the characteristics and use the image processing techniques discussed herein. In some embodiments, control unit 2614 may send the collected image to server 2606 and server 2606 may be configured to identify at least one parameter and determine one or more characteristics of aquatic plant culture 2710 by employing at least one image processing technique on each image received.

In step 3034, control unit 2614 (or server 2606) determines whether or not aquatic plant culture 2710 is viable (i.e., healthy and not contaminated). If aquatic plant culture 2710 is not viable, control unit 2614 may discard cartridge 2700 in step 3036 and send a discard alert to server 2606 in step 3038 telling server 2606 that cartridge 2700 has been discarded. If cartridge 2700 is discarded in step 3038, control unit 2614 may terminate the initialization process and wait for a new cartridge 2700 to be inserted into the input unit of POU bioreactor 2604.

If aquatic plant culture 2710 is deemed viable in step 3034, aquatic plant culture 2710 may be transferred to an incubation-growing chamber (e.g., incubation-growing chamber 321) of POU bioreactor 2604 in step 3040. Control unit 2614 may be configured to operate extractor 322 to transfer aquatic plant culture 2710 from capsule 2702 to incubation-growing chamber 321. Once aquatic plant culture 2710 is received in incubation-growing chamber 321, aquatic plant culture 2710 may mature under the supervision of control unit 2614. While aquatic plant culture 2710 is in incubation-growing chamber 321, control unit 2614 may be configured to fertilize aquatic plant culture 2710 with fertilizer(s) or fertilizer stock solution(s) 2716 contained in capsules 2702 of cartridge 2700. Control unit 2614 may be configured to use the cartridge identification information read from identification label(s) 2720 to determine the amount and/or type of fertilizer to use. Control unit 2614 may also be configured to operate extractor 322 to retrieve the correct type and/or amount of fertilizer(s) or fertilizer stock solution(s) 2716 from capsules 2702. In some embodiments, control unit 2614 may be configured to retrieve the correct type and/or amount of fertilizer stock solution(s) 2716 from fertilizer stock solution containers associated with POU bioreactor 2604 and may be configured to prepare a fertilizer medium using fertilizer stock solution(s) 2716.

After a predetermined amount of time (e.g., ~24 hours), control unit 2614 may image aquatic plant culture 2710 in incubation-growing chamber 321 and identify at least one parameter of a plurality of parameters related to a characteristic of the aquatic plants by employing at least one image processing technique on each image received. And, in turn, control unit 2614 may determine one or more characteristics of aquatic plant culture 2710. In some embodiments, control unit 2614 may send the collected image to server 2606 and server 2606 may be configured to identify at least one parameter and determine one or more characteristics of the aquatic plant culture 2710 by employing at least one image processing technique on each image received.

In step 3046, control unit 2614 (or server 2606) determines whether or not aquatic plant culture 2710 is viable (i.e., healthy and not contaminated). If aquatic plant culture 2710 is not viable, control unit 2614 may attempt to revive aquatic plant culture 2710 by altering the growing conditions and allowing aquatic plant culture 2710 to continue growing in incubation-growing chamber 321. If aquatic plant culture 2710 is not viable, either before or after the growing conditions are altered, control unit 2614 may discard cartridge 2700 in step 3048 and send a discard alert to server 2606 in step 3050 telling server 2606 that cartridge 2700 has been discarded. If cartridge 2700 is discarded in step 3048, control unit 2614 may terminate the initialization process and wait for a new cartridge 2700 to be inserted into the input unit of POU bioreactor 2604.

If aquatic plant culture 2710 is deemed viable in step 3046, aquatic plant culture 2710 may be transferred to a growing unit (e.g., growing unit 330) of POU bioreactor 2604 under the control of control unit 2614 in step 3052. Control unit 2614 may also be configured to send a confirmation alert to server 2606 in step 3054 telling server 2606 the aquatic plant culture 2710 has been successfully received, incubated, and passed onto growing unit 330.

Once in growing unit 330, aquatic plant culture 2710 may continue to grow and will be eventually harvested (e.g., by harvesting unit 340) under control of control unit 2614. Control unit 2614 may be configured to fertilize aquatic plant culture 2710 with fertilizer stock solution(s) 2716 contained in capsules 2702 of cartridge 2700 after aquatic plant culture 2710 is transferred to growing unit 330. And control unit 2614 may be configured to use the cartridge identification information read from identification label(s) 2720 to determine the amount and/or type of fertilizer to use. If other aquatic plant cultures are already present in growing unit 330, aquatic plant culture 2710 will serve to replenish the supply of aquatic plants within growing unit 330, and thus provide a constant supply of viable aquatic plants for harvesting at POU bioreactor 2604. In other words, aquatic plant culture 2710 begins growing alongside the already present aquatic plant culture and becomes a part of the same culture. In some embodiments, the aquatic plants in a POU bioreactor 2604 are harvested at times corresponding to the times they were introduced into the POU bioreactor 2604. In other words, POU bioreactors 2604 may be configured to always harvest the oldest aquatic plants (i.e., a first-in-first-out harvesting).

Control unit 2614 may also be configured to monitor the growth of an aquatic plant culture within growing unit 330 after the initialization process. For example, control unit 2614 may continue to send one or more images to server 2606 or determine one more characteristics and/or states of the aquatic plant culture and send that information to server 2606. In some embodiments, control unit 2614 may be configured to constantly (e.g., once a day or once a week) send information related to the growth within growing unit 330 to server 2606. In some embodiments, control unit 2614 may be configured to continuously send this information in real-time to server 2606.

After receiving information from POU bioreactors 2604, server 2606 may, in turn, be configured to use the information to adjust the distribution of cartridges 2700 in distribution system 2600. For example, if it is determined that an aquatic plant culture in a specific POU bioreactor 2604 is growing slowly, server 2606 may be configured to route additional cartridges 2700 to that POU bioreactor 2604 in order to replenish the supply of aquatic plants in that POU bioreactor 2604. As another example, if is determined that aquatic plant cultures are constantly dying within a specific POU bioreactor 2604, server 2606 may indicate that maintenance is required for that POU bioreactor 2604 and may stop sending cartridges 2700 to that POU bioreactor 2604.

Server 2606 may be configured to track the distribution of cartridges 2700 by processing the information collected from POU bioreactors 2604 (e.g., cartridge identification information, time stamps, discard alters, etc.). Server 2606 may also be configured to store and process the information collected from source bioreactors 2602 (e.g., harvest schedules, species being grown, etc.), along with the information collected from POU bioreactors 2604. Additionally, server 2606 may be configured to perform one or more actions based on the information collected from source bioreactors 2602 and/or POU bioreactors 2604. These actions may adjust one or more events within distribution system 2600.

In some embodiments, as shown in FIG. 26, distribution system 2600 may include a central processing unit 2620 having a control unit 2622. Central processing unit 2620 may include a display 2624 and a user interface 2626. Display 2624 and user interface 2626 may be the same or similar to display 376 and user interface 377. In some embodiments, central processing unit 2620 may not be a standalone unit, but rather may be a component of one of the source bioreactors 2602 in distribution system 2600. In other words, one of the source bioreactors 2602 may be a supervisory bioreactor including central processing unit 2620. Central processing unit 2620 may allow a user to communication with server 2606. For example, central processing unit 2620 may allow a user to send commands to server 2606 and review messages sent from server 2606. Additionally, central processing unit 2620 may allow a user to review all the information collected by server 2606 from source bioreactors 2602 and POU bioreactors 2604.

Server 2606 may be configured to perform one or more of the following actions based on information collected from source bioreactors 2602 and/or POU bioreactors 2604: (i) request a new cartridge shipment for a POU bioreactor 2604; (ii) adjust a shipment date for a subsequent cartridge shipment from a source bioreactor 2602; (iii) adjust the aquatic plant culture 2710 (e.g., the species of the aquatic plant culture, the life stage of the aquatic plant culture, or the amount of aquatic plant culture) in a cartridge 2700 for a subsequent cartridge shipment; (iv) customize the contents of a cartridge 2700 to be sent to a specific location or specific POU bioreactor 2604; (v) send a status report for a POU bioreactor 2604 to central processing unit 2620; (vi) adjust the growth conditions in source bioreactor 2602; (vii) adjust a preservation medium 2712 for a subsequent cartridge shipment; (viii) adjust one or more fertilizer stock solution (s) 2716 (including organic certified solutions) for a subsequent cartridge shipment; and (ix) adjust the harvesting schedule in a source bioreactor 2602; (x) adjust one or more other substances, including, but not limited to, cleaning agents and additives for a subsequent cartridge shipment. Server 2606 may perform one or more these actions automatically or server 2606 may send recommendations to a user (e.g., via central processing unit 2620) for subsequent action by the user.

In some embodiments, server 2606 may confirm with a user of a POU bioreactor 2604 that a new cartridge should be shipped (e.g., via display 376 and user interface 377). In some embodiments, users may subscribe to the automatic shipment of new cartridges for a specific amount of time (e.g., a year). An adjustment of a shipment date may be based on various factors. For example, if a POU bioreactor 2604 sends a discard alter to server 2606, server 2606 may be configured to expedite the shipment of a new cartridge to that POU bioreactor 2604. As another example, if the consumption of aquatic plants at a specific POU bioreactor 2604 increases (i.e., the POU bioreactor 2604 is dispensing larger amounts of aquatic plants), server 2606 may be configured to increase the frequency of shipping cartridges to that POU bioreactor 2604 to meet the increased demand.

In some embodiments, server 2606 may adjust the species of the aquatic plant culture, the life stage of the aquatic plant culture, or the amount of aquatic plant culture in a subsequent cartridge shipment based on information related to the characteristics of aquatic plant cultures growing in specific POU bioreactors 2604. For example, if it is determined that aquatic plant cultures in a specific POU bioreactor 2604 are growing slowly or are stressed, server 2606 may be configured to alter the predetermined life stage of the aquatic plant cultures sent to that POU bioreactor 2604. In some embodiments, adjusting the harvesting schedule in a source bioreactor 2602 changes the life stage at which aquatic plant cultures are harvested and packaged into another cartridge (e.g., from spring life stage to winter life stage). In some embodiments, adjusting the harvesting schedule in a source bioreactor 2602 changes the time within a life stage at which aquatic plant cultures are harvested and packaged into another cartridge (e.g., from two weeks into spring life stage to one week into spring life stage). Changing the life stage and/or time of harvesting and packaging may help alleviate any stress imparted on the aquatic plant cultures during distribution to specific locations.

In some embodiments, adjusting the harvesting schedule in a source bioreactor 2602 accelerates the life cycle for an aquatic plant culture in the source bioreactor 2602 such that the aquatic plant culture is ready for harvesting at an earlier date. For example, if server 2606 determines that there will be a shortage of aquatic plant cultures in spring life stage in the near future, server 2606 may be configured to accelerate the winter life stage of an aquatic plant culture in a specific source bioreactor 102 such the spring life stage occurs earlier in time.

The species of aquatic plant culture harvested and packaged may also be adjusted for various reasons. For example, a specific species may survive better in winter life stage during long distance distribution, or a user may request a different type of species for his or her POU bioreactor 2604. Also, the species of aquatic plant culture harvested and packaged may also be adjusted in order to maintain a biodiversity long-term cultivation mode in a source bioreactor 2602 or POU bioreactor 2604. The species of the aquatic plant culture, the life stage of the aquatic plant culture, the amount of aquatic plant culture, and preservation mediums and/or fertilizer types may be customized for specific POU bioreactors 2604 based on the information received from those POU bioreactors 2604.

In some embodiments, server 2606 may be configured to instruct POU bioreactors 2604 to adjust their growing conditions based on information received from the POU bioreactors 2604. But, in some embodiments, POU bioreactors 2604 may adjust their own growing conditions based on the information they collect and process (or the processed information they receive from server 2606, such as characteristic determinations). In some embodiments, server 2606 may adjust other substances required to be transported into a POU bioreactor 2604 including, but not limited to, cleaning agents and solution additives.

As discussed above, systems 300, 600, and 650 include a bioreactor having one or more growing units 330 adapted to grow one or more aquatic plants, one or more harvesting units 340 adapted to harvest one or more aquatic plants, and one or more processing units 350 adapted to modify and/or customize one or more aquatic plants harvested from the one or more harvesting units 340. Each growing unit 330 may include one or more growing apparatuses, such as growing apparatus 3200 (see, for example, FIGS. 32 and 33A). System 300 may also include an input unit 320 adapted to receive an aquatic organism used as a starter material, fertilizers, water, and/or air, and one or more output units 360 adapted to supply the aquatic plant and/or a culture conditioned medium to a user. The output may be provided as a foodstuff, a medicinal substance, a cosmetic substance, a chemical substance, or other useful products.

In some embodiments, a bioreactor system, and specifically one or more growing apparatus and related methods, are designed for growing aquatic plants in a controlled and compact environment. FIG. 31 shows a schematic of a growing apparatus according to an embodiment. Growing apparatus 3100 may include one or more modules 3120. The one or more modules 3120 may function similar to a horizontal raceway. For example, growing apparatus 3100 may include a bottom module 3120-1 and one or more stacked modules 3120 vertically placed over bottom module 3120 (i.e. modules 3120-2 through 3120-n). Growing apparatus 3100 may include a vertical raceway 3110 for circulating aquatic plants (AP) and liquid growth medium (LGM) between the one or more modules 3120. In some embodiments, vertical raceway 3110 may be formed as a continuous loop interconnecting each module 3120 within growing apparatus 3100. In some embodiments, vertical raceway 3110 may include a plurality of sub-channels 3116 connecting adjacent modules 3120. For example, as shown in FIG. 31, sub-channels 3116 may be connected to an inlet 3112 and an outlet 3114 on each module 3120, inlet 3112 configured to supply AP and/or LGM to a module 3120 and outlet 3114 configured to remove AP and/or LGM from a module 3120.

In some embodiments, AP and LGM may flow into a module 3120 via inlet 3112, circulate within the module, and flow out of the module via outlet 3114. In some embodiments, each module 3120 may include at least one baffle 3118 for directing the flow of AP and/or LGM within the module. While FIG. 31 shows a single straight baffle 3118, each module 3120 may include any number of baffles having any shape and oriented in any fashion. Baffle configurations include, but are not limited to, the baffle configurations described in reference to FIGS. 35A-35D.

Vertical raceway 3110 may facilitate the flow of AP and/or LGM into and out of each module 3120 located within growing apparatus 3100. In some embodiments, AP and/or LGM may continuously flow between modules 3120 via vertical raceway 3110, inlets 3112, and outlets 3114. In some embodiments inlets 3112 and/or outlets 3114 may include one or more valves for controlling the flow of AP and/or LGM between adjacent modules. Valves located at or near inlets 3112 and/or outlets 3114 may include static valves, mechanical valves, and/or electronically actuated valves, including, but not limited to the valve configurations discussed herein. In some embodiments, AP and/or LGM may flow between modules 3120 via gravity and AP and/or LGM may be recirculated from bottom module 3120-1 to top module 3120-n using a pump 3119.

FIG. 32 shows a growing apparatus 3200 according to an embodiment. Growing apparatus 3200 may include a bottom module 3220-1 and one or more modules 3220 placed over bottom module 3220-1 in a vertically stacked configuration. Modules 3220 may be connected to each other by a first vertical raceway 3290. Each module 3220 may be configured to hold a volume of aquatic plants placed in a liquid growth medium, the liquid growth medium being designed to provide growth conditions for the aquatic plants. The liquid growth medium may be composed of, for example, but not limited to, water, essential salts and fertilizers, nutrition enrichment compounds, growth stimulating compounds (e.g., dissolved organic carbon), and anti-microbial agents (e.g., antibiotic and fungicides). In some embodiments, control unit 370 may be configured to control, for example, light, $CO_2$ levels, PH levels, temperature, etc. within growing apparatus 3200 in order to create an ecosystem mimicking natural growth conditions for optimal growth of the aquatic plants. Furthermore, the connection between modules 3220 via first vertical raceway 3290 may enable a homogeneous flow of the liquid growth medium and/or the aquatic plants between the stacked modules 3220. After harvesting the aquatic plants, the liquid growth medium may be recycled for future use.

Control unit 370 may be connected to one or more components that comprise growing apparatus 3200 and may be configured to control the operation of growing apparatus 3200. While a single control unit is shown in FIG. 32, it is appreciated that the control unit may be modular in fashion. In other words, growing apparatus 3200 may have a sub-control unit (not shown), which is controlled by a supervisory control unit, such as control unit 370.

Growing apparatus 3200 may include a stack of modules 3220-1 through 3220-n (n being an integer having a value of 2 or greater) having a bottom module 3220-1 and one or more modules 3220-2 through 3220-n vertically placed over bottom module 3220-1. Growing apparatus 3200 may be designed and configured to mimic natural conditions for the aquatic plants to facilitate optimal growth of the aquatic plants within growing apparatus 3200. For example, growing apparatus 3200 may contain an air ($CO_2$) flow source (i.e., air supply) 3230 that may provide each module 3220 with air ($CO_2$) flow. Moreover, each module 3220 may include a light source 3322-1 through 3222-n, an inlet 3231-1 through 3231-n to receive the air ($CO_2$) flow, and an outlet 3232-1 through 3232-n to release excess air pressure. Light sources 3222 may include, but are not limited to, LED light sources. It should be understood that the entry of air ($CO_2$) into growing apparatus 3200, the release of the excess pressure, and the lighting level may be controlled by control unit 370.

Growing apparatus 3200 may also include a separation unit 3240 for periodically or continuously separating harvested aquatic plants from the liquid growth medium in which the aquatic plants were cultured. In some embodiments, separation unit 3240 may include a mechanical filter to separate the aquatic plants from the liquid growth medium. The mechanical filter may be, but is not limited to, a filter having a permeable membrane that blocks the transfer of particles at the size of aquatic plants or larger while allowing the growth medium and particles having a particle size smaller than the aquatic plants to pass. Separation unit 3240 may further or alternatively contain an additional mechanical filter and/or chemical filter for the purpose of removing any type of unwanted element other than the aquatic plants. For example, the filter(s) within separation unit 3240 may be capable of removing debris, contamination, and/or non-viable aquatic plants from the liquid growth medium. Separation unit 3240 may also include a pump for controlling the flow of liquid growth medium and aquatic plants into and out of separation unit 3240.

According to some embodiments, after the aquatic plants are separated from the liquid growth medium, the liquid growth medium may be transferred to a modification unit 3250 for recycling. Modification unit 3250 may include a system for sterilizing and/or disinfecting the liquid growth medium. Modification unit 3250 may sterilize and/or disinfect the liquid growth medium using at least one of a variety of methods, including but not limited to, UV irradiation methods, ozone ($O_3$) sterilizing/disinfecting methods, and the like. Modification unit 3250 may further or alternatively contain a chemical filter for the purpose removing any type of unwanted element. Moreover, modification unit 3250 may be configured to dissolve one or more essential elements, e.g., fertilizers into the liquid growth medium. Essential fertilizers may be, but are not limited to, nitrogen, phosphorus, iron, potassium, sulfur, calcium, magnesium, zinc, compounds containing at least one of these elements, and combinations thereof. Furthermore, modification unit 3250 may be configured to perform aeration, PH and/or temperature adjustment, and the like. Moreover, modification unit 3250 may direct the liquid growth medium to a first drain outlet channel 3299a for disposal. In some embodiments, each growing apparatus 3200 within bioreactor 310 includes a separation unit 3240 and a modification unit 3250. In some embodiments, a plurality of growing apparatuses 3200 within bioreactor 310 may share one or more separation units 3240 and/or modification units 3250. Modification unit 3250 may also include a pump for controlling the flow of liquid growth medium and aquatic plants into and out of modification unit 3250.

In some embodiments, growing apparatus 3200 may include a storage unit 3260, which may be, for example and without limitation, a canister appropriate for the storage of the liquid growth medium. A pumping unit 3270 may be used to pump the liquid growth medium from storage unit 3260 to top module 3220-n in the stack of modules 3220 via a vertical channel 3297. Pumping may be performed in a controlled manner either manually or automatically under the control of control unit 370. In some embodiments, each growing apparatus 3200 within bioreactor 310 includes a storage unit 3260 and a pumping unit 3270. In some embodiments, a plurality of growing apparatuses 3200 within bioreactor 310 may share one or more storage units 3260 and/or pumping units 3270.

As shown in FIG. 32, first vertical raceway 3290, which is an interconnected vertical channel beginning at the bottom module 3220-1, vertically connects all the modules 3220 placed over bottom module 3220-1. First vertical raceway 3290 may include a plurality of sub-channels 3291, each of which connect one module 3220 to the module directly below it. In some embodiments, as shown for example in FIG. 32, sub-channels 3291 are aligned in a vertical formation. In some embodiments, as shown for example in FIGS. 31 and 33A, sub-channels 3291 may not aligned in a vertical formation such that a first sub-channel 3291 is horizontally off-set from an adjacent second sub-channel 3291. First vertical raceway 3290 may be configured to enable flow of at least one portion of the aquatic plants and/or the liquid growth medium from a higher module 3220 in the stack of modules to the lower modules 3220 in the stack of modules. In some embodiments, one or more valves 3224 control the flow of liquid growth medium and/or aquatic plants from modules 3220 into sub-channels 3291. In some embodiments, the flow rate within sub-channels 3291 may be controlled via flow rate valves 3295 that may be operated manually or under control of control unit 370. In some embodiments, valves 3224 are static valves. In some embodiments, valves 3224 are mechanical or electronic valves controlled by control unit 370. In some embodiments, valves 3224 are manually controlled. In some embodiments, first vertical raceway 3290 may be connected to separation unit 3240 via a channel, such as channel 3294. As such, first vertical raceway 3290 may be further configured to enable flow of at least one portion of aquatic plants to separation unit 3240.

In some embodiments, first vertical raceway 3290 may be connected to a separation unit 3252 and/or modification unit 3255. Separation unit 3252 and modification unit 3255 may perform the function of separation unit 3240 and modification unit 3250, respectively, as described above. In some embodiments, as shown in FIG. 32, pumping unit 3270 is positioned between separation unit 3252 and modification unit 3255. In some embodiments, modification unit 3255 may dispose the liquid growth medium by directing it to a second drain outlet channel 3299*b*. This may be performed either manually or automatically by control unit 370. By providing vertical movement of liquid growth medium, first vertical raceway 3290 allows growing apparatus 3200 to have a compact design that provides many of the advantages discussed herein.

The vertical configuration of modules within a growing apparatus exploits the benefits of using horizontal raceway cultivation while increasing the amount of aquatic plants that can be grown per unit floor area. In some embodiments, this may dramatically increase the yield per unit floor area. For example, a stack of 100 modules (L=180 cm, W=60 cm, and H=180 cm) can produce an annual yield of 8,760 kg/m$^2$ floor area, compared to a maximum of 50 kg/m$^2$ floor area achieved by current state of the art methods. Furthermore, the compact design of the system increases light utilization efficiency. The design of embodiments discussed herein is capable of achieving over 90% LED light to plant transfer for photosynthetic utilization while also emitting only photosynthetic active wavelengths to save energy. In some embodiments, light sources 3222 only emit light with wavelengths in the range of approximately 620 nm to approximately 700 nm and approximately 400 nm to approximately 515 nm.

In some embodiments growing apparatus 3200 also includes one or more transition zones 3280-1 through 3280-*p* in connection with at least one module 3220. Transition zones 3280 may be used in the harvesting process to capture a portion of the aquatic plants, the details of which are explained below. The portion of the aquatic plants may be transferred from transition zone 3280 to separation unit 3240 through a second vertical raceway 3292. Second vertical raceway 3292 may include a plurality of sub-channels 3293, each of which connect one module 3220 to the module directly below it. In some embodiments, as shown for example in FIG. 32, sub-channels 3293 are aligned in a vertical formation. In some embodiments, sub-channels 3293 may not aligned in a vertical formation such that a first sub-channel 3293 is horizontally off-set from an adjacent second sub-channel 3293. Second vertical raceway 3292 may be a vertical channel beginning at bottom transition zone 3280-1 and vertically connecting each transition zone 3280 that is vertically placed over bottom transition zone 3280-1. Second vertical raceway 3292 may also be connected to separation unit 3240 via channel 3294.

In some embodiments, second vertical raceway 3292 is designed to enable the flow of the liquid growth medium together with a portion of aquatic plants from each transition zone (e.g., top transition zone 3280-*p*) to separation unit 3240. Each transition zone 3280 may include a valve 3282, i.e. valves 3282-1 through 3282-*p* (see FIG. 33A). In some embodiments, each valve 3282 is a static valve that allows a predetermined volume of the liquid growth medium and/or a predetermined volume of the aquatic plants to flow through it depending on the level of liquid growth medium and/or aquatic plants in an individual module 3220. In some embodiments, each transition zone 3280 includes more than one valve 3282. In some embodiments, valves 3282 are mechanical valves or electronic valves controlled by control unit 370. In some embodiments, valves 3282 may be manually controlled.

As shown in FIG. 32, growing apparatus 3200 may be connected to harvesting unit 340 via a harvesting valve 3275. Pumping unit 3245 may pump harvested aquatic plants and/or liquid growth medium to harvesting unit 340 via harvesting valve 3275. Harvesting valve 3275 may direct at least a portion of aquatic plants and/or liquid growth medium to harvesting unit 340 during a harvesting operation after being passed through separation unit 3240 and/or a biomass quantification unit 5200. Additionally, pumping unit 3245 and harvesting valve 3275 may allow at least a portion of aquatic plants and/or liquid growth medium to be returned to a module (e.g., top module 3220-*n*) after being passed through separation unit 3240 and/or biomass quantification unit 5200.

Harvesting unit 340 may be configured to collect the aquatic plants from the separation unit 3240 and store them for further use. In some embodiments, the aquatic plants stored in harvesting unit 340 may be modified, analyzed and/or used by one or more external entities. In some embodiments, harvesting unit 340 may store the aquatic plants until control unit 370 sends them to output unit 360. In some embodiments, harvesting unit 340 may store the aquatic plants until control unit 370 sends them to processing unit 350. In some embodiments, the aquatic plants bypass harvesting unit 340 and proceed directly to processing unit 350 and/or output unit 360. In some embodiments, additional liquid growth medium may be loaded into growing apparatus 3200 from a liquid growth medium source 3265. Liquid growth medium source 3265 may be designed to transfer additional liquid growth medium to maintain the level of the liquid growth medium within growing apparatus 3200 and/or each module 3220 at a predetermined level. This may be performed either manually or automatically under the control of control unit 370.

In some embodiments, growing apparatus may include biomass quantification unit 5200. Harvested aquatic plants may be transported to biomass quantification unit 5200 by pumping unit 3245. The details of biomass quantification unit are described in detail below with reference to FIGS. 52A-52C. In some embodiments, each growing apparatus 3200 within bioreactor 310 may include a biomass quantification unit 5200 and a pumping unit 3245. In some embodiments, a plurality of growing apparatuses 3200 within bioreactor 310 may share one or more biomass quantification units 5200 and/or pumping units 3245.

Each module 3220 in the stack of modules 3220 is configured to contain a volume of aquatic plants. Moreover, each module 3220 in the stack of modules 3220 is configured to contain a volume of liquid growth medium, which is designed to provide optimum growth conditions for the aquatic plants. Such growth conditions may be, but are not limited to, water, essential salts, fertilizer, carbon dioxide ($CO_2$), and so on. The essential salts may be, without limitation, nitrogen, potassium, calcium, magnesium, and iron. Moreover, each module 3220 may be configured to function as a horizontal raceway, thereby enabling the circulation of the liquid growth medium, with or without the circulation of aquatic plants, within each module 3220. The circulation of the liquid growth medium and/or aquatic plants is used for culturing aquatic plants in each module 3220.

According to one embodiment, each module 3220 in the stack of modules 3220 comprises a single valve 3224-1 through 3224-$n$. In some embodiments, each module 3220 may contain more than one valve 3224. In some embodiments, each valve 3224 is a static valve 3223 that allows a predetermined volume of the liquid growth medium and/or a predetermined volume of the aquatic plants to flow through it depending on the level of liquid growth medium and/or aquatic plants in an individual module 3220. The flow of liquid growth medium and/or aquatic plants may be controlled by control unit 370. Additionally, the level of the liquid growth medium and/or the level of the aquatic plants in each module 3220 may be determined by control unit 370 using one or more sensors 372 and/or 374. In some embodiments, control unit 370 is configured to control the flow rate of liquid growth medium flowing into top module 3220-$n$, thereby controlling: (1) the level of liquid growth medium in top module 3220-$n$, (2) the flow of liquid growth medium and/or aquatic plants between modules (in some embodiments, flow rate valves 3295 in sub-channels 3291 may also be used to control the flow of liquid medium between modules), and (3) the harvesting of aquatic plants. By controlling the level of liquid growth medium in top module 3220-$n$, control unit 370 may control the level of liquid growth medium in each module 3220 via the flow of liquid growth medium from top module 3220-$n$ to bottom module 3220-1. Moreover, by controlling the flow rate in sub-channels 3291 via flow rate valves 3295, control unit 370 may further control the flow of liquid growth medium from top module 3220-$n$ to bottom module 3220-1. The flow of liquid growth medium and/or aquatic plants between modules 3220 may be facilitated by valves 3224 and first vertical raceway 3290. The flow of liquid growth medium and the harvesting of aquatic plants may be facilitated by transition zones 3280, including valves 3282, and second vertical raceway 3292.

In some embodiments, both valves 3224 and 3282 are static valves, 3223 and 3283, respectively, having a configuration that allows a predetermined volume of liquid growth medium and/or aquatic plants to flow depending on the volume of liquid growth medium and aquatic plants located in a module 3220. In such embodiments, the predetermined volume of liquid growth medium and/or aquatic plants is fixed due the configuration of the static valves, thus facilitating consistent and repeatable transfer and/or harvesting of aquatic plants. Furthermore, in such embodiments each transfer and/or harvesting process automatically cleans the static valves because liquid growth medium that is forced through the static valves automatically washes each component of the valves. This increases the cleanliness of the system, reduces the need for users to manually clean the system, reduces possible valve failure, and reduces the chance of aquatic plants becoming trapped within the valves, which may cause contamination "hot spots."

The use of static valves may also decrease the complexity of the system and provide a simple and reliable way of controlling flow within growing apparatus 3200. Static valves reduce the number of moving parts and thus decrease chances of failure and reduce maintenance costs. Furthermore, in some embodiments, the static valves allow the flow of liquid growth medium and/or aquatic plants to be controlled from a single point. For example, by controlling the flow of liquid growth medium and/or aquatic plants in top module 3220-$n$, the volume of liquid growth medium and/or aquatic plants in each module 3220-$n$ through 3220-1 can be controlled automatically due to the flow of liquid growth medium and the configuration of static valves 3223 and 3283.

In some embodiments, control unit 370 may control the flow of liquid growth medium not just into top module 3220-$n$, but into multiple modules 3220 within a stack of modules. For example, in a growing apparatus having a large number of modules, for example 20 modules, control unit 370 may control the flow of liquid growth medium into, for example, the first module (i.e. the top module), an intermediate module (e.g. the 11$^{th}$ module), and the last module (i.e. the bottom module). Control unit 370 may be configured to control the flow of liquid growth medium into any module within a stack of modules.

In some embodiments, the configuration of static valves 3223 allows a predetermined volume of liquid growth medium to flow from an upper module to a lower module. Each static valve 3223 may be configured to allow liquid growth medium to flow from a module 3220, into first vertical raceway 3290, and to the next module 3220 due to an increase in the level of the liquid growth medium in a module 3220 (see "State B" for valve 3223 in FIG. 33B). For example, an increase in the liquid growth medium in one module 3220, e.g., top module 3220-$n$, may cause the static valve 3223 in that module to allow liquid growth medium to flow into first vertical raceway 3290, via a sub-channel 3291, to the next module 3220-($n$-1). In some embodiments, the flow of the liquid growth medium may be from top module 3220-$n$ to bottom module 3220-1, filling each of the modules in between accordingly.

In some embodiments, the configuration of static valves 3223 also allows a predetermined volume of aquatic plants to flow from an upper module 3220-$n$ to a lower module 3220-($n$-1). For example, when the volume/density of the aquatic plants increases (relative to the aquatic plants that were present before), at least a portion of the aquatic plants may be transferred to the next module 3220-($n$-1) to reduce the aquatic plant density level in the previous module 3220-$n$. When the volume or density of aquatic plants increases, control unit 370 may flood top module 3220-$n$ with liquid growth medium (see "State C" in FIG. 33B). As a result, a portion of aquatic plants is transferred through first vertical raceway 3290 from top module 3220-n to module 3220-(n−1) due to the configuration of the static valve 3223-n. Acceptable levels of the liquid growth medium and/or the volume/density of the aquatic plants may be predetermined by the control unit 370. In some embodiments, the volume/density of the aquatic plants in each module 3220 is monitored using image sensors 374 and/or sensors 372 in communication with control unit 370.

In some embodiments, when a portion of aquatic plants reaches bottom module 3220-1, that portion of aquatic plants is transferred, by a flow of the liquid growth medium, through first vertical raceway 3290 to separation unit 3240. In separation unit 3240, the aquatic plants may go through a filtering process as described in greater detail above. In some embodiments, as shown in FIG. 33A, bottom module 3220-1 does not include a sub-channel 3291 connected to channel 3294, and instead is connected to a vertical line 3296. As an alternative to pumping unit 3270, an air lift pump 3298 in communication with vertical line 3296 may be configured to pump at least a portion of liquid growth medium and/or aquatic plants back to first module 3220-n. In some embodiments, growing apparatus 3200 includes both channel 3294 and vertical line 3296 and bottom module 3220-1 is connected to both.

In some embodiments, valves 3282 in transition zones 3280 are static valves 3283. In some embodiments, the configuration of static valves 3283 in transition zones 3280 allows another predetermined volume of aquatic plants to be harvested via second vertical raceway 3292. At the same time static valves 3223 allow a portion of aquatic plants to be transferred from an upper module to a lower module, at least another portion of the aquatic plants may be harvested via static valves 3283 (see "State C*" in FIG. 33B). The at least another portion of the aquatic plants captured in each transition zone 3280 may be transferred by the flow of liquid growth medium through second vertical raceway 3292 to the separation unit 3240 via channel 3294. In separation unit 3240, the at least another portion of aquatic plants may go through a filtering process as described in greater detail above.

FIG. 33A shows a growing apparatus 3200 according to an embodiment. As shown in FIG. 33A, growing apparatus 3200 may include a number of modules 3220-n through 3220-1 in a stacked configuration. Each module 3220 may include a sub-channel 3291, that in combination, form first vertical raceway 3290. Static valves 3223 connect each module 3220 to each sub-channel 3291. Static valves 3223 may include a first baffle 3225, a second baffle 3226, and a third baffle 3227. The size (e.g., height) and location of first baffle 3225, second baffle 3226, and third baffle 3227 determine how much liquid growth medium and/or aquatic plants flow from an upper module 3220-n to a lower module 3220-(n−1). In other words, the heights and locations of first baffle 3225, second baffle 3226, and third baffle 3227 predetermine the volume of liquid growth medium and/or aquatic plants that flows from an upper module to a lower module depending on the level of liquid growth medium and/or aquatic plants in each module 3220.

Each module 3220 may also include a transition zone 3280, each transition zone 3280 including at least one static valve 3283. As shown in FIG. 33A, each static valve 3283 may connect each module 3220 to a sub-channel 3293 within second vertical raceway 3292. Each static valve 3283 may include a fourth baffle 3284 and a fifth baffle 3286. The heights and locations of fourth baffle 3284 and fifth baffle 3286 predetermine the volume of aquatic plants that is harvested from each module 3220 during a harvesting operation. The sizes and locations of each baffle shown in FIG. 33A are exemplary and may be modified to provide the desired flow of liquid growth medium and/or aquatic plants.

In some embodiments, the height and location of baffles 3225, 3226, 3227, 3284, and 3286 may be adjusted, either manually or under the control of control unit 370, to control the amount of LGM and/or AP exiting modules 3220.

The operation of static valves 3223 and 3283 according to one embodiment will now be described in reference to FIG. 33B. It should be noted that healthy (viable) aquatic plants (AP) will typically float on top of liquid growth medium (LGM). State A and State A* show the levels of (LGM) and (AP) in a module 3220 when no LGM or AP is flowing between modules 3220. In State A and A*, AP in each module may be allowed to grow and increase in volume/density. As shown in State A, third baffle 3227 in static valve 3223 prevents LGM and AP from flowing into sub-channel 3291. Additionally, fifth baffle 3286 in static valve 3283 prevents LGM and AP from flowing into second vertical raceway 3292, as shown in State A*. The height of third baffle 3227 may determine the maximum amount of LGM and AP a module 3220 can hold.

State B shows how static valves 3223 are configured to allow only LGM to flow from one module to another. In some embodiments, if control unit 370 determines that fresh LGM is required or that any module 3220 in the stack of modules requires additional LGM, control unit 370 may cause fresh or additional LGM to flow into top module 3220-n. This may occur, for example, because of a need to change the growth conditions of the liquid growth medium. In some embodiments, the additional liquid growth medium is loaded from liquid growth medium source 3265 and/or storage unit 3260. As a result, the level of LGM in top module 3220-n increases, as shown State B. When this occurs, a portion of LGM is allowed to flow over third baffle 3227 into sub-channel 3291, but no AP is allowed to flow because of second baffle 3226. Because modules 3220 are stacked vertically, flow of LGM from top module 3220-n causes LGM to flow over third baffle 3227 and into the module below top module 3220-n and so on. While static valve 3223 allows LGM to flow into sub-channel 3291, fifth baffle 3286 in static valve 3283 still prevents LGM and AP from flowing into second vertical raceway 3292 as shown in State B*. This allows additional LGM to be added to modules 3220 without transferring or harvesting any AP. A small flow of LGM over third baffle 3227 (see "State B") may be considered the steady state operation of growing apparatus 3200.

In some embodiments, control unit 370 continuously causes a small amount of LGM to flow into top module 3220-n. As such, LGM is constantly and automatically replenished in every module in the stack of modules. LGM may flow continuously from one module to another through first vertical raceway 3290 then back to the top module via vertical line 3296 in a closed loop. Similarly, LGM may flow continuously from one module to another via second vertical raceway 3292 then back to the top module via channel 3294, pumping unit 3245, and harvesting valve 3275.

If control unit 370 determines that a portion of AP needs to be transferred and/or harvested, control unit 370 may cause a larger amount of LGM to flow into top module 3220-n. As a result, the level of LGM in top module 3220-n rises to the level shown in State C and State C*. When this occurs, a portion of AP is simultaneously transferred into sub-channel 3291 and vertical raceway 3292 via valve 3223-n and valve 3283-n, respectively. As shown in State C, the level of LGM rises to a level above second baffle 3226.

This causes only the portion of AP located between second baffle 3226 and first baffle 3225 to flow over second baffle 3226, into sub-channel 3291, and into the module 3220-($n-1$) located below top module 3220-$n$. First baffle 3225 prevents any other portion of AP from flowing over second baffle 3226 and into sub-channel 3291. At the same time, another portion of AP is transferred into second vertical raceway 3292, as shown in State C*. When the level of LGM rises above fifth baffle 3286 only the portion of AP located between fifth baffle 3286 and fourth baffle 3284 flows over fifth baffle 3286, into second vertical raceway 3292, and towards separation unit 3240. Fourth baffle 3284 prevents any other portion of AP from flowing over fifth baffle 3286 and into second vertical raceway.

Increasing the amount of LGM flowing into a module, for example top module 3220$n$, such that the module enters state C and C*, results in a larger amount of LGM flowing into the subsequent lower module (3220$n-1$) via sub-channels 3291 and 3293. This causes the total volume of LGM and AP in module 3220$n-1$ to increase such that it enters state C and C*, which results in an increase of the LGM level in the module below (3220$n-2$) and so on in a sequential cascade to each of the modules 3220 within a stack of modules.

In some embodiments, the maximum heights of second baffle 3226 and fifth baffle 3286 are the same, as shown in FIGS. 33A and 33B. In some embodiments, the maximum heights of second baffle 3226 and fifth baffle 3286 are different. The height and location of the baffles allows AP to be transferred between modules and/or harvested separately into first and second vertical raceways 3290 and 3292 depending on the level of LGM and/or AP in each module 3220. After AP is transfer and/or harvested, control unit 370 may reduce the flow of LGM into top module 3220-$n$ and the system may return to State A/State A* or State B/State B*.

FIG. 34 shows a cross-section of a module 3220 according to one embodiment along the lines A-A' in FIGS. 33A, 35A, 35B, 35C, and 35D. As shown in FIG. 34, module 3220 may include a bottom wall 3234, side walls 3236, and a top wall 3238 defining a channel 3235 that holds a volume of liquid growth medium (LGM), a volume of aquatic plants (AP) and a volume of air. In some embodiments, one or more of the side walls 3236 may be a baffle 3218. In some embodiments, module 3220 may be configured to hold, for example, about 0.5 to about 2 cm of LGM, about 2 mm to about 3 mm of AP, and about 7 mm of air. In some embodiments, air is constantly flowing over the AP and the LGM. The flow of air may be controlled by control unit 370. A light source 3222 may be positioned above module 3220, as shown in FIG. 34, or integrated within top wall 3238. The wavelength and/or intensity of light emitted from light source 3222 may be controlled by control unit 370. In some embodiments, each light source may be independently controlled by control unit 370 so as to adjust light intensity/wavelength in an individual module.

FIGS. 35A, 35B, 35C, and 35D show various exemplary configurations for modules 3220. FIG. 35A shows an exemplary module 3220 including a channel 3235 having a continuous elliptical shape. Module 3220, shown in FIG. 35A, may include a single straight baffle 3218 for creating continuous channel 3235. FIG. 35B shows an exemplary module 3220 including a channel 3235 having a U-shape. Module 3220, shown in FIG. 35B, may include a single straight baffle 3218 for creating U-shaped channel 3235. FIG. 35C shows an exemplary module 3220 including a channel 3235 having a continuous circular shape. Module 3220, shown in FIG. 35C, may include a circular baffle 3218 for creating a continuous circular channel 3235. FIG. 35D shows an exemplary module 3220 including a unique channel configuration. Module 3220 shown in FIG. 35D may include two angled baffles 3218 for creating a desirable flow pattern within module 3220. The flow pattern and the details of the module 3220 shown in FIG. 35D according to some embodiments are described below in reference to FIGS. 38, 47A, 47B, 48A, and 48B.

While FIGS. 33A and 35A-35D show various exemplary shapes for modules 3220, modules 3220 may include any shape and may have any number of baffles for creating a desired flow pattern(s) within a module 3220. Additionally, baffles 3218 may have any shape, size, or orientation for creating a desired flow pattern(s) within a module 3220. In some embodiments, a module may not have a baffle. Moreover, while FIGS. 33A and 35A-35D show modules 3220 having an inlet 3212 and an outlet 3214 located on the same end of module 3220, inlet 3212 and outlet 3214 may be located anywhere along channel 3235 so as to facilitate a desired flow characteristic for module 3220.

FIG. 36 is an exemplary and non-limiting flowchart 3600 describing the operation of growing aquatic plants in growing apparatus 3200 having a stack of modules 3220 according to an embodiment. The operation starts in 3610 when control unit 370 causes a flow of a liquid growth medium into the top module 3220-$n$. When this occurs, liquid growth medium flows from top module 3220-$n$ to bottom module 3220-1 of the stack via first vertical raceway 3290, filling each of the modules 3220 in between. The closed loop flow of the liquid growth medium through first vertical raceway 3290 may create a homogeneous growth platform in the stack of modules 3220. The level of liquid growth medium may be detected by sensors 372 (e.g., level sensors) in communication with control unit 370. Starter material, which has been matured in incubation-growing chamber 321, may also be introduced into each module 3220 of growing apparatus 3200 in 3610.

The liquid growth medium is designed to provide optimal growth conditions for the aquatic plants (e.g., water, essential salts, fertilizers, etc.). According to one embodiment, the liquid growth medium may be pumped by pumping unit 3270 from storage unit 3260 to the top module 3220-$n$ in the stack in a controlled manner, either manually or automatically under the control of the control unit 370.

In 3615, it is checked whether the volume of the liquid growth medium has reaches a predefined level, and if so the execution continues with 3620.

In 3620, according to one embodiment, when the volume of the liquid growth medium reaches to a predefined level of, for example, approximately 1 centimeter in at least one module 3220, for example the top module 3220-$n$, starter aquatic plants, which have been matured in incubation-growing chamber 321, may be transferred to the top module 3220-$n$ via pumping unit 3270 and vertical line 3296, and/or via channel 3294, through pumping unit 3245, and harvesting valve 3275. In 3620, aquatic plants flow into each module 3220. Due to the follow of aquatic plants into top module 3220-$n$, at least one portion of the aquatic plants is transferred from top module 3220-$n$, through vertical raceways 3290 and/or 3292, and to the modules 3220 under the top module 3220-$n$. In other words, aquatic plants are transferred in a controlled cascading manner, either manually or automatically under the control of the control unit 370. This may occur due to the configuration of static valves 3223 (see State C in FIG. 33B) or may occur due to control unit 370 electronically operating dynamic or electronic valves, such as valves 3830 or 4230 described herein. In some embodiments, this may occur due to a user manually operating a valve. During 3620, the culture (aquatic plants) is allowed to grow in each module 3220 under the supervision of control unit 370. In some embodiments, starter aquatic plants may be introduced into each module 3220 of growing apparatus 3200 in 3620 either manually or automatically under the control of the control unit 370.

In 3620, the amount/density of aquatic plants in different modules 3220 may be adjusted manually and/or under the supervision of control unit 370. The flow of aquatic plants may continue until the volume and liquid growth medium reaches a predefined volume and/or the aquatic plants reach a predefined volume/density. In 3625, it is checked whether the volume/density of the aquatic plants in modules 3220 has reached a predefined level, and if so execution continues with 3630.

Once it is determined that the aquatic plants have reached a predefined volume/density, growing apparatus 3200 may shift into steady state in 3630. Steady state within growing apparatus 3200 may be defined as a continuous flow of a relatively small amount of liquid growth medium between modules 3220. This may occur due to the configuration of static valves 3223 (see State B in FIG. 33B), the configuration of dynamic valves 3830 or 4230 described below in reference to FIGS. 38-43, or due to control unit 370 electronically operating other types of mechanical or electronic valves. Steady state may allow aquatic plants to mature and grow under the supervision of control unit 370. During steady state operation AP within one or more modules may be continuously or periodically washed due to the flow of LGM between modules. The washing of AP is described below in more detail in reference to FIGS. 44 and 45. Growing apparatus may stay in steady state until it is determined that a harvest operation is required in 3635. The determination of when to harvest and how much to harvest may be controlled by control unit 370.

In 3640, at least another portion of the aquatic plants may be captured in at least one transition zone 3280-$p$ and harvested via second vertical raceway 3292. This may occur due to the configuration of static valves 3283 (see State C* in FIG. 33B), the configuration of dynamic valves 3830 or 4230 described below in reference to FIGS. 38-43, or due to control unit 370 electronically operating other types of mechanical or electronic valves.

In the case of static valves, control unit 370 may be configured to monitor the volume/density of aquatic plants in each module using, for example, image sensors 374. In some embodiments, control unit 370 is configured to follow a protocol for maintaining an acceptable volume/density of aquatic plants in each module. In such embodiments, control unit 370 may be configured to transfer and/or harvest a predetermined amount of aquatic plants when the volume/density of aquatic plants exceeds a predefined level in one or more module 3220.

For example, the growth conditions in a module 3220 may efficiently enable the growth of up to a predefined volume/density of aquatic plants in each module 3220, for example a layer of aquatic plants approximately 3 millimeters thick. The volume/density of aquatic plants in each module 3220 may be determined by sensors 372 and/or 374 in communication with control unit 370. When the volume/density of aquatic plants in a module increases to the predefined level, a predetermined amount of aquatic plants may be transferred to the module below and/or harvested. For example, if the volume/density of the aquatic plants in the top module 3220-$n$ reaches the predefined volume/density (i.e. a layer of aquatic plants 3 millimeters thick), 0.5 milliliters of the aquatic plants may be transferred from the top module 3220-$n$ to a module 3220-$(n-1)$ under the top module 3220-$n$. These aquatic plants are transferred via valve 3224-$n$ and a sub-channel 3291 of first vertical raceway 3290. As a result, the volume of the aquatic plants in the module 3220-$(n-1)$ increases. Subsequently, a portion of aquatic plants in module 3220-$(n-1)$ may be transferred or harvested from module 3220-$(n-1)$ through the first vertical raceway 3290. This may occur similarly for every module 3220 in a stack of modules.

In some embodiments, harvested aquatic plants may be transferred from each module 3220 via transition zones 3280 and vertical raceway 3292. During a harvest operation, a portion of aquatic plants in module 3220-$n$ may be captured in transition zone 3280-$p$, via valve 3282-$p$ in 3640. In some embodiments, harvesting may occur at the same time that aquatic plants are being transferred between modules 3220 (see, for example, States C and C* in FIG. 33B). In some embodiments, harvesting may be a separate and distinct operation. The harvested portion of aquatic plants, along with liquid growth medium, may be transferred to separation unit 3240 via second vertical raceway 3292 in 3640. After predefined portions of AP are transferred/harvested via valve 3224-$n$ and/or valve 3282-$p$, respectively every module 3220 would have room to grow more aquatic plants. According to some embodiments, the harvesting rate and the total daily harvest volume may be synchronized with the culture growth rate such that only the accumulated growing biomass is harvested. In some embodiments, different amounts of aquatic plants could be harvested to meet user demand.

According to some embodiments, the volume of the aquatic plants that is transferred via first vertical raceway 3290 and the volume of the aquatic plants that is captured in each transition zone 3280 are predetermined by the configuration of static valves 3223 and 3283. In such embodiments, control unit 370 may determine the number of transferring events that occur per day. In some embodiments, the volume of aquatic plants that is transferred via first vertical raceway and/or captured in each transition zone 3280 may be determined by control unit 370 controlling electronic valves or dynamic valves, such as valves 3830 or 4230 described below in reference to FIGS. 38-43.

After the harvesting operation in 3640, the harvested aquatic plants may be separated from the liquid growth medium by separation unit 3240 and the harvested aquatic plants may be sent to harvesting unit 340 in 3645. Separation unit 3240 may include a mechanical filter to separate the aquatic plants from the liquid growth medium. Separation unit 3240 may further or alternatively contain a chemical filter for the purpose of removing any type of unwanted element other than the aquatic plants. In some embodiments, after the aquatic plants are separated from the liquid growth medium in 3645, the aquatic plants may be transferred to harvesting unit 340. The harvesting unit 340 may be used to temporarily store the aquatic plants. Moreover, such aquatic plants may be further analyzed, modified and/or used by one or more external entities.

In 3650, after the separation of the liquid growth medium from the aquatic plants, the liquid growth medium may be cleaned and/or recycled by modification unit 3250. As a non-limiting example, the recycling process may include, a cleaning phase, an analyzing phase, and an enriching phase. Modification unit 3250 may contain a physical filter for the purpose of sterilizing and/or disinfecting the liquid growth medium. Such sterilizing and/or disinfecting may be, but is not limited to, UV irradiation sterilizing and disinfecting methods, ozone ($O_3$) sterilizing and disinfecting methods, and the like. Modification unit 3250 may further or alternatively contain a chemical filter for the purpose of removing any type of unwanted element. After the cleaning phase, the liquid growth medium may be analyzed to identify, for example, the temperature and/or the PH of the liquid growth medium. Moreover, the liquid growth medium may be analyzed to identify the level of one or more essential salts and/or fertilizers found within the liquid growth medium. The essential salts may be, but are not limited to, nitrogen, potassium, calcium, magnesium, and iron. In some embodiments, modification unit 3250 may dispose the liquid growth medium by directing it to first drain outlet channel 3299a. This may be performed either manually or automatically by control unit 370.

In 3650, the liquid growth medium may also be modified by modification unit 3250 (in response to the analysis described above) to provide optimal growth conditions for the aquatic plants. This process may include dissolving one or more essential salts, fertilizer, etc. into the liquid growth medium. Furthermore, this process may include aeration, PH and/or temperature adjustment, and the like. In some embodiments, the liquid growth medium is stored in the storage unit 3260 for later use. According to one embodiment, additional liquid growth medium may be loaded into growing apparatus 3200 from liquid growth medium source 3265. This may be performed either manually or automatically by control unit 370 to maintain the level of the liquid growth medium in the modules 3220.

In 3655, it is checked whether more aquatic plants need to be harvested, and if so execution continues with 3635; otherwise execution continues to 3660. In 3660, it is checked whether the cultivation needs to be continued, and if so execution continues with 3630; otherwise execution terminates. Thereafter, control unit 370 may monitor growing apparatus 3200 to determine when to perform any of the steps shown in FIG. 36. In some embodiments, the volume of the aquatic plants to be harvested may be determined by a user and/or under the control of control unit 370.

FIG. 37 is an image of a bioreactor 310 according to an embodiment. As shown in FIG. 37, bioreactor 310 may include a plurality of modules 3220 with a plurality of light sources 3222 positioned in between the modules 3220. While FIG. 37 shows a bioreactor 310 having multiple modules 3220, a bioreactor 310 may contain any number of modules 3220. FIG. 37 also shows two sub-channels 3291 that make up first vertical raceway 3290 and shows a portion of harvesting unit 340 according to one embodiment.

In some embodiments, a bioreactor (e.g., bioreactor 310) may include one or more dynamic valves for harvesting a portion of a culture. Dynamic valves may include, for example, rotating, oscillating, or gate-like mechanisms configured to harvest an aquatic plant culture. In some embodiments, the dynamic valves may be configured to harvest a specific and repeatable amount of a culture in subsequent harvesting operations. In some embodiments, the dynamic valves may be configured to harvest variable amounts of a culture. A control unit (e.g., control unit 370) may be configured to control the dynamic valves based on determining various conditions with a bioreactor as described herein (e.g., aquatic plant density levels).

FIGS. 38-41 illustrate a module 3800 having a dynamic valve 3830 according to an embodiment. Module 3800 may include a side wall 3802, two baffles 3804, and a floor 3806 defining a flow area for liquid growth medium (LGM) and aquatic plants (AP). Baffles 3804 may define an open ended center channel 3850 having a proximal opening 3852 and a distal opening 3854. An inlet 3812 may be provided on a proximal end 3813 of module 3800 for supplying LGM and/or AP to module 3800 and an outlet 3814 may be provided opposite inlet 3812 on a distal end 3815 of module 3800 for removing LGM and/or AP from module 3800. In embodiments including stacked modules, inlet 3812 of one module may be in fluid communication with outlet 3814 of a module above it (see FIG. 41). A spout 3810 in fluid communication with inlet 3812 may be provided to direct LGM and/or AP from inlet 3812 onto a flow shaper 3808. The operation of flow shaper 3808 is described below in more detail in reference to FIGS. 44 and 45. In some embodiments, floor 3806 may include a ramped floor 3807, the details of which are described in reference to FIG. 50.

In some embodiments, LGM and/or AP may flow from spout 3810, though center channel 3850 towards distal end 3815, out of distal opening 3854, around the end of baffles 3804, and back towards spout 3810 via outer channels 3856. LGM and/or AP flowing back via outer channels 3856 may be pulled back into center channel 3850 via proximal opening 3852. The configuration of module 3800 results in continuous circulation of LGM and/or AP within module 3800 during steady state operation, the continuous circulation facilitated by the structure of dynamic valve 3830.

As shown in FIG. 38, distal end 3815 of module 3800 may include a transition zone 3820 with dynamic valve 3830 situated therein. Transition zone 3820 along with valve 3830 allows a portion of AP to be harvested manually or under the control of control unit 370. As shown in FIGS. 38-41, dynamic valve 3830 may include a mouth 3834 having an opening 3838 for receiving LGM and AP when in an open configuration, the mouth being defined by a mouth wall 3836. Dynamic valve 3830 may also include a valve side wall 3840 connected to and at least partially surrounding mouth wall 3836. Valve side wall 3840 may be configured to seal with an outlet wall 3822 in transition zone 3820 when dynamic valve 3830 is in a closed position. In other words, valve side wall 3840 may contact the ends of outlet wall 3822 when dynamic valve 3830 is in the closed position.

Valve side wall 3840 may be connected to a valve top wall 3842, valve top wall 3842 being connected to an actuator 3832. In some embodiments, actuator 3832 may be operatively coupled to control unit 370 and control unit 370 may be configured to control actuator 3832 so as to rotate dynamic valve 3830 between an open position and a closed position (see FIG. 40). In some embodiments, actuator 3832 may be manually controlled by a user to rotate dynamic valve 3830 between the open position and the closed position. In some embodiments, dynamic valve 3830 may rotate about pivot 3844. The configuration of module 3800 and dynamic valve 3830 results in a module configuration having a single valve. As discussed below, dynamic valve 3830 in effect preforms the function of both static valves 3223 and 3283 (i.e. allows the flow of LGM and/or AP between modules and/or to harvesting unit 340). In some embodiments, module 3800 may include more than one dynamic valve 3830.

The operation of dynamic valve 3830 will now be described in reference to FIGS. 39A-41. FIGS. 38 and 39A show dynamic valve 3830 in a closed position. In the closed position, opening 3838 of mouth 3834 faces towards distal end 3815 of module 3800. In this position, no AP can enter mouth 3834 due to valve side wall 3840. Additionally, valve side wall 3840 is sealed with outlet wall 3822 to prevent AP from entering outlet 3814. However, LGM is allowed to flow underneath valve side wall 3840, into mouth 3834, over an adjustable water gate 3824, and out of module 3800 via outlet 3814.

FIG. 39B shows dynamic valve 3830 in an open position. In the open position, opening 3838 of mouth 3834 faces towards proximal end 3813 of module 3800. In this position LGM and AP are allowed to flow into mouth 3834 via opening 3838. In the open position, LGM is still allowed to flow underneath valve side wall 3840 towards outlet 3814. The height of adjustable water gate 3824 may control the amount of LGM that is allowed to flow in both the open position and the closed position. In some embodiments, the height of adjustable water gate may be controlled by control unit 370.

FIG. 40 shows a full rotation of dynamic valve 3830 during a harvesting operation. Dynamic valve 3830 is shown in the closed position in Stage 1 with only LGM flowing towards outlet 3814 (i.e. steady state operation). When a user and/or control unit 370 determines that a portion of AP needs to be harvested and/or transferred from module 3800, actuator 3832 begins to rotate dynamic valve 3830 towards the open position. As shown in Stage 2, as dynamic valve 3830 is rotated towards the open position, AP floating on top of LGM enters opening 3838 and is captured within mouth 3834. Actuator 3832 continues to rotate dynamic valve to the open position shown in Stage 3. In some embodiments, the rotation of dynamic valve 3830 may stop at Stage 3 to allow AP to fill mouth 3834. In some embodiments, the rotation of dynamic valve may be continuous and may not stop at Stage 3. As shown in Stages 4 and 5, dynamic valve 3830 completes its rotation by returning to the closed position. When dynamic valve 3830 returns to the closed position in Stage 5, the AP captured within mouth 3834 flows into outlet 3814. Once all the AP has flowed out of mouth 3834, module 3800 may return to steady state operation as shown in Stage 6. In some embodiments, valve side wall 3840 remains in sealed contact with outlet wall 3822 during the entire rotation of dynamic valve 3830.

In some embodiments, the complete rotation of dynamic valve 3830 may occur within 1 to 30 seconds. In some embodiments, rather than a complete rotation, the actuator 3832 may be configured to rotate dynamic valve 3830 to the open position (Stage 3) and reverse the rotation so as to return dynamic valve 3830 to the closed position. In some embodiments, the half rotations (i.e. from the closed position to the open position and back to the closed position) may occur in a total of 1 to 30 seconds. In some embodiments, control unit 370 may be configured to repeatedly actuate dynamic valve 3830 via actuator 3832 after a predetermined amount of time has lapsed. This predetermined amount of time may range from a minute to several hours. In some embodiments, control unit 370 may be configured to rotate dynamic valve 3830 via actuator 3832 in response to data collected by sensors 372 and/or 374. In some embodiments, a user may manually, either via control unit 370 or by physical operation, rotate dynamic valve 3830 via actuator 3832.

FIGS. 42 and 43 illustrate a module 4200 having a dynamic valve 4230 according to an embodiment. Module 4200 may include a side wall 4202 and a floor 4206 defining a flow area for LGM and AP. In some embodiments, module 4200 may include a ramped floor 4207. An inlet 4212 may be provided on a proximal end 4213 of module 4200 for supplying LGM and/or AP to module 4200 and an outlet 4214 may be provided opposite inlet 4212 on a distal end 4215 of module 4200 for removing LGM and/or AP from module 4200. In embodiments including stacked modules, inlet 4212 of one module may be in fluid communication with outlet 4214 of a module above it. A spout 4210 in fluid communication with inlet 4212 may be provided to direct LGM and/or AP into module 4200.

In some embodiments, LGM and/or AP may flow from spout 4210 towards a transition zone 4220 located at distal end 4215 of module 4200. The configuration of module 4200 results in continuous circulation of LGM and/or AP within module 4200 during steady state operation, the continuous circulation facilitated by the structure of dynamic valve 4230.

As shown in FIGS. 41 and 42, transition zone 4220 may have dynamic valve 4230 situated therein. Transition zone 4220 along with dynamic valve 4230 allows a portion of AP to be harvested manually or under the control of control unit 370. Dynamic valve 4230 may include a body 4240 having a body wall 4241. Body 4240 may be connected to a pivot 4238 for rotating dynamic valve 4230 between a closed position and an open position. An actuator 4232 coupled to pivot 4238 may be configured to rotate dynamic valve 4230 between the closed position and the open position. In some embodiments, actuator 4232 may be operatively coupled to control unit 370 and control unit 370 may be configured to control actuator 4232 so as to rotate dynamic valve 4230 between the open position and the closed position. In some embodiments, actuator 4232 may be manually controlled by a user to rotate dynamic valve 4230 between the open position and the closed position.

As shown in FIG. 43, body 4240 may include a mouth 4242 having a mouth wall 4244 and an opening 4246. Mouth wall 4244 may be in fluid communication with a first open end 4250 of a canal 4248. Canal 4248 may include first open end 4250 defined by mouth wall 4244 and a second open end 4252 defined by body wall 4241.

The operation of dynamic valve 4230 will now be described in reference to FIG. 43. Stage 1 shows dynamic valve 4230 in a closed position. In the closed position, opening 4246 of mouth 4242 faces towards distal end 4215 of module 4200. In this position, body wall 4241 may be sealed with an outlet wall 4222 such that no AP can enter mouth 4242. Additionally, due to the location of canal 4248, AP floating on top of LGM within module 4200 cannot enter mouth 4242 via canal 4248 in the closed position. However, LGM is allowed to flow into canal 4248, through mouth 4242, and out of module 4200 via outlet 4214. In some embodiments, module 4200 may include an adjustable water gate similar to or the same as adjustable water gate 3824.

When a user and/or control unit 370 determines that a portion of AP needs to be harvested and/or transferred from module 4200, actuator 4232 begins to rotate dynamic valve 4230 towards the open position. As shown in Stage 2, as dynamic valve 4230 is rotated towards the open position, opening 4246 of mouth 4242 rotates towards proximal end 4213 of module 4200. Actuator 4232 continues to rotate dynamic valve to the open position shown in Stage 3. In some embodiments, the rotation of dynamic valve 4230 may stop at Stage 3 to allow AP to fill mouth 4234. In some embodiments, the rotation of dynamic valve may be continuous and may not stop at Stage 3. In either case, AP floating on top of LGM fills mouth 4234 when valve dynamic 4230 is in the open configuration shown in Stage 3. As shown in Stage 4, actuator 4232 causes dynamic valve 4230 to reverse its rotation when returning it to the closed position in Stage 5. When dynamic valve 4230 returns to the closed position in Stage 5, the AP captured within mouth 4242 flows into outlet 4214. Once all the AP has flowed out of mouth 4242, module 4200 may return to steady state operation with only LGM flowing towards outlet 4214 via canal 4248.

In some embodiments, the two rotations of dynamic valve 4230 (i.e. from the closed position to the open position and back to the closed position) may occur within a total of 1 to 30 seconds. In some embodiments, control unit 370 may be configured to repeatedly actuate dynamic valve 4230 via actuator 4232 after a predetermined amount of time has lapsed. This predetermined amount of time may range from a minute to several hours. In some embodiments, control unit 370 may be configured to rotate dynamic valve 4230 via actuator 4232 in response to data collected by sensors 372 and/or 374. In some embodiments, a user may manually, either via control unit 370 or by physical operation, rotate dynamic valve 4230 via actuator 4232.

Dynamic valves 3830 and 4230, allow the level of AP and/or LGM within an individual module to be controlled independently. For example, should control unit 370 determine that AP in a specific module within a stack (e.g., the third module within a stack) needs to be harvested; control unit 370 may actuate the dynamic valve associated with the third module, thereby harvesting AP from only that module. Additionally, the design of dynamic valves 3830 and 4230 provide for a consistent harvesting operation. The amount of AP harvested each time a dynamic valve is actuated, which may be defined as a % of the overall amount of AP determined by the area ratio of the valve mouth area to total culture area, is controlled by the size of mouth 3834/4242. As such, the amount of AP harvested from a module during a single harvesting operation (i.e. a single actuation of valve 3830/4230) is consistent. Consistent harvesting amounts aids in determining how many times a valve 3830/4230 needs to be actuated to harvest a certain amount of AP from a module. Moreover, the design of dynamic valves 3830 and 4230 facilitates the cleanliness of the valve. Each transfer and/or harvesting process automatically cleans the dynamic valves because liquid growth medium that is forced through the dynamic valves automatically washes each component of the valve. This configuration may enable to use of a single output and input channel, thus simplifying the design and increasing the robustness of the system. In addition, no AP is left to dry in or around the valves, thus eliminating potential static contamination "hot spots."

During steady state operation LGM leaving a module (e.g., module 3220, 3800, or 4200) within a stack of modules via outlet (e.g., 2414, 3814, or 4214) may be transferred to the next module within the stack (see, for example, FIG. 41). During a steady state operation, the continuous flow of LGM between modules results in the continuous washing of AP within each module. This washing results from a relatively high speed swirl flow near the inlet of a module followed by a substantially linear slowing down flow rate that allows AP to resurface. The slowing down flow occurs over a sufficient distance so as to allow viable plants to float back to the surface of the LGM before reaching a harvesting valve.

As LGM flows into a module, AP present within that module are forced downward due to the incoming flow of LGM. This forces AP and any contaminates, debris, or non-viable AP towards the floor of the module. Viable AP forced towards the floor will resurface due to $CO_2$ vacuoles naturally present in individual aquatic plants. In contrast, contaminates, debris, and non-viable AP will remain at the bottom of the module near the floor. As such, the contaminates, debris, and non-viable AP are allowed to flow through a valve (e.g., below valve side wall 3840 in FIG. 39A) with the LGM to the next module in the stack. Eventually, due to the continuous flow of LGM, the contaminates, debris, and non-viable AP will be transferred from the stack of modules to a separation unit where the contaminates, debris, and non-viable AP can be removed.

During a harvesting operation, LGM and AP leaving a module via an outlet may be transferred to either: 1) the next module (see e.g., FIG. 41) or 2) directly to the harvesting unit via the second vertical raceway. In embodiments where LGM and AP are transferred to the next module during a harvesting operation, AP is ultimately "harvested" from only specific modules within a stack (e.g., the bottom module within a stack) that are connected to a harvesting unit. Embodiments where LGM and AP are sent directly to the harvesting unit serve to isolate the harvesting operation for each module from the other modules within a stack. Valves associated with a module's outlet may direct LGM and AP to either the next module or directly to the harvesting unit. In some embodiments, these valves may be controlled by control unit 370.

FIG. 44 illustrates a module 4400 having a flow shaper 4408 according to one embodiment. As shown in FIG. 44, module 4400 may include a side wall 4402 and a floor 4406 defining a flow area for LGM and AP. LGM and AP may flow into module 4400 via an inlet 4412 and a spout 4410. Flow shaper 4408 may be located on floor 4406 near a proximal end 4413 of module. Flow shaper 4408 may protrude from floor 4406 and include a top surface 4409. In some embodiments, flow shaper 4408 may be formed as part of floor 4406. In some embodiments, flow shaper 4408 may be a separate piece that is releasably or permanently attached to floor 4406. Flow shaper 4408 may be used to shorten the "re-floating distance" and improve the washing efficiency of aquatic plants flowing within a module, e.g., module 4400. Module 4400 may also include a transition zone 4420 and an outlet 4414 located at a distal end 4415 thereof. Transition zone 4420 may include a valve, such as static valve 3283 or a dynamic valve 3830/4230 as described above, or valve 5030 described below.

As used herein "re-floating distance" means the horizontal distance, measured in the direction of the liquid growth medium flow from a point on top surface 4409 or floor 4406 wherein an aquatic plant may be forced downward by a swirl flow, that is required for a plant to re-surface. The "refloating distance" must be shorter than the distance required to reach an exit point 4411 within transition zone 4420 to ensure that viable AP does not inadvertently escape module 4400 via transition zone 4420 during steady state operation. In some embodiments, the swirl flow may be derived by the flow of aquatic plants and/or liquid growth medium exiting inlet spout 4410. Alternatively or additionally, the swirl flow may be derived locally by a mechanical device, e.g. a propeller, or by directed airflow, or other liquid flow.

As shown in FIG. 44, AP and/or LGM exiting spout 4410 creates a swirl flow below spout 4410. This swirl flow forces AP, either exiting spout 4410 or already present within module 4400, towards floor 4406. The AP forced towards floor 4406 will resurface due to its endogenous natural floating mechanisms, i.e. tiny air bubbles, naturally present in individual aquatic plants. The re-floating distance may influence the dimensions of the modules described herein because the operation of some valves described herein (e.g., valves 3283, 3830, and 4230) requires that AP be floating on top of LGM to function properly. For example, if AP were present below valve side wall 3840 in FIG. 39A, viable AP may be undesirably transferred to a lower module within a stack of modules during steady state operation. In such a circumstance, the higher modules within a stack would eventually contain little to no AP. This would be detrimental to achieving uniform growth conditions within each module within the stack.

As illustrated in FIG. 45, the use of flow shaper 4408 results in a shorter re-floating distance for AP across a range of inlet swirl flow rates. The swirl flow rate facilitates the washing of AP, and a high inlet swirl flow rate enables better washing of AP. However, a high inlet flow rate may also result in a long re-floating distance. Flow shaper 4408 reduces the re-floating distance without reducing the inlet swirl flow rate, thus optimizing the inlet swirl flow rate to facilitate washing of AP, and on a system level, optimizing the overall LGM flow rate through modification units. Optimizing the flow rate of LGM through a modification unit may increase the efficiency of the modification unit. For example, in a modification unit that employs a UV cleaning process, optimizing the flow rate of LGM can increase the speed and efficiency of debris and contamination removal within the modification unit.

In some embodiments, a shorter re-floating distance creates a shorter horizontal race and allows a module to be shorter in length, thereby reducing its footprint. Alternatively or additionally, a shorter refloating distance may remove the need to add baffles to a module to control the flow characteristics and ensure that AP are floating when they reach a valve, such as valves 3283, 3830, or 4230. In some embodiments, a flow shaper may be employed in concert with one or more baffles to create a desirable flow characteristic and/or re-floating distance. In some embodiments, baffles alone may be used to create a desirable flow characteristic and/or re-floating distance within a module.

FIG. 46 shows a module 4600 having flow shaper 4608 and two baffles 4604 used to control the flow characteristics and the re-floating distance of AP according to an embodiment. FIG. 46 shows two inlet swirls formed adjacent to the outlet of a spout 4610. The swirls force AP downward and flow shaper 4608 is used to decrease the re-floating distance of the AP. FIG. 46 also shows how baffles 4604 are used to recirculate AP and LGM back towards spout 4610. This recirculation facilities the washing of all the AP within module 4600.

FIGS. 47A and 47B show an aerial and cross-sectional view of module 4600, respectively. Module 4600 may include an inlet 4612 and an outlet 4614 both located at a proximal end 4613. Module 4600 may also include a side wall 4602, baffles 4604, and floor 4606 defining a flow area for LGM and AP. LGM and/or AP flowing into module 4600 results in a swirl flow that forces AP downward towards flow shaper 4608. The AP is then directed into center channel 4650 defined by baffles 4604, center channel 4650 including a proximal opening 4652 and a distal opening 4654. As LGM and AP move through center channel 4650, the AP is allowed to re-float as it approaches distal opening 4654. When LGM and AP reach distal opening 4654, viable AP have refloated to the top of the LGM while debris, contaminates, and non-viable plants remain near floor 4606. The LGM and AP then circulate around the end of baffles 4604 at distal end 4615 and enter outer channels 4656 on its way back to proximal end 4613.

A portion LGM, and any debris, contamination, or non-viable plants adjacent to floor 4606 returning towards proximal end 4613 may exit module 4600 via outlet 4614. In contrast, the AP floating on top of the LGM and a portion of LGM is recirculated into center channel 4650 due to the suction created at proximal opening 4652 from the swirl flow created by LGM and/or AP flowing into module 4600 via spout 4610. In some embodiments, outlet 4614 may include a valve, such as static valve 3223. In some embodiments, distal end 4615 may include a valve, such as valve 3283 for harvesting AP from module 4600. In some embodiments, the height of baffles 4604 may be equal to or greater than the height LGM present within module 4600 during steady state operation. In some embodiments, the height of baffles 4604 may be equal to or greater than the height of LGM+AP present within module 4600 during steady state operation.

FIGS. 48A and 48B show a module 4800 according to an embodiment. Module 4800 may include a side wall 4802, a baffle 4804, and a floor 4806. A proximal wall 4817 located at a proximal end 4813 of module 4800 along with side wall 4802, baffle 4804, and floor 4806 define a flow area for AP and LGM within module 4800. Module 4800 may also include an inlet 4812 with a spout 4810 located at proximal end 4813 for supplying AP and/or LGM to module 4800. Proximal end 4813 may also include a biomass outlet 4814 having two outlets, a first biomass outlet 4814*a* and a second biomass outlet 4814*b*, for removing AP from module 4800. Additionally, a solution outlet 4816 may be located adjacent to side wall 4802 and near proximal end 4813 for removing LGM from module 4800. Module 4800 may also include one or more valve mechanisms 4830 located in the vicinity of outlets 4814 and 4816 for directing AP to outlet 4814 and LGM to outlet 4816. In some embodiments, valve mechanism(s) 4830 may be located at proximal end 4813 between baffle 4804 and solution outlet 4816. Valve mechanisms 4830 may include, but are not limited to, one or more of the valves discussed herein (e.g., valves 3223, 3283, 3830, 4230, 5030, etc.).

Baffle 4804 may extend from proximal wall 4817 towards distal end 4815. In some embodiments, baffle 4804 has a length ($l_b$) between 200 mm and 250 mm. In some embodiments, baffle 4804 has a length ($l_b$) between 220 mm and 230 mm. In some embodiments, baffle 4804 has a length ($l_b$) of 228.50 mm. In some embodiments, module 4800 may have an overall interior length ($l_{m1}$) between 350 mm and 400 mm. In some embodiments, module 4800 may have an overall interior length ($l_{m1}$) of 373 mm. In some embodiments, the length of the flow area defined by proximal wall 4817 and distal end 4815 ($l_{m2}$) may be between 300 mm and 350 mm. In some embodiments, $l_{m2}$ is 328 mm.

In some embodiments, module 4800 may have an interior width ($w_m$) between 175 mm and 225 mm. In some embodiments, module 4800 may have an interior width ($w_m$) that is 200 mm. In some embodiments, the interior diameter of spout 4810 ($d_s$), and the interior diameter of outlets 4814*a*, 4814*b*, and 4816 ($d_o$) may be between 8 mm and 12 mm. In some embodiments, $d_s$ and $d_o$ are equal to 10 mm. In some embodiments, $d_s$ and $d_o$ are not equal to each other. In some embodiments, spout 4810 is oriented at an angle (θ) relative to floor 4806. The angle θ may influence the swirl flow created adjacent to spout 4810, which facilitates the washing of AP within module 4800. In some embodiments, θ is between 30° and 60°. In some embodiments, θ is 45°.

In some embodiments, module 4800 has a top wall 4818 defining an interior volume height ($h_m$). In some embodiments, $h_m$ is between 20 mm and 30 mm. In some embodiments, $h_m$ is 25 mm. In some embodiments, baffle 4804 may have a height ($h_b$) that is equal to $h_m$. In some embodiments, $h_b$ may be less than $h_m$.

FIGS. 49A and 49B show a module 4900 according to an embodiment. Module 4900 may include a side wall 4902, two baffles 4904, and a floor 4906. A distal wall 4916 located at a distal end 4915 of module 4900 along with side wall 4902, baffles 4904, and floor 4906 define a flow area for AP and LGM with module 4900. Module 4900 may also include an inlet 4912 with a spout 4910 located at a proximal end 4913 for supplying AP and/or LGM to module 4900. Proximal end 4913 may also include an outlet 4914 for removing AP and/or LGM from module 4900. Module 4900 may also include one or more valve mechanisms 4930 located in the vicinity of outlet 4914 for directing LGM to outlet 4914. One or more valve mechanisms 4930 may also be located in the vicinity of distal wall 4916 for removing AP from module 4900. In some embodiments, one or more valve mechanisms 4930 may be located at or may form part of side wall 4902 at proximal end 4913. In some embodiments, one or more valve mechanisms 4930 may be located at or may form part of distal wall 4916 at distal end 4915. Valve mechanisms 4930 may include, but are not limited to, one or more of the valves discussed herein (e.g., valves 3223, 3283, 3830, 4230, 5030, etc.).

Baffles 4904 may extend, at opposing angles relative to distal wall 4916, from proximal end 4913 towards distal end 4915, thereby forming a center channel 4950 having a proximal opening 4952 and a distal opening 4954. Baffles 4904 along with side wall 4902 may also define two outer channels 4956. In some embodiments, baffles 4904 may have a length ($l_b$) between 200 mm and 250 mm. In some embodiments, baffles 4904 may have a length ($l_b$) equal to 231.50 mm. In some embodiments, proximal opening 4952 may have a width ($w_{b1}$) between 30 mm and 35 mm. In some embodiments, $w_{b1}$ may be 32 mm. The width ($w_{b1}$) of proximal opening 4952 along with the swirl flow created by inflowing LGM and/or AP from spout 4910 may create the desired suction to pull LGM and AP into center channel 4950, thus creating continuous circulation of AP and LGM within module 4900. In some embodiments, distal opening 4954 may have a width ($w_{b2}$) between 80 mm and 85 mm. In some embodiments, $w_{b2}$ may be 82 mm.

In some embodiments, module 4900 may have an overall interior length ($l_{m1}$) between 350 mm and 400 mm. In some embodiments, module 4900 may have an overall interior length ($l_{m1}$) of 380 mm. In some embodiments, the length of the flow area defined by distal wall 4916 and proximal end 4913 ($l_{m2}$) may be between 300 mm and 350 mm. In some embodiments, $l_{m2}$ may be 334 mm. In some embodiments, module 4900 may have an interior width ($w_m$) between 175 mm and 225 mm. In some embodiments, module 4900 may have an interior width ($w_m$) that is 198 mm.

In some embodiments, the interior diameter of spout 4910 may change from a first diameter ($d_1$) to a second diameter ($d_2$), the second diameter ($d_2$) being smaller than the first diameter ($d_1$). In some embodiments, $d_1$ may be between 6 mm and 8 mm. In some embodiments, $d_1$ may be 7 mm. In some embodiments, $d_2$ may be between 3 mm and 5 mm. In some embodiments, $d_2$ may be 4 mm. In some embodiments, the interior diameter of spout 4910 may be constant (i.e. $d_1 = d_2$). In some embodiments, the center of spout 4910 may be located a distance ($h_s$) above floor 4906. In some embodiments, $h_s$ may be between 8 and 10 mm. In some embodiments, $h_s$ may be 9 mm. The diameters ($d_1$ and $d_2$) of spout and $h_s$ may influence the swirl flow created adjacent to spout 4910, which facilitates the washing of AP within module 4900. In some embodiments, the interior diameter of outlet 4914 ($d_o$) may be between 8 mm and 12 mm. In some embodiments, $d_o$ may be 10 mm.

In some embodiments, module 4900 has a top wall 4918 defining an interior volume height ($h_m$). In some embodiments, $h_m$ is between 20 mm and 30 mm. In some embodiments, $h_m$ is 25 mm. In some embodiments, baffles 4904 may have a height ($h_b$) that is equal to $h_m$. In some embodiments, $h_b$ may be less than $l_m$. In some embodiments, $h_b$ may be between 12 mm and 18 mm. In some embodiments, $h_b$ may be 15 mm.

While exemplary dimensions have been described above for components of modules 4800 and 4900, the size and shape of modules 4800 and 4900 and the components may be adjusted and/or scaled depending on the desired footprint for a bioreactor and/or growing apparatus. For example, a module having a relatively small size may be preferable for a household bioreactor used to culture and harvest aquatic plants for a single family while a module having a relatively large size may be preferable for a large scale bioreactor used to culture and harvest large amounts of aquatic plants for large scale distribution.

FIG. 50 illustrates the operation of a ramped floor 5040 according to an embodiment. FIG. 50 shows a comparison of a module 5000a without a ramped floor and a module 5000b with ramped floor 5040. Both modules 5000a/b may include a side wall 5002 and a floor 5006 defining a flow area for AP and LGM. Additionally, both modules 5000a/b may include an outlet 5014 in fluid communication with a static valve and/or mechanical valve 5030. Static and/or mechanical valve 5030 may include a first baffle 5032 and a second baffle 5034 that together are configured to allow LGM to exit modules 5000a/b and prevent AP from exiting modules 5000a/b. In some embodiments, the height and location of baffles 5032 and 5034 may be adjusted, either manually or under the control of control unit 370, to control the amount of LGM exiting modules 5000a/b.

As shown on the right side of FIG. 50, floor 5006 of module 5000b includes ramped floor 5040 extending across at least a portion of floor 5006, exclusive of a valve area 5042 located immediately adjacent to valve 5030. The ramped floor 5040 does not extend into valve area 5042 because valve 5030 requires a minimum level of LGM for optimal functionality (a minimum level of LGM is also required for optimal functionality of other valves described herein, e.g., valves 3223, 3283, 3830, or 4230).

As shown in FIG. 50, ramped floor 5040 occupies space that would be occupied by LGM in the absence of ramped floor 5040. This reduces the amount of LGM required to fill a module, but still maintains the amount of surface area on top of the LGM that can be used to culture AP. In some embodiments, ramped floor 5040 may decrease the amount of LGM required to fill a module by up to 80%. In embodiments employing a plurality of stacked modules, this significantly reduces the volume of LGM required to operate a bioreactor, which may significantly reduce the cost of operating the bioreactor and the size/cost of the equipment needed to circulate LGM with the bioreactor.

In some embodiments, ramped floor 5040 also defines a cavity 5044. In some embodiments cavity 5044 may house a light source 5046, such as light source 3222, for illuminating module 5000b and/or a module below module 5000b. In some embodiments, light source 5046 may be light guide for directing light within cavity 5044 and for illuminating module 5000b and/or a module below module 5000b (see FIGS. 51A and 51B). Since cavity 5044 may be used to house at least a portion of light source 5046, the overall height of a growing apparatus can be decreased. In embodiments employing a plurality of stacked modules, a light source for each module may be at least partially received in cavity 5044 defined by ramped floor 5040. In such embodiments, cavities 5044 may reduce the height required for each module and an associated light source. For example, the height may be reduced by 25%. As such, the overall height of a growing apparatus and bioreactor may be reduced by approximately 25%.

While FIG. 50 shows ramped floor 5040 having a rectangular cross-sectional shape, ramped floor 5040 may have any cross-sectional shape including, but not limited to, an elliptical shape or pentagonal shape. Additionally, while FIG. 50, shows ramped floor 5040 employed in combination with valve 5030, a ramped floor may be used in concert with any of the valves described herein, e.g., valves 3223, 3283, 3830, or 4230.

FIGS. 51A and 51B show a module 5100 including a ramped floor 5040 and a dynamic valve 3830 according to an embodiment. As shown in FIG. 51A, two LED light arrays 5102 may be arranged on opposites side of module 5100 with two light guides 5104 located between and in optical communication with LED light arrays 5102. In some embodiments, light guides 5104 may be located in cavity 5044 defined by ramped floor 5040. In some embodiments, module 51000 may include a single light guide extending across module 5100 for illuminating module 5100 and/or a module below module 5100. In some embodiments, module 5100 may include more than two light guides for illuminating module 5100 and/or a module below module 5100. In some embodiments, LED light arrays 5102 may be at least partially disposed within cavity 5044. Module 5100 also includes flow shaper 3808 located on top of ramped floor 5040. Module 5100 provides a good example of how various aspects from different module embodiments described herein can be combined to produce a module having desirable characteristics. It is appreciated at that various aspects of each embodiment described herein, excluding those that are mutually exclusive, may be combined to create a module having desired characteristics.

While various module embodiments have been described or illustrated herein as being within a stack of modules, each module may function as a single module. In other words, a single module connected to appropriate devices, such as, for example, an LGM supply and a harvesting unit, may be used to cultivate and harvest AP. In other words, the various module embodiments described herein may not be dependent on other modules to function properly. Additionally, while various module embodiments have been described or illustrated herein as being a single module, it is appreciated that single modules may be incorporated into module stacks.

FIGS. 52A-52C illustrate a biomass quantification unit 5200 according to an embodiment. In some embodiments, biomass quantification unit 5200 may be in fluid communication with second vertical raceway 3292. In some embodiments, harvested AP may be transferred via second vertical raceway 3292 to separation unit 3240 then to biomass quantification unit 5200 via pumping unit 3245. In some embodiments, as shown in FIGS. 52A-52C, at least a portion of separation unit 3240 may be included within biomass quantification unit 5200.

Harvested AP along with LGM may be delivered to a holding chamber 5202 in biomass quantification unit 5200 via inlet tube 5204. In embodiments where at least a portion of separation unit 3240 is included within biomass quantification unit 5200, holding chamber 5202 and/or a pump tube 5206 connected to holding chamber 5202 may include one or more filters 5201 for separating LGM from AP. In other words, holding chamber 5202 and/or pump tube 5206 in combination with at least one filer 5201 may function as a separation unit. In some embodiments, an inlet valve 5205 may control the flow of LGM and AP into holding chamber 5202.

In some embodiments, under steady state operation, inlet tube 5204 may be connected to bottom module 3220-1 via a sub-channel 3291 or 3293 (described in FIG. 32). In some embodiments, biomass quantification unit 5200 may be in fluid communication with storage unit 3260 or liquid growth medium source 3265 via a pump tube 5206. In some embodiments, LGM may be flushed through filter 5201 and holding chamber 5202 via the flow of LGM through pump tube 5206, either under pressure provided by pump 5208 or due to gravity. Pump tube 5206 may include a pump valve 5207 for controlling the flow of LGM and/or AP within pump tube 5206. Flushing filter 5201 and holding chamber 5202 with LGM forces contamination, particles, debris, and non-viable aquatic plants into holding chamber 5202. The contamination, particles, debris, and non-viable aquatic plants, precipitated or suspended in LGM, can then be sent to modification unit 3250 for removal. If LGM needs to be replaced, pump 5208 may be stopped and valves 5205 and 5207 may block the flow from inlet tube 5204 and to pump tube 5206, respectively. When valves 5205 and 5207 are closed, outlet valve 5213 may be opened to allow LGM with the accumulated contamination particles, debris, and non-viable aquatic plants to flow from holding chamber 5202 to first drain outlet channel 3299a via modification unit 3250.

Holding chamber 5202 may include a container 5203 for increasing the refloating rate of viable AP and the build-up of the floating AP layer. After floating AP has accumulated in holding chamber 5202, inlet valve 5205 may be closed and pump 5208 may deliver fresh LGM into holding chamber 5202 via pump tube 5206, thereby causing all floating AP to rise into measurement tube 5210 (see FIG. 52B). In some embodiments, pump 5208 may control the flow of fresh LGM such that floating AP remains within measurement tube 5210 for a predetermined amount of time. During this predetermined amount of time a measurement device 5214 may measure the plant floating volume (PFV) of the separated AP. In some embodiments, pump 5208 may not suspend the floating AP within measurement tube 5210, but rather push the separated AP through measurement tube 5210 continuously. In such embodiments, measurement device 5214 may be configured to measure the PFV for the floating AP as the floating AP is moving through measurement tube 5210. In some embodiments, measurement device 5214 may include an optical device capable of measuring absorbance and/or transmission of light though measurement tube 5210 and/or the reflection of light off of AP within measurement tube 5210. In some embodiments, measurement device 5214 may include a photometer and/or a camera.

After the PFV is measured in measurement tube 5210, pump 5208 may flush measurement tube 5210 with additional LGM, thereby transferring the separated AP out of biomass quantification unit 5200 via transfer tube 5216. In some embodiments, transfer tube 5216 is in fluid communication with harvesting valve 3275; harvesting valve 3275 being in communication with harvesting unit 340 and growing apparatus 3200 (see FIG. 32). After measurement tube 5210 is flushed with LGM, LGM remaining within biomass quantification unit 5200 may be removed via outlet tube 5212 by opening outlet valve 5213 (see FIG. 52C).

In some embodiments, the operation of biomass quantification unit 5200 is controlled by control unit 370. In some embodiments, control unit 370 may be configured read data collected by measurement device 5214 and to calculate the PVF for separated AP within measurement tube 5210. The calculation of PFV may be used by control unit 370 to monitor and control growth conditions within a growing apparatus and/or bioreactor. As a non-limiting example, control unit 370 may be configured to monitor the growth rate within a module or group of modules by monitoring changes in PFV. Since valves, such as valves 3830 and 4230, are configured to harvest relatively the same amount of AP and LGM each harvesting operation (due to the fixed size of mouths 3834 and 4242) the relative amounts of AP and LGM harvested in one or more harvesting operations may provide information related to the growth rate within a module, growing apparatus, or bioreactor. For example, during optimal growing conditions a single harvesting operation from a single module may result in separated AP having a PFV of x mL. If the PFV for a single harvesting operation from a single module begins to decrease below x mL, this may signal that the growth rate within that module is less than optimal. Control unit 370 may be configured to monitor the PFV for a single module overtime and adjust growing conditions within the module based on PFV values.

In addition to or as an alternative to adjusting growing conditions within a module, control unit 370 may configured to alter the timing of harvesting operations. For example, if the PFV for a single module decreases over time, control unit 370 may increase the time between harvesting operations for that module in order to optimize the amount of AP harvested per harvesting operation. Similarly, if the PFV for a single module increases over time, control unit 370 may decrease the time between harvesting operations for that module.

Moreover, measurements of PFV within biomass quantification unit 5200 allow control unit 370 to monitor the total output from a module, growing apparatus, and/or bioreactor. Total output allows control unit 370 to track amount of AP cultured and harvested and provides information related to the efficiency of a module, growing apparatus, and/or bioreactor that can be used to optimize the operation of the module, growing apparatus, and/or bioreactor.

The in-line PFV measurements performed using biomass quantification unit 5200 offer significant advantages over traditional methods that measure the amount of harvested AP by sampling then counting particles and/or weighing dried biomass of off-line samples. First of all, in-line PFV measurements provide real-time values related to the amount of AP being harvested. Real-time information facilitates quick identification of problems and/or errors and allows these problems or errors to be quickly rectified. Second, in-line viable PFV measurements remove the need for off-line drying and measuring devices, which can be expensive and time consuming. Third, in-line PFV measurements can be performed under conditions that maintain the aquatic plants' viability, thus enabling the continuation of their cultivation post measurement. For example, after a PFV measurement, control unit 370 may return a harvested portion of AP back to a module, growing apparatus, or bioreactor for further cultivation. For example, rather than harvesting potentially immature plants having a low PFV, immature plants may be reintroduced into a module for further cultivation and growth. Forth, in-line PFV measurements do not require the suspension and homogenization of the plants in a solution for accurate sampling. Fifth, in-line PFV measurements do not require counting of individual plants. Sixth, in-line PFV measurements do not require the complete separation of the biomass from the solution, which may be difficult to standardize, yet essential for accurate wet weight measurements.

In the case of aquatic plants, the inventors have discovered a linear relationship between the wet floating form, the wet form (i.e. not floating), and dry form of the same aquatic plants. The details of this relationship are described below in reference to FIGS. 53-55B.

As illustrated in FIG. 53, viable plants will float on top of LGM within a tube. The volume of this mass of floating AP can be measured if the diameter of the tube and the height of the floating AP is known. The PFV volume has a linear correlation to the aquatic plants' wet weight (WW). FIG. 54 shows a graph illustrating a linear correlation between PFV and WW for *Wolffia*. The PFV volume also has a linear correlation to the aquatic plants' dry weight (DW). FIGS. 55A and 55B show graphs illustrating a linear correlation between PFV and DW for *Wolffia globosa* and *Wolffia arrhiza*, respectively. As such, PFV measurements provide accurate measurements related to the amount of harvested biomass and can be used to calculate WW and DW values. Without being limited thereto, the inventors believe these linear relationships are attributable to an "envelope" or "wall" that surrounds each aquatic plant. This "envelope" or "wall" may be rigid enough to maintain the spherical geometrical shape of individual plants, thus maintaining a constant density for each volume unit of plants as plants accumulate, similar to marbles in a jar.

In some embodiments, control unit 370 may store these relationships for any type of aquatic plant in a memory and use them to determine DW and/or WW for a portion of harvested AP.

FIGS. 56-58 illustrate sterilization units 5600, 5700, and 5800 according to various embodiments. The sterilization units may significantly reduce or prevent contamination of a bioreactor 310 at outlet or inlet points where at least one component of the bioreactor may be exposed to the external environment. The sterilization units provide a continuous laminar flow ("air curtain") of sterilized air at the outlets or inlets. This "air curtain" prevents unwanted contamination from entering the bioreactor via the outlets or inlets. In some embodiments, the sterilization units include very little moving parts and no complex mechanisms. The lack of moving parts and complex mechanisms decreases the chance of failure and increases the robustness of the units. In some embodiments, a sterilization unit may be formed as part of other units in the bioreactor 310. For example, as discussed below, sterilization units 5700 and 5700 may be formed as part of output unit 360. While FIGS. 56-58 show specific embodiments of sterilization units, the sterilization units may be used to prevent contamination of a bioreactor via any inlet or outlet located on the bioreactor.

FIG. 56 shows a sterilization unit 5600 for preventing undesirable contamination at an outlet 5616 of an output unit 360 of a bioreactor 310. Sterilization unit 5600 may be connected to an outlet tube 5614 and outlet 5616 configured to deliver foodstuff, a medicinal substance, a cosmetic substance, a chemical substance, or other useful products to a user. Sterilization unit 5600 may include an air pump 5602 operatively connected to ambient air, a HEPA filter 5604, an air supply tube 5606, and a biomass supply tube 5610.

In some embodiments, air pump 5602 and HEPA filter 5604 may also be used in connection with air supply 3230 that supplies air to modules 3220 for culturing aquatic plants. Air pumped from outside the bioreactor (e.g., bioreactor 310) is sterilized using HEPA filter 5604 before entering air supply tube 5606. Biomass (i.e. AP and/or LGM) may be supplied to output unit 360/sterilization unit 5600 from harvesting unit 340 or processing unit 350 via biomass supply tube 5610. A valve 5612 may be used to control the flow of harvested and/or processed biomass into output unit 360/sterilization unit 5600.

As shown in FIG. 56, air supply tube 5606, biomass supply tube 5610, and outlet tube 5614 meet at a junction 5608. In some embodiments, air supply tube 5606, biomass supply tube 5610, and outlet tube 5614 meet at junction 5608 having a "Y" configuration with air supply tube 5606 and biomass supply tube 5610 oriented at an angle θ relative to each other. Preferably, θ is about 45° or less. An angle of 45° or less facilitates laminar flow of biomass and air at junction 5608.

Air and biomass flowing though junction 5608 flow together down outlet tube 5614 towards outlet 5616. The flow of air and biomass through junction 5608 and down outlet tube 5614 creates an "air curtain" that blocks any contamination from entering the bioreactor via outlet 5616. The length of outlet tube 5614 may be adjusted to allow for the highest air flow rate while still maintaining a controlled, unified, laminar flow from junction 5608 to outlet 5616. The laminar air flow is continuous before, during, and after biomass flows into junction 5608 and through outlet 5616. The air flow rate may be controlled and may be altered between batches of biomass delivered from harvesting unit 340 or processing unit 350. Control unit 370 may control the flow of air and/or biomass such that they flow together in a laminar, directed, unified, and controlled manner.

FIG. 57 shows a sterilization unit 5700 for preventing undesirable contamination at an outlet 5716 of an output unit 360 of a bioreactor (e.g., bioreactor 310). The output unit 360 in FIG. 57 may be configured to deliver foodstuff, a medicinal substance, a cosmetic substance, a chemical substance, or other useful products into a cup 5720 placed on a table top 5722 via outlet tube 5714 and outlet 5716. Sterilization unit 5700 may include an air pump 5702, a HEPA filter 5704, an air supply tube 5706, and a biomass supply tube 5710. Air pump 5702, HEPA filter 5704, air supply tube 5706, and biomass supply tube 5710 are the same or similar to air pump 5602, HEPA filter 5604, air supply tube 5606, and biomass supply tube 5610 described above in reference to FIG. 56 and have the same functions and characteristics.

As shown in FIG. 57, air pump 5702, HEPA filter 5704, valve 5712, harvesting unit 340, and other portions or all of a bioreactor may be housed within a housing below a housing surface (e.g., a table top) 5722. While surface 5722 is shown in FIG. 57, the bioreactor may be housed within other suitable enclosures, such as but not limited to, behind a wall, within a bar enclosure, below a floor, or partially or fully within any other suitable enclosure.

Biomass (i.e. AP and/or LGM) may be supplied to output unit 360/sterilization unit 5700 from harvesting unit 340 via biomass supply tube 5710 and valve 5712. Similar to FIG. 56, air supply tube 5706, biomass supply tube 5710, and outlet tube 5714 meet at a junction 5708 having a "Y" configuration with air supply tube 5706 and biomass supply tube 5710 oriented at an angle θ relative to each other. Preferably, 0 is about 45° or less.

FIG. 58 shows a sterilization unit 5800 for preventing undesirable contamination at first drain outlet channel 3299a associated with modification unit 3250 of a bioreactor. Sterilization unit 5800 may include an air pump 5802, a HEPA filter 5804, an air supply tube 5806, and a biomass supply tube 5810. Air pump 5802, HEPA filter 5804, air supply tube 5806, and biomass supply tube 5810 are the same or similar to air pump 5602, HEPA filter 5604, air supply tube 5606, and biomass supply tube 5610 described above in reference to FIG. 56 and have the similar functions and characteristics.

Biomass (i.e. AP and/or LGM) may be supplied to sterilization unit 5800 from modification unit 3250 via biomass supply tube 5810 and valve 5812. Similar to FIG. 56, air supply tube 5806, biomass supply tube 5810, and outlet tube 5814 meet at a junction 5808 having a "Y" configuration with air supply tube 5806 and biomass supply tube 5810 oriented at an angle θ relative to each other. Preferably, θ is about 45° or less. Sterilization unit 5800 creates an "air curtain" that blocks any contamination from entering the bioreactor via first drain outlet channel 3299a when LGM and/or AP is being drained from the bioreactor.

One or more aspects of the inventions shown in FIGS. 1-58, or any part(s) or function(s) thereof, may be implemented using hardware, software modules, firmware, tangible computer readable media having instructions stored thereon, or a combination thereof and may be implemented in one or more computer systems or other processing systems.

FIG. 59 illustrates an exemplary computer system 5900 in which embodiments, or portions thereof, may be implemented as computer-readable code. For example, portions of distribution system 2600 or bioreactor system 300, such as, control units 2612, 2614, and 370, or network 380, may be implemented in computer system 5900 using hardware, software, firmware, tangible computer readable media having instructions stored thereon, or a combination thereof and may be implemented in one or more computer systems or other processing systems.

If programmable logic is used, such logic may execute on a commercially available processing platform or a special purpose device. One of ordinary skill in the art may appreciate that embodiments of the disclosed subject matter can be practiced with various computer system configurations, including multi-core multiprocessor systems, minicomputers, and mainframe computers, computer linked or clustered with distributed functions, as well as pervasive or miniature computers that may be embedded into virtually any device.

For instance, at least one processor device and a memory may be used to implement the above described embodiments. A processor device may be a single processor, a plurality of processors, or combinations thereof. Processor devices may have one or more processor "cores."

Various embodiments of the inventions may be implemented in terms of this example computer system 5900. After reading this description, it will become apparent to a person skilled in the relevant art how to implement one or more of the inventions using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 5904 may be a special purpose or a general purpose processor device. As will be appreciated by persons skilled in the relevant art, processor device 5904 may also be a single processor in a multi-core/multiprocessor system, such system operating alone, or in a cluster of computing devices operating in a cluster or server farm. Processor device 5904 is connected to a communication infrastructure 5906, for example, a bus, message queue, network, or multi-core message-passing scheme.

Computer system 5900 also includes a main memory 5908, for example, random access memory (RAM), and may also include a secondary memory 5910. Secondary memory 5910 may include, for example, a hard disk drive 5912, or removable storage drive 5914. Removable storage drive

5914 may include a floppy disk drive, a magnetic tape drive, an optical disk drive, a flash memory, or the like. The removable storage drive 5914 reads from and/or writes to a removable storage unit 5918 in a well-known manner. Removable storage unit 5918 may include a floppy disk, magnetic tape, optical disk, etc. which is read by and written to by removable storage drive 5914. As will be appreciated by persons skilled in the relevant art, removable storage unit 5918 includes a computer usable storage medium having stored therein computer software and/or data.

Computer system 5900 (optionally) includes a display interface 5902 (which can include input and output devices such as keyboards, mice, etc.) that forwards graphics, text, and other data from communication infrastructure 5906 (or from a frame buffer not shown) for display on display unit 5930.

In alternative implementations, secondary memory 5910 may include other similar means for allowing computer programs or other instructions to be loaded into computer system 5900. Such means may include, for example, a removable storage unit 5922 and an interface 5920. Examples of such means may include a program cartridge and cartridge interface (such as that found in video game devices), a removable memory chip (such as an EPROM, or PROM) and associated socket, and other removable storage units 5922 and interfaces 5920 which allow software and data to be transferred from the removable storage unit 5922 to computer system 5900.

Computer system 5900 may also include a communication interface 5924. Communication interface 5924 allows software and data to be transferred between computer system 5900 and external devices. Communication interface 5924 may include a modem, a network interface (such as an Ethernet card), a communication port, a PCMCIA slot and card, or the like. Software and data transferred via communication interface 5924 may be in the form of signals, which may be electronic, electromagnetic, optical, or other signals capable of being received by communication interface 5924. These signals may be provided to communication interface 5924 via a communication path 5926. Communication path 5926 carries signals and may be implemented using wire or cable, fiber optics, a phone line, a cellular phone link, an RF link or other communication channels.

In this document, the terms "computer program medium" and "computer usable medium" are used to generally refer to media such as removable storage unit 5918, removable storage unit 5922, and a hard disk installed in hard disk drive 5912. Computer program medium and computer usable medium may also refer to memories, such as main memory 5908 and secondary memory 5910, which may be memory semiconductors (e.g. DRAMs, etc.).

Computer programs (also called computer control logic) are stored in main memory 5908 and/or secondary memory 5910. Computer programs may also be received via communication interface 5924. Such computer programs, when executed, enable computer system 5900 to implement the embodiments as discussed herein. In particular, the computer programs, when executed, enable processor device 5904 to implement the processes of the embodiments discussed here. Accordingly, such computer programs represent controllers of the computer system 5900. Where the embodiments are implemented using software, the software may be stored in a computer program product and loaded into computer system 5900 using removable storage drive 5914, interface 5920, and hard disk drive 5912, or communication interface 5924.

Embodiments of the inventions also may be directed to computer program products comprising software stored on any computer useable medium. Such software, when executed in one or more data processing device, causes a data processing device(s) to operate as described herein. Embodiments of the inventions may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

It is to be appreciated that the Detailed Description section, and not the Summary and Abstract sections, is intended to be used to interpret the claims. The Summary and Abstract sections may set forth one or more but not all exemplary embodiments of the present inventions as contemplated by the inventor(s), and thus, are not intended to limit the present inventions and the appended claims in any way.

The present inventions have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the inventions that others can, by applying knowledge within the skill of the art, readily modify and/or adapt for various applications such specific embodiments, without undue experimentation, without departing from the general concept of the present inventions. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present inventions should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A system for monitoring a culture of aquatic plants, the system comprising:
   a processor in communication with at least one image sensor disposed in a bioreactor; and
   a memory in communication with the processor, containing instructions executed by the processor, wherein the processor is configured to:
receive at least one image of a culture of aquatic plants from the at least one image sensor disposed in the bioreactor, the culture of aquatic plants comprising a plurality of aquatic plants;
perform image processing on the at least one image to determine at least one physical characteristic of an aquatic plant of the plurality of aquatic plants in the culture of aquatic plants;
perform an analysis to determine at least one state of the culture based on the image processing; and
control operation of the bioreactor based on one or more of: the determination of the at least one physical characteristic and the determination of the at least one state.

2. The system of claim 1, wherein the at least one physical characteristic is determined based on at least one parameter of the aquatic plant.

3. The system of claim 2, wherein the at least one parameter is selected from the group consisting of: the surface area of the aquatic plant, the amount of light absorbed by the aquatic plant, the wavelength and intensity of light reflected from the surface of the aquatic plant, the wavelength and intensity of light which is transmitted through the aquatic plant, and the distribution of the wavelengths and intensities in the reflected or transmitted light.

4. The system of claim 1, wherein the processor is further configured to store in a database a time stamp of when the at least one image is received together with the at least one physical characteristic of the aquatic plant.

5. The system of claim 1, wherein the processor is further configured to determine the at least one state by monitoring changes in the at least one physical characteristic of aquatic plants in the aquatic plant culture over time.

6. The system of claim 5, wherein the processor is further configured to monitor the changes in the at least one physical characteristic of aquatic plants in the aquatic plant culture by using at least one mathematical model.

7. The system of claim 1, wherein the at least one physical characteristic is any of: a shape of the aquatic plant, a size of the aquatic plant, a pigment of the aquatic plant, a texture of the aquatic plant, a hue of the aquatic plant, a pigmentation intensity of the aquatic plant, a distribution of colors in the aquatic plant's pigmentation, or a transparency of the aquatic plant.

8. The system of claim 1, wherein the at least one state of the culture is at least one of: a healthy culture, a contaminated culture, a growth phase of the culture, a selective nutrient profile, a growth rate of the culture, a culture under stress, a deficiency of a growth condition, a mortality rate, a dead culture, a dying culture, and a viability of the aquatic plants' growth.

9. The system of claim 8, wherein the at least one state of the culture is the growth phase of the culture, and wherein the growth phase of the culture is one of: lag phase, exponential phase, stationary phase, death phase, or any intermediate phase.

10. The system of claim 1, wherein the processor is further configured to store in a database one or more of: the at least one image, the at least one physical characteristic, or the at least one state.

11. The system of claim 1, wherein the processor is in communication with the bioreactor via a server over a network.

12. The system of claim 1, wherein the processor is located in a control unit within the bioreactor.

13. The system of claim 1, wherein the culture of aquatic plants comprises at least one of: the genus *Spirodela, Landoltia, Lemna, Wolffiella*, and *Wolffia*.

14. The system of claim 1, wherein the bioreactor comprises:
at least one input unit for receiving an aquatic organism used as a starter material for the culture of aquatic plants;
at least one growing unit for growing the culture of aquatic plants;
at least one harvesting unit for harvesting the culture of aquatic plants; and
at least one output unit for providing a consumable derived from the culture of aquatic plants.

15. The system of claim 1, wherein the processer is configured to control operation of the bioreactor by adjusting at least one growing condition.

16. The system of claim 15, wherein the at least one growing condition includes at least one of: a light level, light spectrum, light interval, temperature, fertilizer elements level, water level, vapor pressure, humidity, pH, ion concentration, oxygen concentration, $CO_2$ level, culture density, air flow, growth solution flow, and culture flow.

17. A bioreactor for growing an aquatic plant culture comprising:
at least one input unit for receiving an aquatic organism used as a starter material for an aquatic plant culture;
at least one growing unit for growing the aquatic plant culture, the aquatic plant culture comprising a plurality of aquatic plants of at least one of the genus *Spirodela, Landoltia, Lemna, Wolffiella*, and *Wolffia;*
at least one harvesting unit for harvesting the aquatic plant culture;
at least one output unit for providing a consumable derived from the aquatic plant culture; and
a control unit configured to:
receive an image of the aquatic plant culture within the growing unit from an imaging system disposed in the bioreactor, the imaging system comprising at least one image sensor;
determine at least one physical characteristic related to an aquatic plant of the plurality of aquatic plants in the aquatic plant culture by performing at least one image processing technique on the at least one image, wherein the at least one physical characteristic is at least one of: a shape of the aquatic plant, a size of the aquatic plant, a pigment of the aquatic plant, a texture of the aquatic plant, a hue of the aquatic plant, a pigmentation intensity of the aquatic plant, a distribution of colors in the aquatic plant, or a transparency of the aquatic plant; and
control operation of the bioreactor based on the determination of the at least one physical characteristic.

18. The bioreactor of claim 17, wherein the control unit is configured to control operation of the bioreactor by adjusting at least one growing condition.

19. A method for monitoring a culture of aquatic plants in a bioreactor, the method comprising the steps of:
performing an analysis of at least one image of the culture, wherein the analysis includes:
receiving the at least one image of the culture of aquatic plants from at least one image sensor disposed in the bioreactor,
performing an image processing technique on the at least one image to determine at least one physical characteristic of the culture, and performing an analysis to determine at least one state of the culture; and adjusting at least one growing condition based on one or more of the at least one determined physical characteristic and the at least one determined state, wherein the culture comprises at least one of the genus *Spirodela, Landoltia, Lemna, Wolffiella,* and *Wolffia.*

20. The method of claim 19, wherein the at least one growing condition is adjusted based on the at least one determined physical characteristic and the at least one determined state.

21. The system of claim 1, wherein the processor is configured to control operation of the bioreactor in real-time based on one or more of: the determination of the at least one physical characteristic and the determination of the at least one state.

22. The system of claim 1, wherein the processor performs image processing on a plurality of images received from the at least one image sensor to determine the at least one state of the culture.

23. The system of claim 1, wherein upon determining the at least one state of the culture, the processor is configured to promote a change of the at least one state of the culture to a different state by adjusting at least one growing condition for the culture of aquatic plants.

24. The system of claim 1, wherein, during the image processing, the processor is configured to determine at least one physical characteristic of each of a plurality of aquatic plants in the culture of aquatic plants.

25. The system of claim 1, wherein, during the image processing, the processor is configured to determine a plurality of physical characteristics of the aquatic plant.

26. The system of claim 25, wherein one of the plurality of physical characteristics is a shape of the aquatic plant.

27. The system of claim 1, wherein, during the image processing, the processor is configured to determine a plurality of physical characteristics of each of a plurality of aquatic plants in the culture of aquatic plants.

28. The system of claim 27, wherein, during the image processing, the processor is configured to score each of the plurality of physical characteristics in the at least one image of a culture of aquatic plants based on the determined physical characteristics of each of the plurality of aquatic plants.

29. The system of claim 28, wherein the at least one state is determined based on the scoring of each of the plurality of physical characteristics.

30. The system of claim 29, wherein the processor is configured to control an operation of the bioreactor based on the at least one state determined based on the scoring of each of the plurality of physical characteristics.

31. The system of claim 1, wherein the culture of aquatic plants comprises individual aquatic plants and at least one of mother-daughter aquatic plant pairs and mother-daughter aquatic plant colonies.

32. The system of claim 1, wherein the aquatic plant is an individual aquatic plant, a mother-daughter aquatic plant pair, or a mother-daughter aquatic plant colony.

33. The system of claim 1, wherein the at least one state is determined based on a determination of a plurality of physical characteristics of each of a plurality of aquatic plants in the culture of aquatic plants determined during the image processing.

34. The bioreactor of claim 17, wherein the control unit is configured to determine at least one state of the culture based on a determination of the at least one physical characteristic of each of a plurality of aquatic plants in the culture of aquatic plants.

35. The bioreactor of claim 34, wherein the control unit is configured to control operation of the bioreactor based on the determination of the at least one state.

* * * * *